US008552203B2

(12) United States Patent
Lowe et al.

(10) Patent No.: US 8,552,203 B2
(45) Date of Patent: *Oct. 8, 2013

(54) INDANE ACETIC ACID DERIVATIVES AND THEIR USE AS PHARMACEUTICAL AGENTS, INTERMEDIATES, AND METHOD OF PREPARATION

(75) Inventors: Derek B. Lowe, Hamden, CT (US); Philip L. Wickens, Wallingford, CT (US); Xin Ma, Bethany, CT (US); Mingbao Zhang, Stamford, CT (US); William H. Bullock, Easton, CT (US); Philip D. G. Coish, New Haven, CT (US); Ingo A. Mugge, New Haven, CT (US); Andreas Stolle, Wuppertal (DE); Ming Wang, Milford, CT (US); Yamin Wang, Sandy Hook, CT (US); Chengzhi Zhang, Orange, CT (US); Hai-Jun Zhang, Middletown, CT (US); Lei Zhu, Milford, CT (US); Manami Tsutsumi, Stratford, CT (US); James N. Livingston, Guilford, CT (US)

(73) Assignee: Bayer Healthcare LLC, Tarrytown, NY (US)

( * ) Notice: Subject to any disclaimer, the term of this patent is extended or adjusted under 35 U.S.C. 154(b) by 153 days.

This patent is subject to a terminal disclaimer.

(21) Appl. No.: 13/035,638

(22) Filed: Feb. 25, 2011

(65) Prior Publication Data
US 2011/0152331 A1 Jun. 23, 2011

Related U.S. Application Data

(60) Continuation of application No. 12/369,736, filed on Feb. 11, 2009, which is a continuation of application No. 12/059,706, filed on Mar. 31, 2008, now abandoned, which is a division of application No. 11/429,136, filed on May 5, 2006, now Pat. No. 7,358,386, which is a division of application No. 10/949,119, filed on Sep. 22, 2004, now Pat. No. 7,112,597, which is a continuation of application No. 10/205,839, filed on Jul. 25, 2002, now Pat. No. 6,828,335.

(60) Provisional application No. 60/308,500, filed on Jul. 27, 2001, provisional application No. 60/373,048, filed on Apr. 16, 2002.

(51) Int. Cl.
C07D 277/22 (2006.01)
C07D 263/30 (2006.01)

(52) U.S. Cl.
USPC .......................................... 548/203; 548/235

(58) Field of Classification Search
None
See application file for complete search history.

(56) References Cited

U.S. PATENT DOCUMENTS

| 3,929,923 A | 12/1975 | Hosler et al. |
|---|---|---|
| 4,393,240 A | 7/1983 | Stille |
| 5,466,833 A | 11/1995 | Ivanics et al. |
| 5,480,896 A | 1/1996 | Malamas et al. |
| 5,595,991 A | 1/1997 | Shoop et al. |
| 5,851,988 A | 12/1998 | Sportsman et al. |
| 6,150,564 A | 11/2000 | Brocker et al. |
| 6,214,850 B1 | 4/2001 | Evans et al. |
| 6,329,431 B1 | 12/2001 | Sportsman et al. |
| 6,828,335 B2 | 12/2004 | Lowe et al. |
| 7,112,597 B2 | 9/2006 | Lowe et al. |
| 7,358,386 B2 | 4/2008 | Lowe et al. |

FOREIGN PATENT DOCUMENTS

| EP | 0490772 | 6/1992 |
|---|---|---|
| JP | 1087602 A | 3/1989 |
| WO | WO-9640128 | 12/1996 |
| WO | WO 99/11255 A1 | 3/1999 |
| WO | WO 00/16798 A1 | 3/2000 |
| WO | WO-0064876 | 11/2000 |
| WO | WO-0064888 | 11/2000 |
| WO | WO-0116120 | 3/2001 |
| WO | WO-0218355 | 3/2002 |

OTHER PUBLICATIONS

Sarma et al. "Sesquiterpenic Indanes of Bicyclonidorellane Skeleton: Synthesis of 1,6-Diisopropylindane & Ethyl 2-(6-Isopropyl-1-indanyl)propionate", *Indian J. Chemistry* 25B:953-954 (1986).
"Crystallization", *Kirk-Othmer Encyclopedia of Chemical Technology* Copyright © 2002 by John Wiley & Sons, Inc. pp. 1-63.
Examination Report corresponding to Australian Patent Application No. 2002319693 dated Apr. 27, 2007.
Examination Report corresponding to Australian Patent Application No. 2008237581 dated May 10, 2010.
Jarvill-Taylor et al. "A Hydroxychalcone Derived from Cinnamon Functions as a Mimetic for Insulin in 3T3-L1 Adipocytes", *J. Am. College of Nutrition* 20(4):327-336 (2001).
Kletzien et al. "Enhancement of Adipocyte Differentiation by an Insulin-Sensitizing Agent", *Molecular Pharmacology* 41:393-398 (1991).
Zhang et al. "Discovery of a Small Molecule Insulin Mimetic with Antidiabetic Activity in Mice", *Science* 284:974-977 (1999).
Office Action corresponding to Canadian Patent Application No. 2,455,620 issued Jul. 8, 2010.
Office Action corresponding to Canadian Patent Application No. 2,455,620 issued Jul. 21, 2009.
First Office Action corresponding to Chinese Patent Application No. 02818676.1 issued Sep. 9, 2005.
Second Office Action corresponding to Chinese Patent Application No. 02818676.1 issued Aug. 8, 2008.
Third Office Action corresponding to Chinese Patent Application No. 02818676.1 issued Dec. 12, 2008.
First Office Action corresponding to Chinese Patent Application No. 200610004609.1 issued Feb. 1, 2008.

(Continued)

*Primary Examiner* — Johann R Richter
*Assistant Examiner* — Jennifer C Sawyer
(74) *Attorney, Agent, or Firm* — James G. Passé; Passé Intellectual Property, LLC

(57) ABSTRACT

This invention relates to novel indane acetic acid derivatives which are useful in the treatment of diseases such as diabetes, obesity, hyperlipidemia, and atherosclerotic diseases. The invention also relates to intermediates useful in preparation of indane acetic derivatives and to methods of preparation.

11 Claims, No Drawings

(56) References Cited

OTHER PUBLICATIONS

Second Office Action corresponding to Chinese Patent Application No. 200610004609.1 issued Sep. 26, 2008.
Third Office Action corresponding to Chinese Patent Application No. 200610004609,1 issued May 8, 2009.
Hoffsommer et al. "Structure of the Indenylacetic Acids", *J. Org. Chemistry* 34(12):4182-4184 (1969).
Examination Report corresponding to Indian Patent Application No. 00258/DELNP/2004 dated Jul. 31, 2007.
Notice of Reasons for Rejection corresponding to Japanese Patent Application No. 2003-517034 dated Mar. 31, 2009.
Final Rejection corresponding to Japanese Patent Application No. 2003-517034 dated Oct. 27, 2009.
Notice of Preliminary Rejection corresponding to Korean Patent Application No. 10-2004-7001188.
Notice of Preliminary Rejection corresponding to Korean Patent Application No. 10-2009-7023801.
Office Action corresponding to Mexican Patent Application No. PA/a/2004/000599 dated Apr. 25, 2006.
Office Action corresponding to Mexican Patent Application No. PA/a/2006/007672 dated Mar. 3, 2008.
Office Action corresponding to Mexican Patent Application No. PA/a/2006/007672 dated Sep. 9, 2008.
Office Action corresponding to Mexican Patent Application No. PA/a/2006/007672 dated May 13, 2009.
Office Action corresponding to Mexican Patent Application No. PA/a/2006/007672 dated Sep. 4, 2009.
Office Action corresponding to Mexican Patent Application No. MX/a/2008/007663 dated Jun. 3, 2010.
Office Action corresponding to Mexican Patent Application No. MX/a/2008/007663 dated Jan. 20, 2011.
Examination Report corresponding to Malaysian Patent Application No. PI 20022806 dated Jan. 5, 2007.
Examination Report corresponding to Malaysian Patent Application No. PI 20063359 dated Jun. 26, 2009.
Examination Report corresponding to Malaysian Patent Application No. PI 20063359 dated May 13, 2011.
Office Action corresponding to Norwegian Patent Application No. 20040356 dated Feb. 1, 2008.
Office Action corresponding to Norwegian Patent Application No. 20040356 dated Sep. 4, 2008.
Office Action corresponding to Norwegian Patent Application No. 20040356 dated Dec. 18, 2008.
Office Action corresponding to Russian Patent Application No. 2004105925/04.
Subramaniam, "The Emerging Role of Thiazolidinediones in the Treatment of Diabetes-Mellitus and Related Disorders," *Clin. Exper. Hypertension*, 21:121-136 (1999).
Bhattacharyya et al. "Selective Reduction of Dienones Synthesis of Intermediates for Sesqui-and Diterpenes", *Synthetic Communications* 19:673-678 (1989).

INDANE ACETIC ACID DERIVATIVES AND THEIR USE AS PHARMACEUTICAL AGENTS, INTERMEDIATES, AND METHOD OF PREPARATION

The present application is a continuation of and claims priority from U.S. patent application Ser. No. 12/369,736, filed Feb. 11, 2009, which is a continuation of U.S. patent application Ser. No. 12/059,706, filed Mar. 31, 2008, now abandoned, which is a divisional application of U.S. patent application Ser. No. 11/429,136, filed on May 5, 2006, now U.S. Pat. No. 7,358,386, which is a divisional application of U.S. patent application Ser. No. 10/949,119, filed on Sep. 22, 2004, now U.S. Pat. No. 7,112,597, which is a continuation application of U.S. patent application Ser. No. 10/205,839, filed Jul. 25, 2002, now U.S. Pat. No. 6,828,335, which claims benefit of U.S. Provisional Application Ser. No. 60/308,500, filed Jul. 27, 2001 and U.S. Provisional Application Ser. No. 60/373,048, filed on Apr. 16, 2002, the contents of each of these applications is are incorporated herein by reference in their entirety.

FIELD OF THE INVENTION

This invention is directed to indane acetic acid derivatives and their use in pharmaceutical compositions for the treatment of diseases such as diabetes, obesity, hyperlipidemia, and atherosclerotic disease. The invention is also directed to intermediates useful in preparation of indane acetic derivatives and to methods of preparation.

BACKGROUND OF THE INVENTION

Type II diabetes is the more common form of diabetes, with 90-95% of hyperglycemic patients experiencing this form of the disease. In Type II diabetes, there appears to be a reduction in the pancreatic β-cell mass, several distinct defects in insulin secretion, and a decrease in tissue sensitivity to insulin. The symptoms and consequences of this form of diabetes include fatigue, frequent urination, thirst, blurred vision, frequent infections and slow healing of sores, diabetic nerve damage, retinopathy, micro and macro blood vessel damage, and heart and renal disease.

Resistance to the metabolic actions of insulin is one of the key features of Type II diabetes. Insulin resistance is characterized by impaired uptake and utilization of glucose in insulin-sensitive target organs, for example, adipocytes and skeletal muscle, and by impaired inhibition of hepatic glucose output. Functional insulin deficiency, insulin resistance in the periphery, and the failure of insulin to suppress hepatic glucose output results in fasting hyperglycemia. Pancreatic β-cells compensate for the insulin resistance by secreting increased levels of insulin. However, the β-cells are unable to maintain this high output of insulin, and eventually, the glucose-induced insulin secretion falls, leading to the deterioration of glucose homeostasis and to the subsequent development of overt diabetes. Hyperinsulinemia is also linked to insulin resistance, hypertriglyceridemia, low high-density lipoprotein (HDL) cholesterol, and increased plasma concentration of low-density lipoproteins (LDL). The association of insulin resistance and hyperinsulinemia with these metabolic disorders has been termed "Syndrome X," and has been strongly linked to an increased risk of hypertension and coronary artery disease.

Obesity is an excessive accumulation of adipose tissue. Excess adipose tissue is associated with the development of serious medical conditions, for example, Type II diabetes, hypertension, coronary artery disease, hyperlipidemia, obesity, and certain malignancies. The adipocyte may also influence glucose homeostasis through the production of tumor necrosis factor α (TNFα) and other molecules.

Atherosclerotic disease is known to be caused by a number of factors, for example, hypertension, diabetes, low levels of HDL, and high levels of LDL.

Atherosclerotic-related diseases include cardiovascular disease, coronary heart disease (CHD), cerebrovascular disease, and peripheral vessel disease. Coronary heart disease includes CHD death, myocardial infarction, and coronary revascularization. Cerebrovascular disease includes ischemic or hemorrhagic stroke, and transient ischemic attacks.

Accordingly, despite the presence of some pharmaceuticals that are used to treat these diseases, there remains a need for new pharmaceuticals that are both safe and effective agents for the treatment of disease, and for useful methods to prepare them.

The present invention relates to compounds which are useful in the treatment of diabetes and related disorders such as Syndrome X, impaired glucose tolerance, impaired fasting glucose, and hyperinsulinemia; obesity; atherosclerotic disease, dyslipidemia, and related disorders such as hypertriglyceridemia, low HDL cholesterol, and hypercholesteremia; cardiovascular disease; and cerebrovascular disease.

DESCRIPTION OF THE INVENTION

The present invention encompasses the compounds of Formula I,

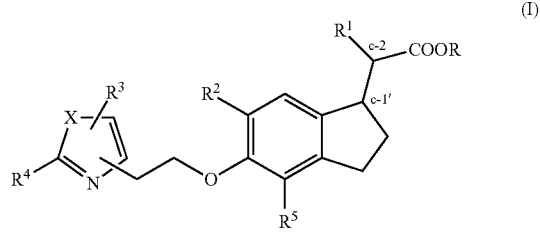

wherein
R is H or $C_1$-$C_6$ alkyl;
$R^1$ is H, COOR, $C_3$-$C_8$ cycloalkyl, or
  $C_1$-$C_6$ alkyl, $C_2$-$C_6$ alkenyl, or $C_1$-$C_6$ alkoxy each of which may be unsubstituted or substituted with fluoro, methylenedioxyphenyl, or phenyl which may be unsubstituted or substituted with $R^6$;
$R^2$ is H, halo, or $C_1$-$C_6$ alkyl which may be unsubstituted or substituted with $C_1$-$C_6$ alkoxy, oxo, fluoro, or
$R^2$ is phenyl, furyl, thienyl, pyrrolyl, oxazolyl, thiazolyl, imidazolyl, pyrazolyl, isoxazolyl, isothiazolyl, triazolyl, oxadiazolyl, thiadiazolyl, tetrazolyl, pyridyl, pyrrolidinyl, piperidinyl, tetrahydropyranyl, tetrahydrothiopyranyl, piperazinyl, or morpholinyl,
  each of which may be unsubstituted or substituted with $R^6$;
$R^3$ is H, $C_1$-$C_6$ alkyl, or phenyl which may be unsubstituted or substituted with $R^6$;
X is O or S;
$R^4$ is $C_1$-$C_6$ alkyl or $C_3$-$C_8$ cycloalkyl, either of which may be unsubstituted or substituted with fluoro, oxo, or $C_1$-$C_6$ alkoxy which may be unsubstituted or substituted with $C_1$-$C_6$ alkoxy, or phenyl optionally substituted with $R^6$,
  or either of which may be substituted with phenyl, naphthyl, furyl, thienyl, pyrrolyl, tetrahydrofuryl, pyrrolidinyl, pyrrolinyl, tetrahydrothienyl, oxazolyl, thiazolyl, imidazolyl, pyrazolyl, isoxazolyl, isothiazolyl, triazolyl, oxadiazolyl, thiadiazolyl, tetrazolyl, pyridyl, piperidinyl, tetrahydropyranyl, tetrahydrothiopyranyl, pyrimidinyl, pyrazinyl, pyridazinyl, piperazinyl, morpholinyl, benzofuryl, dihydrobenzofuryl, benzothienyl, dihydrobenzothienyl, indolyl, indolinyl, indazolyl, benzoxazolyl, benzothiazolyl, benzimidazolyl, benzisoxazolyl, benzisothiazolyl, benzodioxolyl, quinolyl, isoquinolyl, quinazolinyl, quinoxazolinyl, dihydrobenzopyranyl, dihydrobenzothiopyranyl, or 1,4-benzodioxanyl, each of which may be unsubstituted or substituted with $R^6$, or $C_1$-$C_6$ alkyl may also be substituted with $C_3$-$C_8$ cycloalkyl or with phenoxy which may be unsubstituted or substituted with $R^6$ or with phenyl, naphthyl, furyl, thienyl, pyrrolyl, tetrahydrofuryl, pyrrolidinyl, pyrrolinyl, tetrahydrothienyl, oxazolyl, thiazolyl, imidazolyl, pyrazolyl, isoxazolyl, isothiazolyl, triazolyl, oxadiazolyl, thiadiazolyl, tetrazolyl, pyridyl, piperidinyl, tetrahydropyranyl, tetrahydrothiopyranyl, pyrimidinyl, pyrazinyl, pyridazinyl, piperazinyl, morpholinyl, benzofuryl, dihydrobenzofuryl, benzothienyl, dihydrobenzothienyl, indolyl, indolinyl, indazolyl, benzoxazolyl, benzothiazolyl, benzimidazolyl, benzisoxazolyl, benzisothiazolyl, benzodioxolyl, quinolyl, isoquinolyl, quinazolinyl, quinoxazolinyl, dihydrobenzopyranyl, dihydrobenzothiopyranyl, or 1,4-benzodioxanyl, each of which may be unsubstituted or substituted with $R^6$, or $R^4$ is phenyl, naphthyl, furyl, thienyl, pyrrolyl, tetrahydrofuryl, pyrrolidinyl, pyrrolinyl, tetrahydrothienyl, oxazolyl, thiazolyl, imidazolyl, pyrazolyl, isoxazolyl, isothiazolyl, triazolyl, oxadiazolyl, thiadiazolyl, tetrazolyl, pyridyl, piperidinyl, tetrahydropyranyl, tetrahydrothiopyranyl, pyrimidinyl, pyrazinyl, pyridazinyl, piperazinyl, morpholinyl, benzofuryl, dihydrobenzofuryl, benzothienyl, dihydrobenzothienyl, indolyl, indolinyl, benzoxazolyl, benxothiazolyl, benzimidazolyl, benzisoxazolyl, benzisothiazolyl, benzodioxolyl, quinolyl, isoquinolyl, quinazolinyl, quinoxazolinyl, dihydrobenzopyranyl, dihydrobenzothiopyranyl, or 1,4-benzodioxanyl, each of which may be unsubstituted or substituted with $R^6$, or with phenyl, furyl, thienyl, pyrrolyl, oxazolyl, thiazolyl, imidazolyl, pyrazolyl, isoxazolyl, isothiazolyl, triazolyl, oxadiazolyl, thiadiazolyl, tetrazolyl, pyridyl, pyrrolidinyl, piperidinyl, tetrahydropyranyl, tetrahydrothiopyranyl, piperazinyl, morpholinyl, benzodioxolyl, dihydrobenzofuranyl, indolyl, pyrimidinyl or phenoxy, each of which may be unsubstituted or substituted with $R^6$;

$R^5$ is H, halo or $C_1$-$C_6$ alkyl optionally substituted with oxo;

$R^6$ is halo, $CF_3$, $C_1$-$C_6$ alkyl optionally substituted with oxo or hydroxy, or $C_1$-$C_6$ alkoxy optionally substituted with fluoro; and pharmaceutically acceptable salts and esters thereof.

The terms identified above have the following meaning throughout:

"$C_1$-$C_6$ alkyl" means straight or branched chain alkyl groups having from one to about six carbon atoms. Such groups include methyl, ethyl, n-propyl, isopropyl, n-butyl, isobutyl, sec-butyl, tert-butyl, n-pentyl, neo-pentyl, 2-pentyl, n-hexyl, 2-hexyl, 3-hexyl, 2,3-dimethylbutyl, and the like.

"$C_2$-$C_6$ alkenyl" means straight or branched chain alkenyl groups having from two to about six carbon atoms and containing one or more double bonds. Such groups include ethenyl, propenyl, isopropenyl, 2-isobutenyl, 4-pentenyl, 5-hexenyl, and the like.

"$C_3$-$C_8$ cycloalkyl" means saturated monocyclic alkyl groups having from 3 to about 8 carbon atoms and includes such groups as cyclopropyl, cyclopentyl, cyclohexyl, and the like.

"$C_1$-$C_6$alkoxy" means straight or branched chain alkoxy groups having from one to about six carbon atoms and includes such groups as methoxy, ethoxy, n-propoxy, isopropoxy, n-butoxy, isobutoxy, sec-butoxy, tert-butoxy, and the like.

"Halo" means fluoro, chloro, bromo, or iodo.

When an alkyl, cycloalkyl, alkenyl, or alkoxy group is described as being substituted with fluoro, it may be substituted with one or more fluorine atoms at any available carbon atom up to the perfluoro level.

When an alkyl substituent is described as being substituted by oxo, it means substitution by a doubly bonded oxygen atom, which forms together with the carbon to which it is attached, a carbonyl group —(C=O)—.

When any moiety is described as being substituted, it can have one or more of the indicated substituents that may be located at any available position on the moiety. When there are two or more substituents on any moiety, each substituent may be defined independently of any other substituent and may, accordingly, be the same or different.

The term "optionally substituted" means that the moiety so modified may be unsubstituted or substituted with the identified substituent(s).

$R^3$ may be attached to the heterocyclic moiety of the compound of Formula I at either the 4 or 5 position (i.e., at either available carbon atom) and, accordingly, the remaining portion of the molecule will be attached at the remaining available carbon atom.

Examples of the compounds of Formula I, which are illustrative of the present invention but not limiting in any way, are listed in Table 1.

TABLE 1

Illustrative Examples of Compounds of Formula I

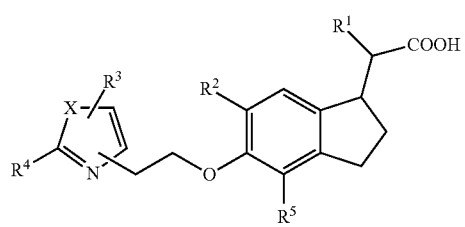

(I)

| Entry No. | $R^1$ | $R^2$ | $R^3$ | $R^4$ | $R^5$ | X |
|---|---|---|---|---|---|---|
| 1 | H | H | H | $CH_3$ | H | O |
| 2 | H | H | H | n-butyl | H | O |
| 3 | H | H | H | cyclopropyl | H | O |
| 4 | H | H | H | cyclopentyl | H | O |

TABLE 1-continued

Illustrative Examples of Compounds of Formula I (I)

| Entry No. | R¹ | R² | R³ | R⁴ | R⁵ | X |
|---|---|---|---|---|---|---|
| 5 | H | H | H | cyclooctyl | H | O |
| 6 | H | H | H | Ph | H | O |
| 7 | H | H | H | Ph | H | S |
| 8 | H | H | H | 2-Cl Ph | H | O |
| 9 | H | H | H | 2,3-d-F Ph | H | O |
| 10 | H | H | H | 2,4-di-CH₃ Ph | H | O |
| 11 | H | H | H | 2-thienyl | H | O |
| 12 | H | H | H | (4-phenyl-5-trifluoromethyl-2-thienyl group) | H | O |
| 13 | H | H | H | 2-furyl | H | O |
| 14 | H | H | H | 2-furyl | H | S |
| 15 | H | H | H | 2-(4-CH₃)furyl | H | O |
| 16 | H | H | H | (5-(3,5-dichlorophenoxy)-2-furyl group) | H | O |
| 17 | H | H | H | 4-F Ph | H | O |
| 18 | H | H | H | 4-F Ph | H | S |
| 19 | H | H | CH₃ | 4-F Ph | H | O |
| 20 | H | H | Et | 4-F Ph | H | O |
| 21 | H | H | Et | 4-F Ph | H | S |
| 22 | H | H | Et | 3-pyridyl | H | O |
| 23 | H | H | Et | (6-(2-thienyl)-2-methyl-3-pyridyl group) | H | O |
| 24 | H | H | isopropyl | 4-F Ph | H | O |
| 25 | H | H | isopropyl | 2,4-di-F Ph | H | O |
| 26 | H | H | n-butyl | 2,4-di-F Ph | H | O |
| 27 | H | H | n-hexyl | 2,4-di-F Ph | H | O |
| 28 | H | H | Ph | 2,4-di-F Ph | H | O |
| 29 | H | H | 4-F Ph | 2,4-di-F Ph | H | O |
| 30 | H | CH₃ | Et | Ph | H | O |
| 31 | H | CH₃ | Et | Ph | H | S |
| 32 | H | CH₃ | Et | 3-CH₃O Ph | H | O |
| 33 | H | H | Et | 3-CH₃O Ph | H | O |
| 34 | H | H | Et | 3-CH₃O Ph | H | S |
| 35 | H | H | Et | 4-CH₃O Ph | H | O |
| 36 | H | H | Et | 4-CH₃O Ph | H | S |
| 37 | H | H | Et | 4-EtO Ph | H | S |
| 38 | H | H | Et | 4-EtO Ph | H | O |

TABLE 1-continued

Illustrative Examples of Compounds of Formula I (I)

| Entry No. | $R^1$ | $R^2$ | $R^3$ | $R^4$ | $R^5$ | X |
|---|---|---|---|---|---|---|
| 39 | H | H | Me | (benzo[d][1,3]dioxol-5-yl)-C(CH₃)₂– | H | O |
| 40 | H | H | Me | PhCH₂ | H | O |
| 41 | H | H | Me | 3-Cl-4-F—Ph | H | O |
| 42 | H | H | Me | 3-F-4-Me—Ph | H | O |
| 43 | H | H | Me | 3-Me-4-F—Ph | H | O |
| 44 | H | H | Me | 3-NH₂-4-Me—Ph | H | O |
| 45 | H | H | Et | 4-Et—Ph | H | O |
| 46 | H | H | Me | 4-Et—Ph | H | O |
| 47 | H | H | Et | 4-CN—Ph | H | O |
| 48 | H | H | Et | 4-(Et)₂N—Ph | H | O |
| 49 | H | H | Me | 4-i-Pr—Ph | H | O |
| 50 | H | H | Me | 4-t-Bu—Ph | H | O |
| 51 | H | H | Me | 4-Et—Ph | H | O |
| 52 | H | H | Me | 4-n-Bu—Ph | H | O |
| 53 | H | H | Et | 4-n-Pr—Ph | H | O |
| 54 | H | CH₃ | Et | 4-CH₃O Ph | H | O |
| 55 | H | CH₃ | Et | 4-CH₃O Ph | H | S |
| 56 | H | CH₃ | Et | 4-CH₃O Ph | CH₃ | O |
| 57 | H | CH₃ | Et | 3,4-di-CH₃O Ph | CH₃ | O |
| 58 | H | CH₃ | Et | 4-Ph Ph | CH₃ | O |
| 59 | H | CH₃ | Et | 4-Ph Ph | CH₃ | S |
| 60 | H | CH₃ | Et | 4-(4-t-Bu-phenyl)-1,2,3-thiadiazol-5-yl | CH₃ | O |
| 61 | H | CH₃ | Ph | cyclopropyl | H | O |
| 62 | H | CH₃ | Ph | cyclohexyl | H | O |
| 63 | H | CH₃ | Ph | cyclohexyl | H | S |
| 64 | H | CH₃ | p-F Ph | cyclohexyl | H | O |
| 65 | H | Cl | i-Pr | Ph | H | O |
| 66 | H | Cl | i-Pr | Ph | H | S |
| 67 | H | Cl | i-Pr | Ph | Cl | O |
| 68 | H | Cl | i-Pr | 4-CH₃ Ph | Cl | O |
| 69 | H | Br | CH₃ | Ph | Br | O |
| 70 | H | Br | CH₃ | 3-F Ph | Br | O |
| 71 | H | Br | CH₃ | 3-F Ph | Br | S |
| 72 | H | CH₃CO | CH₃ | n-propyl | CH₃CO | O |
| 73 | H | CH₂OCH₃ | Et | 2-thienyl | H | O |
| 74 | H | Ph | H | 2,4-di-Cl Ph | H | O |
| 75 | H | Ph | H | 2,4-di-Cl Ph | H | S |
| 76 | H | Ph | CH₃ | 2,4-di-Cl Ph | H | O |
| 77 | H | Ph | Et | 2,4-di-Cl Ph | H | O |
| 78 | H | Ph | Ph | 2,4-di-Cl Ph | H | O |
| 79 | H | Ph | Ph | 2,4-di-Cl Ph | H | S |
| 80 | H | Ph | 4-CH₃O—Ph | 2,4-di-Cl Ph | H | O |
| 81 | H | 4-F Ph | CH₃ | 4-F Ph | H | O |
| 82 | H | 4-F Ph | CH₃ | 2,4-di-Cl Ph | H | O |
| 83 | H | 3-pyridyl | CH₃ | 2,4-di-Cl Ph | H | O |
| 84 | H | 3-pyridyl | CH₃ | 2,4-di-Cl Ph | H | S |
| 85 | H | 2-thienyl | CH₃ | Ph | H | O |
| 86 | H | 2-thienyl | CH₃ | 2,4-di-Cl Ph | H | O |
| 87 | H | 2-thienyl | CH₃ | 2,4-di-Cl Ph | H | S |

TABLE 1-continued

Illustrative Examples of Compounds of Formula I (I)

| Entry No. | R¹ | R² | R³ | R⁴ | R⁵ | X |
|---|---|---|---|---|---|---|
| 88 | H | 2-thienyl | CH₃ | 3-pyridyl | H | O |
| 89 | H | 2-thienyl | CH₃ | cyclopentyl | H | O |
| 90 | H | 2-thienyl | CH₃ | (phenyl-cyclopentyl) | H | O |
| 91 | H | 2-thienyl | CH₃ | Ph | 2-thienyl | O |
| 92 | CH₃ | H | H | Ph | H | O |
| 93 | CH₃ | H | H | Ph | H | S |
| 94 | CH₃ | H | H | 2-thienyl | H | O |
| 95 | CH₃ | H | H | 2-thienyl | H | S |
| 96 | CH₃ | H | H | (5-methyl-3-isoxazolyl) | H | O |
| 97 | CH₃ | H | H | (thiadiazolyl-isoxazolyl) | H | O |
| 98 | CH₃ | H | H | (1-methyl-imidazol-2-yl) | H | O |
| 99 | CH₃ | H | H | 2-pyridyl | H | O |
| 100 | CH₃ | H | H | (2-pyrazinyl) | H | O |
| 101 | CH₃ | H | CH₃ | cyclobutyl | H | O |
| 102 | CH₃ | H | CH₃ | cyclohexyl | H | O |
| 103 | CH₃ | H | CH₃ | cyclohexyl | H | S |
| 104 | CH₃ | H | CH₃ | 3,4-di-F Ph | H | O |
| 105 | CH₃ | H | CH₃ | 3,4-di-F Ph | H | S |
| 106 | CH₃ | H | CH₃ | 2-pyridyl | H | O |

TABLE 1-continued

Illustrative Examples of Compounds of Formula I (I)

| Entry No. | R¹ | R² | R³ | R⁴ | R⁵ | X |
|---|---|---|---|---|---|---|
| 107 | CH₃ | H | CH₃ | 4-methyl-1,2,3-thiadiazol-5-yl | H | O |
| 108 | CH₃ | H | CH₃ | quinoxalin-2-yl | H | O |
| 109 | CH₃ | H | Et | Ph | H | O |
| 110 | CH₃ | H | Et | Ph | H | S |
| 111 | CH₃ | H | Et | 4-CF₃ Ph | H | O |
| 112 | CH₃ | H | Et | 4-methyl-1,2,3-thiadiazol-5-yl | H | O |
| 113 | CH₃ | H | Et | 2-napthyl | H | O |
| 114 | CH₃ | H | Et | 5-methylbenzo[d]isothiazol-3-yl | H | O |
| 115 | CH₃ | H | Et | benzo[b]thiophen-2-yl | H | O |
| 116 | CH₃ | H | Et | benzo[b]thiophen-2-yl | H | S |
| 117 | CH₃ | H | Et | 4-tert-butyl-5-methyl-2-phenylfuran-3-yl | H | O |

TABLE 1-continued
Illustrative Examples of Compounds of Formula I
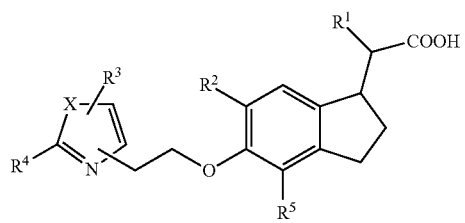
(I)
| Entry No. | R¹ | R² | R³ | R⁴ | R⁵ | X |
|---|---|---|---|---|---|---|
| 118 | CH₃ | H | Et | 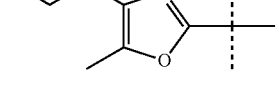 | H | O |
| 119 | CH₃ | H | i-Pr | Ph | H | O |
| 120 | CH₃ | H | i-Pr | Ph | H | S |
| 121 | CH₃ | H | i-Pr | 3,4-di-F Ph | H | O |
| 122 | CH₃ | H | i-Pr | 3,4-di-Cl Ph | H | O |
| 123 | CH₃ | H | i-Pr | 4-Ph Ph | H | O |
| 124 | CH₃ | H | i-Pr | 4-Ph Ph | H | S |
| 125 | CH₃ | H | i-Pr | 4-(4-ClPh)Ph | H | O |
| 126 | CH₃ | H | i-Pr | 4-(4-ClPh)Ph | H | S |
| 127 | CH₃ | H | i-Pr | 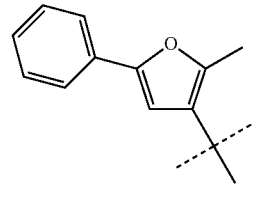 | H | O |
| 128 | CH₃ | H | i-Pr | 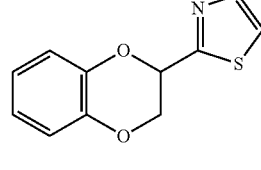 | H | O |
| 129 | CH₃ | H | i-Pr | 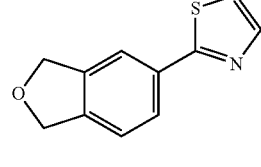 | H | O |
| 130 | CH₃ | H | i-Pr | 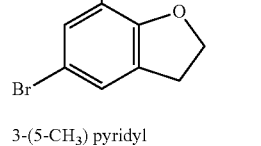 | H | O |
| 131 | CH₃ | H | i-Pr | 3-(5-CH₃) pyridyl | H | O |

TABLE 1-continued

Illustrative Examples of Compounds of Formula I $$\text{(I)}$$

| Entry No. | R¹ | R² | R³ | R⁴ | R⁵ | X |
|---|---|---|---|---|---|---|
| 132 | CH₃ | H | i-Pr | 6-methyl-2-(thiophen-2-yl)pyridin-3-yl | H | O |
| 133 | CH₃ | H | i-Pr | 6-methyl-2-(thiophen-2-yl)pyridin-3-yl | H | S |
| 134 | CH₃ | H | i-Pr | 3-tert-butyl-1-methyl-1H-pyrazol-5-yl | H | O |
| 135 | CH₃ | CH₃ | i-Pr | 3,4-di-Cl Ph | CH₃ | O |
| 136 | CH₃ | n-propyl | i-Pr | 3,4-di-Cl Ph | n-propyl | O |
| 137 | CH₃ | Cl | i-Pr | 4-Cl Ph | H | O |
| 138 | CH₃ | Cl | i-Pr | 4-Cl Ph | H | S |
| 139 | CH₃ | Cl | i-Pr | 3-CH₃O Ph | H | O |
| 140 | CH₃ | Cl | i-Pr | 3-CH₃O Ph | Cl | O |
| 141 | CH₃ | Cl | i-Pr | 3-CH₃O Ph | Cl | S |
| 142 | CH₃ | Cl | i-Pr | benzothiophen-2-yl | Cl | O |
| 143 | CH₃ | Br | i-Pr | Ph | H | O |
| 144 | CH₃ | Br | i-Pr | 3-Cl Ph | H | O |
| 145 | CH₃ | Br | i-Pr | Ph | Br | O |
| 146 | CH₃ | Br | i-Pr | Ph | Br | S |
| 147 | CH₃ | CH₃ | i-Pr | Ph | H | O |
| 148 | CH₃ | CH₃ | i-Pr | Ph | H | S |
| 149 | CH₃ | CH₃ | i-Pr | 2-Cl Ph | H | O |
| 150 | CH₃ | CH₃ | i-Pr | benzothiophen-2-yl | H | O |
| 151 | CH₃ | CH₃CO | i-Pr | 3-F Ph | H | O |
| 152 | CH₃ | CH₃CO | i-Pr | 3-F Ph | H | S |
| 153 | CH₃ | n-PrCO | i-Pr | 3-F Ph | H | O |

TABLE 1-continued

Illustrative Examples of Compounds of Formula I (I)

| Entry No. | R¹ | R² | R³ | R⁴ | R⁵ | X |
|---|---|---|---|---|---|---|
| 154 | CH₃ | n-BuCO | i-Pr | 3-F Ph | H | O |
| 155 | CH₃ | H | n-Bu | Ph | H | O |
| 156 | CH₃ | H | n-Bu | benzothiophen-2-yl | H | O |
| 157 | CH₃ | H | n-Bu | benzothiophen-2-yl | H | S |
| 158 | CH₃ | H | n-Bu | 2-Cl Ph | H | O |
| 159 | CH₃ | H | n-Bu | 2,4 di-F Ph | H | O |
| 160 | CH₃ | H | n-Bu | 3,4 di-CH₃O Ph | H | O |
| 161 | CH₃ | H | n-Bu | phenethyl-substituted | H | O |
| 162 | CH₃ | H | n-Bu | 2-furyl | H | O |
| 163 | CH₃ | H | n-Bu | di-t-butyl methylfuryl | H | O |
| 164 | CH₃ | H | n-Bu | thiophen-2-yl-propyl | H | O |
| 165 | CH₃ | H | n-Bu | thiophen-2-yl-propyl | H | S |
| 166 | CH₃ | H | n-Bu | methyl-(thiophen-2-yl)pyridinyl | H | O |

TABLE 1-continued
Illustrative Examples of Compounds of Formula I
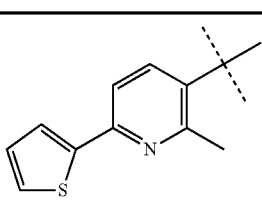
(I)
| Entry No. | R¹ | R² | R³ | R⁴ | R⁵ | X |
|---|---|---|---|---|---|---|
| 167 | CH₃ | H | n-Bu | 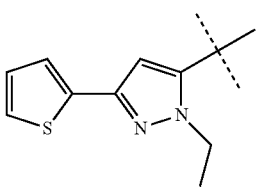 | H | S |
| 168 | CH₃ | H | n-Bu | 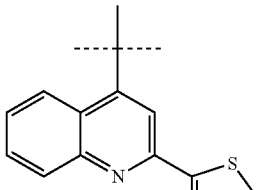 | H | O |
| 169 | CH₃ | H | n-Bu | 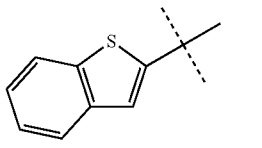 | H | O |
| 170 | CH₃ | Br | n-Bu | 2,4 di-F Ph | Br | O |
| 171 | CH₃ | Cl | n-Bu | 2,4 di-F Ph | H | O |
| 172 | CH₃ | H | n-pentyl | Ph | H | O |
| 173 | CH₃ | H | n-pentyl | 2,4 di-F Ph | H | O |
| 174 | CH₃ | H | n-pentyl | 2,4 di-F Ph | H | S |
| 175 | CH₃ | H | n-pentyl | 4-pyridyl | H | O |
| 176 | CH₃ | H | n-pentyl | 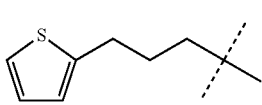 | H | O |
| 177 | CH₃ | Cl | n-pentyl | Ph | H | O |
| 178 | CH₃ | Cl | n-pentyl | Ph | H | S |
| 179 | CH₃ | H | Ph | 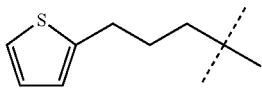 | H | O |
| 180 | CH₃ | H | 2-Cl Ph | 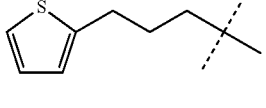 | H | O |
| 181 | CH₃ | H | 2-Cl Ph | 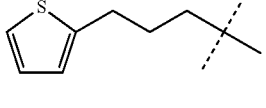 | H | S |

TABLE 1-continued

Illustrative Examples of Compounds of Formula I

| Entry No. | R¹ | R² | R³ | R⁴ | R⁵ | X |
|---|---|---|---|---|---|---|
| 182 | $CH_3$ | H | H | $PhOCH_2$ | H | O |
| 183 | $CH_3$ | H | H | $(4-CH_3Ph)OCH_2$ | H | O |
| 184 | $CH_3$ | H | H | $C(CF_3)(F)(OPh)-$ (attached) | H | O |
| 185 | $CH_3$ | H | $CH_3$ | Et | H | O |
| 186 | $CH_3$ | H | $CH_3$ | Et | H | S |
| 187 | $CH_3$ | H | $CH_3$ | $CF_3CF_2$ | H | O |
| 188 | $CH_3$ | H | $CH_3$ | t-butyl | H | O |
| 189 | $CH_3$ | H | Et | 3-(5-$CH_3$) pyridyl | H | O |
| 190 | $CH_3$ | H | Et | 4-pyridyl | H | O |
| 191 | $CH_3$ | H | Et | 4-pyridyl | H | S |
| 192 | $CH_3$ | Et | $CH_3$ | $PhOCH_2$ | H | O |
| 193 | $CH_3$ | Et | $CH_3$ | $PhOCH_2$ | H | S |
| 194 | $CH_3$ | Et | $CH_3$ | $PhCH_2OCH_2$ | H | O |
| 195 | $CH_3$ | n-propyl | $CH_3$ | $PhOCH_2$ | H | O |
| 196 | $CH_3$ | n-propyl | $CH_3$ | $PhOCH_2$ | n-propyl | O |
| 197 | $CH_3$ | n-butyl | $CH_3$ | $PhOCH_2$ | H | O |
| 198 | $CH_3$ | n-hexyl | $CH_3$ | $PhOCH_2$ | H | O |
| 199 | $CH_3$ | n-hexyl | $CH_3$ | $PhOCH_2$ | H | S |
| 200 | $CH_3$ | n-hexyl | isopropyl | 3-Cl Ph | H | O |
| 201 | $CH_3$ | n-hexyl | Ph | 3-Cl Ph | H | O |
| 202 | $CH_3$ | $CH_3OCH_2$ | $CH_3$ | $PhOCH_2$ | H | O |
| 203 | $CH_3$ | Ph | n-butyl | 3,4-di-F Ph | H | O |
| 204 | $CH_3$ | 3-F Ph | $CH_3$ | 1-napthyl | H | O |
| 205 | $CH_3$ | 4-pyridyl | H | $4-CF_3$ Ph | H | O |
| 206 | $CH_3$ | 4-pyridyl | H | $4-CF_3$ Ph | H | S |
| 207 | $CH_3$ | Cl | $CH_3$ | 3,5-di-F—Ph | H | O |
| 208 | $CH_3$ | Br | $CH_3$ | $CF_3CF_2$ | H | O |
| 209 | $CH_3$ | Br | n-butyl | $CF_3CF_2$ | H | O |
| 210 | $CH_3$ | Br | n-butyl | $CF_3CF_2$ | Br | O |
| 211 | $CH_3$ | Br | Ph | $CF_3CF_2$ | Br | O |
| 212 | $CH_3$ | 2-furyl | $CH_3$ | isobutyl | H | O |
| 213 | $CH_3$ | 2-furyl | $CH_3$ | isobutyl | H | S |
| 214 | $CH_3$ | 2-furyl | $CH_3$ | $2-F-4-CF_3$ Ph | H | O |
| 215 | $CH_3$ | 2-furyl | $CH_3$ | 2-napthyl | H | O |
| 216 | $CH_3$ | 2-furyl | i-Pr | isobutyl | H | O |
| 217 | $CH_3$ | EtCO | n-propyl | $3-CH_3O$ Ph | EtCO | O |
| 218 | Et | H | H | cyclopropyl | H | O |
| 219 | Et | H | H | 4-F Ph | H | O |
| 220 | Et | H | H | 3,5-di-F—Ph | H | O |
| 221 | Et | H | H | 4-Cl $PhCH_2$ | H | O |
| 222 | Et | H | H | 2-quinolinyl | H | O |
| 223 | Et | H | $CH_3$ | $PhCH_2$ | H | O |
| 224 | Et | H | $CH_3$ | 4-F $PhCH_2$ | H | O |
| 225 | Et | H | $CH_3$ | 3,4-di-F—$PhOCH_2$ | H | O |
| 226 | Et | H | $CH_3$ | phenethyl (attached) | H | O |

TABLE 1-continued
Illustrative Examples of Compounds of Formula I
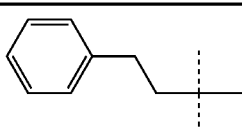
(I)
| Entry No. | R¹ | R² | R³ | R⁴ | R⁵ | X |
|---|---|---|---|---|---|---|
| 227 | Et | H | CH₃ | 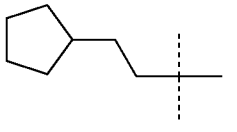 | H | S |
| 228 | Et | H | CH₃ | 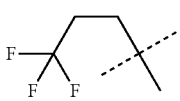 | H | O |
| 229 | Et | H | CH₃ | 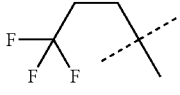 | H | O |
| 230 | Et | H | CH₃ | 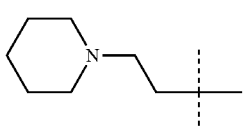 | H | S |
| 231 | Et | H | CH₃ | 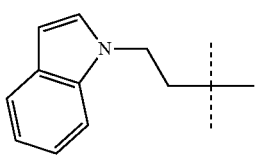 | H | O |
| 232 | Et | H | CH₃ | 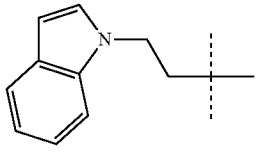 | H | O |
| 233 | Et | H | CH₃ | 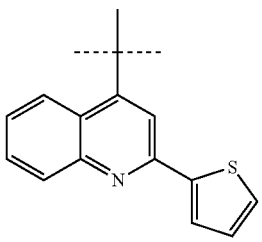 | H | S |
| 234 | Et | H | CH₃ | 2-quinolinyl | H | O |
| 235 | Et | H | CH₃ |  | H | O |

TABLE 1-continued
Illustrative Examples of Compounds of Formula I
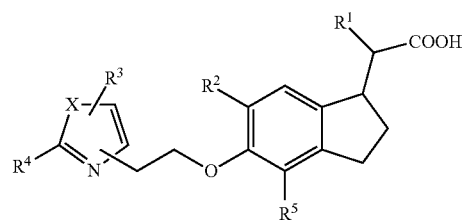
(I)
| Entry No. | R¹ | R² | R³ | R⁴ | R⁵ | X |
|---|---|---|---|---|---|---|
| 236 | Et | H | CH₃ | 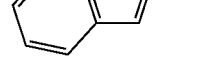 | H | O |
| 237 | Et | H | CH₃ | 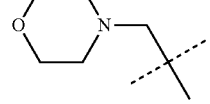 | H | O |
| 238 | Et | H | CH₃ | 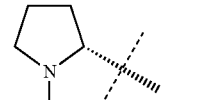 | H | O |
| 239 | Et | H | CH₃ | 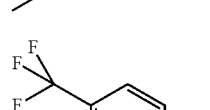 | H | O |
| 240 | Et | H | CH₃ | 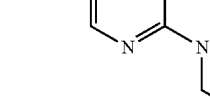 | H | O |
| 241 | Et | H | CH₃ | 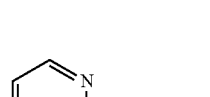 | H | O |
| 242 | Et | H | CH₃ | 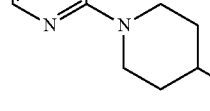 | H | O |
| 243 | Et | H | CH₃ | (4-CH₃O) PhCH₂CH₂ | H | O |

TABLE 1-continued

Illustrative Examples of Compounds of Formula I (I)

| Entry No. | R¹ | R² | R³ | R⁴ | R⁵ | X |
|---|---|---|---|---|---|---|
| 244 | Et | H | CH₃ | 4-methyl-1,2,3-thiadiazol-5-yl (t-Bu substituted) | H | O |
| 245 | Et | Cl | CH₃ | 2,5-disubstituted furan (t-Bu, CH₃, t-Bu) | H | O |
| 246 | Et | Br | CH₃ | 5-phenyl-2-methyl-3-t-Bu-furan | H | O |
| 247 | Et | H | Et | 4-Ph Ph | H | O |
| 248 | Et | H | Et | 4-Ph Ph | H | S |
| 249 | Et | H | Et | 4-(4-CH₃Ph)Ph | H | O |
| 250 | Et | CH₃ | CH₃ | 2-F Ph | H | O |
| 251 | Et | CH₃ | CH₃ | 2-F Ph | CH₃ | O |
| 252 | Et | CH₃ | CH₃ | 2-F Ph | CH₃ | O |
| 253 | Et | CH₃ | CH₃ | 2-F Ph | CH₃ | S |
| 254 | Et | 3-Cl Ph | Et | 4-Ph Ph | H | O |
| 255 | Et | 3-Cl Ph | Et | 4-Ph Ph | H | S |
| 256 | Et | CH₃CO | H | 4-F Ph | H | O |
| 257 | Et | CH₃CO | isopropyl | 4-F Ph | H | O |
| 258 | Et | CH₃CO | Ph | 4-F Ph | H | O |
| 259 | Et | CH₃CO | CH₃ | cyclohexyl | CH₃CO | O |
| 260 | Et | CH₃CO | CH₃ | 4-F Ph | CH₃CO | O |
| 261 | Et | CH₃CO | Ph | 4-F Ph | CH₃CO | O |
| 262 | Et | CH₃CO | Ph | 4-F Ph | CH₃CO | S |
| 263 | Et | Cl | Et | 4-(4-CH₃Ph)Ph | H | O |
| 264 | Et | Cl | Et | 4-(4-CH₃Ph)Ph | Cl | O |
| 265 | Et | Cl | Et | benzothiophen-2-yl | Cl | O |
| 266 | Et | Br | Ph | 2-OCH₃ Ph | Br | O |
| 267 | CF₃CH₂ | H | H | n-butyl | H | O |
| 268 | CF₃CH₂ | H | H | Ph | H | O |
| 269 | CF₃CH₂ | H | H | 3-pyridyl | H | O |
| 270 | CF₃CH₂ | H | CH₃ | cyclopentyl | H | O |
| 271 | CF₃CH₂ | H | CH₃ | 4-(CF₃O)Ph | H | O |
| 272 | CF₃CH₂ | H | CH₃ | 4-(CF₃O)Ph | H | S |
| 273 | CF₃CH₂ | H | CH₃ | 4-(CHF₂O)Ph | H | O |

TABLE 1-continued

Illustrative Examples of Compounds of Formula I

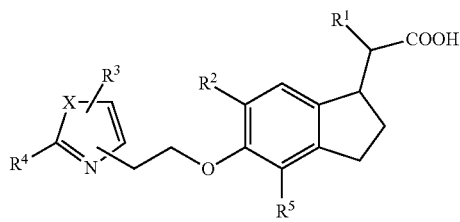

(I)

| Entry No. | R¹ | R² | R³ | R⁴ | R⁵ | X |
|---|---|---|---|---|---|---|
| 274 | $CF_3CH_2$ | H | $CH_3$ | 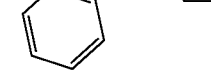 | H | O |
| 275 | $CF_3CH_2$ | H | n-butyl | (4-F Ph)$OCH_2$ | H | O |
| 276 | $CF_3CH_2$ | H | Ph | Ph | H | O |
| 277 | $CF_3CH_2$ | H | Ph | Ph | H | S |
| 278 | $CF_3CH_2$ | H | Ph | 2-(5-$CF_3$) furyl | H | O |
| 279 | $CF_3CH_2$ | H | Ph | 2-thienyl | H | O |
| 280 | $CF_3CH_2$ | H | 4-F Ph | Ph | H | O |
| 281 | $CF_3CH_2$ | $CH_3$ | H | 2-F Ph | H | O |
| 282 | $CF_3CH_2$ | $CH_3$ | H | 2-F Ph | H | S |
| 283 | $CF_3CH_2$ | $CH_3$ | H | 2-F Ph | $CH_3$ | O |
| 284 | $CF_3CH_2$ | $CH_3$ | Et | 3-$CF_3$ Ph | H | O |
| 285 | $CF_3CH_2$ | $CH_3$ | n-butyl | (4-F Ph)$OCH_2$ | H | O |
| 286 | $CF_3CH_2$ | $CH_3$ | n-butyl | (4-F Ph)$OCH_2$ | H | S |
| 287 | $CF_3CH_2$ | $CH_3$ | Ph | 2-thienyl | H | O |
| 288 | n-propyl | H | H | $CH_3$ | H | O |
| 289 | n-propyl | H | H | $CH_3$ | H | S |
| 290 | n-propyl | H | H | n-propyl | H | O |
| 291 | n-propyl | H | H | cyclobutyl | H | O |
| 292 | n-propyl | H | H | cycloheptyl | H | O |
| 293 | n-propyl | H | H | 3,4-di-$CH_3$ Ph | H | O |
| 294 | n-propyl | H | H | 2-thienyl | H | O |
| 295 | n-propyl | H | H | 2-thienyl | H | S |
| 296 | n-propyl | H | H | 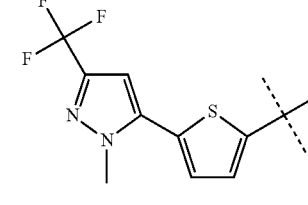 | H | O |
| 297 | n-propyl | H | $CH_3$ | $CH_3$ | H | O |
| 298 | n-propyl | H | $CH_3$ | $CH_3$ | H | S |
| 299 | n-propyl | H | $CH_3$ | 3-$CF_3$ Ph | H | O |
| 300 | n-propyl | H | $CH_3$ | 2-thienyl | H | O |
| 301 | n-propyl | H | $CH_3$ | 3-(4-($OCH_3$)thienyl) | H | O |
| 302 | n-propyl | H | $CH_3$ | 2-(5-($CH_3$)thienyl) | H | O |
| 303 | n-propyl | H | $CH_3$ | 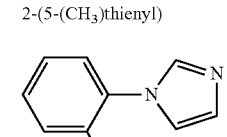 | H | O |

TABLE 1-continued

Illustrative Examples of Compounds of Formula I (I)

| Entry No. | R¹ | R² | R³ | R⁴ | R⁵ | X |
|---|---|---|---|---|---|---|
| 304 | n-propyl | H | CH₃ | [5-trifluoromethyl-1-phenyl-1H-pyrazol-4-yl] | H | O |
| 305 | n-propyl | CH₃ | CH₃ | 3-Br Ph | H | O |
| 306 | n-propyl | CH₃ | CH₃ | 3-Br Ph | H | S |
| 307 | n-propyl | CH₃ | CH₃ | 3-Br Ph | CH₃ | O |
| 308 | n-propyl | CH₃ | CH₃ | [4-phenyl-2-trifluoromethyl-thiophen-5-yl] | H | O |
| 309 | n-propyl | CH₃ | CH₃ | [5-trifluoromethyl-1-phenyl-1H-pyrazol-4-yl] | H | O |
| 310 | n-propyl | n-propyl | CH₃ | 3-Cl Ph | H | O |
| 311 | n-propyl | n-propyl | CH₃ | 3-Cl Ph | H | S |
| 312 | n-propyl | CH₃OCH₂ | CH₃ | 3-Cl Ph | H | O |
| 313 | n-propyl | CH₃CO | CH₃ | 3-Cl Ph | H | O |
| 314 | n-propyl | PrCO | CH₃ | 3-Cl Ph | H | O |
| 315 | n-propyl | PrCO | CH₃ | 3-Cl Ph | PrCO | O |
| 316 | n-propyl | Cl | CH₃ | [5-trifluoromethyl-1-phenyl-1H-pyrazol-4-yl] | H | O |
| 317 | n-propyl | Cl | CH₃ | [3,5′-dimethyl-3,4′-biisoxazol-4-yl] | H | O |

TABLE 1-continued

Illustrative Examples of Compounds of Formula I

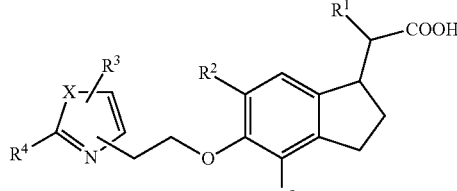

(I)

| Entry No. | R¹ | R² | R³ | R⁴ | R⁵ | X |
|---|---|---|---|---|---|---|
| 318 | n-propyl | Cl | CH₃ | 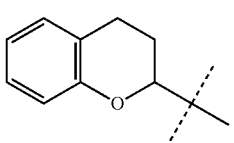 | H | O |
| 319 | n-propyl | Cl | H | Ph | Cl | O |
| 320 | n-propyl | Cl | CH₃ | Ph | Cl | O |
| 321 | n-propyl | Cl | CH₃ | Ph | Cl | S |
| 322 | n-propyl | Cl | n-propyl | 3-CH₃O Ph | Cl | O |
| 323 | n-propyl | Cl | n-propyl | 3-pyridyl | Cl | O |
| 324 | isopropyl | H | H | Ph | H | O |
| 325 | isopropyl | H | H | 2-quinolinyl | H | O |
| 326 | isopropyl | H | H | 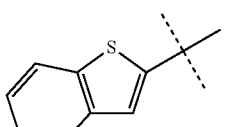 | H | O |
| 327 | isopropyl | H | CH₃ | CH₃ | H | O |
| 328 | isopropyl | H | CH₃ | t-butyl | H | O |
| 329 | isopropyl | H | CH₃ | n-heptyl | H | O |
| 330 | isopropyl | H | CH₃ | n-heptyl | H | S |
| 331 | isopropyl | H | CH₃ | 2,4-di-F Ph | H | O |
| 332 | isopropyl | H | CH₃ | 2,4-di-F Ph | H | S |
| 333 | isopropyl | H | CH₃ | 2-F-4-CF₃ Ph | H | O |
| 334 | isopropyl | H | n-propyl | 2-F-4-CF₃ Ph | H | O |
| 335 | isopropyl | H | n-propyl | 3,5-di-Cl Ph | H | O |
| 336 | isopropyl | H | Ph | 2,4-di-CF₃ Ph | H | O |
| 337 | isopropyl | H | 4-F Ph | 2-F-4-CF₃ Ph | H | O |
| 338 | isopropyl | CH₃ | Et | 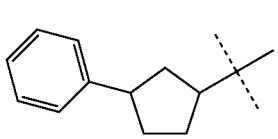 | H | O |
| 339 | isopropyl | CH₃ | Et | | H | O |
| 340 | isopropyl | CH₃ | Et | 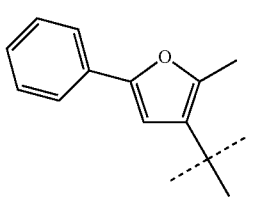 | H | O |

TABLE 1-continued

Illustrative Examples of Compounds of Formula I

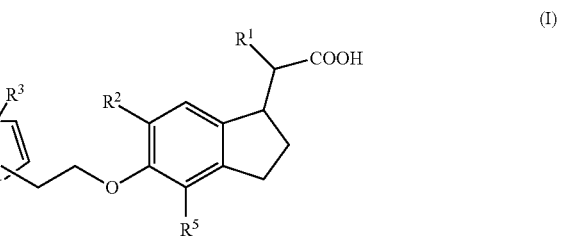

(I)

| Entry No. | R¹ | R² | R³ | R⁴ | R⁵ | X |
|---|---|---|---|---|---|---|
| 341 | isopropyl | CH₃ | Et | 2-methyl-5-phenyl-3-tert-butyl-furan | H | S |
| 342 | isopropyl | CH₃ | Et | 5-methyl-4-phenyl-2-tert-butyl-oxazole | H | O |
| 343 | isopropyl | CH₃ | Et | 2-(2,4-difluorophenyl)-4-tert-butyl-thiazole | H | O |
| 344 | isopropyl | CH₃ | Et | 1-ethyl-3-(2-thienyl)-5-tert-butyl-pyrazole | H | O |
| 345 | isopropyl | Et | CH₃ | 3-CF₃ Ph | H | O |
| 346 | isopropyl | Et | CH₃ | 3-Et Ph | H | O |
| 347 | isopropyl | n-propyl | H | PhOCH₂ | H | O |
| 348 | isopropyl | n-propyl | H | PhOCH₂ | n-propyl | O |
| 349 | isopropyl | n-propyl | H | 2-(2-methyl)chromanyl | H | O |
| 350 | isopropyl | n-propyl | H | 2-(2-methyl)chromanyl | n-propyl | O |
| 351 | isopropyl | n-propyl | H | 2-(2-methyl)chromanyl | H | S |

TABLE 1-continued
Illustrative Examples of Compounds of Formula I
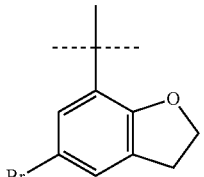
(I)
| Entry No. | R¹ | R² | R³ | R⁴ | R⁵ | X |
|---|---|---|---|---|---|---|
| 352 | isopropyl | n-propyl | H | 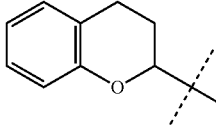 | H | O |
| 353 | isopropyl | n-propyl | n-butyl | 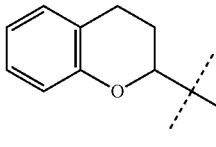 | H | O |
| 354 | isopropyl | n-propyl | Ph | 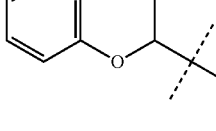 | H | O |
| 355 | isopropyl | n-butyl | H | 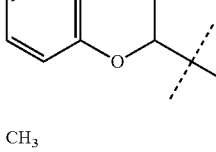 | H | O |
| 356 | isopropyl | n-hexyl | H | 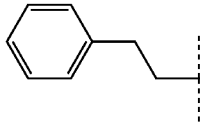 | H | O |
| 357 | isopropyl | Ph | H | CH₃ | H | O |
| 358 | isopropyl | Ph | H | n-propyl | H | O |
| 359 | isopropyl | Ph | H | n-propyl | H | S |
| 360 | isopropyl | Ph | H | 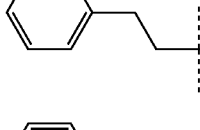 | H | O |
| 361 | isopropyl | Ph | H | 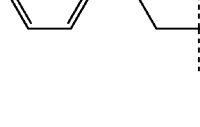 | H | S |
| 362 | isopropyl | Ph | CH₃ |  | H | O |

TABLE 1-continued

Illustrative Examples of Compounds of Formula I

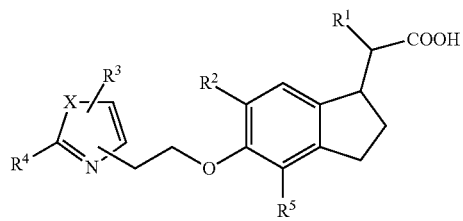

(I)

| Entry No. | R¹ | R² | R³ | R⁴ | R⁵ | X |
|---|---|---|---|---|---|---|
| 363 | isopropyl | Ph | CH₃ | 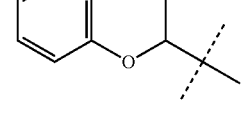 | H | O |
| 364 | isopropyl | Cl | Et | Ph | H | O |
| 365 | isopropyl | Cl | Et | Ph | H | S |
| 366 | isopropyl | Cl | Et | 2-CH₃ Ph | Cl | O |
| 367 | isopropyl | Cl | n-propyl | 3-F Ph | H | O |
| 368 | isopropyl | Cl | isopropyl | 3-F Ph | H | O |
| 369 | isopropyl | Cl | 4-F Ph | 3-F Ph | H | O |
| 370 | isopropyl | Br | Et | 2-CH₃ Ph | Br | O |
| 371 | isopropyl | Br | Et | 2-CH₃ Ph | Br | S |
| 372 | n-butyl | H | H | Cyclohexyl | H | O |
| 373 | n-butyl | H | H | Ph | H | O |
| 374 | n-butyl | H | H | 4-F Ph | H | O |
| 375 | n-butyl | H | H | 3,5-di-Cl Ph | H | O |
| 376 | n-butyl | H | H | 3,5-di-Cl Ph | H | S |
| 377 | n-butyl | H | CH₃ | 3,4-di-CH₃OPh | H | O |
| 378 | n-butyl | H | CH₃ | 4-F PhOCH₂ | H | O |
| 379 | n-butyl | H | CH₃ | 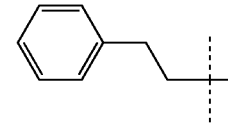 | H | O |
| 380 | n-butyl | H | CH₃ | (4-CH₃O) PhCH₂CH₂ | H | O |
| 381 | n-butyl | H | CH₃ | 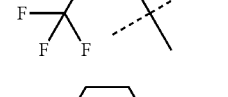 | H | O |
| 382 | n-butyl | H | CH₃ | 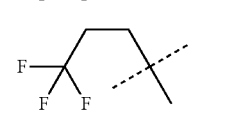 | H | S |
| 383 | n-butyl | H | Et |  | H | O |
| 384 | n-butyl | H | n-propyl | cyclobutyl | H | O |
| 385 | n-butyl | H | n-propyl | 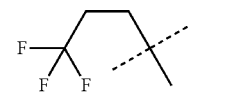 | H | O |
| 386 | n-butyl | H | isopropyl |  | H | O |
| 387 | n-butyl | H | Ph | n-propyl | H | O |

TABLE 1-continued

Illustrative Examples of Compounds of Formula I

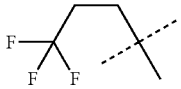

(I)

| Entry No. | R¹ | R² | R³ | R⁴ | R⁵ | X |
|---|---|---|---|---|---|---|
| 388 | n-butyl | H | Ph | 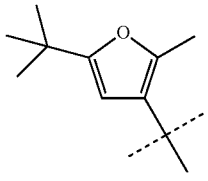 | H | O |
| 389 | n-butyl | H | Ph | Ph | H | O |
| 390 | n-butyl | H | Ph | Ph | H | S |
| 391 | n-butyl | CH₃ | CH₃ | 4-CH₃ Ph | H | O |
| 392 | n-butyl | CH₃ | CH₃ | 4-CH₃ Ph | CH₃ | O |
| 393 | n-butyl | CH₃ | Et | 4-CH₃ Ph | H | O |
| 394 | n-butyl | CH₃ | Ph | 4-CH₃ Ph | H | O |
| 395 | n-butyl | CH₃OCH₂ | CH₃ | 2,4-di-CH₃ Ph | H | O |
| 396 | n-butyl | Cl | CH₃ | 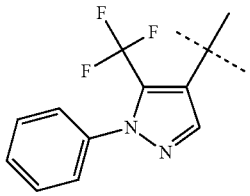 | H | O |
| 397 | n-butyl | Cl | CH₃ | 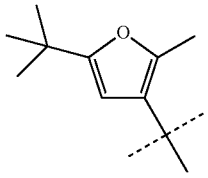 | H | O |
| 398 | n-butyl | Cl | Ph | (same furyl as 396) | H | O |
| 399 | n-pentyl | H | H | CH₃ | H | O |
| 400 | n-pentyl | H | H | CH₃ | H | S |
| 401 | n-pentyl | H | H | Et | H | O |
| 402 | n-pentyl | H | H | cyclopentyl | H | O |
| 403 | n-pentyl | H | H | cyclopentyl | H | S |
| 404 | n-pentyl | H | H | cycloheptyl | H | O |
| 405 | n-pentyl | H | H | Ph | H | O |
| 406 | n-pentyl | H | H | Ph | H | S |
| 407 | n-pentyl | H | H | 2-furyl | H | O |
| 408 | n-pentyl | H | H | 2-(5-CF₃) furyl | H | O |
| 409 | n-pentyl | H | H | 2-thienyl | H | O |
| 410 | n-pentyl | H | H | 3,4-di-Cl Ph | H | O |
| 411 | n-pentyl | H | CH₃ | n-butyl | H | O |
| 412 | n-pentyl | H | CH₃ | n-butyl | H | S |

TABLE 1-continued

Illustrative Examples of Compounds of Formula I

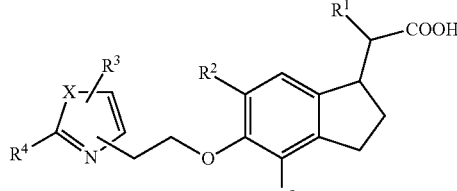

(I)

| Entry No. | R¹ | R² | R³ | R⁴ | R⁵ | X |
|---|---|---|---|---|---|---|
| 413 | n-pentyl | H | CH₃ | 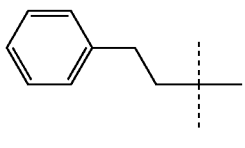 | H | O |
| 414 | n-pentyl | H | CH₃ | PhOCH₂ | H | O |
| 415 | n-pentyl | H | CH₃ | PhCH₂OCH₂ | H | O |
| 416 | n-pentyl | H | Et | 2-F Ph | H | O |
| 417 | n-pentyl | H | Et | 2-F Ph | H | S |
| 418 | n-pentyl | H | 4-CH₃ Ph | 2-F Ph | H | O |
| 419 | n-pentyl | CH₃ | Et | 4-CH₃ Ph | H | O |
| 420 | n-pentyl | Cl | CH₃ | n-butyl | H | O |
| 421 | n-pentyl | Cl | CH₃ | Ph | H | O |
| 422 | n-pentyl | Cl | CH₃ | Ph | H | S |
| 423 | n-pentyl | Cl | CH₃ | 4-Ph Ph | H | O |
| 424 | n-pentyl | Cl | CH₃ | 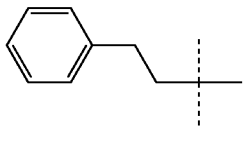 | H | O |
| 425 | n-pentyl | Cl | CH₃ | 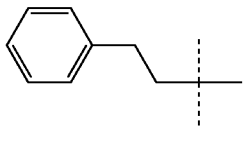 | Cl | O |
| 426 | n-pentyl | PrCO | CH₃ | 4-CH₃ Ph | PrCO | O |
| 427 | n-pentyl | Ph | CH₃ | 3-Br Ph | H | O |
| 428 | n-pentyl | 2-thienyl | CH₃ | 3-Br Ph | 2-thienyl | O |
| 429 | n-hexyl | H | H | 2-F Ph | H | O |
| 430 | n-hexyl | H | CH₃ | cyclopentyl | H | O |
| 431 | n-hexyl | H | CH₃ | cycloheptyl | H | O |
| 432 | n-hexyl | H | CH₃ | 2-F Ph | H | O |
| 433 | n-hexyl | H | CH₃ | 2-F Ph | H | S |
| 434 | n-hexyl | H | Et | 2-F Ph | H | O |
| 435 | n-hexyl | H | n-propyl | 2-F Ph | H | O |
| 436 | n-hexyl | H | isopropyl | 2-F Ph | H | O |
| 437 | n-hexyl | H | Ph | 2-F Ph | H | O |
| 438 | n-hexyl | CH₃CO | CH₃ | 2,4-di-CH₃ Ph | H | O |
| 439 | n-hexyl | CH₃OCH₂ | CH₃ | 2,4-di-CH₃ Ph | H | O |
| 440 | n-hexyl | Ph | Et | Ph | H | O |
| 441 | n-hexyl | Ph | Et | Ph | H | S |
| 442 | n-hexyl | Ph | Et | 4-pyridyl | H | O |
| 443 | n-hexyl | Br | Et | Ph | Br | O |
| 444 | n-hexyl | Br | Et | 2-F Ph | Br | O |
| 445 | cyclopropyl | H | H | cyclopentyl | H | O |
| 446 | cyclopropyl | H | H | 2,4-di-Cl Ph | H | O |
| 447 | cyclopropyl | H | H | 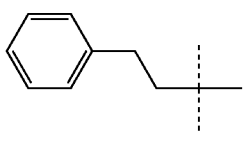 | H | O |
| 448 | cyclopropyl | H | CH₃ | 3-F Ph | H | O |

TABLE 1-continued

Illustrative Examples of Compounds of Formula I (I)

| Entry No. | R¹ | R² | R³ | R⁴ | R⁵ | X |
|---|---|---|---|---|---|---|
| 449 | cyclopropyl | H | CH₃ | 3-F Ph | H | S |
| 450 | cyclopropyl | H | CH₃ | benzothiophen-2-yl (t-Bu) | H | O |
| 451 | cyclopropyl | H | Et | benzothiophen-2-yl (t-Bu) | H | O |
| 452 | cyclopropyl | H | n-propyl | 4-CF₃ Ph | H | O |
| 453 | cyclopropyl | H | isopropyl | Ph | H | O |
| 454 | cyclopropyl | H | isopropyl | 3-pyridyl | H | O |
| 455 | cyclopropyl | H | n-butyl | 4-CF₃ Ph | H | O |
| 456 | cyclopropyl | H | n-hexyl | Ph | H | O |
| 457 | cyclopropyl | H | n-hexyl | 4-CF₃ Ph | H | O |
| 458 | cyclopropyl | H | Ph | Ph | H | O |
| 459 | cyclobutyl | H | CH₃ | 4-CH₃ Ph | H | O |
| 460 | cyclobutyl | H | Et | benzothiophen-2-yl (t-Bu) | H | O |
| 461 | cyclobutyl | H | Et | 2-(2,4-difluorophenyl)thiazol-4-yl (t-Bu) | H | O |
| 462 | cyclobutyl | H | Et | 5-methylbenzo[d]isothiazol-3-yl (t-Bu) | H | O |
| 463 | cyclobutyl | H | Et | morpholinomethyl (gem-dimethyl) | H | O |
| 464 | cyclobutyl | H | Et | (S)-1-ethylpyrrolidin-2-yl (gem-dimethyl) | H | O |

TABLE 1-continued

Illustrative Examples of Compounds of Formula I (I)

| Entry No. | R¹ | R² | R³ | R⁴ | R⁵ | X |
|---|---|---|---|---|---|---|
| 465 | cyclobutyl | H | 4-F Ph | [2-methyl-5-phenylfuran-3-yl, gem-dimethyl linker] | H | O |
| 466 | cyclobutyl | Cl | CH₃ | 3-Cl Ph | Cl | O |
| 467 | cyclobutyl | Cl | CH₃ | 3-Cl Ph | Cl | S |
| 468 | cyclopentyl | H | H | 3-CF₃ Ph | H | O |
| 469 | cyclopentyl | H | CH₃ | 2,4-di-CF₃ Ph | H | O |
| 470 | cyclopentyl | H | CH₃ | 2,4-di-CF₃ Ph | H | S |
| 471 | cyclopentyl | H | n-butyl | [5-tert-butyl-2-methylfuran-3-yl, gem-dimethyl linker] | H | O |
| 472 | cyclopentyl | H | 3-F Ph | 4-CH₃ Ph | H | O |
| 473 | cyclopentyl | CH₃ | CH₃ | Ph | H | O |
| 474 | cyclopentyl | CH₃ | CH₃ | 3,5-di-Cl Ph | H | O |
| 475 | cyclopentyl | CH₃ | CH₃ | Ph | H | S |
| 476 | cyclopentyl | Et | CH₃ | Ph | H | O |
| 477 | cyclopentyl | Cl | CH₃ | Ph | Cl | O |
| 478 | cyclopentyl | Cl | CH₃ | Ph | Cl | S |
| 479 | cyclohexyl | H | H | 3-F Ph | H | O |
| 480 | cyclohexyl | H | H | 2,4-di-CH₃ Ph | H | O |
| 481 | cyclohexyl | H | H | [2-phenylethyl, gem-dimethyl linker] | H | O |
| 482 | cyclohexyl | H | CH₃ | n-propyl | H | O |
| 483 | cyclohexyl | H | CH₃ | n-propyl | H | S |
| 484 | cyclohexyl | H | CH₃ | [4,4,4-trifluoro, gem-dimethyl linker] | H | O |
| 485 | cyclohexyl | H | CH₃ | 3-Cl Ph | H | O |
| 486 | cyclohexyl | H | CH₃ | 3-Cl Ph | H | S |
| 487 | cyclohexyl | H | CH₃ | [benzo[b]thiophen-2-yl, gem-dimethyl linker] | H | O |

TABLE 1-continued

Illustrative Examples of Compounds of Formula I (I)

| Entry No. | R¹ | R² | R³ | R⁴ | R⁵ | X |
|---|---|---|---|---|---|---|
| 488 | cyclohexyl | H | Et | (benzothiophen-2-yl) | H | O |
| 489 | cyclohexyl | H | n-propyl | 4-CF₃ Ph | H | O |
| 490 | cyclohexyl | H | n-propyl | 3-pyridyl | H | O |
| 491 | cyclohexyl | H | isopropyl | Ph | H | O |
| 492 | cyclohexyl | H | isopropyl | 3-pyridyl | H | O |
| 493 | cyclohexyl | H | n-butyl | 3-Cl Ph | H | O |
| 494 | cyclohexyl | H | n-pentyl | 3-Cl Ph | H | O |
| 495 | cyclohexyl | H | n-hexyl | 4-CF₃ Ph | H | O |
| 496 | cyclohexyl | H | 4-F Ph | Ph | H | O |
| 497 | cyclohexyl | CH₃ | CH₃ | 3-CH₃ Ph | H | O |
| 498 | cyclohexyl | CH₃ | CH₃ | 3-CH₃ Ph | H | S |
| 499 | cyclohexyl | CH₃ | Et | 3-pyridyl | CH₃ | O |
| 500 | cyclohexyl | Et | CH₃ | 2-F-4-CF₃ Ph | Et | O |
| 501 | cyclohexyl | 2-thienyl | i-Pr | 3-pyridyl | H | O |
| 502 | cyclohexyl | Cl | CH₃ | 2,3-di-CH₃ Ph | H | O |
| 503 | cyclohexyl | Cl | CH₃ | 2,3-di-CH₃ Ph | H | S |
| 504 | 2-propenyl | H | H | CH₃ | H | O |
| 505 | 2-propenyl | H | H | isopentyl | H | O |
| 506 | 2-propenyl | H | H | cyclopentyl | H | O |
| 507 | 2-propenyl | H | H | Ph | H | O |
| 508 | 2-propenyl | H | H | Ph | H | S |
| 509 | 2-propenyl | H | H | 2-quinolinyl | H | O |
| 510 | 2-propenyl | H | H | (2-(thiophen-2-yl)quinolin-4-yl) | H | O |
| 511 | 2-propenyl | H | CH₃ | (chroman-2-yl) | H | O |
| 512 | 2-propenyl | H | CH₃ | 2,4-di-F Ph | H | O |
| 513 | 2-propenyl | H | CH₃ | 2,4-di-F Ph | H | S |
| 514 | 2-propenyl | H | CH₃ | 2-F-4-CF₃ Ph | H | O |
| 515 | 2-propenyl | H | Et | 2-napthyl | H | O |
| 516 | 2-propenyl | H | Et | 2-napthyl | H | S |
| 517 | 2-propenyl | H | Et | (benzothiophen-2-yl) | H | O |

TABLE 1-continued

Illustrative Examples of Compounds of Formula I

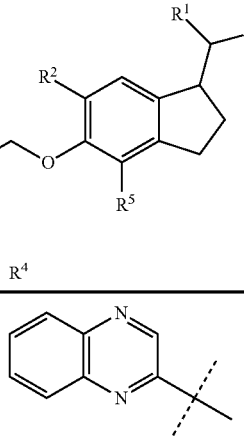

(I)

| Entry No. | R¹ | R² | R³ | R⁴ | R⁵ | X |
|---|---|---|---|---|---|---|
| 518 | 2-propenyl | H | Et | 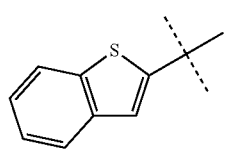 | H | O |
| 519 | 2-propenyl | H | n-propyl | 2-F-4-CF₃ Ph | H | O |
| 520 | 2-propenyl | H | Ph | 2,4-di-CF₃ Ph | H | O |
| 521 | 2-propenyl | H | 4-F Ph | 2-F-4-CF₃ Ph | H | O |
| 522 | 2-propenyl | CH₃ | Et | 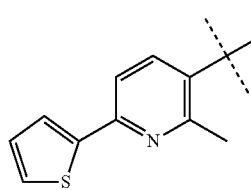 | H | O |
| 523 | 2-propenyl | Cl | CH₃ | 3-CF₃ Ph | Cl | O |
| 524 | 2-propenyl | Cl | CH₃ | 3-CF₃ Ph | Cl | S |
| 525 | 2-propenyl | Br | Et | 3-CF₃ Ph | Br | O |
| 526 | 2-isobutenyl | H | H | 3-pyridyl | H | O |
| 527 | 2-isobutenyl | H | H |  | H | O |
| 528 | 2-isobutenyl | H | CH₃ | 4-(CF₃O)Ph | H | O |
| 529 | 2-isobutenyl | H | CH₃ | 4-(CF₃O)Ph | H | O |
| 530 | 2-isobutenyl | H | CH₃ | 4-(CF₃O)Ph | H | S |
| 531 | 2-isobutenyl | H | n-butyl | 4-(CH₃O)Ph | H | O |
| 532 | 2-isobutenyl | H | n-butyl | (4-F Ph)OCH₂ | H | O |
| 533 | 2-isobutenyl | H | n-butyl | (4-CH₃O) PhCH₂CH₂ | H | O |
| 534 | 2-isobutenyl | H | Ph | 2-thienyl | H | O |
| 535 | 2-isobutenyl | H | 4-F Ph | Ph | H | O |
| 536 | 2-isobutenyl | CH₃CO | Ph | cyclohexyl | H | O |
| 537 | 2-isobutenyl | CH₃CO | Ph | 3-F Ph | H | O |
| 538 | 4-pentenyl | H | CH₃ | Ph | H | O |
| 539 | 4-pentenyl | H | CH₃ | Ph | H | S |
| 540 | 5-hexenyl | H | H | Ph | H | O |
| 541 | 5-hexenyl | H | CH₃ | 2-F Ph | H | O |
| 542 | 5-hexenyl | H | CH₃ | 2-F Ph | H | S |

TABLE 1-continued

Illustrative Examples of Compounds of Formula I (I)

| Entry No. | R¹ | R² | R³ | R⁴ | R⁵ | X |
|---|---|---|---|---|---|---|
| 543 | 5-hexenyl | H | CH₃ | 3-(2-Cl-Ph)-5-methylisoxazol-4-yl (t-substituted) | H | O |
| 544 | 5-hexenyl | H | isopropyl | 4-(CF₃O)Ph | H | O |
| 545 | 5-hexenyl | H | Ph | 4-(CF₃O)Ph | H | O |
| 546 | 5-hexenyl | CH₃CO | CH₃ | 2-CH₃ Ph | CH₃CO | O |
| 547 | CH₃O | H | H | cyclobutyl | H | O |
| 548 | CH₃O | H | H | 2,4-di-F Ph | H | O |
| 549 | CH₃O | H | H | (4-CH₃) PhCH₂ | H | O |
| 550 | CH₃O | H | H | 2-quinolinyl | H | O |
| 551 | CH₃O | H | CH₃ | CH₃ | H | O |
| 552 | CH₃O | H | CH₃ | CH₃ | H | S |
| 553 | CH₃O | H | CH₃ | 3-CF₃ Ph | H | O |
| 554 | CH₃O | H | CH₃ | 2-furyl | H | O |
| 555 | CH₃O | H | CH₃ | 2-furyl | H | S |
| 556 | CH₃O | H | CH₃ | 2-thienyl | H | O |
| 557 | CH₃O | H | CH₃ | 3-(4-(OCH₃)thienyl) | H | O |
| 558 | CH₃O | H | CH₃ | 2-(1H-imidazol-1-yl)phenyl (t-substituted) | H | O |
| 559 | CH₃O | H | n-propyl | 4-(CF₃O)Ph | H | O |
| 560 | CH₃O | H | 4-F Ph | 4-(CF₃O)Ph | H | O |
| 561 | CH₃O | Br | isobutyl | 3-CF₃ Ph | Br | O |
| 562 | CH₃O | H | CH₃ | 2-phenyl-4-t-butyl-2H-1,2,3-triazol-5-yl | H | O |
| 563 | EtO | 3-F Ph | Et | cyclopentyl | H | O |
| 564 | EtO | H | H | CH₃ | H | O |
| 565 | EtO | H | H | CH₃ | H | S |
| 566 | EtO | H | H | 3,4-di-CH₃ Ph | H | O |
| 567 | EtO | H | CH₃ | n-propyl | H | O |
| 568 | EtO | H | CH₃ | cyclobutyl | H | O |
| 569 | EtO | H | CH₃ | cycloheptyl | H | O |
| 570 | EtO | H | CH₃ | cycloheptyl | H | S |
| 571 | EtO | H | CH₃ | 3-(1H-indol-1-yl)-2,2-dimethylpropyl | H | O |
| 572 | EtO | H | CH₃ | 3,4-di-F Ph | H | O |

TABLE 1-continued

Illustrative Examples of Compounds of Formula I

| Entry No. | R¹ | R² | R³ | R⁴ | R⁵ | X |
|---|---|---|---|---|---|---|
| 573 | EtO | H | CH₃ | 3,5-dimethylisoxazol-4-yl (t-Bu substituted) | H | O |
| 574 | EtO | H | n-butyl | 2-thienyl | H | O |
| 575 | EtO | H | Ph | 2-thienyl | H | O |
| 576 | EtO | CH₃ | CH₃ | 4-Br Ph | H | O |
| 577 | EtO | Cl | CH₃ | n-hexyl | H | O |
| 578 | EtO | Cl | CH₃ | 2-Cl Ph | H | S |
| 579 | EtO | Cl | CH₃ | 2-Cl Ph | H | S |
| 580 | EtO | Cl | n-butyl | Ph | Cl | O |
| 581 | (i-Pr)O | H | H | CH₃ | H | O |
| 582 | (i-Pr)O | H | H | CH₃ | H | S |
| 583 | (i-Pr)O | H | H | 3,5-di-Cl Ph | H | O |
| 584 | (i-Pr)O | H | CH₃ | 1,1-difluoro-neopentyl | H | O |
| 585 | (i-Pr)O | H | CH₃ | 3-Cl-5-F Ph | H | O |
| 586 | (i-Pr)O | H | CH₃ | 3-Cl-5-F Ph | H | S |
| 587 | (i-Pr)O | H | CH₃ | 4-methyl-1,2,3-thiadiazol-5-yl | H | O |
| 588 | (i-Pr)O | H | isopropyl | 4-Br Ph | H | O |
| 589 | (i-Pr)O | H | 4-F Ph | 3,4-di-F Ph | H | O |
| 590 | (i-Pr)O | CH₃ | Et | 2-thienyl | H | O |
| 591 | (i-Pr)O | CH₃CO | Et | 2-thienyl | CH₃CO | O |
| 592 | (i-Pr)O | Cl | 3-F Ph | 2,4-di-F Ph | Cl | O |
| 593 | n-BuO | H | H | cyclpentyl | H | O |
| 594 | n-BuO | H | H | cyclooctyl | H | O |
| 595 | n-BuO | H | H | cyclooctyl | H | S |
| 596 | n-BuO | H | Et | cyclooctyl | H | O |
| 597 | n-BuO | H | Et | Ph | H | O |
| 598 | n-BuO | H | Et | 2,4-di-F Ph | H | O |
| 599 | n-BuO | H | Et | PhOCH₂ | H | O |
| 600 | n-BuO | H | isopropyl | cyclooctyl | H | O |
| 601 | n-BuO | H | n-hexyl | cyclooctyl | H | O |
| 602 | n-BuO | CH₃ | CH₃ | 3,5-di-F Ph | H | O |
| 603 | n-BuO | PrCO | Et | 3,5-di-CH₃ Ph | H | O |
| 604 | n-BuO | Br | Ph | cyclooctyl | Br | O |
| 605 | (n-pentyl)O | H | CH₃ | 3-Br Ph | H | O |
| 606 | (n-pentyl)O | H | CH₃ | 3-Br Ph | H | S |
| 607 | (n-pentyl)O | H | CH₃ | 2-napthyl | H | O |
| 608 | (n-pentyl)O | H | CH₃ | benzothiophen-2-yl (t-Bu) | H | O |

TABLE 1-continued

Illustrative Examples of Compounds of Formula I

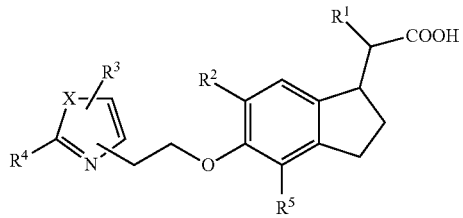
(I)

| Entry No. | R¹ | R² | R³ | R⁴ | R⁵ | X |
|---|---|---|---|---|---|---|
| 609 | (n-hexyl)O | H | $CH_3$ | cyclopropyl | H | O |
| 610 | (n-hexyl)O | H | $CH_3$ | n-pentyl | H | O |
| 611 | (n-hexyl)O | H | $CH_3$ | 3-Br Ph | H | O |
| 612 | (n-hexyl)O | H | $CH_3$ | 2-napthyl | H | O |
| 613 | (i-hexyl)O | $CH_3OCH_2$ | Et | Ph | H | O |
| 614 | (i-hexyl)O | $CH_3OCH_2$ | Et | Ph | H | S |
| 615 | $CO_2H$ | H | H | 3,5-di-Cl Ph | H | O |
| 616 | $CO_2H$ | H | $CH_3$ | 3,5-di-Cl Ph | H | O |
| 617 | $CO_2H$ | H | propyl | Ph | H | O |
| 618 | $CO_2H$ | H | propyl | 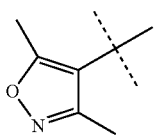 | H | O |
| 619 | $CO_2H$ | H | $CH_3$ | Ph | H | O |
| 620 | $CO_2H$ | H | $CH_3$ | 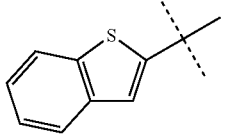 | H | O |
| 621 | $CO_2H$ | H | $CH_3$ | 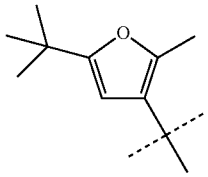 | H | O |
| 622 | $CO_2H$ | $CH_3$ | $CH_3$ | 3,5-di-Cl Ph | H | O |
| 623 | $CO_2H$ | $CH_3$ | isopropyl | 3-Br Ph | H | O |
| 624 | $CO_2H$ | $CH_3$ | isopropyl | 3-Br Ph | $CH_3$ | O |
| 625 | $CO_2H$ | $CH_3$ | 4-F Ph | propyl | H | O |
| 626 | $CO_2H$ | Et | H | 4-F Ph | H | O |
| 627 | $CO_2H$ | Et | H | 4-F Ph | Et | O |
| 628 | $CO_2H$ | Et | $CH_3$ | 4-F Ph | Et | O |
| 629 | $CO_2H$ | Et | propyl | Ph | H | O |
| 630 | $CO_2H$ | Et | propyl | Ph | H | S |
| 631 | $CO_2H$ | Ph | $CH_3$ | 2-furyl | H | O |
| 632 | $CO_2H$ | Ph | $CH_3$ | 2-furyl | H | S |
| 633 | $CO_2H$ | 3-Br Ph | Ph | 2-thienyl | H | O |
| 634 | $CO_2H$ | n-PrCO | H | 3-Cl Ph | H | O |
| 635 | $CO_2H$ | n-PrCO | H | 3-pyridyl | H | O |
| 636 | $CO_2H$ | n-PrCO | H | 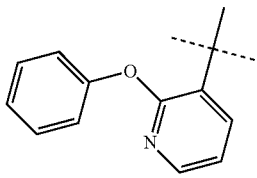 | H | O |

TABLE 1-continued

Illustrative Examples of Compounds of Formula I

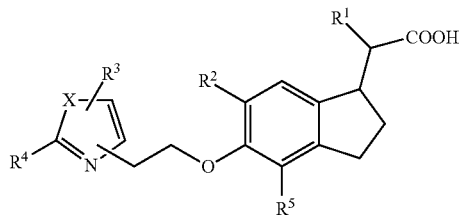

(I)

| Entry No. | R$^1$ | R$^2$ | R$^3$ | R$^4$ | R$^5$ | X |
|---|---|---|---|---|---|---|
| 637 | CO$_2$H | n-PrCO | CH$_3$ | 3-Cl Ph | H | O |
| 638 | CO$_2$H | n-PrCO | CH$_3$ | 3-Cl Ph | n-PrCO | O |
| 639 | CO$_2$H | n-pentylCO | Ph | 3-Cl Ph | H | O |

A salt of a compound of Formula I may be prepared in situ during the final isolation and purification of a compound or by separately reacting the purified compound in its free base form with a suitable organic or inorganic acid and isolating the salt thus formed. Likewise, when the compound of Formula I contains a carboxylic acid moiety, (e.g., R=H), a salt of said compound of Formula I may be prepared by separately reacting it with a suitable inorganic or organic base and isolating the salt thus formed. The term "pharmaceutically acceptable salt" refers to a relatively non-toxic, inorganic or organic acid addition salt of a compound of the present invention (see, e.g., Berge at al., J. Pharm. Sci. 66:1-19, 1977).

Representative salts of the compounds of Formula I include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, undecanoate, and the like.

Base salts include, for example, alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups in the conjugate base may be quaternized with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and stearyl chlorides, bromides and iodides; aralkyl halides like benzyl and phenethyl bromides, and the like.

The esters of Formula I in the present invention are non-toxic, pharmaceutically acceptable esters, for example, alkyl esters such as methyl, ethyl, propyl, isopropyl, butyl, isobutyl, or pentyl esters. Additional esters such as, for example, methyl ester or phenyl-C$_1$-C$_5$ alkyl may be used. The compound of Formula I may be esterified by a variety of conventional procedures including reacting the appropriate anhydride, carboxylic acid, or acid chloride with the alcohol group of the Formula I compound. The appropriate anhydride may be reacted with the alcohol in the presence of a base to facilitate acylation such as 1,8-bis[dimethylamino]naphthalene or N,N-dimethylaminopyridine. An appropriate carboxylic acid may be reacted with the alcohol in the presence of a dehydrating agent such as dicyclohexylcarbodiimide, 1-[3-dimethylaminopropyl]-3-ethylcarbodiimide, or other water soluble dehydrating agents which are used to drive the reaction by the removal of water, and optionally, an acylation catalyst. Esterification may also be effected using the appropriate carboxylic acid in the presence of trifluoroacetic anhydride and optionally, pyridine, or in the presence of N,N-carbonyldiimidazole with pyridine. Reaction of an acid chloride with the alcohol may be carried out with an acylation catalyst such as 4-DMAP or pyridine.

One skilled in the art would readily know how to successfully carry out these as well as other methods of esterification of alcohols.

Additionally, sensitive or reactive groups on the compound of Formula I may need to be protected and deprotected during any of the above methods for forming esters. Protecting groups in general may be added and removed by conventional methods well known in the art (see, e.g., T. W. Greene and P. G. M. Wuts, *Protective Groups in Organic Synthesis*; Wiley: New York, (1999)).

The compounds of Formula I may contain one or more asymmetric centers, depending upon the location and nature of the various substituents desired. Asymmetric carbon atoms may be present in the (R) or (S) configuration. Preferred isomers are those with the absolute configuration which produces the compound of Formula I with the more desirable biological activity. In certain instances, asymmetry may also be present due to restricted rotation about a given bond, for example, the central bond adjoining two aromatic rings of the specified compounds.

Substituents on a ring may also be present in either cis or trans form, and a substituent on a double bond may be present in either Z or E form.

It is intended that all isomers (including enantiomers and diastereomers), either by nature of asymmetric centers or by restricted rotation as described above, as separated, pure or partially purified isomers or racemic mixtures thereof, be included within the scope of the instant invention. The purification of said isomers and the separation of said isomeric mixtures may be accomplished by standard techniques known in the art.

The particular process to be utilized in the preparation of the compounds of this invention depends upon the specific compound desired. Such factors as the selection of the specific X moiety, and the specific substituents possible at various locations on the molecule, all play a role in the path to be followed in the preparation of the specific compounds of this invention. Those factors are readily recognized by one of ordinary skill in the art.

In general, the compounds of this invention may be prepared by standard techniques known in the art and by known processes analogous thereto. The compounds of Formula I may generally be synthesized according to Reaction Schemes 1, 2, and 3. Reaction Schemes 1 and 2 demonstrate how to make intermediates that are coupled in Reaction Scheme 3 to provide the compounds of Formula I.

Route (A) of Reaction Scheme 1 provides a method to prepare compounds 4 and 5 where R" is $C_1$-$C_6$ lower alkyl or benzyl, $R^3$ is not hydrogen, and X is O. The first step shows protection of the acid group of a commercially available aspartate derivative compound 1 by means well known in the art such as, for example, by forming a silyl ester, followed by N-acylation with the appropriate $R^4$-acid derivative, $R^4COY$, where Y is a leaving group such as halo. Finally, the compound is deprotected by means well known in the art such as, for example, in the case of a silyl ester, an aqueous work up, to give compound 2. Alternatively, condensation of the protected form of compound 1 with a free carboxylic acid such as $R^4COOH$ in the presence of a dehydrating reagent, such as DCC or EDCI, also provides compound 2. Compound 2 may then be converted to compound 3, where $R^3$ is as defined for Formula I compounds by several methods. For example, one such method, when $R^3$=Me, is the well known Dakin-West reaction which is typically performed using acetic anhydride and pyridine. When $R^3$ is other than hydrogen, compound 2 may be converted to an acid chloride with a reagent such as thionyl chloride and reacted with a Grignard reagent such as $R^3Mg$-halo, to provide compound 3. Other methods for the formation of ketones of compound 3 from acids and acid derivatives may also be employed, for example, by using Weinreb amides, which are known to those skilled in the art. Compound 3 is then cyclized under acid dehydrative conditions using, for example, phosphorus oxychloride, or a mixture of sulfuric acid and acetic anhydride, generally with heating, to provide compound 4 where X is O and the $R^3$ group is attached at the 5 position.

It will be recognized by those skilled in the art that compound 4 and thus, compound 5, may exist in two regioisomeric forms with respect to the attachment point of the $R^3$, $CH_2CO_2R"$, and $CH_2CH_2OH$ groups. Using Route (B), one can prepare compound 4 in which the $R^3$ is attached at the 4-position and carboxymethyl side chain is attached at the 5-position, that is, the groups are reversed from that of Route (A). In Route (B), a commercially available amino acid, compound 6, may be acylated under basic conditions, for example, with aqueous sodium hydroxide, with an appropriate $R^4$-acid derivative, (e.g., $R^4COY$), where Y is a leaving group such as chloro, to provide the N-acylated product 7. Compound 7 may be then coupled with an acetic acid ester in the presence of a strong non-nucleophilic base to make the keto ester 8, where R" is $C_1$-$C_6$ alkyl or benzyl. Cyclization of compound 8 using a dehydrating reagent such as $POCl_3$ provides compound 4 where X=O and $R^3$ is attached at the 4 position. Reaction of compound 8 with a nucleophilic S reagent such as $P_2S_5$ in solvents such as pyridine or acetonitrile/triethylamine, with heating as necessary, gives compound 4 where X=S and $R^3$ is attached at the 4 position.

Route (C) of Reaction Scheme 1 depicts the preparation of compound 4 from ketoesters 9 or 10, where Y is a leaving group such as halo and R" is $C_1$-$C_6$ alkyl or benzyl. Either compound 9 or 10 may be chosen as the starting material depending on whether the $R^3$ group in the desired end product is hydrogen or is attached at the 4 or 5 position. Accordingly, compound 9 or 10 may be reacted with an amide or thioamide where X is either O or S to yield compound 4. Ketoesters 9 or 10 are commercially available, or may be prepared by methods well known in the art such as by bromination of commercially available ketoesters 9 and 10 where Y is hydrogen. Amides ($R^4C$(=X)$NH_2$) where X is O may be commercially available carboxylic amides, or may be prepared from the corresponding available acids or acid chlorides by well known methods. Thioamides ($R^4C$(=X)$NH_2$) where X is S may be commercially available thioamides, or may be prepared from the corresponding available amides by known methods such as through the use of Lawesson's reagent. Reaction of ketoester 9 with an amide or thioamide in the presence of a base provides compound 4 as an oxazole or a thiazole, respectively, where $R^3$ is other than hydrogen and located at the 4-position. Reaction of ketoester 10 with an amide or thioamide in the presence of base provides compound 4 as an oxazole or thiazole, where $R^3$ is located at the 5-position.

Routes (A), (B), and (C) each provide compound 4 where $R^3$ and $R^4$ are each as described for a compound of Formula I and where R" is a lower alkyl or benzyl. Compound 4 may then be reduced to compound 5 using reducing agents such as lithium aluminum hydride, lithium borohydride, or other suitable hydride donors under conditions well known in the art.

Reaction Scheme 1

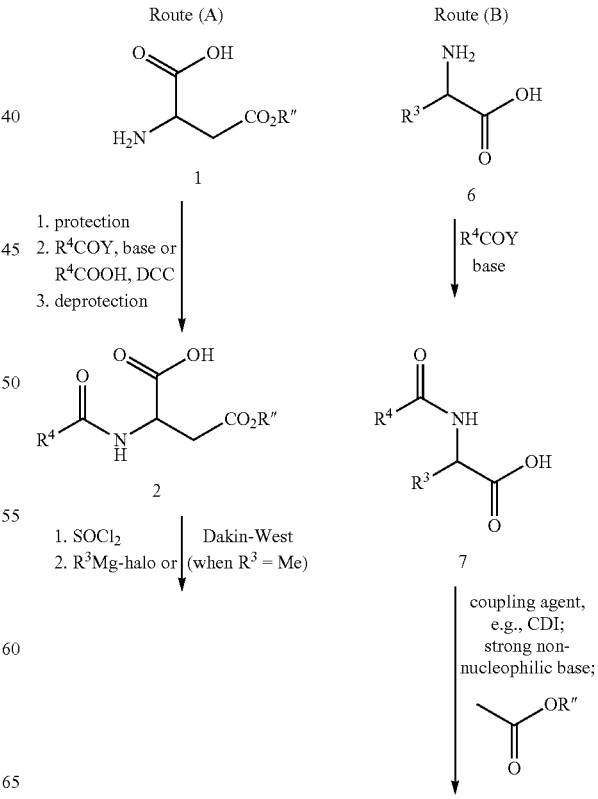

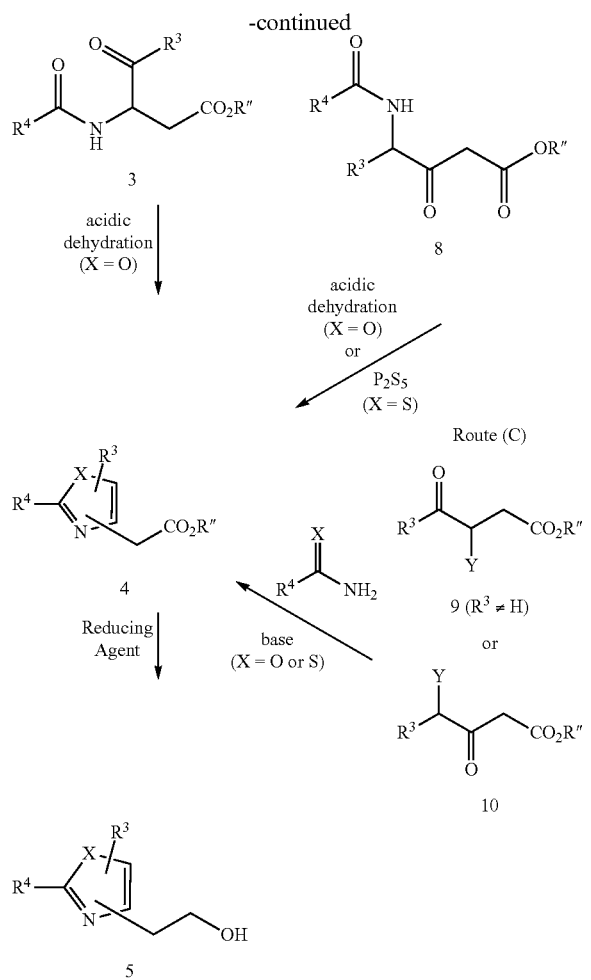

Reaction Scheme 2 depicts the conversion of commercially available hydroxy ketone 11 to a protected derivative 12, by reaction with $R^7$—Y in the presence of a base, where $R^7$ is $C_1$-$C_6$ alkyl optionally substituted with phenyl or oxo, $C_1$-$C_6$-trialkylsilyl, arylalkylsilyl, or $COR^8$; and $R^8$ is $C_1$-$C_6$ alkyl or phenyl optionally substituted with $C_1$-$C_6$ alkyl, halo, or nitro; and Y is a leaving group. "$C_1$-$C_6$ trialkylsilyl" means three independently selected straight or branched chain alkyl groups having from one to about six carbon atoms, each of which are bound to silicon and includes such groups as trimethylsilyl, tert-butyldimethyl silyl, and the like. "Arylalkylsilyl" means at least one phenyl or substituted phenyl group bound to silicon, with an appropriate number of independently selected straight or branched chain alkyl groups having from one to about six carbon atoms, each of which are also bound to silicon, and includes such groups as t-butyldiphenylsilyl methyldiphenylsilyl, dimethylpentafluorophenylsilyl, and the like. "Leaving group" includes halides such as I, Br, and Cl; carboxylates such as acetates, and trifluoroacetates; and aryl and alkyl sulfonates such as methanesulfonates (mesylates) and p-toluene sulfonates (tosylates), and the like.

Compound 12 is substituted with $R^2$ (as described in Formula I) by means of, for example, reaction with a source of electrophilic halogen, or a Friedel-Crafts reaction in the presence of a Lewis acid and $R^2$—Y where Y is as described above, to form a substituted ketone 13. Alternatively, a halogenated compound formed in this manner (for example, substituted with bromine or iodine) may be reacted with a range of coupling partners under metal catalysis, using complexes and compounds of elements such as palladium and nickel well known to those skilled in the art, to form further substituted ketone 13. Examples of such catalysts include tetrakis (triphenylphosphine)palladium(0) and [1,1'-bis(diphenylphosphino)ferrocene]dichloropalladium(II), and similar nickel(0) and nickel(II) compounds; and examples of coupling partners include boronic acids and esters (the well known Suzuki coupling, carried out in solvents such as toluene in the presence of a base such as potassium carbonate), and organometallics such as Grignard reagents, organozincs (Negishi coupling), and organotin derivatives (Stille coupling), reaction conditions for which are widely known. Furthermore, such halogenated compounds may be coupled with secondary amines such as piperidine using similar palladium or nickel catalysts (Hartwig or Buchwald coupling) to provide further substituted ketones 13.

Further reaction of compound 13 with a halogen source or $R^5$—Y, (where $R^5$ is as described in Formula I), under similar conditions gives disubstituted compound 14. A Wittig reaction, or the Horner-Emmons-Wadsworth variation, each well known in the art, may be used to convert 14 to compound 15. For example, reaction of compound 14 with a trialkylphosphonoacetate, where R" is lower alkyl and R is as described in Formula I, in the presence of a strong base such as sodium hydride, provides compound 15. In like manner, compound 13 may be converted to compound 15 where $R^5$ is H.

Regardless of the isomeric mixture of isomers of 15 produced in the reaction, either isomer (E or Z) or a mixture of both, may be converted to the corresponding compound 17 by catalytic hydrogenation or reduction with a hydride reagent capable of 1,4 (conjugate) addition, which are known to those skilled in the art. This route is particularly advantageous for preparing compound 17 where $R^1$ is hydrogen.

Compound 17 where $R^1$ is COOR, may be prepared through standard condensation reactions, for example, the well known Knoevenagel reaction. In such cases, the ketone 13 or 14 may be reacted with a suitable active-hydrogen coupling partner, under the influence of acidic reagents such as titanium tetrachloride, or basic reagents such as piperidine, in appropriate solvents. The product 15b (compound 15 where $R^1$ is COOR), may be reduced to 17b (compound 17 where $R^1$ is COOR), which may be further alkylated with another $R^1$ group in the presence of base, hydrolyzed and decarboxylated to give 17d (compound 17 where $R^1$ is other than COOH and R is H). Reesterification of 17d and removal of the protecting group $R^7$ would afford 17c. Reesterification may be performed using standard conditions using the well known Fischer esterification by treatment with an acid and an alcohol or by reaction with diazoalkyl reagents or with an electrophilic species such as, for example, methyl iodide or dimethyl sulfate. Compound 17 where $R^1$ is alkoxy may be prepared by a similar condensation reaction of ketone 13 or 14 with a silylated enol ester of Formula $R^1CH=C(OR")O$-alkylsilyl, where $R^1$ is alkoxy, under the influence of acidic reagents such as titanium tetrachloride, and reducing the intermediate compound 15, where $R^1$ is alkoxy, in the presence of hydrogen and a catalyst as described above.

A general coupling reaction of compound 13 or 14 via the Reformatsky reaction produces compound 16 (Formula II), when $R^1$ is alkyl, or compound 15a when $R^1$ is H. The ketone is condensed with an appropriate organozinc reagent prepared in situ from Zn and $R^1CHYCO_2R$, where Y is halo. The alpha-halo ester compounds of formula $R^1CHYCO_2R$, are either commercial reagents or are prepared by halogenation of commercially available $R^1CH_2CO_2R$ compounds by methods well known to those skilled in the art.

The conversion of 16 to 17 may be accomplished by standard hydrogenation conditions, for example, Pd/C and hydrogen; and deprotection of compound 17, where $R^7$ is a protecting group, to compound 17c, where $R^7$ is hydrogen, may be accomplished by standard means. For example, when the $R^7$ group is alkyl (e.g., methyl), the compound 17a may be generated by nucleophilic cleavage with a reagent such as an alkali metal thiolate. Alternatively, compound 17 when $R^7$ is methyl, may be converted to compound 17c by reaction with a Lewis acid such as a bromoborane. When $R^7$ is benzyl, the compound 17 may be converted to 17c under hydrogenation conditions, typically carried out using a catalyst such as palladium. Other conditions for the removal of the protecting group $R^7$ from compound 17, where $R^7$ is other than hydrogen which produces the hydroxy compound 17c, are dependent on the specific protecting group chosen from among those which are well known by those skilled in the art.

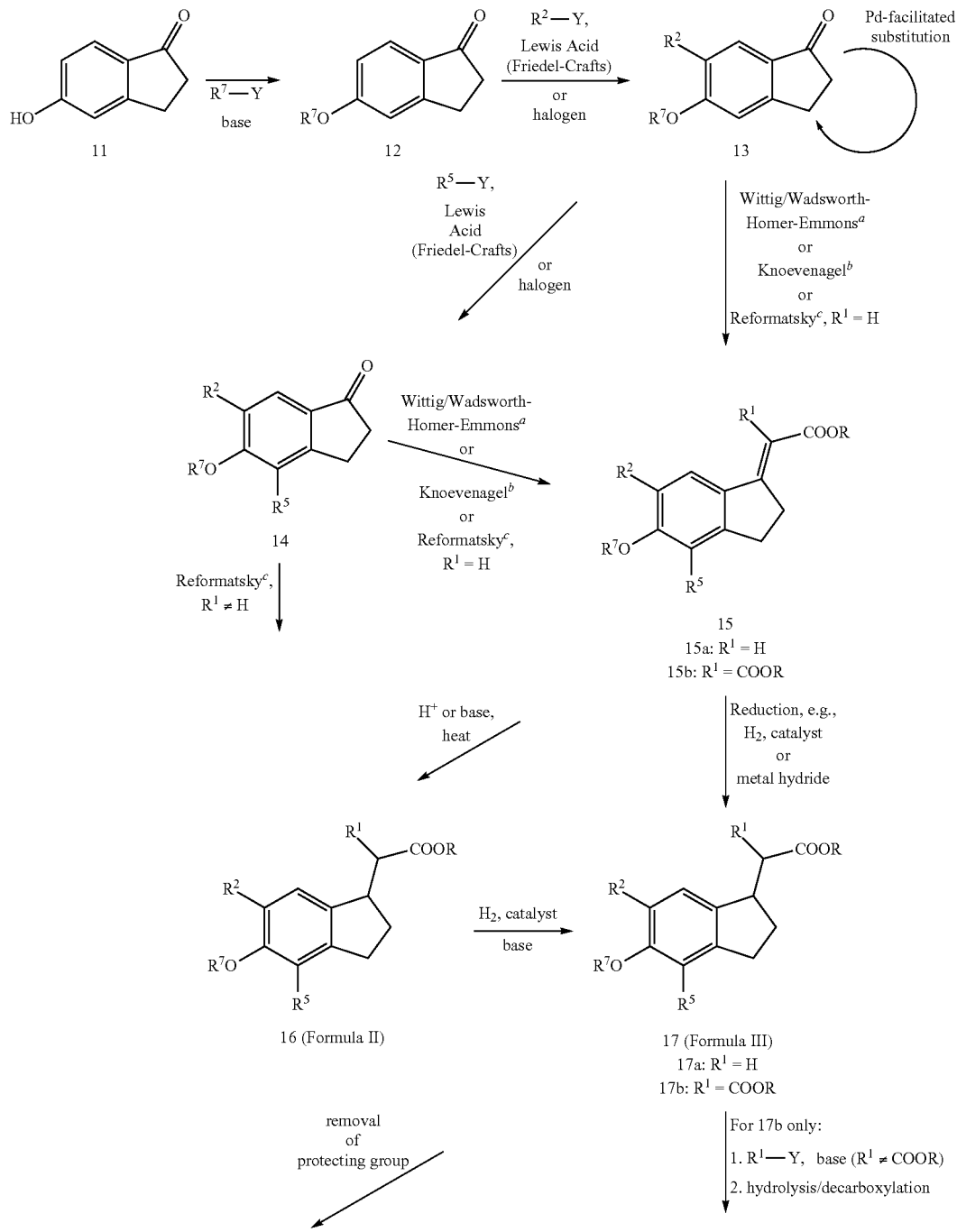

Reaction Scheme 2

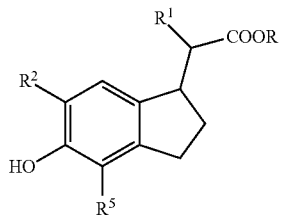
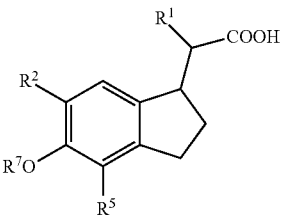

17c (Formula III)  →  1) Reesterification  2) Removal of protecting group  ←  17d (Formula III, $R^1 \neq$ COOR)

Notes:
a. $(R^2O)_2P(=O)CHR^1COOR$, where $R^1$ = H, strong base
b. $R^1CH_2COOR$, where $R^1$ = COOR, acid or base catalyst
c. $R^1CHBrCO_2R$, Zn The final step in the preparation of Formula I compounds is shown in Reaction Scheme 3. The alcohol 5 (from Reaction Scheme 1) is coupled with the hydroxy indane 17c (from Reaction Scheme 2) via a Mitsunobu coupling, facilitated by an azodicarboxylate reagent such as DEAD, and a phosphine such as triphenylphosphine to make the compounds of Formula I. Alternatively, the hydroxy group of alcohol 5 is converted to a leaving group such as halo, tosylate (OTs), or mesylate (OMs), by reaction with a halogenating agent such as thionyl chloride or $CCl_4$/triphenylphosphine; or by reaction with a Y-halo compound, where Y is tosyl (Ts) or mesyl (Ms), in the presence of a base, providing compound 18. Compound 18 may be reacted with compound 17c in the presence of a base, providing the compounds of Formula I.

Compounds of Formula I in which R is alkyl, may be converted to compounds of Formula I in which R is H by treatment with a base (e.g., KOH) in a suitable solvent (e.g., methanol, THF, or water, or mixtures thereof) with heating. Alternatively, this conversion may be accomplished by reaction with a nucleophile such as iodide or cyanide, in a suitable solvent, such as pyridine. In addition, when R is benzyl, the cleavage to compounds of Formula I in which R is H may be effected through hydrogenolysis by means well known in the art.

Reaction Scheme 3

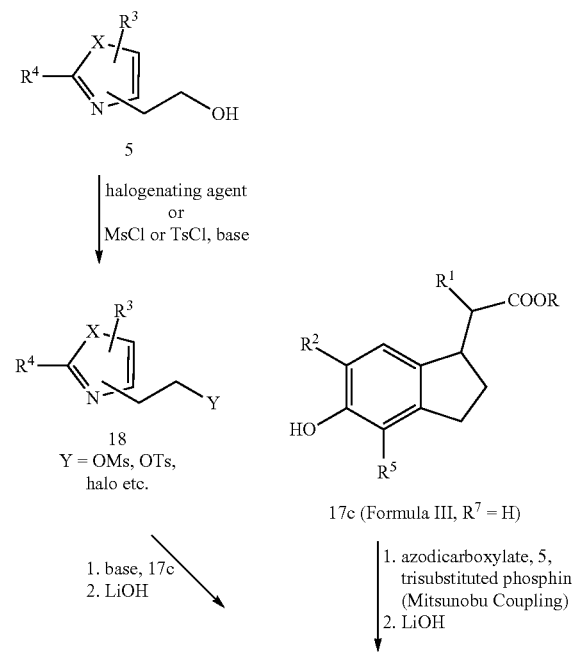

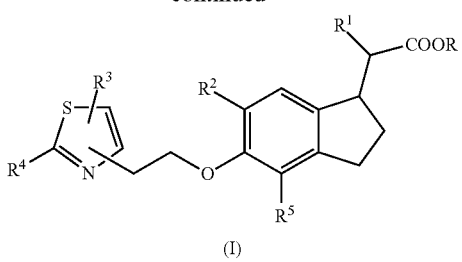

(I)

An alternative route to Formula I compounds, useful when X=S and the $R^4$ group contains one or more $R^6$ substituents labile to the reaction conditions of Scheme 1 or 2, is shown in Reaction Scheme 3a.

Reaction Scheme 3a

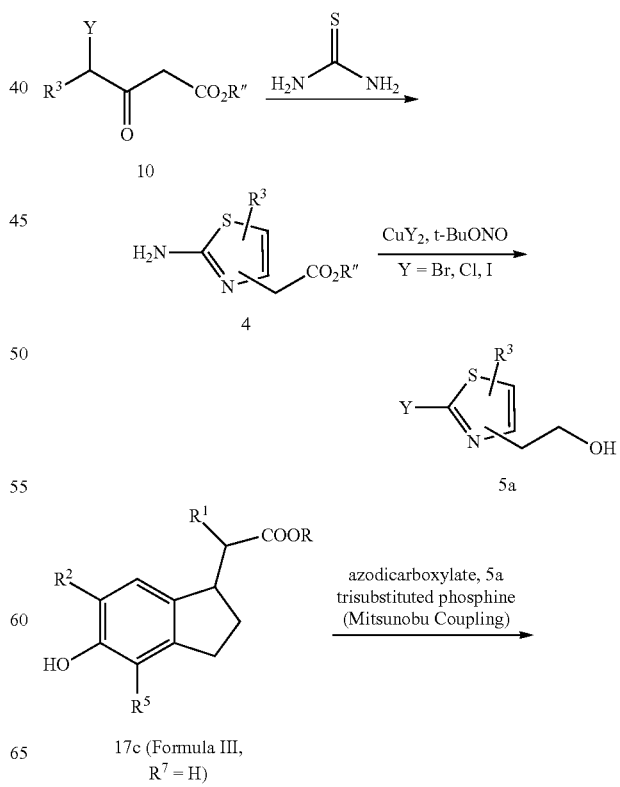

-continued

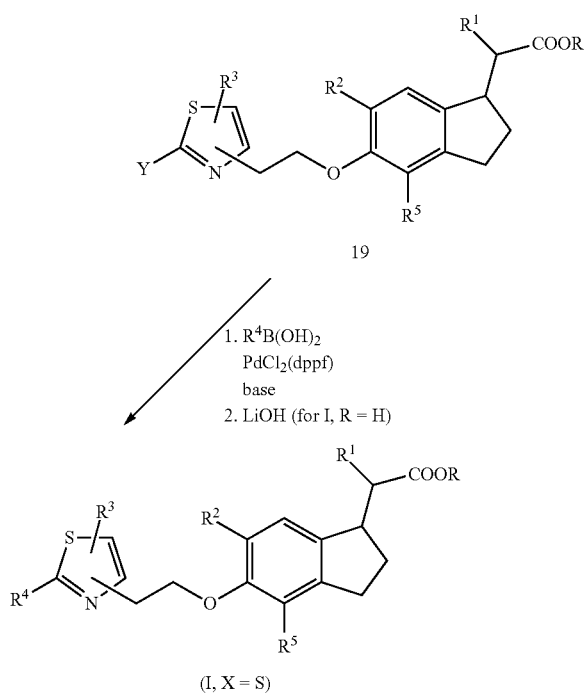

(I, X = S)

In Scheme 3a, a 2-aminothiazole 4 may be prepared using thiourea (similar to Route C, Reaction Scheme 1) and converted to a 2-halo thiazole 5a as shown above (Erlenmeyer et al., Helv. Chim. Acta 28:362-363, 1945). Mitsunobu coupling of 5a by a method analogous to Reaction Scheme 3 is then accomplished, and product 19 is further elaborated by a Palladium-catalyzed cross-coupling reaction to introduce the $R^4$ substituent. Hydrolysis as described in Reaction Scheme 3 gives Formula I compounds where R=H.

The foregoing reaction schemes are further illustrated by the specific Examples described herein.

The salts and esters of this invention may be readily prepared by conventional chemical processes as described previously herein.

The invention is further directed to novel Formula II compounds (compound 16) and Formula III (compounds 17, including compounds 17a-d) compounds shown in Reaction Scheme 2. These compounds are useful in the preparation of the compounds of Formula I, and are further described as follows.

The present invention encompasses the compounds of Formula II and Formula III,

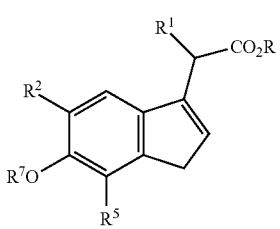

(II)

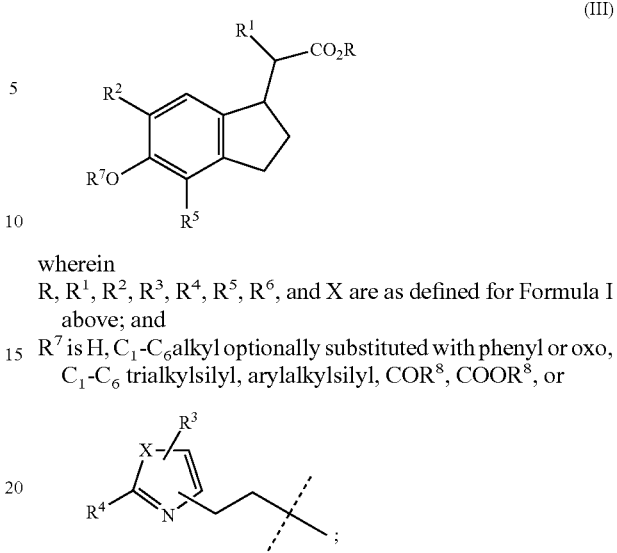

wherein
R, $R^1$, $R^2$, $R^3$, $R^4$, $R^5$, $R^6$, and X are as defined for Formula I above; and
$R^7$ is H, $C_1$-$C_6$ alkyl optionally substituted with phenyl or oxo, $C_1$-$C_6$ trialkylsilyl, arylalkylsilyl, $COR^8$, $COOR^8$, or $R^8$ is $C_1$-$C_6$ alkyl, or phenyl optionally substituted with $C_1$-$C_6$ alkyl, halo, or nitro; and
the salts thereof.

$C_1$-$C_6$ trialkylsilyl means three independently selected straight or branched chain alkyl groups having from one to about six carbon atoms, each of which are bound to silicon and includes such groups as trimethylsilyl, tert-butyldimethyl silyl, and the like.

Arylalkylsilyl means at least one phenyl or substituted phenyl group bound to silicon, with an appropriate number of independently selected straight or branched chain alkyl groups having from one to about six carbon atoms, each of which are also bound to silicon, and includes such groups as t-butyldiphenylsilyl methyldiphenylsilyl, dimethylpentafluorophenylsilyl, and the like.

The salts of this invention may be readily prepared by conventional chemical processes as described previously herein.

The compounds of Formula II and Formula III may each contain one or more asymmetric centers, depending upon the location and nature of the various substituents desired. Asymmetric carbon atoms may be present in the (R) or (S) configuration. Preferred isomers are those with the absolute configuration which produces the compound of Formula II or Formula III that will be useful in producing the compounds of Formula I having a more desirable biological activity. In certain instances, asymmetry may also be present due to restricted rotation about a given bond, for example, the central bond adjoining two aromatic rings of the specified compounds.

Substituents on a ring may also be present in either cis or trans form, and a substituent on a double bond may be present in either Z or E form.

It is intended that all isomers (including enantiomers and diastereomers), either by nature of asymmetric centers or by restricted rotation as described above, as separated, pure or partially purified isomers or racemic mixtures thereof, be included within the scope of the present invention. The purification of said isomers and the separation of said isomeric mixtures may be accomplished by standard techniques known in the art, as well as by the novel means described herein.

For example, Formula II compounds may contain an asymmetric center (labeled C-2) and Formula III compounds may contain two asymmetric centers (labeled C-2 and C-1') which give rise to enantiomers and diastereomers. Examples of these and other compounds of Formula II and Formula III, which are illustrative of the present invention, are shown in Table 2.

TABLE 2

Illustrative Examples of Compounds II and III

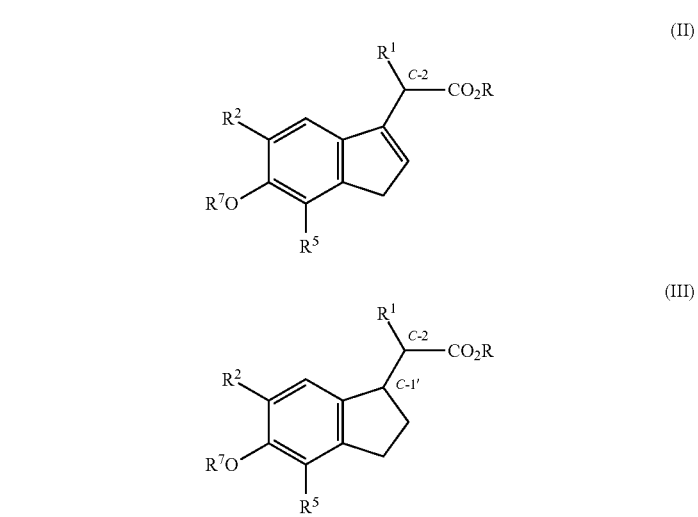

| Entry No. | Formula | absolute configuration C-2 | C-1' | $R^1$ | $R^2$ | $R^5$ | $R^7$ |
|---|---|---|---|---|---|---|---|
| 1 | II | R | — | H | H | H | $CH_3$ |
| 2 | III | R | R | H | H | H | $CH_3$ |
| 3 | II | R | — | Cl | H | H | $t\text{-Bu}(CH_3)_2Si$ |
| 4 | III | R | S | Cl | H | H | $t\text{-Bu}(CH_3)_2Si$ |
| 5 | II | S | — | H | H | H | $CH_3$ |
| 6 | III | S | S | H | H | H | $CH_3$ |
| 7 | II | R | — | $CH_3$ | H | H | $CH_3$ |
| 8 | III | R | R | $CH_3$ | H | H | $CH_3$ |
| 9 | II | S | — | $CH_3$ | H | H | $CH_3$ |
| 10 | III | S | R | $CH_3$ | H | H | $CH_3$ |
| 11 | II | R | — | $CH_3$ | H | H | $PhCH_2$ |
| 12 | III | R | S | $CH_3$ | H | H | $PhCH_2$ |
| 13 | II | S | — | $CH_3$ | H | H | $PhCH_2$ |
| 14 | III | S | S | $CH_3$ | H | H | $PhCH_2$ |
| 15 | II | R | — | $CH_3$ | H | H | $t\text{-Bu}(CH_3)_2Si$ |
| 16 | III | R | R | $CH_3$ | H | H | $t\text{-Bu}(CH_3)_2Si$ |
| 17 | II | S | — | $CH_3$ | H | H | $t\text{-Bu}(CH_3)_2Si$ |
| 18 | II | R | — | $CH_3$ | H | H | $t\text{-BuCO}$ |
| 19 | III | R | S | $CH_3$ | H | H | $t\text{-BuCO}$ |
| 20 | II | S | — | $CH_3$ | H | H | $t\text{-BuCO}$ |
| 21 | III | S | S | $CH_3$ | H | H | $t\text{-BuCO}$ |
| 22 | II | R | — | $CH_3$ | $CH_3$ | H | $PhCH_2$ |
| 23 | II | R | — | $CH_3$ | $CH_3CO$ | H | $PhCH_2$ |
| 24 | II | S | — | $CH_3$ | 2-thienyl | H | $t\text{-Bu}(CH_3)_2Si$ |
| 25 | III | S | R | $CH_3$ | 2-thienyl | H | $t\text{-Bu}(CH_3)_2Si$ |
| 26 | II | S | — | $CH_3$ | Ph | H | $CH_3$ |
| 27 | II | R | — | $CH_3$ | Cl | H | $CH_3$ |
| 28 | II | S | — | $CH_3$ | Cl | H | $CH_3$ |
| 29 | III | S | S | $CH_3$ | Cl | H | $CH_3$ |
| 30 | II | R | — | $CH_3$ | Br | H | $Ph(CH_3)_2Si$ |
| 31 | III | R | R | $CH_3$ | Br | H | $Ph(CH_3)_2Si$ |
| 32 | II | S | — | $CH_3$ | Br | H | $Ph(CH_3)_2Si$ |
| 33 | III | S | R | $CH_3$ | Br | H | $Ph(CH_3)_2Si$ |
| 34 | II | S | — | $CH_3$ | Cl | Cl | $CH_3$ |
| 35 | II | R | — | Et | H | H | $CH_3$ |
| 36 | III | R | R | Et | H | H | $CH_3$ |
| 37 | II | S | — | Et | H | H | $PhCH_2$ |
| 38 | III | S | S | Et | H | H | $PhCH_2$ |
| 39 | II | R | — | Et | H | H | $t\text{-Bu}$ |
| 40 | II | S | — | Et | H | H | $t\text{-Bu}$ |
| 41 | II | S | — | Et | $CH_3$ | H | $Ph(CH_3)_2Si$ |
| 42 | III | S | S | Et | $CH_3$ | H | $Ph(CH_3)_2Si$ |
| 43 | II | R | — | Et | n-propyl | H | $CH_3$ |
| 44 | II | S | — | Et | Ph | H | $CH_3$ |
| 45 | II | S | — | Et | 3-Cl Ph | H | $t\text{-Bu}(CH_3)_2Si$ |

TABLE 2-continued

Illustrative Examples of Compounds II and III

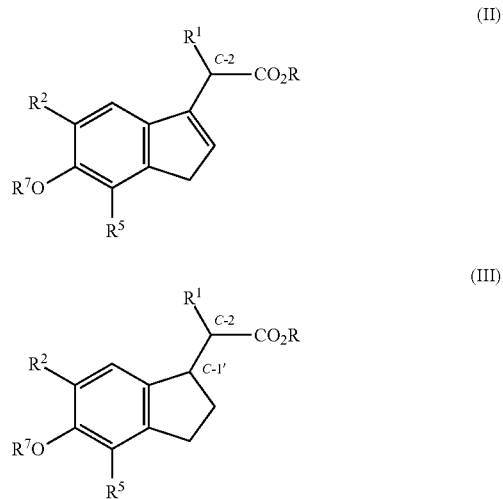

| Entry No. | Formula | absolute configuration C-2 | absolute configuration C-1' | R¹ | R² | R⁵ | R⁷ |
|---|---|---|---|---|---|---|---|
| 46 | III | S | R | Et | 3-Cl Ph | H | t-Bu(CH$_3$)$_2$Si |
| 47 | II | S | — | Et | 4-pyridyl | H | t-Bu(CH$_3$)$_2$Si |
| 48 | III | S | S | Et | 4-pyridyl | H | t-Bu(CH$_3$)$_2$Si |
| 49 | II | S | — | Et | CH$_3$ | H | Ph(CH$_3$)$_2$Si |
| 50 | II | R | — | Et | n-propyl | Cl | CH$_3$ |
| 51 | II | R | — | Et | Br | Br | t-Bu(CH$_3$)$_2$Si |
| 52 | III | R | R | Et | Br | Br | t-Bu(CH$_3$)$_2$Si |
| 53 | II | S | — | CF$_3$CH$_2$ | H | H | CH$_3$ |
| 54 | II | S | — | CF$_3$CH$_2$ | CH$_3$ | CH$_3$ | (4-CH$_3$O)PhCH$_2$ |
| 55 | III | S | S | CF$_3$CH$_2$ | CH$_3$ | CH$_3$ | (4-CH$_3$O)PhCH$_2$ |
| 56 | II | S | — | n-propyl | H | H | (i-Pr)$_3$Si |
| 57 | II | R | — | n-propyl | PrCO | PrCO | t-Bu |
| 58 | II | R | — | n-propyl | Cl | Cl | (i-Pr)$_3$Si |
| 59 | III | R | R | n-propyl | Cl | Cl | (i-Pr)$_3$Si |
| 60 | II | S | — | isopropyl | CH$_3$ | H | CH$_3$ |
| 61 | III | S | R | isopropyl | CH$_3$ | H | CH$_3$ |
| 62 | II | R | — | isopropyl | n-hexyl | H | (4-CH$_3$O)PhCH$_2$ |
| 63 | III | R | S | isopropyl | n-hexyl | H | (4-CH$_3$O)PhCH$_2$ |
| 64 | II | S | — | n-butyl | H | H | PhCH$_2$ |
| 65 | II | S | — | n-butyl | CH$_3$OCH$_2$ | H | t-Bu(CH$_3$)$_2$Si |
| 66 | III | S | S | n-butyl | CH$_3$OCH$_2$ | H | t-Bu(CH$_3$)$_2$Si |
| 67 | II | R | — | n-butyl | Cl | H | CH$_3$ |
| 68 | II | R | — | n-pentyl | Cl | Cl | (4-CH$_3$O)PhCH$_2$ |
| 69 | II | S | — | n-pentyl | 2-thienyl | 2-thienyl | CH$_3$ |
| 70 | III | S | S | n-pentyl | 2-thienyl | 2-thienyl | CH$_3$ |
| 71 | II | R | — | n-hexyl | CH$_3$CO | H | t-Bu(CH$_3$)$_2$Si |
| 72 | III | R | S | n-hexyl | CH$_3$CO | H | t-Bu(CH$_3$)$_2$Si |
| 73 | II | R | — | n-hexyl | Ph | H | Ph(CH$_3$)$_2$Si |
| 74 | III | R | R | n-hexyl | Ph | H | Ph(CH$_3$)$_2$Si |
| 75 | II | R | — | cyclopropyl | H | H | t-BuCO |
| 76 | II | S | — | cyclopropyl | CH$_3$ | H | (i-Pr)$_3$Si |
| 77 | II | S | — | cyclobutyl | H | H | CH$_3$ |
| 78 | III | S | S | cyclobutyl | H | H | CH$_3$ |
| 79 | II | S | — | cyclobutyl | Cl | Cl | (4-CH$_3$O)PhCH$_2$ |
| 80 | II | R | — | cyclopentyl | CH$_3$ | H | t-Bu(CH$_3$)$_2$Si |
| 81 | III | R | S | cyclopentyl | CH$_3$ | H | t-Bu(CH$_3$)$_2$Si |
| 82 | II | S | — | cyclohexyl | Et | Et | CH$_3$ |
| 83 | II | R | — | cyclohexyl | 2-thienyl | H | CH$_3$CO |
| 84 | II | R | — | cyclohexyl | Cl | H | CH$_3$ |
| 85 | III | R | R | cyclohexyl | Cl | H | CH$_3$ |
| 86 | II | S | — | 2-propenyl | H | H | t-Bu(CH$_3$)$_2$Si |
| 87 | II | R | — | 2-propenyl | CH$_3$ | H | CH$_3$CO |
| 88 | II | S | — | 2-isobutenyl | CH$_3$CO | H | CH$_3$ |
| 89 | II | S | — | 5-hexenyl | CH$_3$CO | CH$_3$CO | CH$_3$ |
| 90 | II | S | — | CH$_3$O | H | H | PhCH$_2$ |
| 91 | III | S | R | CH$_3$O | H | H | PhCH$_2$ |
| 92 | II | R | — | CH$_3$O | 3-F Ph | H | (4-CH$_3$O)PhCH$_2$ |
| 93 | II | S | — | EtO | Cl | Cl | PhCH$_2$ |

TABLE 2-continued

Illustrative Examples of Compounds II and III

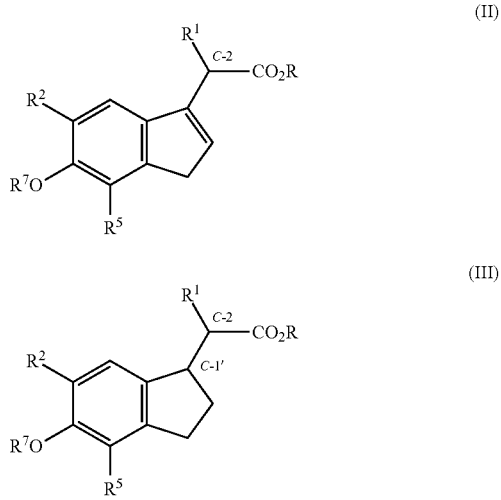

| Entry | | absolute configuration | | | | | |
|---|---|---|---|---|---|---|---|
| No. | Formula | C-2 | C-1' | $R^1$ | $R^2$ | $R^5$ | $R^7$ |
| 94 | III | S | R | EtO | Cl | Cl | $PhCH_2$ |
| 95 | II | R | — | (i-Pr)O | H | H | $PhCH_2$ |
| 96 | III | R | R | (i-Pr)O | H | H | $PhCH_2$ |
| 97 | II | S | — | (n-pentyl)O | $CH_3$ | H | $t\text{-}Bu(CH_3)_2Si$ |
| 98 | III | S | S | (n-pentyl)O | $CH_3$ | H | $t\text{-}Bu(CH_3)_2Si$ |
| 99 | II | S | — | $CO_2H$ | H | H | $(4\text{-}CH_3O)PhCH_2$ |

Another embodiment of the present invention is an improved process for the preparation of compounds having a specific isomeric configuration when that specific configuration is desired for the ultimate desired end product of Formula I. The improved process yields these intermediate compounds in significantly greater diastereomeric excess than was heretofore possible.

Previously, for example, in the absence of stereocontrol during the hydrogenation step of Reaction Scheme 2, hydrogenation of a Formula II compound, where $R^1$ is alkyl may produce an unequal mixture of diastereomeric products of Formula III, in which one pair of enantiomers is favored because of the asymmetric nature of the starting material. Separation of such compounds may be accomplished by stepwise separation of the enantiomeric pairs, then by resolution of each enantiomer by crystallization or by chiral HPLC. Prior resolution of the starting material into a single enantiomer produces mixtures with enrichment of a single enantiomer that may likewise be separated.

However, when a compound of a specific relative configuration, namely a syn form (defined below) is desired, the yield is low when $R^1$ is alkyl, because the conditions of the hydrogenation step described in the art may favor the other (i.e., anti) diastereomers.

The desired isomeric configurations realized from this improved process are in the syn form where, for example, in compounds of Formula Va and Vb (depicted in Reaction Schemes 4 and 5), the $R^9$ group and the 2' methylene carbon of the cyclopentane ring are both below the plane or are both above the plane. Anti diastereomers are those compounds where, for example, $R^9$ is above the plane and 2' methylene is below the plane. This is further exemplified in Figures 1 and 2 below, in which solid wedge bonds are used to indicate projection of the bond above the plane and dashed wedge bonds are used to indicate projection of the bond below the plane.

FIG. 1. syn diastereomers of Formula V

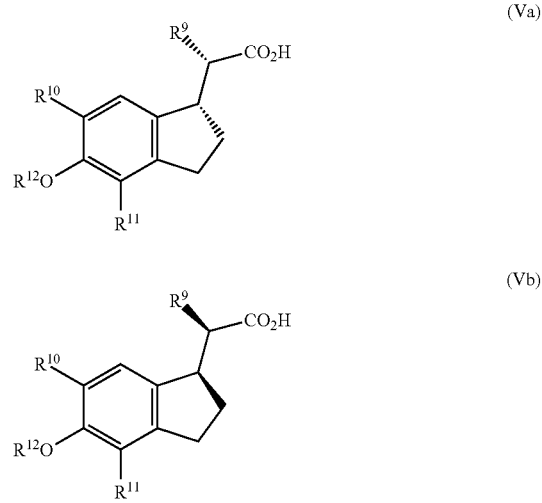

FIG. 2. anti diastereomers of Formula V

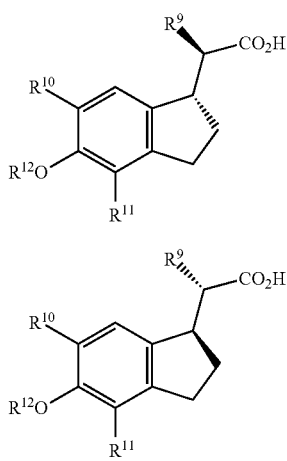

The improved process of this invention yields compounds in the syn form (Formulas Va and Vb, as drawn in Figure 1 and Reaction Schemes 4 and 5) in significantly higher diastereomeric excess than was generally possible.

The intermediate compounds used as starting materials for this process (compound IV of Reaction Schemes 4 and 5) are related to the compounds of Formula II (compound 16) in Reaction Scheme 2, and may be prepared by the same or analogous methods. These intermediates may be reacted under certain conditions to yield Formula V compounds that are related to compounds of Formula III (compounds 17 and 17a of Reaction Scheme 2), or to directly yield compounds of Formula I. However, due to the constraints of the improved process, only certain substituents are appropriate for completing this process.

Accordingly, the present invention relates to an improved process for the preparation of a substantially enriched syn form of a compound of Formula V,

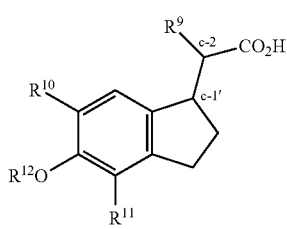

wherein
$R^9$ is methoxy optionally substituted by fluoro, $C_2$-$C_6$ alkoxy, $C_1$-$C_6$ alkyl, or $C_4$-$C_8$ cycloalkyl each optionally substituted by fluoro, methylenedioxyphenyl or phenyl optionally substituted with $R^{13}$;
$R^{10}$ is hydrogen, fluoro, methyl optionally substituted with fluoro, oxo, or
$C_2$-$C_6$ alkyl which may be unsubstituted or substituted with $C_1$-$C_6$ alkoxy, oxo, fluoro, or with phenyl, furyl, thienyl, pyrrolyl, oxazolyl, thiazolyl, imidazolyl, pyrazolyl, isoxazolyl, isothiazolyl, triazolyl, oxadiazolyl, thiadiazolyl, tetrazolyl, pyridyl, pyrrolidinyl, piperidinyl, tetrahydropyranyl, tetrahydrothiopyranyl, piperazinyl, or morpholinyl,
each of which may be unsubstituted or substituted with $R^{13}$, or
$R^{10}$ is phenyl, furyl, thienyl, pyrrolyl, oxazolyl, thiazolyl, imidazolyl, pyrazolyl, isoxazolyl, isothiazolyl, triazolyl, oxadiazolyl, thiadiazolyl, tetrazolyl, pyridyl, pyrrolidinyl, piperidinyl, tetrahydropyranyl, tetrahydrothiopyranyl, piperazinyl, or morpholinyl,
each of which may be unsubstituted or substituted with $R^{13}$;
$R^{11}$ is halo or $C_1$-$C_6$ alkyl optionally substituted with oxo;
$R^{12}$ is hydrogen, methyl optionally substituted with fluoro or oxo,
$C_2$-$C_6$ alkyl optionally substituted with phenyl, fluoro, or oxo,
$C_1$-$C_6$ trialkylsilyl, arylalkylsilyl, $COR^{14}$, $COOR^{14}$, or

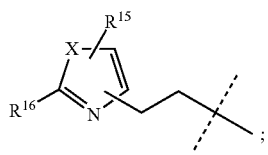

$R^{13}$ is fluoro, $CF_3$, $C_1$-$C_6$ alkyl optionally substituted with oxo, or $C_1$-$C_6$ alkoxy optionally substituted with fluoro;
$R^{14}$ is $C_1$-$C_6$ alkyl, or phenyl optionally substituted with $C_1$-$C_6$ alkyl or fluoro;
$R^{15}$ is hydrogen, $C_1$-$C_6$ alkyl or phenyl substituted with $R^{13}$;
$R^{16}$ is methyl optionally substituted with fluoro, oxo or
with phenyl, naphthyl, furyl, thienyl, pyrrolyl, tetrahydrofuryl, pyrrolidinyl, pyrrolinyl, tetrahydrothienyl, oxazolyl, thiazolyl, imidazolyl, pyrazolyl, isoxazolyl, isothiazolyl, triazolyl, oxadiazolyl, thiadiazolyl, tetrazolyl, pyridyl, piperidinyl, tetrahydropyranyl, tetrahydrothiopyranyl, pyrimidinyl, pyrazinyl, pyridazinyl, piperazinyl, morpholinyl, benzofuryl, dihydrobenzofuryl, benzothienyl, dihydrobenzothienyl, indolyl, indolinyl, indazolyl, benzoxazolyl, benxothiazolyl, benzimidazolyl, benzisoxazolyl, benzisothiazolyl, benzodioxolyl, quinolyl, isoquinolyl, quinazolinyl, quinoxazolinyl, dihydrobenzopyranyl, dihydrobenzothiopyranyl, or 1,4-benzodioxanyl,
each of which may be unsubstituted or substituted with $R^{13}$, or
$C_4$-$C_8$ cycloalkyl or $C_2$-$C_6$ alkyl, either of which may be unsubstituted or substituted with fluoro, methoxy, $C_2$-$C_6$ alkoxy optionally substituted with phenyl or $C_1$-$C_6$ alkoxy, oxo or with, phenyl, naphthyl, furyl, thienyl, pyrrolyl, tetrahydrofuryl, pyrrolidinyl, pyrrolinyl, tetrahydrothienyl, oxazolyl, thiazolyl, imidazolyl, pyrazolyl, isoxazolyl, isothiazolyl, triazolyl, oxadiazolyl, thiadiazolyl, tetrazolyl, pyridyl, piperidinyl, tetrahydropyranyl, tetrahydrothiopyranyl, pyrimidinyl, pyrazinyl, pyridazinyl, piperazinyl, morpholinyl, benzofuryl, dihydrobenzofuryl, benzothienyl, dihydrobenzothienyl, indolyl, indolinyl, indazolyl, benzoxazolyl, benxothiazolyl, benzimidazolyl, benzisoxazolyl, benzisothiazolyl, benzodioxolyl, quinolyl, isoquinolyl, quinazolinyl, quinoxazolinyl, dihydrobenzopyranyl, dihydrobenzothiopyranyl, or 1,4-benzodioxanyl,
each of which may be unsubstituted or substituted with $R^{13}$, or
$C_2$-$C_6$ alkyl which may also be substituted with $C_4$-$C_8$ cycloalkyl or with phenoxy which may be unsubstituted or substituted with $R^6$ or with phenyl, naphthyl, furyl, thienyl, pyrrolyl, tetrahydrofuryl, pyrrolidinyl, pyrrolinyl, tetrahydrothienyl, oxazolyl, thiazolyl, imidazolyl, pyrazolyl, isoxazolyl, isothiazolyl, triazolyl, oxadiazolyl, thiadiazolyl, tetrazolyl, pyridyl, piperidinyl, tetrahydropyranyl, tetrahydrothiopyranyl, pyrimidinyl, pyrazinyl, pyridazinyl, piperazinyl, morpholinyl, benzofuryl, dihydrobenzofuryl, benzothienyl, dihydrobenzothienyl, indolyl, indolinyl, indazolyl, benzoxazolyl, benxothiazolyl, benzimidazolyl, benzisoxazolyl, benzisothiazolyl, benzodioxolyl, quinolyl, isoquinolyl, quinazolinyl, quinoxazolinyl, dihydrobenzopyranyl, dihydrobenzothiopyranyl, or 1,4-benzodioxanyl, each of which may be unsubstituted or substituted with $R^{13}$, or $R^{16}$ is phenyl, naphthyl, furyl, thienyl, pyrrolyl, tetrahydrofuryl, pyrrolidinyl, pyrrolinyl, tetrahydrothienyl, oxazolyl, thiazolyl, imidazolyl, pyrazolyl, isoxazolyl, isothiazolyl, triazolyl, oxadiazolyl, thiadiazolyl, tetrazolyl, pyridyl, piperidinyl, tetrahydropyranyl, tetrahydrothiopyranyl, pyrimidinyl, pyrazinyl, pyridazinyl, piperazinyl, morpholinyl, benzofuryl, dihydrobenzofuryl, benzothienyl, dihydrobenzothienyl, indolyl, indolinyl, indazolyl, benzoxazolyl, benxothiazolyl, benzimidazolyl, benzisoxazolyl, benzisothiazolyl, benzodioxolyl, quinolyl, isoquinolyl, quinazolinyl, quinoxazolinyl, dihydrobenzopyranyl, dihydrobenzothiopyranyl, or 1,4-benzodioxanyl, each of which may be unsubstituted or substituted with $R^{13}$, or with phenyl, furyl, thienyl, pyrrolyl, oxazolyl, thiazolyl, imidazolyl, pyrazolyl, isoxazolyl, isothiazolyl, triazolyl, oxadiazolyl, thiadiazolyl, tetrazolyl, pyridyl, pyrrolidinyl, piperidinyl, tetrahydropyranyl, tetrahydrothiopyranyl, piperazinyl, morpholinyl, pyrimidinyl or phenoxy each of which may be unsubstituted or substituted with $R^{13}$, and X is O or S;

comprising hydrogenation of a racemic mixture or isolated optical isomer of a compound of Formula IV,

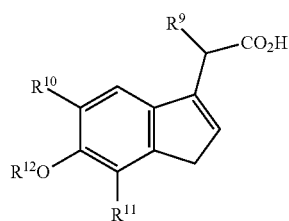

(IV)

wherein the substituents are as defined above, in the presence of hydrogen source, a catalyst, optionally in the presence of a base.

Substantially enriched syn form means at least about seventy percent (70%) or greater of one or both of the compounds of the configuration of Va or Vb. This is equivalent to at least about 40% de (diastereomeric excess) of the syn diastereomer. Diastereomeric excess of the syn diastereomer is calculated from the following formula:

$$\% \ de \ (syn) = \frac{[syn] - [anti]}{[syn] + [anti]} \times 100 = \% \ syn \ \text{diastereomer} - \% \ anti \ \text{diastereomer}$$

in which
% de (syn) represents the diastereomeric excess of the syn diastereomer
[syn] represents the concentration of the syn diastereomer
[anti] represents the concentration of the anti diastereomer, and where %syn+%anti=100%.

Thus, a 40% de of the syn diastereomer is calculated from a mixture of 70% syn diastereomer and 30% anti diastereomer:

40% de(syn)=70% syn diastereomer−30% anti diastereomer

Catalyst means any of the transition metal catalysts well known in the art to effect hydrogenation reactions (P. A. Chaloner, *Handbook of Co-ordination Catalysis in Organic Chemistry*, Butterworth, 1986), and includes homogeneous hydrogenation catalysts. A homogeneous catalyst is a catalyst which is at least partially soluble in the reaction medium and which effects the reduction of a double bond in the presence of hydrogen. Such catalysts include, for example, ClRh[P(Ph)$_3$]$_3$ (Wilkinson's catalyst), (1,5-cyclooctadiene)tricyclohexylphosphinepyridinoiridium(I) hexafluorophosphate, (1,5-cyclooctadiene)bis(methyldiphenylphosphine)iridium (I) hexafluorophosphate (Crabtree's catalysts), and the like.

Base means a substance with a pK$_b$ sufficient to form a salt in situ with a carboxylic acid (see, e.g., *Advanced Organic Chemistry*, 3rd Ed., Jerry March, pp 220-222). The base which is used in this reaction may be any inorganic or organic base, and may be soluble in the reaction medium. Such bases include, for example, mono, di, and tri(C$_1$-C$_6$alkyl)amines such as isopropyl amine, diisopropyl amine, triethylamine, and the like; additional primary amines such as, for example, cyclohexane methylamine and ethanolamine; additional secondary amines such as, for example, morpholine and piperidine; and additional tertiary amines such as, for example, 1,8-diazaobicyclo[5.4.0]undec-7-ene and 1,5-diazabicyclo[4.3.0]non-5-ene as well as inorganic bases such as alkali metal and alkaline earth hydroxides, carbonates, bicarbonates, and optically active bases such as quinine, cinchonine or (+) or (−)-alpha-methylbenzylamine.

Such bases also include, for example, the chiral bases named below that are useful for resolution.

Hydrogen source refers to any means of delivering hydrogen to the reaction medium and includes the use of hydrogen gas. Hydrogenation may by performed under a broad range of hydrogen pressures, that is, from about atmospheric pressure to about 1000 psi, preferably from about 20 to about 100 psi. Suitable hydrogenation solvents include, but are not limited to, protic solvents such as ethanol, methanol, water, 2-proponal, tert-butanol, methyl cellosolve and the like, and mixtures thereof, or optionally mixtures thereof with a miscible aprotic solvent such as THF, such that the hydrogenation catalyst, the base, and the starting material are each at least partially soluble.

The resolution of the starting indene acetic acid derivatives of Formula IV or of the indane acetic acid derivatives of Formula V may be accomplished by means well known in the art, for example, by using optically active bases as resolving agents such as, for example, a readily available base such as quinine, cinchonine or (+)- or (−)-alpha-methylbenzylamine. Choice of the base will depend on the solubility properties of the salt formed, so that resolution by differential recrystallization may be readily accomplished. By selecting bases with opposite absolute configuration, separation of the salt of each enantiomer may be accomplished. For example, for the embodiment illustrated in Reaction Scheme 4, the desired enantiomer IVc or IVd may be separated, and the undesired isomer may be recycled by racemization under basic conditions to the starting material of Formula IV.

Suitable crystallization solvents refer to those solvents in which one diastereomeric salt of a mixture is more soluble than the other, enabling them to be separated by recrystallization. Such solvents include, for example, acetonitrile, acetone, t-butanol, 2-propanol, ethanol, methanol, and the like, and mixtures thereof.

Aqueous mineral acids include, for example, the commonly used inorganic acids such as hydrochloric or sulfuric acid, and the like.

The process may be carried out starting with a racemate of Formula IV (see Reaction Scheme 4), or with a Formula V compound with the configuration at one asymmetric carbon which corresponds to that desired for the end product (see Reaction Scheme 5). Starting with the generally pure configuration is preferred, although either process will yield the desired configuration of the end product (V) in substantially enriched syn form.

One embodiment of this process is shown in the example of Reaction Scheme 4 and comprises the steps of
(1) formation of diastereomeric salts of IVc and IVd by treatment of IV with a suitable basic resolving agent,
(2) separation of the diastereomeric salts IVc and IVd by crystallization in a suitable crystallization solvent,
(3) optionally liberating the individual antipodes IVa and IVb from the separated salts by treatment with aqueous mineral acid, and
(4) reduction of either the separated diastereomeric salts IVc and Vd or the individual antipodes IVa and IVb by hydrogenation in the presence of a homogeneous hydrogenation catalyst, a suitable solvent and a base, wherein M+ is a cation selected from an alkali metal, alkaline earth metal, ammonium, and mono-, di-, tri- or quaternary alkylammonium or aralkylammonium, and $R^9$-$R^{12}$ are as defined above.

The enantiomeric purity of the product Va and Vb will correspond to the enantiomeric purity of the isomer IVa or IVb used, respectively, but will not include any substantial amount of the other (anti) diastereoisomer.

Reaction Scheme 4

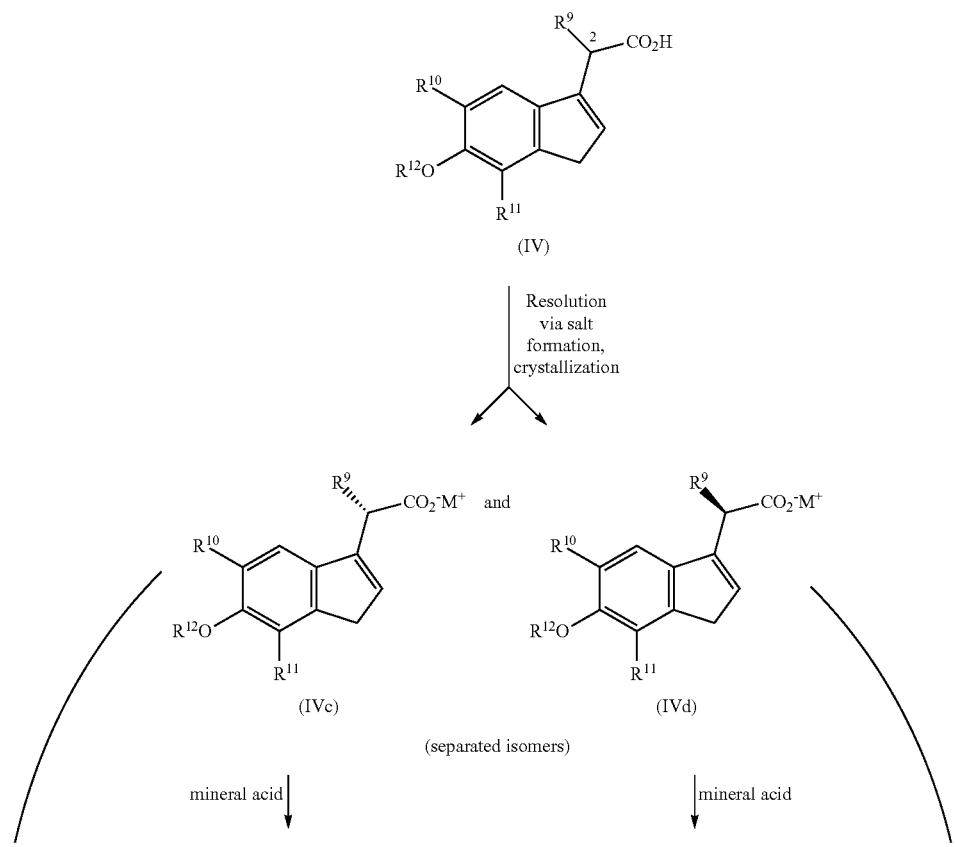

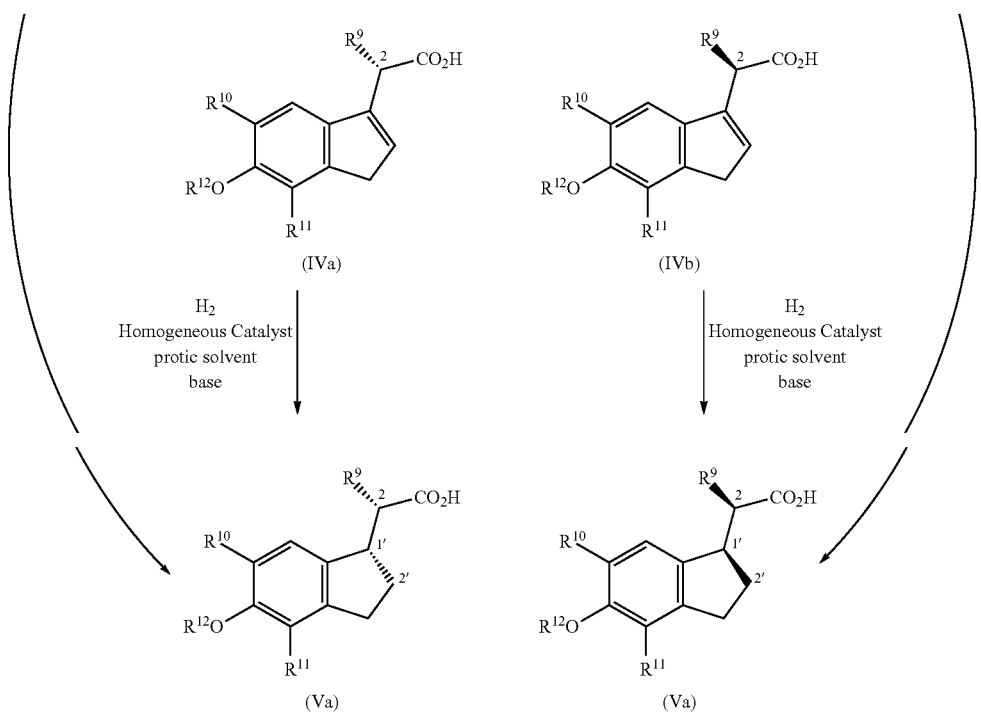

A second embodiment of this process is shown in Reaction Scheme 5 and comprises the steps of (1) reduction of the indene carboxylic acid of Formula IV by hydrogenation in the presence of a homogeneous hydrogenation catalyst, a suitable solvent, and a base, (2) formation of diastereomeric salts of Vc and Vd by treatment of V with a suitable basic resolving agent, (3) separation of the diastereomeric salts Vc and Vd by crystallization in a suitable crystallization solvent, and (4) liberating the individual antipodes Va and Vb from the separated salts by treatment with aqueous mineral acid.

Reaction Scheme 5

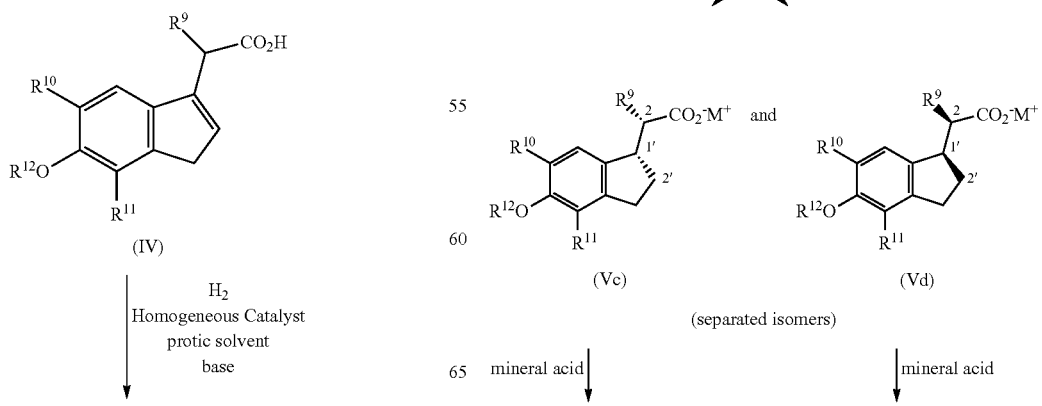

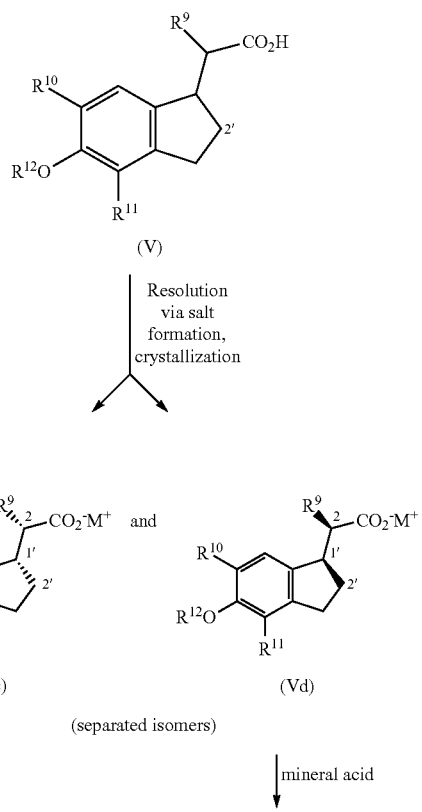

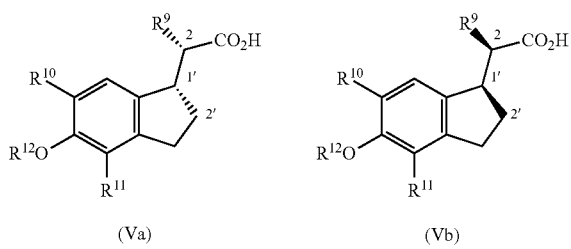

(Va)   (Vb)

The resolution of the racemate of either Formula IV or Formula V compounds may be accomplished by means well known in the art, such as by chiral HPLC, crystallization of chiral salt derivatives, chiral ester derivatives, and the like.

The determination of absolute chirality of IVa, IVb, IVc, IVd, Va, and Vb may be accomplished by several means known to those skilled in the art. X-ray crystallographic methods may provide such information under certain well-established conditions. For example, the presence in the crystallographic unit cell of another component of known chirality, such as a chiral resolving agent or auxiliary in the form of a salt, complex, or covalently attached group, may allow such determination. Another method known in the art, heavy atom scattering technique may be utilized when the compound to be assayed contains an atom of sufficient mass (for example, bromine or iodine). Other methods involving optical properties and the use of plane-polarized light may also be employed. For example, one skilled in the art would recognize that such techniques as circular dichroism may be applicable to a given structure or structural class.

Specific examples of the intermediates that may be made with the process of the present invention are shown below by way of example, and not by way of limitation, and may be used for the preparation of compounds of Formula I of the same absolute configuration.

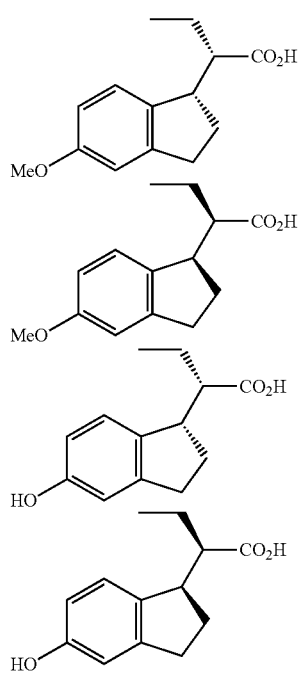

Compounds of Formula III in which $R^1$=H may also be prepared in an optically active fashion by the methods summarized in Reaction Scheme 6. Resolution of racemic ester 17a (Formula III, where $R^1$ is H) may be accomplished by selective enzymatic hydrolysis using Amano Lipase PS to yield 17f. Alternatively, 17e, which may be prepared by hydrolysis of 17a, may be resolved by crystallization of the diastereomeric salts formed with an optically active amine, for example, (S)-(−)-α-methyl-benzylamine, followed by regeneration of the carboxylic acid by treating the salt with mineral acid. Further conversion of 17f to the intermediates 17g and 17h may be accomplished by means analogous to that described for the preparation of 17c in Reaction Scheme 2: reesterification and removal of the $R^7$ protecting group.

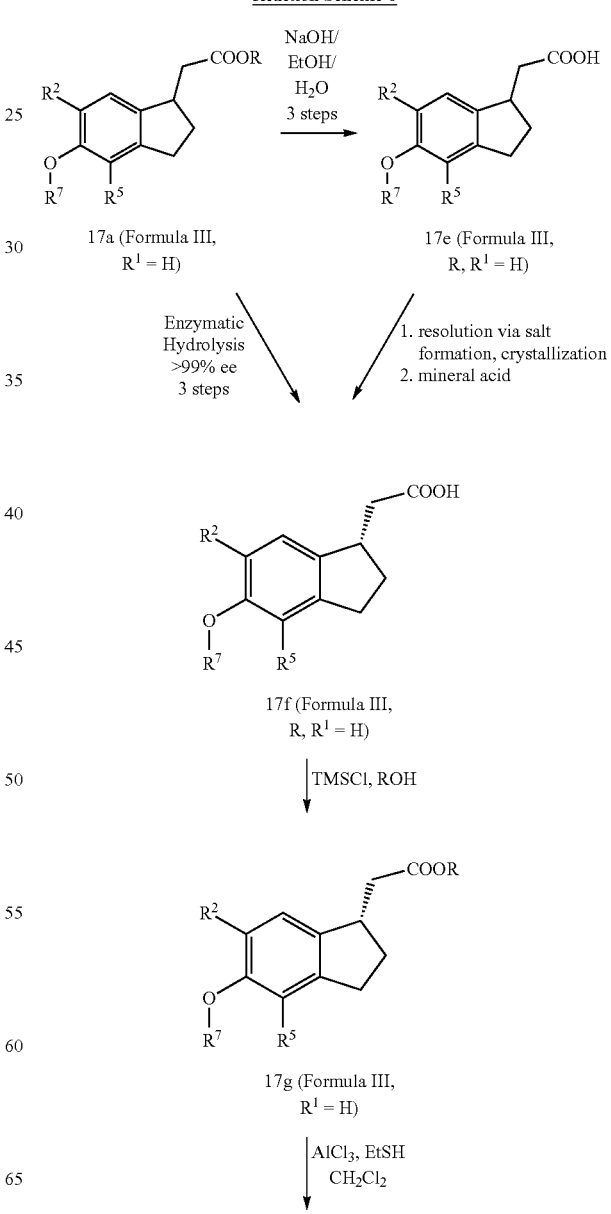

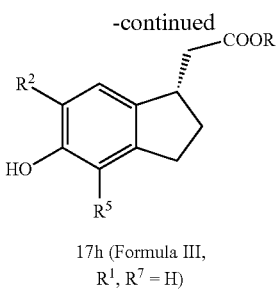

17h (Formula III, $R^1, R^7 = H$)

The compounds of Formula I are effective in the treatment of Type II diabetes mellitus (including associated diabetic dyslipidemia and other diabetic complications), as well as for a number of other pharmaceutical uses associated therewith, such as hyperglycemia, hyperinsulinemia, impaired glucose tolerance, impaired fasting glucose, dyslipidemia, hypertriglyceridemia, Syndrome X, and insulin resistance. In addition, the compounds of the present invention are also effective in the regulation of appetite and food intake in such disorders as obesity, and in the treatment of atherosclerotic disease, hyperlipidemia, hypercholesteremia, low HDL levels, hypertension, cardiovascular disease (including atherosclerosis, coronary heart disease, coronary artery disease, and hypertension), cerebrovascular disease and peripheral vessel disease; and for the treatment of lupus, polycystic ovary syndrome, carcinogenesis, and hyperplasia. The compounds of Formula I are also useful for treating physiological disorders related to, for example, cell differentiation to produce lipid accumulating cells, regulation of insulin sensitivity and blood glucose levels, which are involved in, for example, abnormal pancreatic beta cell function, insulin secreting tumors and/or autoimmune hypoglycemia due to autoantibodies to insulin, autoantibodies to the insulin receptor, or autoantibodies that are stimulatory to pancreatic beta cells), macrophage differentiation which leads to the formation of atherosclerotic plaques, inflammatory response, carcinogenesis, hyperplasia, adipocyte gene expression, adipocyte differentiation, reduction in the pancreatic β-cell mass, insulin secretion, tissue sensitivity to insulin, liposarcoma cell growth, polycystic ovarian disease, chronic anovulation, hyperandrogenism, progesterone production, steroidogenesis, redox potential and oxidative stress in cells, nitric oxide synthase (NOS) production, increased gamma glutamyl transpeptidase, catalase, plasma triglycerides, HDL, and LDL cholesterol levels, and the like.

Particularly useful compounds of Formula I of the present invention are those with efficacy in lowering blood glucose concentration and serum triglyceride levels, and raising serum HDL cholesterol levels.

Therefore, the compounds of Formula I of this invention are expected to be valuable as therapeutic agents. Accordingly, an embodiment of this invention includes a method of treating the various conditions identified above in a patient (including mammals) which comprises administering to said patient a composition containing an amount of the compound of Formula I that is effective in treating the target condition.

As indicated above, a compound of Formula I may be administered alone or in combination with one or more additional hypoglycemic agents. Combination therapy includes administration of a single pharmaceutical dosage formulation which contains a compound of Formula I and one or more additional hypoglycemic agent, as well as administration of the compound of Formula I and each additional hypoglycemic agents in its own separate pharmaceutical dosage formulation. For example, a compound of Formula I and hypoglycemic agent may be administered to the patient together in a single oral dosage composition such as a tablet or capsule, or each agent may be administered in separate oral dosage formulations.

Where separate dosage formulations are used, the compound of Formula I and one or more additional hypoglycemic agents may be administered at essentially the same time (e.g., concurrently) or at separately staggered times (e.g., sequentially).

For example, the compound of Formula I may be administered in combination with one or more of the following additional hypoglycemic agents: insulin; biguanidines such as metformin or buformin; sulfonylureas such as acetohexamide, chloropropamide, tolazamide, tolbutamide, glyburide, glipizide, glyclazide; or any other insulin secretagogue such as, for example, repaglinide and nateglinide; α-glycosidase inhibitors such as acarbose, voglibose, or miglitol; or β₃-adrenoreceptor agonists such as CL-316,243.

The compounds of Formula I may also be utilized, in free base form or in compositions, as well as in research and diagnostics or as analytical reference standards, and the like, which are well known in the art. Therefore, the present invention includes compositions which are comprised of an inert carrier and an effective amount of a compound of Formula I, or a salt, or ester thereof. An inert carrier is any material which does not interact with the compound to be carried and which lends support, means of conveyance, bulk, traceable material, and the like to the compound to be carried. An effective amount of the compound is that amount which produces a result or exerts an influence on the particular procedure being performed.

In another aspect, the present invention provides a method for treating a disease state in a patient, wherein the disease is associated with a physiological detrimental level of insulin, glucose, free fatty acids (FFA), cholesterol, or triglycerides in the blood, comprising administering to the patient a therapeutically effective amount of a compound of Formula I. In a further embodiment, the present invention provides a method for treating a disease state in a patient, wherein the disease is associated with a physiological detrimental level of insulin, glucose, free fatty acids (FFA), or triglycerides in the blood, comprising administering to the patient a therapeutically effective amount of a compound of Formula I and also administering a therapeutically effective amount of an additional hypoglycemic agent such as, for example, insulin, a biguanidine compound, and the like.

Since sulfonylureas and other insulin secretagogues are known to be capable of stimulating insulin release, but are not capable of acting on insulin resistance, and compounds of Formula I are able to act on insulin resistance, it is envisaged that a combination of these medicaments may be used as a remedy for conditions associated with both deficiency in insulin secretion and insulin resistance. Therefore, the invention also provides a method of treating Type II diabetes mellitus in a patient comprising administering a compound of Formula I and one or more additional hypoglycemic agents such as, for example, sulfonylureas, biguanidines, β-adrenoreceptor agonists, α-glycosidase inhibitors, and insulin. Also, compounds of Formula I may be used in combination with HMG Co-A reductase inhibitors (statins), bile acid binding resin, or fibric acid derivatives to improve the lipid profile of subjects with dyslipidemia and insulin resistance. Compounds of Formula I may also be used in combination with agents that regulate hypertension (e.g., inhibitors of angiotension converting enzyme (ACE), β-blockers, calcium channel blockers) and body weight of subjects with insulin resistance or type 2 diabetes.

The following specific examples are presented to illustrate the invention described herein, but should not be construed as limiting the scope of the invention in any way.

SPECIFIC EXAMPLES

HPLC-electrospray mass spectra (HPLC ES-MS) were obtained using a Hewlett-Packard 1100 HPLC equipped with a quaternary pump, a variable wavelength detector, a YMC Pro C18 2.0 mm×23 mm column, and a Finnigan LCQ ion trap mass spectrometer with electrospray ionization. Gradient elution from 90% A to 95% B over 4 minutes was used on the HPLC. Buffer A was 98% water, 2% Acetonitrile, and 0.02% TFA, and Buffer B was 98% Acetonitrile, 2% water, and 0.018% TFA. Spectra were scanned from 140-1200 amu using a variable ion time according to the number of ions in the source.

Proton ($^1$H) nuclear magnetic resonance (NMR) spectra were measured with a General Electric GN-Omega 300 (300 MHz) spectrometer with either Me$_4$Si (δ 0.00) or residual protonated solvent (CHCl$_3$ δ 7.26; MeOH δ 3.30; DMSO δ 2.49) as standard. Carbon ($^{13}$C) NMR spectra were measured with a General Electric GN-Omega 300 (75 MHz) spectrometer with solvent (CDCl$_3$ δ 77.0; d$_3$-MeOD; δ 49.0; d$_6$-DMSO δ 39.5) as standard.

Chiral separations were performed using a commercially available Chiracel® AD HPLC column, eluting with a gradient of isopropanol in hexane (from 1% to 15%) with addition of 0.1% trifluoroacetic acid.

Abbreviations and Acronyms

When the following abbreviations are used herein, they have the following meaning:

| | |
|---|---|
| Ac$_2$O | acetic anhydride |
| ADDP | 1,1'-(azodicarbonyl)dipiperidine |
| anhy | anhydrous |
| BOC | tert-butoxycarbonyl |
| n-BuOH | n-butanol |
| t-BuOH | tert-butanol |
| t-BuOK | potassium tert-butoxide |
| CDI | carbonyl diimidazole |
| CD$_3$OD | methanol-d$_4$ |
| Celite ® | diatomaceous earth filter agent, ® Celite Corp. |
| CH$_2$Cl$_2$ | methylene chloride |
| CI-MS | chemical ionization mass spectroscopy |
| conc | concentrated |
| DCC | dicyclohexylcarbodiimide |
| DCM | dichloromethane |
| de | diastereomeric excess |
| DEAD | diethyl azodicarboxylate |
| dec | decomposition |
| DIA | diisopropyl amine |
| DIBAL-H | diisobutylaluminum hydroxide |
| DMAP | 4-(N,N-dimethylamino)pyidine |
| DME | dimethoxyethane |
| DMF | N,N-dimethylformamide |
| DMSO | dimethylsulfoxide |
| EDCI | 1-(3-dimethylaminopropyl)-3-ethylcarbodiimide hydrochloride |
| ee | enantiomeric excess |
| ELSD | evaporative light scattering detector |
| ES-MS | electrospray mass spectroscopy |
| EtOAc | ethyl acetate |
| EtOH | ethanol (100%) |
| EtSH | ethanethiol |
| Et$_2$O | diethyl ether |
| Et$_3$N | triethylamine |
| GC-MS | gas chromatography-mass spectroscopy |
| HPLC | high performance liquid chromatography |
| IPA | isopropylamine |
| LAH | lithium aluminum hydride |
| LC-MS | liquid chromatography-mass spectroscopy |
| LDA | lithium diisopropylamide |
| m/z | mass-to-charge ratio |
| MeCN | acetonitrile |
| NMM | 4-methylmorpholine |
| Ph$_3$P | triphenylphosphine |
| Pd(dppf)Cl$_2$ | [1,1'-bis(diphenylphosphino)ferrocene]dichloropalladium(II) |
| Pd(PPh$_3$)$_4$ | tetrakis(triphenylphosphine)palladium(0) |
| Pd(OAc)$_2$ | palladium acetate |
| P(O)Cl$_3$ | phosphorous oxychloride |
| Rf | retention factor (TLC) |
| RT | retention time (HPLC) |
| rt | room temperature |
| TEA | triethyl amine |
| THF | tetrahydrofuran |
| TFA | trifluoroacetic acid |
| TLC | thin layer chromatography |
| TMAD | N,N,N',N'-tetramethylethylenediamine |
| TMSCI | trimethylsilyl chloride |

Example 1

Preparation of methyl 2-(6-methoxy-1H-inden-3-yl)butanoate

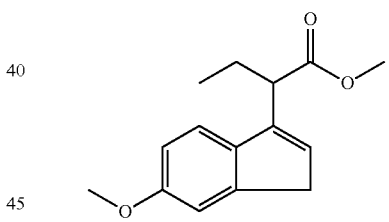

An oven dried 5-L four-necked round-bottomed flask was fitted with a thermometer, a condenser, an addition funnel, and a mechanical stirrer. Under Ar protection, a suspension of 5-methoxy-1-indanone (80.0 g, 494 mmol), Zn powder (Lancaster, 56.2 g, 865 mmol) in 2 L anhydrous THF was stirred at 60° C. (internal temperature), while a solution of methyl bromobutyrate (134.1 g, 741 mmol) in 400 mL anhydrous THF was added slowly through an addition funnel. After completion of the addition, the reaction mixture was stirred at 60° C. (internal temperature) for 1 hour. The reaction was followed by TLC analysis of aliquots following 1N aqueous HCl work-up. After the reaction was completed, it was cooled in an ice-water bath followed by slow addition of 3 L of 1N HCl solution. The pot temperature was kept below 20° C. The mixture was then extracted with 1 L EtOAc. The organic layer was washed with water until pH 6.0-7.0, then saturated NaCl solution, and dried over Na$_2$SO$_4$. The product (127 g, >99%), a yellow oil, was obtained after solvent removal and drying under vacuum. $^1$H NMR (DMSO-d$_6$) δ 7.28(d, 1H), 7.05(d, 1H), 6.82(dd, 1H), 6.22(s, 1H), 3.72(s, 3H), 3.60(m, 1H), 3.58(s, 3H), 3.28(s, 2H), 1.95(m, 1H), 1.80(m, 1H), 0.88(t, 3H).

Example 2a

Preparation of 2-(6-methoxy-1H-inden-3-yl)butanoic acid

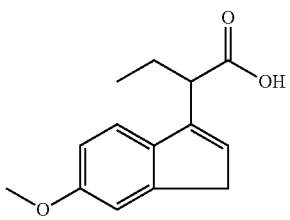 [SMILES: CCC(C(=O)O)C1=CCc2cc(OC)ccc21]

To a solution of the ester prepared in Example 1 (14.0 g, 58.9 mmol) in 140 mL MeOH, was added a solution of KOH (6.4 g, 113.8 mmol) in 5 mL water. The reaction mixture was stirred at 60° C. (pot temperature) for 2 hours. TLC showed 70% conversion. A solution of KOH (3.0 g, 53.6 mmol) in 100 mL water was then slowly added to the pot. After 1 hour, the reaction was completed. After cooling to room temperature, the solvents were removed at a reduced pressure. The residue was dissolved in 500 mL water, and then washed with EtOAc. The aqueous layer was cooled in an ice-water bath, and then acidified with conc. HCl to pH<3.0. The product was extracted into 300 mL $CH_2Cl_2$, washed with water (2×100 mL), then dried over $Na_2SO_4$. After $Na_2SO_4$ was filtered off, the $CH_2Cl_2$ solution was stirred with 3.0 g of charcoal for 2 hours. The charcoal was removed by filtration through a pad of Celite®. The title product (12.5 g, 95%) was obtained as a light brown solid after solvent removal and vacuum drying. $^1$H NMR (DMSO-$d_6$) δ12.20(b, 1H), 7.30(d, 1H), 7.06(d, 1H), 6.82(dd, 1H), 6.22(s, 1H), 3.75(s, 3H), 3.45(t, 1H), 3.30(s, 2H), 1.90(m, 1H), 1.78(m, 1H), 0.90(t, 3H).

Example 2b

Preparation of 2-(6-methoxy-1H-inden-3-yl)propanoic acid

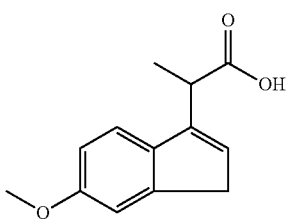 [SMILES: COc1ccc2c(c1)CC=C2C(C)C(=O)O]

This substrate was prepared using the same procedures as described for Examples 1 and 2a, starting with 5-methoxyl-1-indanone and methyl 2-bromopropionate. Yield: 68%. $^1$H NMR ($CD_2Cl_2$) δ 7.34 (d, J=9, 1H), 7.07 (d, J=2, 1H), 6.85 (dd, J=9, J=2, 1H), 6.32 (m, 1H), 3.82 (m, 4H), 3.36 (m, 2H), 1.56 (d, J=7, 3H).

Example 3

Preparation of (2S)-2-(6-methoxy-1,4-inden-3-yl)butanoic acid

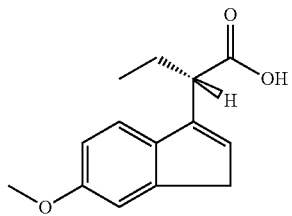

To a solution of the racemic indene acid prepared in Example 2a (300 g, 1.29 mol) in 4.5 L $CH_3CN$, was added quinine (324 g, 1.0 mol) at rt. The mixture was stirred for 1 hour, and became a solution. A small amount of insoluble particles was removed by filtration through a microfiber filter under vacuum. The filtrate was then mechanically stirred under Ar over night. After 24 hours, a small sample of solid was taken and analyzed, showing 76.2% ee. The agitation was stopped after two more days. The suspension was filtered. The filter cake was washed with $CH_3CN$ (3×200 mL), and then dried under vacuum at 40° C. for 3 hours. This solid was stirred with 4.5 L $CH_3CN$ at 70° C. until all solids went into solution. The solution was allowed to cool down to rt slowly. The resulting suspension was stirred at rt for 24 hours. The suspension was filtered. The filter cake was washed with $CH_3CN$ (3×250 mL), and then dried under vacuum at 40° C. for 24 hours. This quinine salt was collected as a white solid (254.6 g, 35.4% yield, 96.8% ee).

The quinine salt (544.3 g, 0.98 mol) was dissolved in 4.0 L $CH_2Cl_2$ to obtain a clear solution. It was stirred vigorously with 4.0 L of 2N HCl solution in a 22-L round-bottomed flask with a bottom valve. After 30 minutes, the mixture was allowed to settle. The bottom layer was separated and top aqueous layer was extracted with 1 L $CH_2Cl_2$. The combined $CH_2Cl_2$ layers were washed with water (3×2.0 L) until pH 5.0-6.0, and then dried over $Na_2SO_4$. The product (230.8 g, 99%, 96.8% ee) was obtained as an off white solid after solvent removal and vacuum drying. $^1$H NMR was identical to that of the racemic material described in Example 2a.

Treatment of the mother liquor in similar fashion gave the (R) isomer. Alternatively, the mother liquor may be subjected to aqueous basic conditions in order to effect racemization and recovery of racemic starting material.

Example 4

Preparation of (2S)-2-[(1S)-5-methoxy-2,3-dihydro-1H-inden-1-yl]butanoic acid

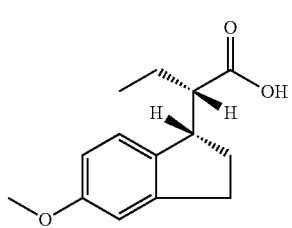

A solution of the product obtained in Example 3 (105 g, 453 mmol), ClRh(PPh$_3$)$_3$ (21.0 g, 5% eq.) and triethylamine (68.8 g, 679.5 mmol) in EtOH (945 mL) and THF (105 mL) was shaken in a 2-L pressure bottle under 60 psi H$_2$ for 16 hours. The solvents were removed at a reduced pressure. The resulting mixture was stirred in 1.5 L of 1N HCl solution and 1.5 L CH$_2$Cl$_2$. The aqueous layer was extracted with CH$_2$Cl$_2$ (2×250 mL). The combined CH$_2$Cl$_2$ layers were washed with 1 L of 1N HCl solution and stirred with 1 L of 1N NaOH solution. The organic layer was extracted with 1N NaOH solution (2×0.5 L). The combined aqueous layer was washed with CH$_2$Cl$_2$ (2×250 mL), and acidified (pH 2.0-3.0) by a slow addition of conc. HCl solution at below 15° C. The acidic mixture was extracted with CH$_2$Cl$_2$ (2×1.5 L), and washed with water (2×0.5 L) until pH 5.0-6.0. After washing with brine and drying over anhydrous Na$_2$SO$_4$, solvent was evaporated under a reduced pressure. The product (101.0 g, 95% yield, 96.8% ee) was obtained as a light yellow oil. $^1$H NMR (DMSO-d$_6$) δ12.20(s, 1H), 7.04(d, 1H), 6.78(d, 1H), 6.66(dd, 1H), 3.70(s, 3H), 3.28(m, 1H), 2.72(m, 2H), 2.32(m, 1H), 2.06(m, 1H), 1.80(m, 1H), 1.50(m, 1H), 1.36(m, 1H), 0.82(t, 3H).

Example 5a

Preparation of syn-2-[5-methoxy-2,3-dihydro-1H-inden-1-yl]butanoic acid

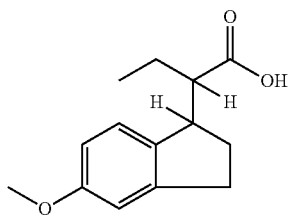 [SMILES: CCC(C(=O)O)C1CCc2cc(OC)ccc21]

A suspension of racemic indene acid (Example 2, 980 mg, 4.2 mmol), ClRh(PPh$_3$)$_3$ (139 mg, 0.15 mmol), NaHCO$_3$ (378 mg, 4.5 mmol) in EtOH (20 mL), and H$_2$O (10 mL) was shaken in a 500 mL pressure bottle under 60 psi H$_2$ for 30 hours. Additional ClRh(PPh$_3$)$_3$ (300 mg, 0.33 mmol) was added to the reaction mixture and hydrogenation was continued for 3 more days. After this time, EtOH was removed at a reduced pressure and the residue was diluted with 200 mL water. The black solid was removed by filtration and the filtrate was washed with EtOAc (2×200 mL). The aqueous solution was then acidified with conc. HCl, and extracted with CH$_2$Cl$_2$ (2×100 mL). The combined CH$_2$Cl$_2$ layer was washed with brine and dried over Na$_2$SO$_4$. Removal of the solvent in vacuum afforded the indane acid as light yellow oil (600 mg, 60%). The product mixture resulted a diastereomeric mixture (87:13) in favor of the syn isomers as determined by NMR analysis, using the ratio of integration of NMR peaks δ 7.11(d, 1H) for the anti, and δ 7.03(d, 1H) for the syn isomers.

Resolution of the product into optical isomers may be accomplished as follows: to a mechanically stirred solution of the syn indane acetic acid [(2R,1R) and (2S,1S), 14.69 g, 62.7 mmol] in acetonitrile (290 mL) at rt, was added (R)-(+)-α-methylbenzylamine (8.49 mL, 65.9 mmol) in one portion. The resulting mixture was stirred overnight. Little solid formation was observed. The reaction mixture was concentrated to dryness and the residue was redissolved in acetonitrile (200 mL) with heating. Magnetic stirring was begun to initiate precipitation. The mixture was stirred overnight. The solids were collected by filtration, and washed three times with a small amount of cold acetonitrile. The solids were then dried under vacuum for 1.5 hours (8.1 g, 86% ee). The slightly wet solids were recrystallized in acetonitrile (120 mL) to give 6.03 g of the (2S)-2-((1S)-5-methoxy-2,3-dihydro-1H-inden-1-yl)butanoic acid, (R)-α-methylbenzylamine salt (94.4% ee). A second crop was collected from various filtrates (0.89 g, 97.6% ee). The overall yield of resolution was 31% (62% based on the maximum content of (2S,1S) acid in the racemate). The material was identical to that obtained in Example 4.

Optical purity for this Example and that of Example 4 may also be analyzed by chiral HPLC; Column: Chiracel AD, 4.6 (I.D.)×250 mm; Mobile Phase, A: 0.1% TFA (trifluoroacetic acid) in hexanes, B: 0.1% TFA in IPA (isopropyl alcohol); Method, Isocratic 95% A (5% B), 20 min.; Flow Rate, 1.5 ml/min.; Detector (UV), 284 nm. Retention times for the four possible diastereomers are 5.163 min. (2S,1R), 6.255 min. (2R,1S), 10.262 min. (2R,1R) and 14.399 min. (2S,1S). The first locator (2S or 2R) denotes the absolute configuration of the carbon adjacent to the carboxyl group (the 2-position); the second locator (1S or 1R) denotes the absolute configuration of the indane ring carbon (its 1-position).

The stereochemical assignment for each peak was determined by chiral HPLC analysis of a non-equal (syn/anti) racemic diastereomeric mixture of compound 5, which provided four baseline-resolved peaks. Peaks 3 and 4, and peaks 1 and 2 represented enantiomer pairs, based on UV integration. The absolute configuration of the compound of peak 4 was determined to be 2S,1S by X-ray structural analysis. Peak 3, the corresponding enantiomer, was then assigned a 2R,1R configuration with certainty. Peak 1 was assigned to the (2S, 1R)-diastereomer (retention time: 5.363 min., ca. 0.97% area) by comparison to the minor product obtained from the reduction of the chiral acid (Example 3) as described in Example 4. The remaining peak 2, could then be assigned with certainty to the compound with 2R,1S configuration.

Example 5b

Preparation of syn-2-[5-methoxy-2,3-dihydro-1H-inden-1-yl]propanoic acid

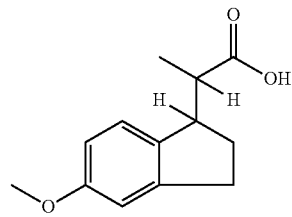 [SMILES: COc1ccc2c(c1)CCC2C(C)C(=O)O]

The compound was prepared in 71% yield and >99% de using the same procedure as described for Example 4 starting with (racemic) Example 2b: $^1$H NMR (DMSO-d$_6$) δ 12.18 (s, 1H), 7.03 (d, J=8, 1H), 6.75 (d, J=2, 1H), 6.67 (dd, J$_1$=8, J$_2$=2, 1H), 3.68 (s, 3H), 3.37 (m, 1H), 2.72 (m, 3H), 2.03 (m, 1H), 1.75 (m, 1H), 0.89 (d, J=7, 3H); $^{13}$C NMR (CD$_2$Cl$_2$) δ 12.626, 28.228, 31.950, 43.300, 46.445, 55.607, 110.054, 112.510, 124.552, 136.702, 146.411, 159.464, 182.330.

Example 6

Preparation of methyl(2S)-2-[(1S)-5-methoxy-2,3-dihydro-1H-inden-1-yl]butanoate

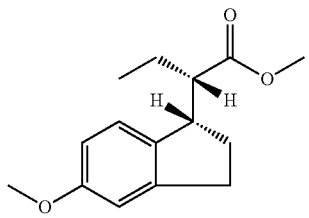

A suspension of acid prepared in Example 4 (220.0 g, 0.94 mol), NaHCO$_3$ (237.0 g, 2.82 mol), CH$_3$I (200 g, 1.41 mol) in 2.0 L DMF was stirred under Ar at rt for 18 hours. NMR analysis showed 95% reaction. Adding CH$_3$I (100 g), and stirring for additional 24 hours at rt caused completion of the reaction. The reaction mixture was poured into 4.0 L water, and extracted with EtOAc (2×2 L). The organic layer was sequentially washed with water (2×1 L), 1 L of 1N NaOH solution, water (2×1 L), and 500 mL brine, and dried over Na$_2$SO$_4$. The product (233 g, 99%) was obtained as a light yellow oil after solvent removal and vacuum drying. $^1$H NMR (DMSO-d$_6$) δ 6.90(d, 1H), 6.78(d, 1H), 6.66(dd, 1H), 3.70(s, 3H), 3.60(s, 3H), 3.20(m, 1H), 2.80(m, 2H), 2.40(m, 1H), 2.08(m, 1H), 1.80(m, 1H), 1.58(m, 1H), 1.40(m, 1H), 0.80(t, 3H).

Example 7

Preparation of methyl(2S)-2-[(1S)-5-hydroxy-2,3-dihydro-1H-inden-1-yl]butanoate

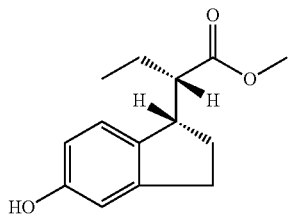

To a cold solution (ice water bath) of the compound prepared in Example 6 (233 g, 0.94 mol) in 2.5 L CH$_2$Cl$_2$, was added AlCl$_3$ (630 g, 4.7 mol) slowly under Ar. The pot temperature was kept below 20° C., and the color of the reaction turned purple. EtSH (345 mL, 4.7 mol) was added slowly via an addition funnel to the reaction mixture, and the inside temperature was kept below 15° C. After 2 hours of stirring at below 20° C., the reaction went to completion by NMR analysis. The pot mixture was slowly poured into 2.5 L ice water with a strong agitation. The organic layer was separated, and the aqueous layer was extracted with 1 L CH$_2$Cl$_2$. The combined CH$_2$Cl$_2$ layers were washed with water (4×1 L) until pH 6.0-7.0, and then dried over Na$_2$SO$_4$. The product (216 g, 98%) was obtained as a white solid after solvent removal and vacuum drying. $^1$H NMR (DMSO-d$_6$) δ 9.10(s, 1H), 6.78(d, 1H), 6.58(d, 1H), 6.50(dd, 1H), 3.60(s, 3H), 3.20(q, 1H), 2.70(m, 2H), 2.40(m, 1H), 2.08(m, 1H), 1.80(m, 1H), 1.50(m, 2H), 0.80(t, 3H).

Example 8

Preparation of methyl 3-[(4-methylbenzoyl)amino]-4-oxopentanoate

To a suspension of L-aspartic acid β-methyl ester hydrochloride (250 g, 1.36 mol) in chilled (<5° C.) CH$_2$Cl$_2$ (4 L) was added Et$_3$N (440 g, 4.35 mol) in a steady flow followed by a slow addition of Me$_3$SiCl (324 g, 2.99 mol). The mixture was warmed to 25° C. and stirred for one hour, cooled again (<10° C.), and p-toluoyl chloride (205 g, 1.36 mol) was added dropwise. The mixture was allowed to warm to ambient slowly with stirring for 16 hours. The reaction mixture was then diluted with CH$_2$Cl$_2$ (500 mL) and washed with 1N HCl (500 mL), brine (500 ml), and dried over Na$_2$SO$_4$. The resultant amide product (310 g, 91%), a white solid, was obtained after solvent removal and drying under vacuum. It was then dissolved in pyridine (1.25 L) and DMAP (5 g) was added. Acetic anhydride (840 mL) was added slowly and then the reaction was heated at 90° C. for 2 hours. The cooled solution was poured into 7 L ice water and extracted with 6 L EOM. The organic layer was washed with 2N HCl (3×1 L) and 1N NaOH (1 L), dried over MgSO$_4$ and concentrated to afford the title compound as a white solid (301 g, 93%).

Example 9

Preparation of methyl[5-methyl-2-(4-methylphenyl)-1,3-oxazol-4-yl]acetate

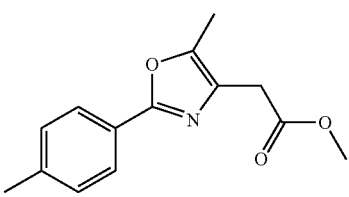

The intermediate prepared in Example 8 (280 g, 1.06 mol) was dissolved in acetic anhydride (650 mL) followed by slow addition of conc. H$_2$SO$_4$ (60 ml). The pot temperature reached 80° C. The reaction was then held at 85° C. for 1 hour, cooled, and the acetic anhydride removed in vacuo. The residue was poured into ice water (2 L) and extracted with EtOAc (4 L total). The organic layer was then stirred with 1 N NaOH (500 mL) for 1 hour, separated, then dried with MgSO$_4$ and concentrated to afford the title ester as a clear oil (223 g, 87%), which slowly solidified to a white solid.

Example 10

Preparation of 2-[5-methyl-2-(4-methylphenyl)-1,3-oxazol-4-yl]ethanol

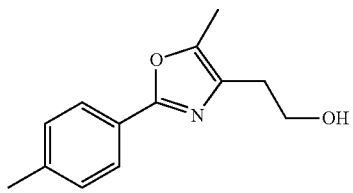 [SMILES: Cc1ccc(-c2nc(CCO)c(C)o2)cc1]

The oxazole ester prepared in Example 9 (300 g, 1.22 mol) was dissolved in THF (2.7 L) and solid LiBH$_4$ (26.6 g, 1.22 mol) was added in 5-g portions while maintaining temperature below 45° C. Reaction was complete within an hour after addition. Solvent was reduced to half volume and then poured into ice water (3 L). The mixture was then acidified by slowly adding 1 N HCl (1 L). A white precipitate formed and was collected by filtration and oven dried over P$_2$O$_5$ to give the desired oxazole ester (214 g, 83%).

Example 11

Preparation of methyl(2S)-2-((1S)-5-{2-[5-methyl-2-(4-methylphenyl)-1,3-oxazol-4-yl]ethoxy}-2,3-dihydro-1H-inden-1-yl)butanoate

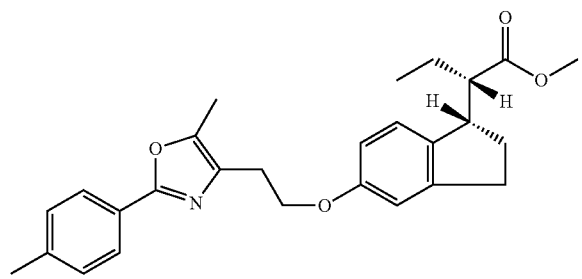

A suspension of the hydroxyindane carboxylate prepared in Example 7 (208 g, 889 mmol), oxazole alcohol prepared in Example 10 (212 g, 977 mmol), ADDP (335 g, 1.33 mol), Ph$_3$P (348 g, 1.33 mol) in 6.0 L anhydrous THF was stirred at rt under Ar. The reaction was followed by $^1$H NMR. No further progress was observed after 2 days. After solids were removed by filtration, THF was removed under reduced pressure. The remaining mixture was stirred in 3 L of 50/50 mixture EtOAc/hexane for 10 minutes, and more solids were formed and removed by filtration. The filtrate was concentrated and subjected to the same procedure with 25/75 mixture of EtOAc/hexane. After solvents were removed, the resulting oily mixture was purified on a silica gel (3.0 kg) column using CH$_2$Cl$_2$ (10.0 L) and 20% CH$_3$CN/CH$_2$Cl$_2$ (10.0 L) as solvent. Fractions containing product were collected, and then concentrated. The crude mixture was dissolved in 4.0 L CH$_2$Cl$_2$, and the unreacted hydroxy compound was removed by washing with 1N NaOH (3×1 L). The CH$_2$Cl$_2$ layer was dried over Na$_2$SO$_4$. The product (358 g, 93%) was obtained as a light yellow oil after solvent removal and vacuum drying. $^1$H NMR (DMSO-d$_6$) δ 7.78(d, 2H), 7.30(d, 2H), 6.90(d, 1H), 6.75(d, 1H), 6.65(dd, 1H), 4.15(t, 2H), 3.60(s, 3H), 3.25(q, 1H), 2.90(t, 2H), 2.75(m, 2H), 2.40 (m, 1H), 2.35(s, 3H), 2.32(s, 3H), 2.05(m, 1H), 1.80(m, 1H), 1.50(m, 2H), 0.80(t, 3H).

Example 12

Preparation of (2S)-2-((1S)-5-{2-[5-methyl-2-(4-methylphenyl)-1,3-oxazol-4-yl]ethoxy}-2,3-dihydro-1H-inden-1-yl)butanoic acid

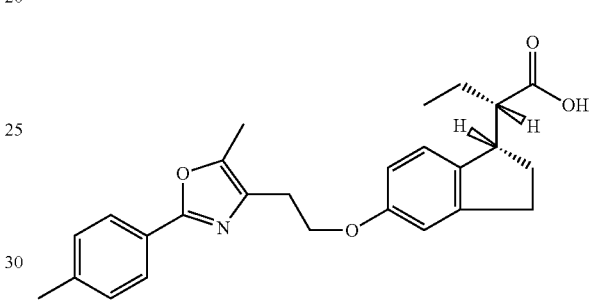

To a solution of LiOH (90.4 g, 3.76 mol) in 1.3 L water and 1.3 L MeOH, was added a solution of the ester prepared in Example 11 (325 g, 0.75 mol) in 3.9 L THF at rt.

The solution turned cloudy. This mixture was heated at 60° C. (pot temperature) for 4 hours, and TLC (50% EtOAc/hexane) analysis showed ca. 50% conversion. A solution of LiOH (30.1 g, 1.25 mol) in water (200 mL) was added to the reaction mixture. After 2 hours, TLC analysis showed ca. 85% reaction. Again, a solution of LiOH (30.1 g, 1.25 mol) in water (200 mL) was added to the reaction mixture. After 2 hours, TLC analysis showed very little starting ester left. After the reaction mixture was cooled to rt, THF and MeOH were removed at a reduced pressure. The residue was diluted with water until the solids dissolved (a total of 60 L of water used). Conc. HCl solution was slowly added to this aqueous solution until pH 2.0-3.0. The solid was collected by filtration, and dried under house vacuum overnight. This solid was stirred with 15 L EtOAc and 2 L of 1N HCl solution for 30 minutes. The EtOAc layer was separated and washed with 1N HCl solution (2×1 L). The organic phase was then washed with water (4×2 L) until pH=5.0-6.0. Under Ar protection, the EtOAc solution was reduced to 2.5 L by normal pressure distillation, then cooled to rt without disturbance. White solid precipitated out. After further cooling in an ice water bath for 2 hours, the solid was filtrated and washed with 500 mL cold EtOAc. After drying under high vacuum at 35° C. to a constant weight, the final product (266 g, 81%, 98% ee,) was collected as a white crystal. $^1$H NMR (CDCl$_3$) δ 7.82(d, 2H), 7.20(d, 2H), 7.05(d, 1H), 6.75(d, 1H), 6.70(dd, 1H), 4.20(t, 2H), 3.42(q, 1H), 2.95(t, 2H), 2.80(m, 2H), 2.50(m, 1H), 2.35(s, 3H), 2.32(s, 3H), 2.20(m, 1H), 1.90(m, 1H), 1.65(m, 1H), 1.45(m, 1H), 3H). Chiral purity, 99% ee, [α]$_D$=+16.11 (CHCl$_3$), mp 149.5-150.5° C.

Example 13

Preparation of 2-{5-[2-(5-methyl-2-phenyl-1,3-oxazol-4-yl)ethoxy]-2,3-dihydro-1H-inden-1-yl}butanoic acid

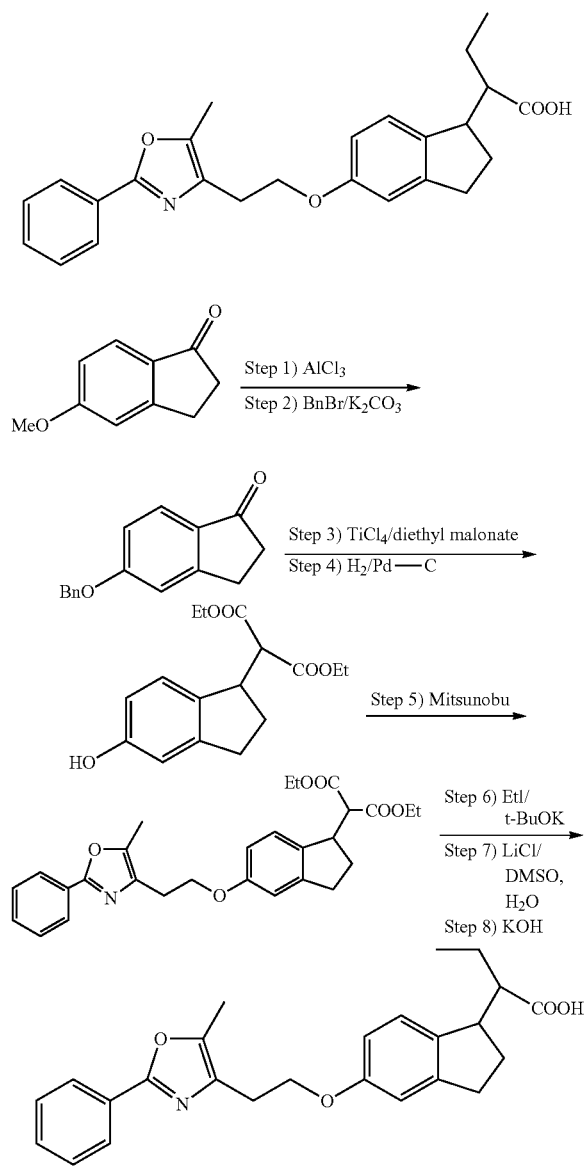

Step 1. To a solution of 5-methoxy-indanone (10 g) dissolved in toluene (150 mL) was added AlCl$_3$ (15 g). The mixture was refluxed for 4 hours until a precipitate appeared. The resulting mixture was cooled and poured into ice water (150 mL). The precipitate was filtered and washed with water, then air-dried to give the desired product (8.5 g, 90%).

Step 2. Benzyl bromide (17 g), 5-hydroxyl-indanone (15 g), K$_2$CO$_3$ (20 g), and 200 mL acetone were mixed in a round-bottom flask (500 mL). The mixture was refluxed for 1 hour. The K$_2$CO$_3$ was filtered off, and the filtrate was evaporated. The resulting residue was crystallized from EtOAc to give 18 g product (75%).

Step 3. A solution of 5-benzyloxyl-indanone (1.14 g, 4.79 mmol) and diethyl malonate (0.844 g, 5.29 mmol) in THF (20 mL) was cooled to 0° C. under argon, and TiCl$_4$ (10 mL, 1M in CH$_2$Cl$_2$) was added dropwise. Pyridine (2 mL) was added finally. The resulting mixture was stirred overnight at rt. After filtration, EtOAc (30 mL) was added into the filtrate. The organic layer was washed with brine (20 mL×3), dried with Na$_2$SO$_4$, and evaporated. The residue was separated by silica gel chromatography to give 800 mg product (50%).

Step 4. The product of step 3 (1.7 g) was dissolved in MeOH (25 mL), and Pd—C (300 mg) was added as a slurry in MeOH, and placed under 60 psi H$_2$ in a Parr shaker for 6 hours. After filtration and concentration, 1.2 g product was obtained (92%).

Step 5. P(Ph)$_3$ (420 mg) and ADDP (420 mg) were dissolved in THF (5 mL) at 0° C., and stirred for 10 minutes. A THF solution of oxazole (300 mg) and phenol (430 mg) was added to the flask. The resulting mixture was stirred for 24 hours, and filtered. The filtrate was evaporated and the resulting residue was separated by silica gel chromatography to give product (320 mg, 45%).

Step 6. The intermediate prepared in step 5 (160 mg) was dissolved in THF (5 mL), and iodoethane (0.5 mL) and t-BuOK (50 mg) were added to the solution and stirred overnight. After filtration, the product was separated by using TLC, providing 100 mg (65%).

Step 7. The intermediate prepared in step 6 (30 mg) was dissolved in DMSO (1 mL). LiCl (160 mg) was added into the flask. The mixture was refluxed for 5 hours. From the resulting mixture, the product was separated by TLC, giving 13 mg (52%).

Step 8. The intermediate prepared in step 7 was subjected to hydrolysis in aqueous KOH as described for Example 2 to obtain the product: LC-MS, RT 3.57 min., M+1 406; $^1$H NMR (CD$_2$Cl$_2$): δ 0.93 (t, 3H), 1.40-1.70 (m, 2H), 1.80-2.20 (m, 2H), 2.30 (s, 3H), 2.40 (m, 1H), 2.60-2.80 (m, 2H), 2.90 (t, 2H), 3.20-3.40 (m, 1H), 4.10 (t, 2H), 6.60 (dd, 1H), 6.70 (d, 1H), 7.00 (d, 1H), 7.30 (m, 3H), 7.90 (m, 2H).

By using the procedures from Examples 1-13 together in some cases with the chiral HPLC separation method described in the general section, and by using the appropriate starting materials, the following were prepared and characterized in a similar manner:

Example 14

2-(5-{2-[5-methyl-2-(4-methylphenyl)-1,3-oxazol-4-yl]ethoxy}-2,3-dihydro-1H-inden-1-yl)butanoic acid

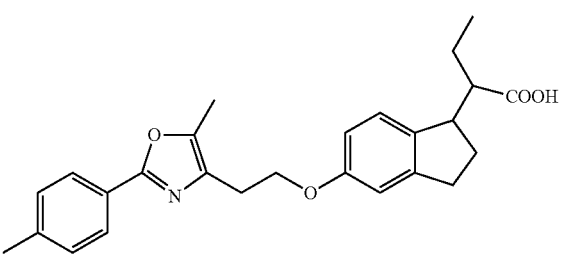 [SMILES: CCC(C(=O)O)C1CCc2cc(OCCc3nc(-c4ccc(C)cc4)oc3C)ccc21]

LC-MS, RT 3.70 min., M+1 420; $^1$H NMR (CD$_2$Cl$_2$): δ 0.93 (t, 3H), 1.40-1.70 (m, 2H), 1.80-2.20 (m, 2H), 2.30 (s, 3H), 2.35 (s, 3H), 2.40 (m, 1H), 2.60-2.80 (m, 2H), 2.90 (t, 2H), 3.20-3.40 (m, 1H), 4.10 (t, 2H), 6.60 (dd, 1H), 6.70 (d, 1H), 7.00 (d, 1H), 7.20 (m, 3H), 7.80 (m, 2H).

Example 15

(2S)-2-{(1S)-5-[2-(5-methyl-2-phenyl-1,3-oxazol-4-yl)ethoxy]-2,3-dihydro-1H-inden-1-yl}butanoic acid

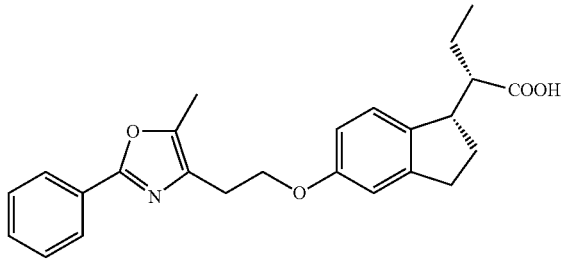 [SMILES: CC[C@H](C(=O)O)[C@@H]1CCc2cc(OCCc3nc(-c4ccccc4)oc3C)ccc21]

The enantiomer was isolated by chiral HPLC. LC-MS, RT 3.57 min., M+1 406; $^1$H NMR (CD$_2$Cl$_2$): δ 0.93 (t, 3H), 1.48 (ddq, 1H), 1.68 (ddq, 1H), 1.93 (dddd, 1H), 2.18 (dddd, 1H), 2.34 (s, 3H), 2.50 (ddd, 1H), 2.77 (ddd, 1H), 2.87 (ddd, 1H), 2.96 (t, 2H), 3.42 (ddd, 1H), 4.19 (t, 2H), 6.68 (dd, 1H) 6.77 (d, 1H), 7.08 (d, 1H), 7.42 (m, 2H), 7.44 (m, 1H), 7.97 (dd, 2H). $^{13}$C NMR: δ 10.4, 12.4, 22.4, 26.6, 29.5, 31.8, 46.5, 51.8, 67.2, 110.9, 113.0, 124.7, 126.2, 128.1, 129.1, 130.2, 133.2, 137.1, 145.6, 146.3, 158.7, 159.7, 180.4.

Example 16

(2S)-2-{(1R)-5-[2-(5-methyl-2-phenyl-1,3-oxazol-4-yl)ethoxy]-2,3-dihydro-1H-inden-1-yl}butanoic acid

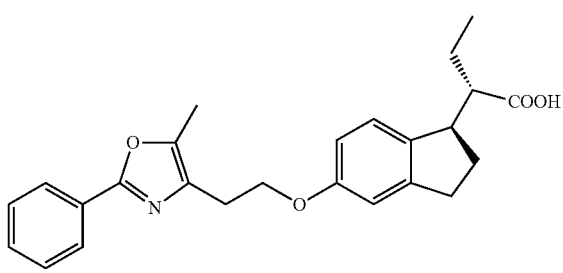 [SMILES: CC[C@H](C(=O)O)[C@H]1CCc2cc(OCCc3nc(-c4ccccc4)oc3C)ccc21]

The enantiomer was isolated by chiral HPLC. LC-MS, RT 3.57 min., M+1 406; $^1$H NMR (CD$_2$Cl$_2$): δ 0.93 (t, 3H), 1.61 (ddq, 1H), 1.69 (ddq, 1H), 1.99 (dddd, 1H), 2.19 (dddd, 1H), 2.47 (s, 3H), 2.52 (ddd, 1H), 2.73 (ddd, 1H), 2.89 (ddd, 1H), 3.11 (t, 2H), 3.31 (ddd, 1H), 4.21 (t, 2H), 6.66 (dd, 1H) 6.74 (d, 1H). 7.13 (d, 1H), 7.55 (m, 2H), 7.61 (m, 1H), 8.05 (dd, 2H). $^{13}$C NMR: δ 10.5, 12.2, 23.8, 24.8, 30.3, 31.5, 46.4, 50.9, 66.1, 110.8, 112.6, 125.9, 127.4, 123.6, 129.8, 133.3, 129.7, 137.0, 148.4, 146.5, 158.2, 160.5, 181.0.

Example 17

(2R)-2-{(1R)-5-[2-(5-methyl-2-[4-methylphenyl]-1,3-oxazol-4-yl)ethoxy]-2,3-dihydro-1H-inden-1-yl}butanoic acid

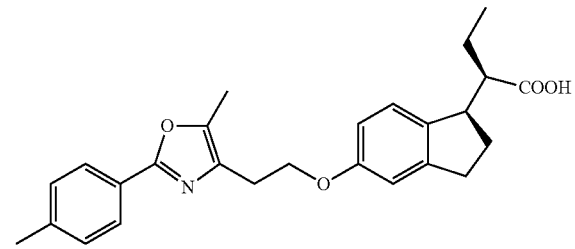 [SMILES: CC[C@@H](C(=O)O)[C@H]1CCc2cc(OCCc3nc(-c4ccc(C)cc4)oc3C)ccc21]

The enantiomer was isolated by chiral HPLC. LC-MS, RT 3.70 min., M+1 420; $^1$H NMR (CD$_2$Cl$_2$): δ 0.95 (t, 3H), 1.40 (m, 1H), 1.70 (m, 1H), 1.90 (m, 1H), 2.20 (m, 1H), 2.30 (s, 3H), 2.35 (s, 3H), 2.50 (m, 1H), 2.60-2.80 (m, 2H), 2.90 (t, 2H), 3.40 (dd, 1H), 4.20 (t, 2H), 6.60 (dd, 1H), 6.70 (d, 1H), 7.10 (d, 1H), 7.20 (m, 3H), 7.80 (m, 2H).

Example 18

2-(5-{2-[5-methyl-2-phenyl-1,3-oxazol-4-yl]ethoxy}-2,3-dihydro-1H-inden-1-yl)propanoic acid

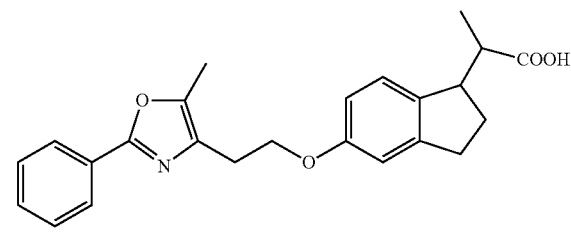 [SMILES: Cc1oc(-c2ccccc2)nc1CCOc1ccc2c(c1)CCC2C(C)C(=O)O]

LC-MS, RT 3.41 min., M+1 392; $^1$H NMR (CD$_2$Cl$_2$): δ 1.10 (d, 3H), 1.90 (m, 2H), 2.20 (m, 1H), 2.40 (s, 3H), 2.70-3.00 (m, 2H), 2.95 (t, 2H), 3.45 (m, 1H), 4.20 (t, 2H), 6.70 (dd, 1H), 6.80 (d, 1H), 7.10 (d, 1H), 7.45 (m, 3H), 8.00 (m, 2H).

Example 19

2-{5-[2-(5-methyl-2-phenyl-1,3-oxazol-4-yl)ethoxy]-2,3-dihydro-1H-inden-1-yl}malonic acid

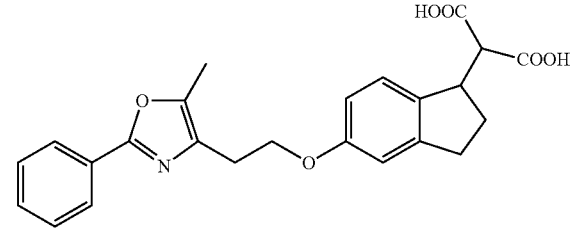 [SMILES: Cc1oc(-c2ccccc2)nc1CCOc1ccc2c(c1)CCC2C(C(=O)O)C(=O)O]

LC-MS, RT 3.00 min., M+1 422; $^1$H NMR (CD$_2$Cl$_2$): δ 1.90 (m, 2H), 2.40 (t, 3H), 2.60-3.00 (m, 3H), 3.40(t, 2H), 3.70 (m, 1H), 4.20 (t, 2H), 6.60 (dd, 1H), 6.80 (d, 1H), 7.10 (d, 1H), 7.50 (m, 3H), 7.95 (m, 2H).

Example 20

3-ethoxy-2-{5-[2-(5-methyl-2-phenyl-1,3-oxazol-4-yl)ethoxy]-2,3-dihydro-1H-inden-1-yl}-3-oxopropanoic acid

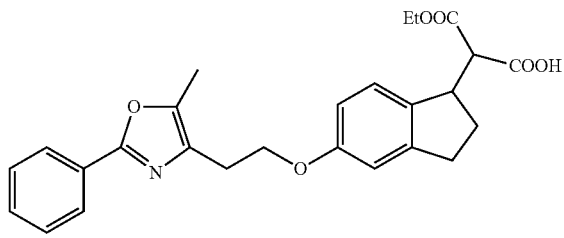 [SMILES: CCOC(=O)C(C(=O)O)C1CCc2cc(OCCc3nc(-c4ccccc4)oc3C)ccc21]

LC-MS, RT 3.39 min., M+1 450; $^1$H NMR (CD$_2$Cl$_2$): δ 1.20 (t, 3H), 2.00(m, 1H), 2.30 (m, 1H), 2.40 (s, 3H), 2.90 (m, 2H), 3.10 (t, 2H), 3.80 (m, 1H), 4.20 (t & q, 4H), 6.70 (dd, 1H), 6.80 (d, 1H), 7.10(d, 1H), 7.50 (m, 3H), 8.00 (m, 2H).

Example 21

2-{5-[2-(5-methyl-2-phenyl-1,3-oxazol-4-yl)ethoxy]-2,3-dihydro-1H-inden-1-yl}-5-phenylpentanoic acid

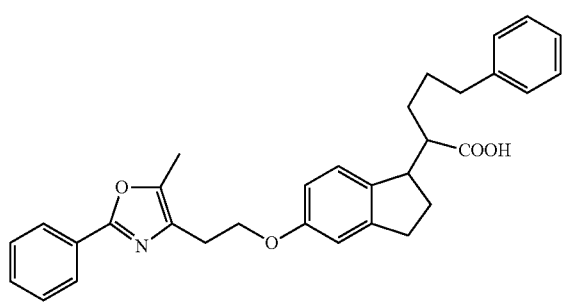 [SMILES: Cc1oc(-c2ccccc2)nc1CCOc1ccc2c(c1)CCC2C(CCCc1ccccc1)C(=O)O]

LC-MS, RT 3.98 min., M+1 396; $^1$H NMR (CD$_2$Cl$_2$): δ 1.40-1.80 (m, 4H), 1.90-2.20 (m, 2H), 2.35 (s, 3H), 2.40-3.00 (m, 5H), 2.90 (t, 2H), 3.35 (m, 1H), 4.10 (t, 2H), 6.60 (dd, 1H), 6.70 (d, 1H), 6.90-7.20 (m, 6H), 7.30 (m, 3H), 7.95 (m, 2H).

Example 22

2-(5-{2-[5-methyl-2-(4-methylphenyl)-1,3-oxazol-4-yl]ethoxy}-2,3-dihydro-1H-inden-1-yl)propanoic acid

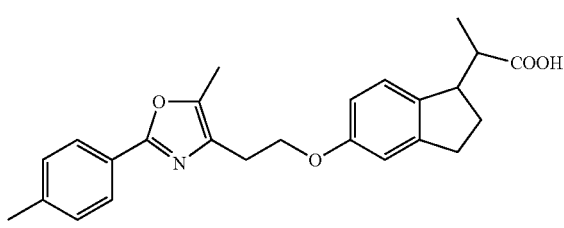 [SMILES: Cc1ccc(-c2nc(CCOc3ccc4c(c3)CCC4C(C)C(=O)O)c(C)o2)cc1]

LC-MS, RT 3.52 min., M+1 406; $^1$H NMR (CD$_2$Cl$_2$): δ 1.10 (d, 3H), 1.90 (m, 2H), 2.20 (m, 1H), 2.30 (s, 3H), 2.31(s, 3H), 2.70-3.00 (m, 2H), 2.95 (t, 2H), 3.40 (m, 1H), 4.10 (t, 2H), 6.60 (dd, 1H), 6.70 (d, 1H), 7.00 (d, 1H), 7.20 (d, 2H), 7.80 (d, 2H).

Example 23

2-(5-{2-[5-methyl-2-(4-methylphenyl)-1,3-oxazol-4-yl]ethoxy}-2,3-dihydro-1H-inden-1-yl)hexanoic acid

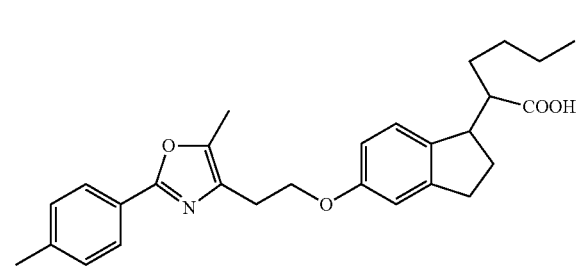 [SMILES: CCCCC(C(=O)O)C1CCc2cc(OCCc3nc(-c4ccc(C)cc4)oc3C)ccc21]

LC-MS, RT 3.92 min., M+1 448; $^1$H NMR (CD$_2$Cl$_2$): δ 0.93 (t, 3H), 1.10-1.30 (m, 4H), 1.40-1.70 (m, 2H), 1.80-2.20 (m, 2H), 2.30 (s, 3H), 2.31 (s, 3H), 2.40 (m, 1H), 2.60-2.80 (m, 2H), 2.90 (t, 2H), 3.20-3.40 (m, 1H), 4.10 (t, 2H), 6.60 (dd, 1H), 6.70 (d, 1H), 7.00 (d, 1H), 7.20 (d, 2H), 7.80 (d, 2H).

Example 24

4-methyl-2-(5-{2-[5-methyl-2-(4-methylphenyl)-1,3-oxazol-4-yl]ethoxy}-2,3-dihydro-1H-inden-1-yl)pentanoic acid

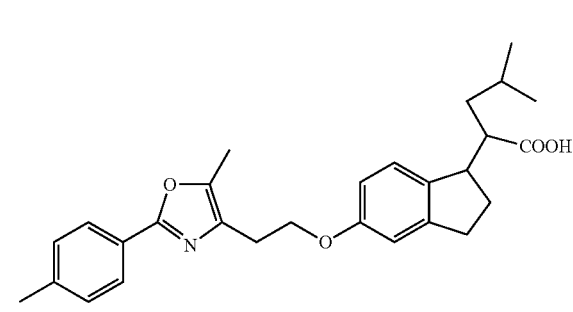 [SMILES: Cc1ccc(-c2nc(CCOc3ccc4c(c3)CCC4C(CC(C)C)C(=O)O)c(C)o2)cc1]

LC-MS, RT 4.00 min., M+1 448; $^1$H NMR (CD$_2$Cl$_2$): δ 0.93 (m, 6H), 1.20 (m, 1H), 1.40-1.70 (m, 2H), 1.80-220 (m, 2H), 2.30 (s, 3H), 2.31 (s, 3H), 2.40 (m, 1H), 2.60-2.80 (m, 2H), 2.90 (t, 2H), 3.20-3.40 (m, 1H), 4.10 (t, 2H), 6.60 (dd, 1H), 6.70 (d, 1H), 7.00 (d, 1H), 7.40 (d, 2H), 8.40 (d, 2H).

Example 25

4-methyl-2-(5-{2-[5-methyl-2-(4-methylphenyl)-1,3-oxazol-4-yl]ethoxy}-2,3-dihydro-1H-inden-1-yl)-4-pentenoic acid

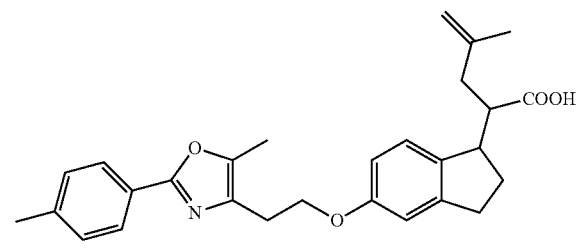 [SMILES: C=C(C)CC(C(=O)O)C1CCc2cc(OCCc3nc(-c4ccc(C)cc4)oc3C)ccc21]

LC-MS, RT 3.74 min., M+1 446; $^1$H NMR (CD$_2$Cl$_2$): δ 1.60 (s, 3H), 1.70 (m, 2H), 1.80-2.20 (m, 2H), 2.30 (s, 3H), 2.31 (s, 3H), 2.40 (m, 1H), 2.60-2.80 (m, 2H), 2.90 (t, 2H), 3.20-3.40 (m, 1H), 4.10 (t, 2H), 5.60 (m, 2H), 6.60 (dd, 1H), 6.70 (d, 1H), 7.00 (d, 1H), 7.20 (d, 2H), 7.80 (d, 2H).

Example 26

Preparation of 2-{6-chloro-5-[2-(5-methyl-2-phenyl-1,3-oxazol-4-yl)ethoxy]-2,3-dihydro-1H-inden-1-yl}butanoic acid via 2-(5-methyl-2-phenyl-1,3-oxazol-4-yl)ethyl methanesulfonate and methyl 2-(6-chloro-5-hydroxy-2,3-dihydro-1H-inden-1-yl) butanoate

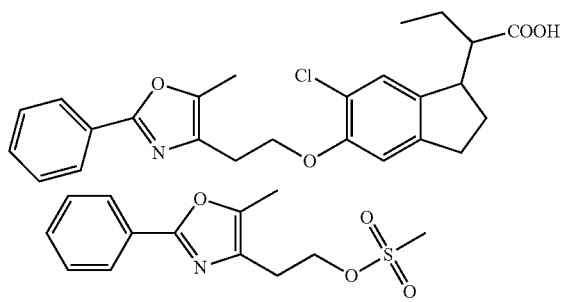

Step 1. To a solution of 2-phenyl-4-methyl-5-hydroxyethyloxazole (500 mg, 2.5 mmol) in 12.5 mL THF, was added methanesulfonyl chloride (0.21 mL, 2.75 mmol) and triethylamine (0.42 mL, 3 mmol). The reaction solution was stirred at rt under argon for two hours then concentrated in vacuo. The resulting residue was taken up in ethyl acetate, washed with 1% aqueous hydrochloric acid (three times) and brine. It was then dried over sodium sulfate, filtered, and concentrated in vacuo to provide (617 mg, 88%): ES-MS m/z 282 ((M+H)$^+$); HPLC RT 2.67; $^1$H NMR (d$_6$-DMSO) δ 2.33 (s, 3H), 2.89 (t, 2H), 3.13 (s, 3H), 4.41 (t, 2H), 7.47-7.51 (m, 3H), 7.88-7.91 (m, 2H).

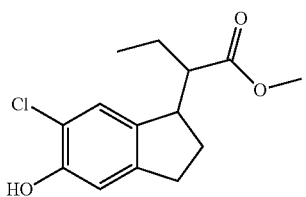 [SMILES: CCC(C(=O)OC)C1CCc2cc(O)c(Cl)cc21]

Step 2. Sulfuryl chloride (0.035 mL, 0.43 mmol) was added to a solution of methyl-5-hydroxy-2,3-dihydro-1-(2-butanoate) (100 mg, 0.43 mmol) in 2.15 mL acetic acid. The reaction solution was stirred at rt for 30 minutes, then concentrated in vacuo. The resulting residue was taken up in ethyl acetate and washed with water, saturated aqueous sodium bicarbonate, and brine. It was then dried over sodium sulfate, filtered, and concentrated in vacuo to provide 63 mg of the desired intermediate as a crude yellow oil which was carried on without further purification: GC-MS 269, ((M+H)$^+$); GC RT (min.) 8.71; $^1$H NMR (d$_6$-DMSO) δ 0.81 (t, 3H), 1.40-1.63 (m, 2H), 1.77-1.88 (m, 1H), 2.00-2.15 (m, 1H), 2.40-2.80 (m, 3H), 3.15-3.22 (m, 1H), 3.50 (s, 3H), 6.76 (s, 1H), 7.13 (s, 1H), 9.84 (s, 1H).

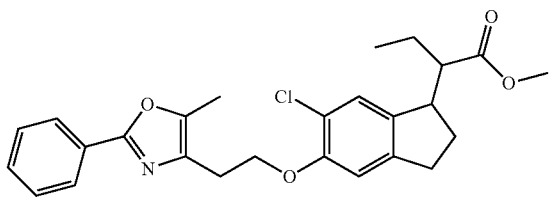 [SMILES: CCC(C(=O)OC)C1CCc2cc(OCCc3nc(-c4ccccc4)oc3C)c(Cl)cc21]

Step 3. A solution of the product obtained in step 2 (30.5 mg, 0.12 mmol) in 0.6 mL DMF was cooled to 0° C. in an ice bath. A 60% dispersion of sodium hydride in oil (5.2 mg, 0.13 mmol) was then added and the ice bath was removed. After stirring the reaction mixture for 1 hour at rt, the mesylate from step 1 (34 mg, 0.12 mmol) was added. The reaction mixture was heated at 50° C. for 24 hours, then cooled to 0° C. An additional 9.6 mg NaH (60% dispersion in oil) was added and heating was resumed for two hours, after which the reaction mixture was cooled to rt and stirred for 48 hours. At this time, ethyl acetate was added and the organic solution was washed with water and brine (three times), dried over sodium sulfate, filtered, and concentrated in vacuo. The resulting residue was purified through silica gel flash chromatography by using 5:1 hexane:ethyl acetate as the eluant to provide product (19 mg, 35%) as a mixture of diastereomers (3:1): ES-MS m/z 454 ((M+H)$^+$); HPLC RT (min.) 4.21; $^1$H NMR (d$_6$-DMSO) δ 0.80 (t, 3H), 1.38-1.63 (m, 2H), 1.79-1.90 (m, 1H), 2.02-2.14 (m, 1H), 2.34 (s, 3H), 2.51-2.57 (m, 1H), 2.63-2.84 (m, 2H), 2.91 (t, 2H), 3.19-3.25 (m, 1H), 3.49 (s, 2.3H), 3.58 (s, 0.7H), 4.22 (t, 2H), 7.00 (s, 1H), 7.21 (s, 1H), 7.43-7.51 (m, 3H), 7.85-7.90 (m, 2H).

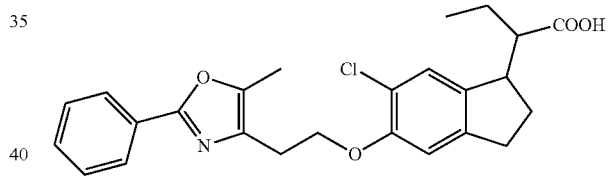

Step 4. Under the standard hydrolysis conditions, the ester from step 3 was converted to the acid (a mixture of diastereomers 3:2): ES-MS m/z 440 ((M+H)$^+$); HPLC RT (min.) 3.69; $^1$H NMR (d$_6$-DMSO) δ 0.83 (t, 3H), 2.34 (s, 3H), 2.92 (t, 2H), 4.21 (t, 2H), 7.00-7.02 (d, 1H), 7.12 (s, 0.24H), 7.21 (s, 0.37H), 7.47-7.48 (m, 3H), 7.87-7.90 (m, 2H).

Example 27

Preparation of ethyl 2-{5-[2-(5-methyl-2-phenyl-1,3-oxazol-4-yl)ethoxy]-2,3-dihydro-1H-inden-1-yl}pentanoate

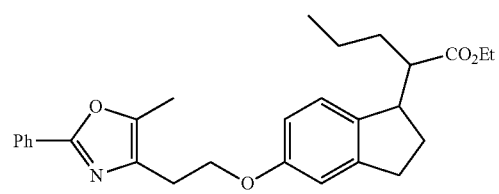 [SMILES: CCCC(C(=O)OCC)C1CCc2cc(OCCc3nc(-c4ccccc4)oc3C)ccc21]

An oven dried 15 mL round-bottom flask and stir bar, cooled under a stream of Ar(g), was charged with ethyl 2-{5-

[2-(5-methyl-2-phenyl-1,3-oxazol-4-yl)ethoxy]-2,3-dihydro-1H-inden-1-yl}acetate (0.070 g, 0.17 mmol) followed by addition of 0.2 mL THF. The stirred solution was then cooled to −78° C. followed by dropwise addition of lithium bis(trimethylsilyl)amide (1.0 M hexane solution, 0.86 mL, 0.86 mmol). Upon complete addition of base, the solution was allowed to stir at −78° C. for 1 hour, then iodopropane (0.142 g, 0.86 mmol) was added via syringe. The contents were then slowly warmed to rt and maintained for 1 hour. The contents of the flask were poured into 5 mL NH$_4$Cl(aq), then extracted with ethyl acetate (3×10 mL). The organic layers were combined and dried over Na$_2$SO$_4$ and concentrated in vacuo yielding 3.0 mg (4.0% yield) of a colorless film. The product had: $^1$H NMR (300 MHz, d$_6$-acetone) δ 7.96 (dd, 8.1, 1.5 Hz, 2H), 7.48 (m, 3H), 6.99 (d, 8.4 Hz, 1H), 6.79 (d, 2.7 Hz, 1H), 6.70 (dd, 8.1, 2.7 Hz, 1H), 4.22 (t, 6.9 Hz, 2H), 4.11 (q, 7.2 Hz, 2H), 3.33 (q, 6.6 Hz, 1H), 2.94 (t, 6.9 Hz, 2H), 2.78 (m, 3H), 2.54 (m, 1H), 2.39 (s, 3H), 2.14 (m, 2H), 1.91 (m, 1H), 1.63 (qt, 10.2, 3.9 Hz, 2H), 1.21 (t, 7.2 Hz, 3H), 0.852 (t, 7.5 Hz, 3H); mass spectroscopy gave MH$^+$ of 448.2 (calc'd molecular weight for C$_{28}$H$_{33}$NO$_4$=447.57).

Example 28

Preparation of 2-{5-[2-(5-methyl-2-phenyl-1,3-oxazol-4-yl)ethoxy]-2,3-dihydro-1H-inden-1-yl}pentanoic acid

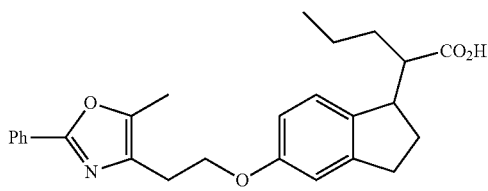 [SMILES: CCCC(C(=O)O)C1CCc2cc(OCCc3nc(-c4ccccc4)oc3C)ccc21]

Hydrolysis of the product of Example 27 by the method described above for Example 2 gave a product with the following, $^1$H NMR (300 MHz, d$_6$-acetone); δ 7.96 (dd, 8.1, 1.5 Hz, 2H), 7.48 (m, 3H), 7.10 (d, 8.4 Hz, 1H), 6.79 (d, 2.7 Hz, 1H), 6.71 (dd, 8.1, 2.7 Hz, 1H), 4.22 (t, 6.9 Hz, 2H), 3.40 (m, 1H), 2.91 (t, 6.9 Hz, 2H), 2.74 (m, 1H), 2.58 (m, 1H), 2.39 (s, 3H), 2.26 (m, 1H), 2.11 (m, 1H), 1.95 (m, 2H), 1.84 (m, 1H), 1.62 (m, 2H), 0.859 (td, 6.9, 1.5 Hz, 3H); mass spectroscopy gave MH$^+$ of 420.1 (calc'd molecular weight for C$_{26}$H$_{29}$NO$_4$=419.51).

Example 29

Preparation of 2-{6-bromo-5-[2-(5-methyl-2-phenyl-1,3-oxazol-4-yl)ethoxy]-2,3-dihydro-1H-inden-1-yl}butanoic acid via methyl 2-(6-bromo-5-hydroxy-2,3-dihydro-1H-inden-1-yl)butanoate

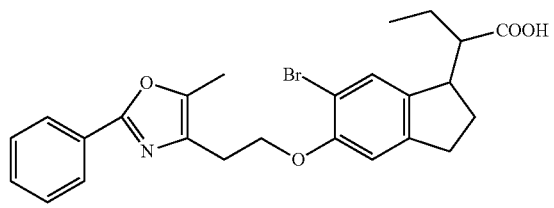 [SMILES: CCC(C(=O)O)C1CCc2cc(OCCc3nc(-c4ccccc4)oc3C)c(Br)cc21]

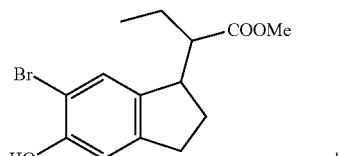

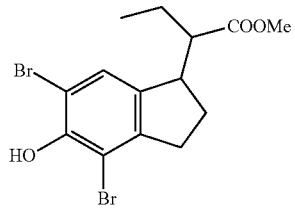

Step 1. A solution of bromine (0.032 mL, 0.60 mmol) in dioxane (3 mL) was cooled to 0° C. for 15 minutes after which a solution of 2-(5-hydroxy-indan-1-yl)-butyric acid methyl ester (141 mg, 0.60 mmol) in dioxane (3 mL) was added. After 5 minutes, the ice bath was removed and the reaction was stirred at rt for 4 hours. Solvent was removed by rotary evaporation. The residue was purified by column chromatography (8% EtOAc in hexane) to obtain a colorless oil of mono-bromo intermediate (A) (145 mg, 77%) and dibromo intermediate (B) (20 mg).

A: R$_f$=0.46 (4:1 hexane:EtOAc); GC-MS (+Cl): m/z=313 (M$^+$); $^1$H NMR (DMSO-d$_6$): δ 0.840 (m, 3H), 1.511 (m, 2H), 1.905 (m, 1H), 2.091 (m, 1H), 2.410-2.793 (m, 3H), 3.212 (m, 1H), 3.505 and 3.512 (s, 3H), 6.713 and 6.753 (s, 1H), 7.034 and 7.274 (s, 1H), 9.932 and 9.934 (s, OH).

B: R$_f$=0.30 (4:1 hexane:EtOAc); GC-MS (+Cl): m/z=393 (M$^+$); $^1$H NMR (DMSO-d$_6$): δ 0.817 (m, 3H), 1.459-1.596 (m, 2H), 1.910 (m, 1H), 2.101 (m, 1H), 2.433-2.768 (m, 3H), 3.371 (m, 1H), 3.400 and 3.596 (s, 3H), 7.168 and 7.357 (s, 1H), 9.535 and 9.542 (s, OH).

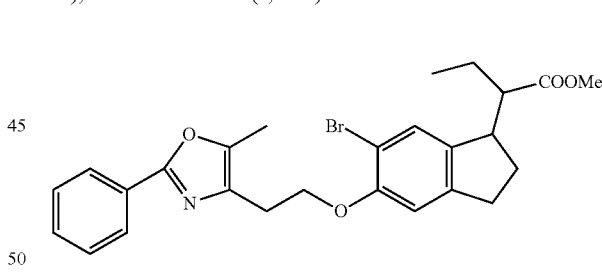

Step 2. To a solution of (A) from step 1 above (118 mg, 0.38 mmol) in DMF (3.8 mL) at 0° C., was added NaH (60% in mineral oil, 30 mg). After 1 hour, the mesylate as prepared in step 1, Example 26 was added. The mixture was heated to 50° C. for 30 hours. The solution was diluted with water, and then extracted with ethyl acetate three times. The combined organic layer was washed with water and brine, then dried (Na$_2$SO$_4$) and concentrated. The residue was purified by column chromatography (10% ethyl acetate in hexane) to give product (63 mg, 34%); R$_f$=0.46 (2:1 hexane:EtOAc); ESLC-MS: m/z=498 (MH$^+$); $^1$H NMR (DMSO-d$_6$): δ 0.847 (m, 3H), 1.468 (m, 2H), 1.812 (m, 1H), 2.146 (m, 1H), 2.340 (s, 3H), 2.525-2.788 (m, 3H), 2.902 (m, 2H), 3.236 (m, 1H), 3.481 and 3.586 (s, 3H), 4.211 (m, 2H), 6.969 (s, 1H), 7.347 and 7.386 (s, 1H), 7.452 (m, 3H), 7.833 (m, 2H).

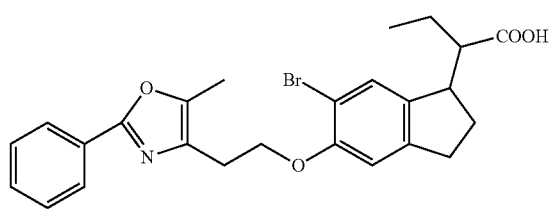

Step 3. To a solution of product from step 2 (5.6 mg) in methanol, was added 3 N KOH (1 mL) followed by addition of THF until the cloudy solution became clear. The mixture was refluxed overnight. Conc. HCl was added to adjust the pH to 2, then extracted three times with ethyl acetate. The organic layers were combined, dried, and concentrated to give white solid (4 mg). $R_f$=0.18 (2:1 hexane:EtOAc); ESLC-MS: m/z=484 (MH$^+$); $^1$H NMR (DMSO-d$_6$): δ 0.832 (m, 3H), 1.468 (m, 2H), 1.812 (m, 1H), 2.146 (m, 1H), 2.405 (m, 1H), 2.788 (m, 2H), 2.904 (m, 2H), 3.015 (m, 1H), 3.136 and 3.138 (s, 3H), 4.209 (m, 2H), 6.987 and 7.344 (s, 1H), 6.972 and 7.251 (s, 1H), 7.487 (m, 3H), 7.882 (m, 2H).

Example 30

Preparation of 2-{5-[2-(5-methyl-2-phenyl-1,3-oxazol-4-yl)ethoxy]-6-phenyl-2,3-dihydro-1H-inden-1-yl}butanoic acid via methyl 2-{5-[2-(5-methyl-2-phenyl-1,3-oxazol-4-yl)ethoxy]-6-phenyl-2,3-dihydro-1H-inden-1-yl}butanoate

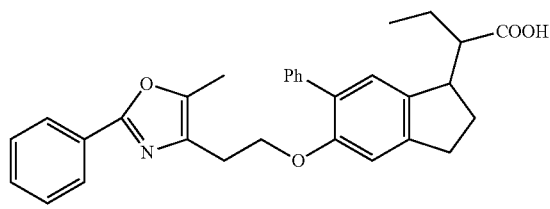

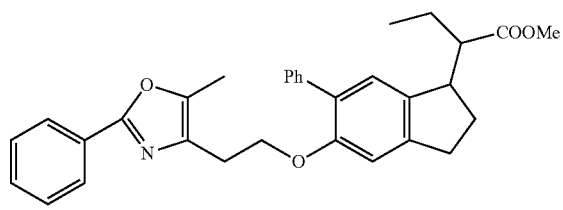 [SMILES: CCC(C(=O)OC)C1CCc2cc(OCCc3nc(-c4ccccc4)oc3C)c(-c3ccccc3)cc21]

Step 1. A mixture of the product of step 2, Example 29 and Pd(PPh$_3$)$_4$ in THF (1.5 mL) was stirred at rt for 30 minutes. Phenylboronic acid (13.2 mg, 0.108 mmol) and 2 N NaOH were then added into the solution. The mixture was heated to reflux for 14 hours. The solution was allowed to cool down, diluted with water, and extracted with ethyl acetate three times. The combined organic layers were washed with brine and dried over sodium sulfate. The crude product was purified by column chromatography eluting with 5% ethyl acetate in hexane to obtain the desired product (8.6 mg). $R_f$=0.48 (2:1 hexane:EtOAc); ESLC-MS: m/z=496 (MH$^+$); $^1$H NMR (DMSO-d$_6$): δ 0.804 (m, 3H), 1.541 (m, 2H), 1.880 (m, 1H), 1.987 (m, 1H), 2.090 (s, 3H), 2.247-2.698 (m, 3H), 2.791 (m, 2H), 3.199 (m, 1H), 3.524 and 3.537 (s, 3H), 4.190 (m, 2H), 6.970 (s, 1H), 7.062 (s, 1H), 7.275 (m, 5H), 7.472 (m, 3H), 7.868 (m, 2H).

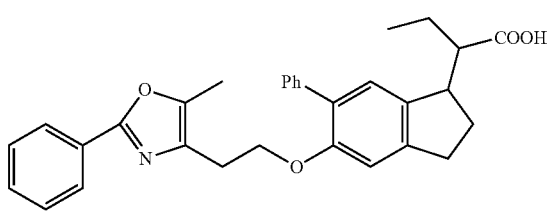

Step 2. The ester was hydrolyzed by methods described above to give product: $R_f$=0.16 (2:1 hexane:EtOAc); ESLC-MS: m/z=482 (MIT); $^1$H NMR (DMSO-d$_6$): δ 0.923 (m, 3H), 1.504 (m, 2H), 1.812 (m, 1H), 2.146 (m, 1H), 2.188 (s, 3H), 2.334 (m, 2H), 2.432 (m, 2H), 2.539 (m, 1H), 2.625 (m, 1H), 4.287 (m, 2H), 7.059 (s, 1H), 7.160 (s, 1H), 7.351 (m, 5H), 7.544 (m, 3H), 7.971 (m, 2H).

Example 31

Preparation of methyl 2-{6-(4-chlorophenyl)-5-[2-(5-methyl-2-phenyl-1,3-oxazol-4-yl)ethoxy]-2,3-dihydro-1H-inden-1-yl}butanoate

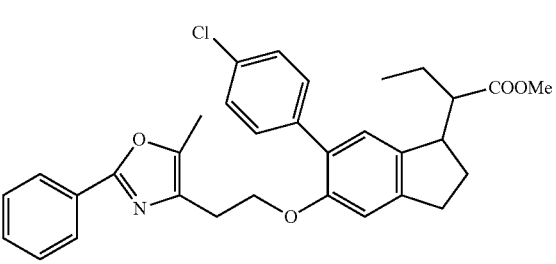 [SMILES: CCC(C(=O)OC)C1CCc2cc(OCCc3nc(-c4ccccc4)oc3C)c(-c3ccc(Cl)cc3)cc21]

A mixture of the product prepared in step 2, Example 29 (71.4 mg, 0.14 mmol), NaHCO$_3$ (14.3 mg, 0.17 mmol), 4-chlorophenylboronic acid (26.8 mg, 0.17 mmol) in ethylene glycol dimethyl ether (1.5 mL) and water (0.4 mL) was degassed for 20 minutes. Pd(dppf)Cl$_2$ was then added to the solution. The mixture was heated to reflux for 2 days. The mixture was then concentrated and purified with column chromatography (10% EtOAc in hexane) to obtain desired product (25 mg). $R_f$=0.51 (2:1 hexane:EtOAc); ESLC-MS: m/z=530 (MH$^+$); $^1$H NMR (DMSO-d$_6$): δ 0.841 (m, 3H), 1.557 (m, 2H), 1.888 (m, 1H), 1.987 (m, 1H), 2.146 (s, 3H), 2.247-2.698 (m, 3H), 2.791 (m, 2H), 3.214 (m, 1H), 3.487 and 3.5538 (s, 3H), 4.189 (m, 2H), 6.993 (s, 1H), 7.080 (s, 1H), 7.308 (s, 4H), 7.493 (m, 3H), 7.868 (m, 2H).

By using the above described methods for Examples 26-31 and substituting the appropriate starting materials, the following were made and characterized:

Example 32

2-{6-chloro-5-[2-(5-methyl-2-phenyl-1,3-oxazol-4-yl)ethoxy]-2,3-dihydro-1H-inden-1-yl}butanoic acid

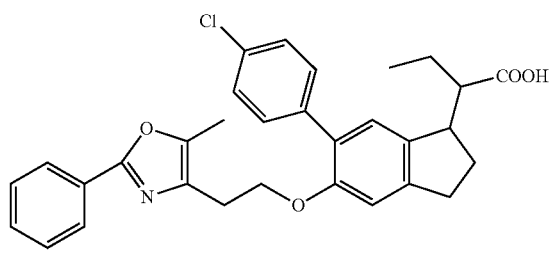 [SMILES: CCC(C(=O)O)C1CCc2cc(OCCc3nc(-c4ccccc4)oc3C)c(-c3ccc(Cl)cc3)cc21]

ESLC-MS: m/z=516 (MH+); $^1$H NMR (DMSO-d$_6$): δ 0.847 (m, 3H), 1.557 (m, 2H), 1.888 (m, 1H), 1.987 (m, 1H), 2.137 (s, 3H), 2.247-2.687 (m, 3H), 2.819 (m, 2H), 3.234 (m, 1H), 4.187 (m, 2H), 6.994 (s, 1H), 7.089 (s, 1H), 7.298 and 7.308 (m, 4H), 7.484 (m, 3H), 7.869 (m, 2H).

Example 33

Methyl 2-{6-methyl-5-[2-(5-methyl-2-phenyl-1,3-oxazol-4-yl)ethoxy]-2,3-dihydro-1H-inden-1-yl}butanoate

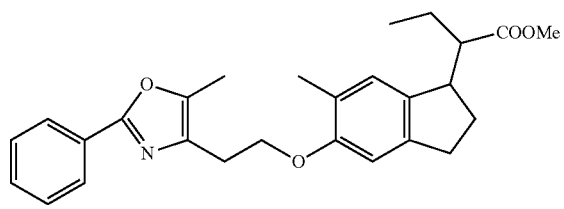 [SMILES: CCC(C(=O)OC)C1CCc2cc(OCCc3nc(-c4ccccc4)oc3C)c(C)cc21]

R$_f$=0.23 (2:1 hexane:EtOAc); ESLC-MS: m/z=434 (MH+); $^1$H NMR (DMSO-d$_6$): δ 0.804 (m, 3H), 1.522 (m, 2H), 1.830 (m, 1H), 1.987 (m, 1H), 2.037 (s, 3H), 2.335 (s, 3H), 2.410-2.550 (m, 3H), 2.901 (m, 2H), 3.146 (m, 1H), 3.507 (s, 3H), 4.163 (m, 2H), 6.777 (s, 1H), 6.939 (s, 1H), 7.483 (m, 3H), 7.875 (m, 2H).

Example 34

2-{6-methyl-5-[2-(5-methyl-2-phenyl-1,3-oxazol-4-yl)ethoxy]-2,3-dihydro-1H-inden-1-yl}butanoic acid

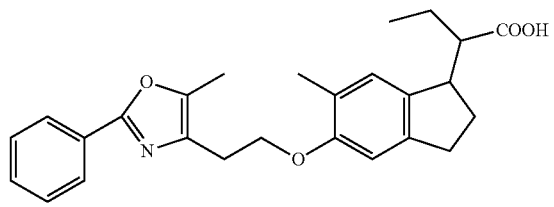 [SMILES: CCC(C(=O)O)C1CCc2cc(OCCc3nc(-c4ccccc4)oc3C)c(C)cc21]

R$_f$=0.31 (2:1 hexane:EtOAc); ESLC-MS: m/z=420 (MH+); $^1$H NMR (DMSO-d$_6$): δ 0.827 (m, 3H), 1.508 (m, 2H), 1.828 (m, 1H), 1.987 (m, 1H), 2.017 (s, 3H), 2.333 (s, 3H), 2.410-2.550 (m, 3H), 2.894 (m, 2H), 3.146 (m, 1H), 4.116 (m, 2H), 6.773 (s, 1H), 6.942 (s, 1H), 7.467 (m, 3H), 7.880 (m, 2H).

Example 35

Methyl 2-[5-[2-(5-methyl-2-phenyl-1,3-oxazol-4-yl)ethoxy]-6-(2-thienyl)-2,3-dihydro-1H-inden-1-yl]butanoate

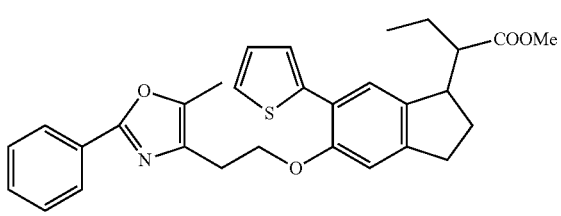 [SMILES: CCC(C(=O)OC)C1CCc2cc(OCCc3nc(-c4ccccc4)oc3C)c(-c3cccs3)cc21]

R$_f$=0.60 (2:1 hexane:EtOAc); ESLC-MS: m/z=502 (MH+); $^1$H NMR (DMSO-d$_6$): δ 0.801 (m, 3H), 1.535 (m, 2H), 1.891 (m, 1H), 1.987 (m, 1H), 2.299 (s, 3H), 2.410-2.550 (m, 3H), 2.988 (m, 2H), 3.146 (m, 1H), 3.506 (s, 3H), 4.337 (m, 2H), 7.011-7.041 (m, 2H), 7.405-7.493 (m, 5H), 7.884 (m, 2H).

Example 36

2-[5-[2-(5-methyl-2-phenyl-1,3-oxazol-4-yl)ethoxy]-6-(2-thienyl)-2,3-dihydro-1H-inden-1-yl]butanoic acid

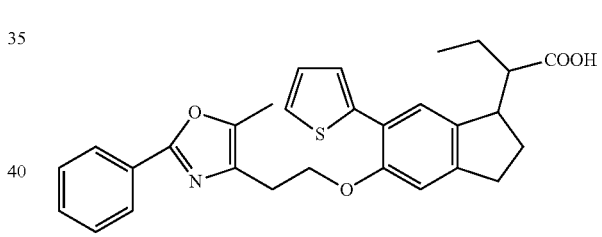

R$_f$=0.18 (2:1 hexane:EtOAc); ESLC-MS: m/z=488 (MH+); $^1$H NMR (DMSO-d$_6$): δ 0.801 (m, 3H), 1.535 (m, 2H), 1.891 (m, 1H), 1.987 (m, 1H), 2.299 (s, 3H), 2.410-2.550 (m, 3H), 2.988 (m, 2H), 3.146 (m, 1H), 4.337 (m, 2H), 7.078 (m, 2H), 7.472 (m, 5H), 7.896 (m, 2H).

Example 37

Methyl 2-{4,6-dibromo-5-[2-(5-methyl-2-phenyl-1,3-oxazol-4-yl)ethoxy]-2,3-dihydro-1H-inden-1-yl}butanoate

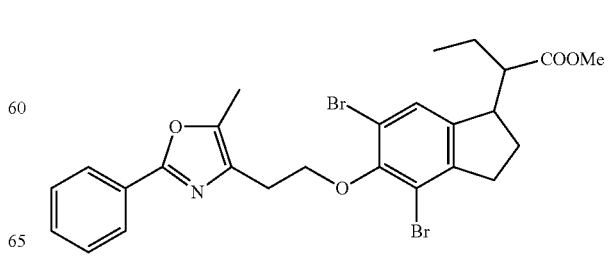

$R_f$=0.35 (4:1 hexane:EtOAc); ESLC-MS: m/z=578 (MH$^+$); $^1$H NMR (DMSO-d$_6$): δ 0.847 (m, 3H), 1.468 (m, 2H), 1.812 (m, 1H), 2.146 (m, 1H), 2.350 (s, 3H), 2.407-2.788 (m, 3H), 2.982 (m, 2H), 3.225 (m, 1H), 3.480 and 3.588 (s, 3H), 4.145 (m, 2H), 7.276 (s, 1H), 7.458 (m, 3H), 7.866 (m, 2H).

Example 38

2-{4,6-dibromo-5-[2-(5-methyl-2-phenyl-1,3-oxazol-4-yl)ethoxy]-2,3-dihydro-1H-inden-1-yl}butanoic acid

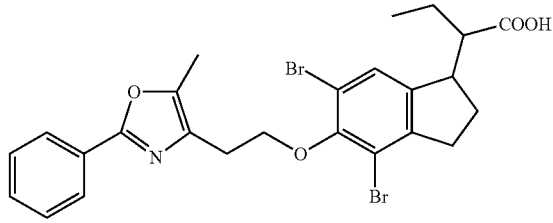 [SMILES: CCC(C(=O)O)C1CCc2c1cc(Br)c(OCCc1nc(-c3ccccc3)oc1C)c2Br]

$R_f$=0.17 (2:1 hexane:EtOAc); ESLC-MS: m/z=564 (MH$^+$); $^1$H NMR (DMSO-d$_6$): δ 0.847 (m, 3H), 1.468 (m, 2H), 1.812 (m, 1H), 2.146 (m, 1H), 2.361 (s, 3H), 2.414-2.781 (m, 3H), 2.995 (m, 2H), 3.123 (m, 1H), 4.125 (m, 2H), 7.345 (s, 1H), 7.437 (m, 3H), 7.886 (m, 2H).

Example 39

Preparation of 2-{6-acetyl-5-[2-(5-methyl-2-phenyl-1,3-oxazol-4-yl)ethoxy]-2,3-dihydro-1H-inden-1-yl}butanoic acid via methyl 2-(6-acetyl-5-methoxy-2,3-dihydro-1H-inden-1-yl)butanoate

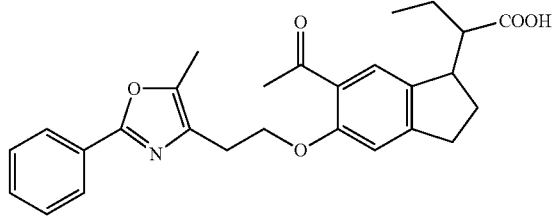 [SMILES: CCC(C(=O)O)C1CCc2cc(OCCc3nc(-c4ccccc4)oc3C)c(C(C)=O)cc21]

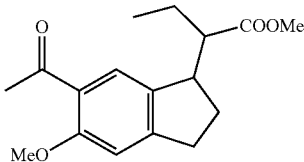 [SMILES: CCC(C(=O)OC)C1CCc2cc(OC)c(C(C)=O)cc21]

Step 1. To a solution of AlCl$_3$ (103 mg, 0.78 mmol) in methylene chloride (2.5 mL) at 0° C., was added acetyl chloride (0.044 mL, 0.63 mmol), followed by the addition of a solution of methyl 5-methoxy-2,3-dihydro-1H-indene-1-yl-butanoate (130 mg, 0.52 mmol) in methylene chloride (2.7 mL) dropwise. The mixture was stirred at 0° C. for 15 minutes. The ice bath was removed and the mixture stirred at rt for 16 hours. The mixture was poured over ice and 4 drops of conc. HCl were added. This mixture was extracted with methylene chloride twice. The combined organic layers were washed with water, 0.05 N NaOH and water. The organic layer was dried, concentrated, and purified by chromatography with 10% EtOAc:hexane to give desired product (103 mg, 68%). $R_f$=0.28 (4:1 hexane:EtOAc); GC-MS (+Cl): m/z=291 (M$^+$); $^1$H NMR (DMSO-d$_6$): δ 0.840 (m, 3H), 1.536 (m, 2H), 1.876 (m, 1H), 2.108 (m, 1H), 2.505 (s, 3H), 2.521 (m, 1H), 2.760-2.889 (m, 2H), 3.236 (m, 1H), 3.511 and 3.589 (s, 3H), 3.836 (s, 3H), 7.012 and 7.253 (s, 1H), 7.440 (s, 1H).

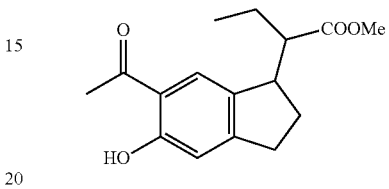

Step 2. To a solution of AlCl$_3$ (238 mg, 1.77 mmol) in CH$_2$Cl$_2$ (1 mL), was added the product of step 1 (103 mg, 0.35 mmol) in CH$_2$Cl$_2$ (2 mL). The mixture was cooled to 0° C. for 5 minutes, then EtSH (0.13 mL, 1.77 mmol) was added slowly. The mixture was stirred at this temperature for 4.5 hours. The mixture was then poured over ice water, stirred for 10 minutes, and extracted with CH$_2$Cl$_2$ twice. The combined organic layers were washed with water, dried over sodium sulfate, and concentrated to give product (86 mg, 89%). $R_1$=0.51 (4:1 hexane:EtOAc); GC-MS (+Cl): m/z=276 (M$^+$); $^1$H NMR (DMSO d$_6$): δ 0.841 (m, 3H), 1.574 (m, 2H), 1.888 (m, 1H), 2.094 (m, 1H), 2.585 (s, 3H), 2.639 (m, 1H), 2.729-2.847 (m, 2H), 3.244 (m, 1H), 3.513 and 3.628 (s, 3H), 6.774 and 7.503 (s, 1H), 6.792 and 7.715 (s, 1H), 12.117 and 12.143 (s, 1H).

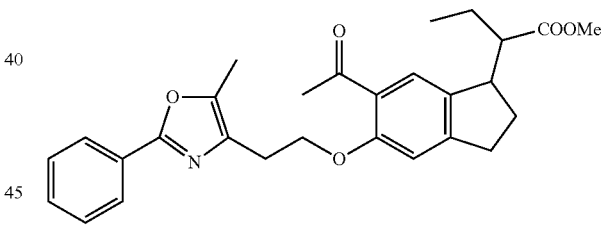

Step 3. The coupling of the hydroxy indene acetic acid ester of step 2 with the mesylate of step 2, Example 26. ESLC-MS: m/z=462 (MH$^+$);

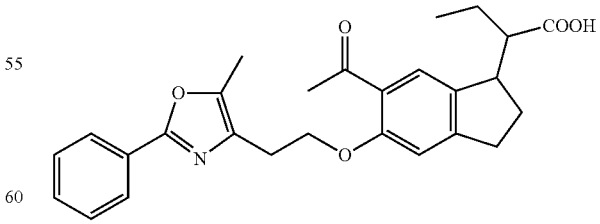

Step 4. The hydrolysis of the product from step 3 was carried out in similar fashion as described above to give product: $R_f$=0.08 (2:1 hexane:EtOAc); ESLC-MS: m/z=448 (MH$^+$); $^1$H NMR (DMSO-d$_6$): δ 0.648 (m, 3H), 1.468 (m, 2H), 1.812 (m, 1H), 2.146 (m, 1H), 2.305 (s, 3H), 2.368 (s, 3H), 2.405 (m, 1H), 2.788 (m, 2H), 2.971 (m, 2H), 3.015 (m, 1H), 4.332 (m, 2H), 7.039 and 7.441 (s, 1H), 7.446 (s, 1H), 7.465 (m, 3H), 7.875 (m, 2H).

Using a combination of the above described procedures and substituting the appropriate starting materials, a variety of compounds were prepared and are described below.

Example 40

Methyl 2-{5-[2-(2,5-diphenyl-1,3-oxazol-4-yl)ethoxy]-2,3-dihydro-1H-inden-1-yl}butanoate

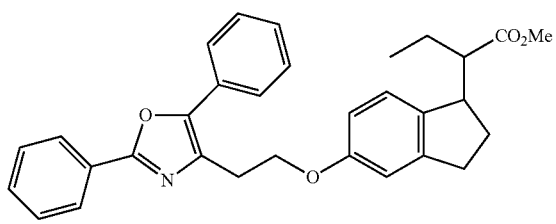 [SMILES: CCC(C(=O)OC)C1CCc2cc(OCCc3nc(-c4ccccc4)oc3-c3ccccc3)ccc21]

Yield: 0.09 g, 46%; $^1$H NMR (CDCl$_3$, 400 MHz) δ 0.83-0.93 (t, 3 H), 1.55-1.78 (m, 2 H), 1.87-1.97 (m, 1 H), 2.10-2.22 (m, 1 H), 2.44-2.52 (m, 1 H), 2.67-2.80 (m, 1 H), 2.81-2.93 (m, 1 H), 3.21-3.29 (m, 1 H), 3.23-3.33 (t, 2 H), 3.62 (s, 3 H), 4.34-4.43 (t, 2 H), 6.66-6.72 (m, 1 H), 6.76 (s, 1 H), 7.05-7.14 (d, 1 H), 7.33-7.39 (t, 1 H), 7.43-7.51 (m, 5 H), 7.78-7.84 (d, 2 H), 8.06-8.12 (m, 2 H).

Example 41

2-{5-[2-(2,5-diphenyl-1,3-oxazol-4-yl)ethoxy]-2,3-dihydro-1H-inden-1-yl}butanoic acid

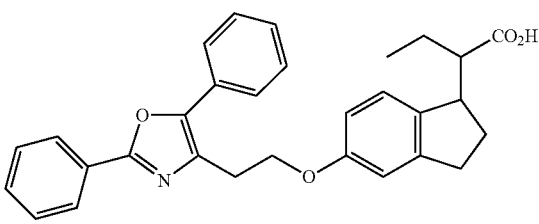 [SMILES: CCC(C(=O)O)C1CCc2cc(OCCc3nc(-c4ccccc4)oc3-c3ccccc3)ccc21]

Yield: 0.07 g, 70%; NMR (CDCl$_3$, 400 MHz) δ 0.85-0.98 (m, 3 H), 1.23-1.47 (m, 1 H), 1.57-1.78 (m, 1 H), 1.88-2.07 (m, 1 H), 2.12-2.27 (m, 1 H), 2.43-2.56 (m, 1 H), 2.68-2.97 (m, 2 H), 3.27-3.35 (t, 2 H), 3.42-3.50 (m, 1 H), 4.34-4.41 (t, 2 H), 6.66-6.73 (d, 1 H), 6.77 (s, 1 H), 7.02-7.16 (d, 1 H), 7.34-7.40 (t, 1 H), 7.43-7.52 (m, 5 H), 7.78-7.83 (d, 2 H), 8.05-8.12 (m, 2 H).

Example 42

Methyl 2-{5-[2-(5-isopropyl-2-phenyl-1,3-oxazol-4-yl)ethoxy]-2,3-dihydro-1H-inden-1-yl}butanoate

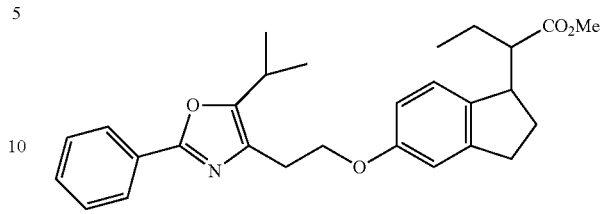

Yield: 0.09 g, 45%; $^1$H NMR (CDCl$_3$, 400 MHz) δ 0.78-0.96 (t, 3 H), 1.26-1.32 (d, 6 H), 1.51-1.62 (m, 1 H), 1.64-1.75 (m, 1 H), 1.81-1.93 (m, 1 H), 2.07-2.21 (m, 1 H), 2.40-2.51 (m, 1 H), 2.65-2.75 (m, 1 H), 2.77-2.98 (m, 1 H), 2.91-2.98 (t, 2 H), 3.09-3.16 (m, 1 H), 3.21-3.28 (m, 1 H), 3.62 (s, 3 H), 4.10-4.17 (t, 2 H), 6.60-6.68 (d, 1 H), 6.72 (s, 1 H), 7.01-7.13 (d, 1 H), 7.33-7.45 (m, 3 H), 7.94-8.00 (d, 2 H).

Example 43

2-{5-[2-(5-isopropyl-2-phenyl-1,3-oxazol-4-yl)ethoxy]-2,3-dihydro-1H-inden-1-yl}butanoic acid

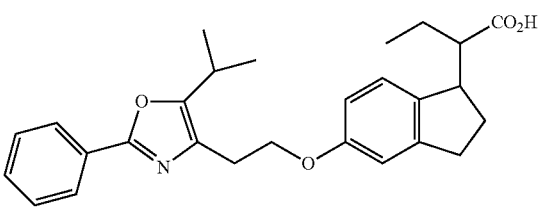 [SMILES: CCC(C(=O)O)C1CCc2cc(OCCc3nc(-c4ccccc4)oc3C(C)C)ccc21]

Yield: 0.08 g, 97%; $^1$H NMR (CDCl$_3$, 400 MHz) δ 0.91-0.98 (t, 3 H), 1.30-1.36 (d, 6 H), 1.58-1.79 (m, 2 H), 1.89-2.05 (m, 1 H), 2.12-2.27 (m, 1 H), 2.44-2.57 (m, 1 H), 2.69-2.80 (m, 1 H), 2.83-2.96 (m, 1 H), 2.97-3.02 (t, 2 H), 3.10-3.21 (m, 1 H), 3.24-3.32 (m, 1 H), 4.14-4.21 (t, 2 H), 6.63-6.71 (d, 1 H), 6.75 (s, 1 H), 7.04-7.16 (d, 1 H), 7.36-7.45 (m, 3 H), 7.94-8.00 (d, 2 H).

Example 44

Methyl 2-{5-[2-(5-ethyl-2-phenyl-1,3-oxazol-4-yl)ethoxy]-2,3-dihydro-1H-indenyl}butanoate

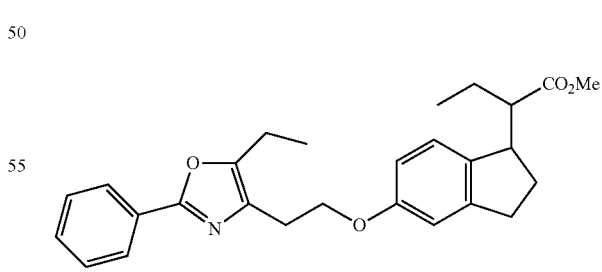

Yield: 0.14 g, 60%; $^1$H NMR (CDCl$_3$, 400 MHz) δ 0.85-0.91 (t, 3 H), 1.25-1.35 (t, 3 H), 1.58-1.77 (m, 2 H), 1.85-1.97 (m, 1 H), 2.10-2.22 (m, 1 H), 2.44-2.64 (m, 2 H), 2.68-2.80 (q, 2 H), 2.82-2.93 (m, 1 H), 2.95-3.01 (t, 2 H), 3.25-3.34 (m, 1 H), 3.62 (s, 3 H), 4.16-425 (t, 2 H), 6.66-6.71 (d, 1 H), 6.75 (s, 1 H), 7.08-7.14 (d, 1 H), 7.38-7.46 (m, 3 H), 7.95-8.01 (m, 2 H).

Example 45

2-{5-[2-(5-ethyl-2-phenyl-1,3-oxazol-4-yl)ethoxy]-2,3-dihydro-1H-inden-1-yl}butanoic acid

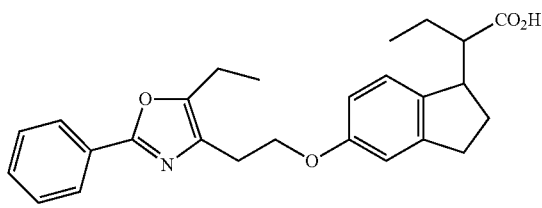 [SMILES: CCc1oc(-c2ccccc2)nc1CCOc1ccc2c(c1)CCC2C(CC)C(=O)O]

Yield: 0.05 g, 60%; $^1$H NMR (CDCl$_3$, 400 MHz) δ 0.85-0.98 (m, 3 H), 1.21-1.33 (m, 3 H), 1.37-1.54 (m, 1 H), 1.56-1.78 (m, 2 H), 1.87-2.29 (m, 2 H), 2.45-2.60 (m, 1 H), 2.69-2.79 (q, 2 H), 2.85-2.95 (m, 1 H), 2.96-3.01 (t, 2 H), 3.27-3.49 (m, 1 H), 4.14-4.23 (t, 2 H), 6.65-6.71 (d, 1 H), 6.75 (s, 1 H), 7.03-7.17 (d, 1 H), 7.38-7.46 (m, 3 H), 7.95-8.01 (d, 2 H).

Example 46

Methyl 2-{5-[2-(2-phenyl-1,3-oxazol-4-yl)ethoxy]-2,3-dihydro-1H-indenyl}butanoate

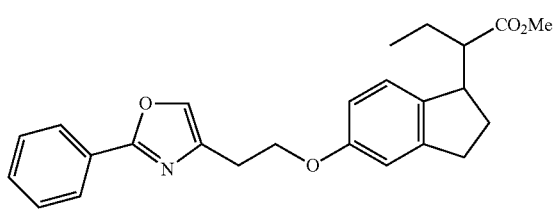 [SMILES: CCC(C(=O)OC)C1CCc2cc(OCCc3coc(-c4ccccc4)n3)ccc21]

Yield: 0.18 g, 80%; $^1$H NMR (CDCl$_3$, 400 MHz) δ 0.82-0.92 (t, 3 H), 1.56-1.66 (m, 1 H), 1.67-1.77 (m, 1 H), 1.88-1.99 (m, 1 H), 2.12-2.23 (m, 1 H), 2.43-2.52 (m, 1 H), 2.68-2.81 (m, 1 H), 2.84-2.97 (m, 1 H), 3.02-3.11 (t, 2 H), 3.25-3.33 (m, 1 H), 3.63 (s, 3 H), 4.21-4.30 (t, 2 H), 6.69-6.74 (d, 1 H), 6.79 (s, 1 H), 7.11-7.16 (d, 1 H), 7.41-7.47 (m, 3 H), 7.55-7.58 (m, 1 H), 7.99-8.05 (m, 2 H).

Example 47

2-{5-[2-(2-phenyl-1,3-oxazol-4-yl)ethoxy]-2,3-dihydro-1H-inden-1-yl}butanoic acid

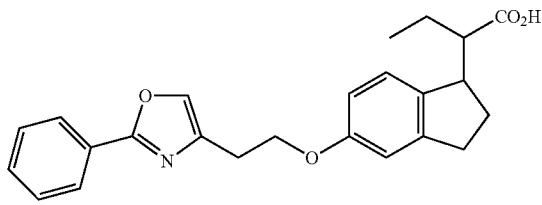 [SMILES: CCC(C(=O)O)C1CCc2cc(OCCc3coc(-c4ccccc4)n3)ccc21]

Yield: 0.07 g, 46%; $^1$H NMR (CDCl$_3$, 400 MHz) δ 0.84-1.01 (m, 3 H), 1.36-1.51 (m, 1 H), 1.59-1.81 (m, 1 H), 1.88-2.00 (m, 1 H), 2.11-2.29 (m, 1 H), 2.43-2.64 (m, 1 H), 2.68-2.81 (m, 1 H), 2.82-3.00 (m, 2 H), 3.02-3.11 (t, 2 H), 3.23-3.37 (m, 1 H), 4.17-4.28 (t, 2 H), 6.66-6.74 (d, 1 H), 6.78 (s, 1 H), 7.04-7.19 (m, 1 H), 7.39-7.47 (m, 2 H), 7.55 (s, 1 H), 7.98-8.05 (m, 2 H).

Example 48

Methyl 2-(5-{2-[2-(2,3-dihydro-1-benzofuran-6-yl)-5-methyl-1,3-oxazol-4-yl]ethoxy}-2,3-dihydro-1H-inden-1-yl)butanoate

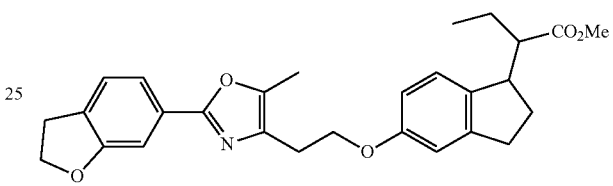

Yield: 0.17 g, 58%; $^1$H NMR (CDCl$_3$, 400 MHz) δ 0.86-0.97 (t, 3 H), 1.41-1.53 (m, 1 H), 1.61-1.77 (m, 1 H), 1.92-2.01 (m, 1 H), 2.04-2.20 (m, 1 H), 2.40 (s, 3 H), 2.49-2.56 (m, 1 H), 2.71-2.92 (m, 2 H), 3.93-3.00 (t, 2 H), 3.21-3.32 (t, 2 H), 3.34-3.49 (m, 1 H), 3.75 (s, 3 H), 4.18-4.24 (t, 2 H), 4.54-4.70 (t, 2 H), 6.70-6.76 (d, 1 H), 6.79 (s, 1 H), 6.82-6.89 (d, 1 H), 6.92-7.01 (d, 1 H), 7.75-7.80 (d, 1 H), 7.87 (s, 1 H).

Example 49

2-(5-{2-[2-(2,3-dihydro-1-benzofuran-6-yl)-5-methyl-1,3-oxazol-4-yl]ethoxy}-2,3-dihydro-1H-inden-1-yl)butanoic acid

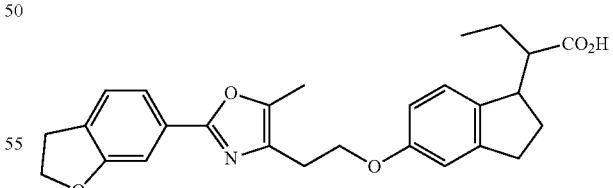

Yield: 0.10 g, 99%; 1H NMR (CDCl$_3$, 400 MHz) δ 0.90-1.04 (t, 3 H), 1.41-1.54 (m, 1 H), 1.60-1.76 (m, 1 H), 1.83-1.97 (m, 1 H), 2.12-2.23 (m, 1 H), 2.35 (s, 3 H), 2.48-2.60 (m, 1 H), 2.69-2.90 (m, 2 H), 2.92-3.01 (t, 2 H), 3.18-3.28 (t, 2 H), 3.39-3.50 (m, 1 H), 4.08-4.12 (t, 2 H), 4.46-4.64 (t, 2 H), 6.76-6.71 (d, 1 H), 6.73 (s, 1 H), 6.77-6.84 (d, 1 H), 7.01-7.09 (d, 1 H), 7.71-7.78 (d, 1 H), 7.83 (s, 1 H).

Example 50

Preparation of ethoxy{5-[2-(5-methyl-2-phenyl-1,3-oxazol-4-yl)ethoxy]-2,3-dihydro-1H-inden-1-yl}acetic acid via ethyl[5-(benzyloxy)-2,3-dihydro-1H-inden-1-ylidene](ethoxy)ethanoate

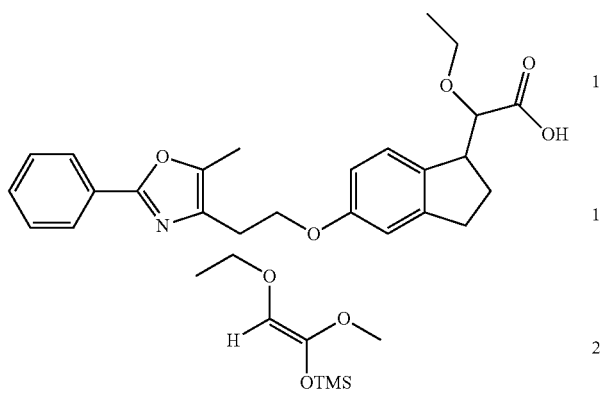

Step 1. LDA (prepared from 11 mmol DIA and 11 mmole BuLi) was added to methyl 2-ethoxyacetate (10 mmol) in 50 mL THF at −78° C., stirred for 1 hour, then TMSCl (30 mmol) was added. The mixture was concentrated in vacuo, and was carried to the next step directly without purification.

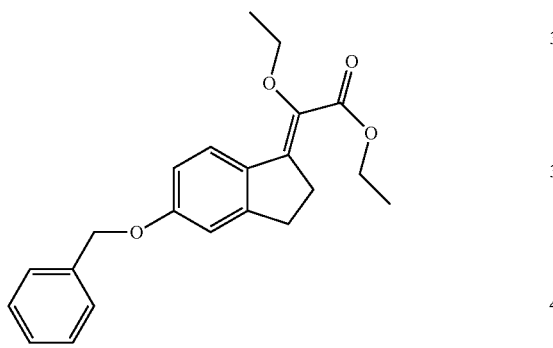

Step 2. 5-Benzyloxy-1-indanone in $CH_2Cl_2$ (5 mL) was slowly added to $TiCl_4$ in $CH_2Cl_2$ (10 mL) at −78° C., stirred at −60° C. for 10 minutes, and cooled to −78° C. The product of step 1 in $CH_2Cl_2$ (5 mL) was slowly added and stirred for 10 minutes. The reaction was quenched with saturated $K_2CO_3$, filtered, extracted with ethyl acetate, and dried over sodium sulfate. Column chromatography yielded a colorless oil as product. LC-MSMH$^+$=353.1, RT=4.00 min.; NMR (CDCl$_3$, 400 MHz) δ 7.9 (1H, d), 7.25 (5H, m), 6.78 (2H, m), 4.93 (2H, s), 4.15 (2H, q), 3.75 (2H, q), 3.05 (2H, m), 2.85 (2H, m), 1.22 (6H, m)

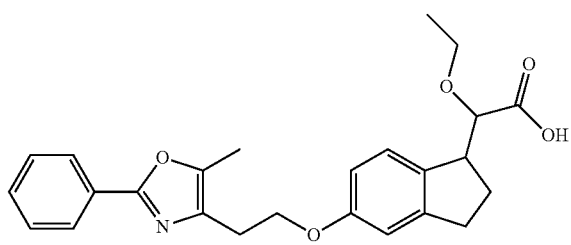 [SMILES: CCOC(C(=O)O)C1CCc2cc(OCCc3nc(-c4ccccc4)oc3C)ccc21]

Step 3. Using the product of step 2 as starting material and procedures similar to that described for Example 13, steps 4-8, the desired final product was prepared and characterized: LC-MS [MH$^+$]=422.2, RT=3.25 min.; NMR (CDCl$_3$, 400 MHz) δ 8.26 (1H, d), 7.55 (2H, m), 7.16 (2H, d), 6.70 (3H, m), 4.16 (2H, q), 3.63 (2H, t) 3.5 (2H, m), 3.30 (1H, m), 3.20 (1H, m), 2.50 (3H, s), 1.10 (3H, m).

Example 51

Preparation of 2-{5-[2-(5-methyl-2-phenyl-1,3-oxazol-4-yl)ethoxy]-2,3-dihydro-1H-inden-1-yl}butanoic acid via 2-(4-methyl-2-phenyl-1,3-oxazol-5-yl)ethanol

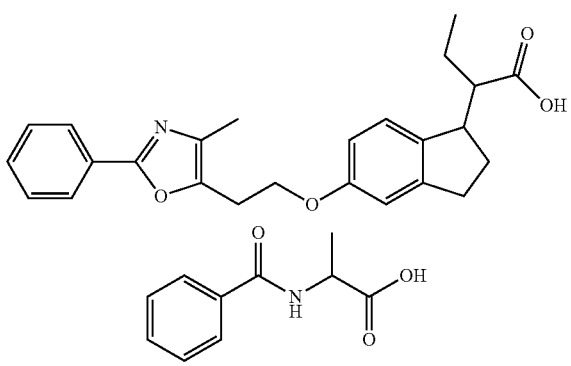

Step 1. To a solution of sodium hydroxide (8.98 g, 224.49 mmol) in water (112.25 mL), was added at rt DL-Alanine (10 g, 112.25 mmol). The resulting solution was heated at 75° C. and the benzoyl chloride (15.77 g, 112.25 mmol) was slowly added. The reaction was heated for 30 minutes, and cooled down to 0° C. with an ice bath. Conc. HCl was added to adjust the pH to 1, then the white solid was filtrated through a fritted glass funnel and vacuum dried with $P_2O_5$ overnight. No purification was needed. This gave N-benzoylalanine (19.6 g, 90.4% yield) as white solid. $^1$H NMR (DMSO-d$_6$) δ 12.61 (s br, 1H), 8.64 (d, 1H), 7.87-7.85 (m, 2H), 7.52-7.43 (m, 3H), 4.40 (q, 1H), 1.39 (d, 3H).

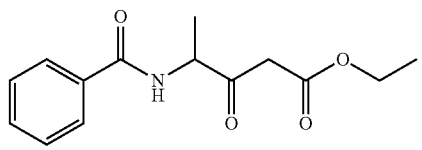 [SMILES: CCOC(=O)CC(=O)C(C)NC(=O)c1ccccc1]

Step 2. In the first flask, N-benzoylalanine (2 g, 10.35 mmol) was dissolved in THF (20 mL), and carbonyl diimidazole (CDI) (1.84 g, 11.39 mmol) was added. The resulting mixture was stirred 1 hour at rt and cooled down to −78° C. Into a second flask, ethyl acetate (3.83 g, 43.48 mmol) in THF (40 mL) was cooled down to −78° C. and LDA (24.3 mL, 48.51 mmol, 2 M in THF) pre-cooled to −78° C. was added. The resulting solution was stirred 30 minutes at −78° C., and the lithium enolate generated was cannulated into the first flask. The resulting white slurry was stirred 30 minutes at −78° C. and warmed up to −10° C. The reaction was quenched with a saturated aqueous solution of NH$_4$Cl. Phases were separated and the organics were dried over MgSO$_4$ and solvents removed under reduced pressure. The crude product was carried to the next step without purification. This gave ethyl 4-(benzoylamino)-3-oxopentanoate (2.6 g, 95.5% yield) as a white solid. ES-MS m/z 263.4 ((MH)$^+$); HPLC RT (min.) 1.53; $^1$H NMR (Acetone-d$_6$) δ 8.13 (s br, 1H), 7.93-7.91 (m, 2H), 7.58-7.43 (m, 3H), 4.72 (m, 1H), 4.19-4.01 (q, 2H), 3.67 (s, 2H), 1.47 (d, 3H), 1.15 (t, 3H).

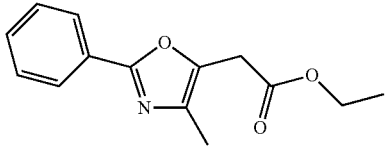 [SMILES: CCOC(=O)Cc1oc(-c2ccccc2)nc1C]

Step 3. To a crude mixture of ethyl 4-(benzoylamino)-3-oxopentanoate (0.6 g, 2.28 mmol) in DMF (4 mL) at rt, was added POCl$_3$ (1.04 g, 6.84 mmol). The resulting solution was heated at 90° C. for 1 hour, then cooled down to rt, and poured into ice for 30 minutes. The aqueous solution was carefully added to a saturated aqueous solution of NaHCO$_3$. Phases were separated with EtOAc and the combined organic extracts were dried over MgSO4 and solvent removed under reduced pressure. The crude material was purified on Biotage small column using a solvent gradient of 0 to 50% EtOAc/Hexane. This gave ethyl(4-methyl-2-phenyl-1,3-oxazol-5-yl)acetate (0.269 g 48% yield) as yellowish oil. ES-MS m/z 246.2 ((MH)$^+$); HPLC RT (min.) 2.77; $^1$H NMR (CDCl$_3$) δ 8.01-7.98 (m, 2H), 7.45-7.41 (m, 3H), 4.20 (q, 2H), 3.71 (s, 2H), 2.21 (s, 3H), 1.28 (t, 3H).

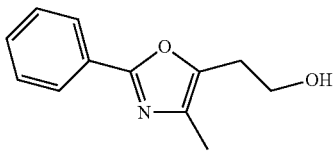

Step 4. Ethyl(4-methyl-2-phenyl-1,3-oxazol-5-yl)acetate (0.922 g, 3.76 mmol) in THF (6 mL) at rt, was added LiBH$_4$ 2M/THF (9.41 mL, 4.70 mmol). The reaction was stirred overnight at rt, then treated with 2 N HCl until pH 7. The solvent THF was removed under reduced pressure, EtOAc was added, and phases separated. The combined organic extracts were dried over MgSO$_4$ and solvent concentrated in vacuo. The crude material was purified by Biotage using a gradient of 10 to 100% EtOAc/Hexane as solvent mixture. This gave 2-(4-methyl-2-phenyl-1,3-oxazol-5-yl)ethanol (0.193 g, 25% yield) as colorless oil. ES-MS m/z 204.2 (MH$^+$)$^4$); HPLC RT (min.) 2.02; $^1$H NMR (Acetone-d$_6$) δ 7.98-7.95 (m, 2H), 7.52-7.42 (m, 3H), 3.95 (s br, 1H), 3.82 (t, 2H)m, 2.90 (t, 2H), 2.13 (s, 3H).

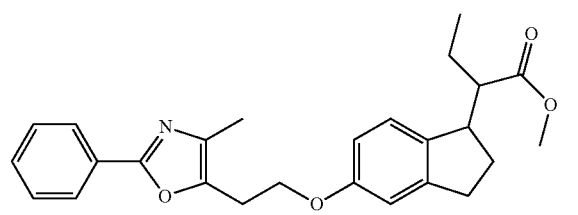 [SMILES: CCC(C(=O)OC)C1CCc2cc(OCCc3oc(-c4ccccc4)nc3C)ccc21]

Step 5. DEAD (0.84 mL, 5.28 mmol) in THF (1.5 mL) was slowly added to a solution of the product of step 3 (4.95 mmol), methyl 5-hydroxy-2,3-dihydro-inden-1yl-2-butanoate (0.78 g, 3.3 mmol), PPh$_3$ (1.4 g, 5.28 mmol) in THF (13 mL). The mixture was stirred at rt overnight. The mixture was filtered, washed with water, brine, dried over sodium sulfate, and concentrated. Column chromatography yielded a colorless oil as product. LC-MS [C$_{25}$H$_{29}$NO$_4$H]$^+$=420.4, RT=4.00 min.; NMR (CDCl$_3$): δ 7.9 (2H, d), 7.45 (2H, dd), 7.1(d), 6.6-6.8 (3H, m), 4.2 (2H, t), 3.62 (3H, s), 3.3 (1H, m), 3.15 (2H, t), 2.6-3.0 (2H, m, br), 2.5 (1H, m),2.21 (3H, s), 1.95 (1H, m), 1.56-1.6 (3H, br, m), 0.88 (3H, t).

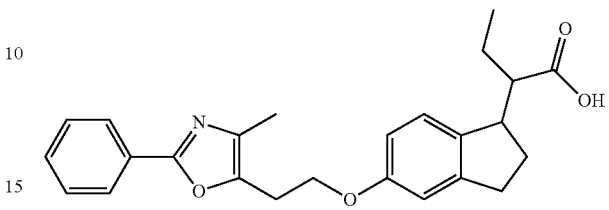

Step 6. KOH (0.5 mL, 3 N) was added to a solution of the product of step 4 (42 mg, 0.1 mmol) in THF/MeOH (1 mL, THF:MeOH 8:2). The mixture was stirred at 70° C. for 6 hours, then cooled down. The pH was adjusted to 4 with 1 N HCl. The mixture was extracted with ethyl acetate (3×2 mL). The combined organic layers were dried over sodium sulfate and concentrated in vacuo. Column chromatography (2:8/hexane:ethyl acetate) gave a white solid as the product (33 mg, 81%). LC-MS [C$_{26}$H$_{27}$NO$_4$H]$^+$=408.3, RT=3.37 min.; $^1$H NMR (CDCl$_3$): δ 8.0 (2H, d), 7.45 (2H, dd), 7.15 (1H, d), 6.7-6.8 (3H, m), 4.2 (2H, t), 3.3 (1H, m), 3.15 (2H, t), 2.6-3.0 (2H, m, br), 2.5 (1H, m), 2.21 (3H, s), 1.95 (1H, m), 1.56-1.6 (3H, br, m), 0.88 (3H, t)

By using the procedure described above for Example 51 and substituting the appropriate starting materials, the following were similarly prepared and characterized.

Example 52

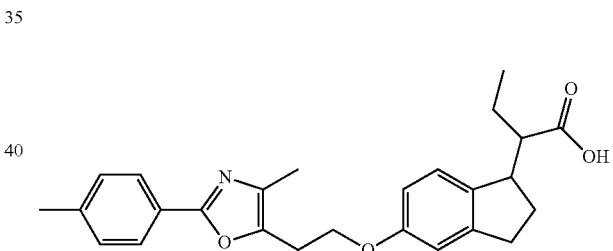

LC-MS [C$_{26}$H$_{29}$NO$_4$H]$^+$=420.3, RT=3.52 min.; $^1$H NMR (CDCl$_3$): δ 7.87 (2H, d), 7.25 (2H, dd), 7.1 (1H, d), 6.6-6.8 (3H, m), 4.2 (2H, t), 3.45 (1H, m), 3.30 (1H, m), 3.15 (2H, t), 2.7-3.0 (2H, m, br), 2.5 (1H, m), 2.4 (3H, s) 1.95 (1H, m), 1.56-1.60 (3H, br, m), 0.88 (3H, t)

Example 53

2-{5-[2-(4-methyl-2-propyl-1,3-oxazol-5-yl)ethoxy]-2,3-dihydro-1H-inden-1-yl}butanoic acid

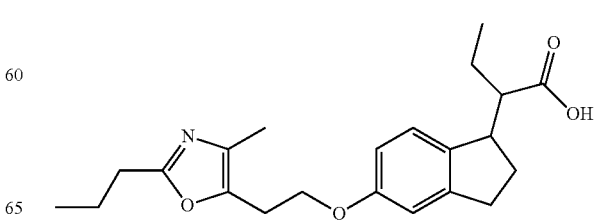

LC-MS $[C_{22}H_{29}NO_4H]^+$=372.3, RT=3.16 min.; $^1$H NMR (CDCl$_3$): δ 7.1 (1H, d), 6.6 (2H, d), 4.2 (2H, t), 3.3 (1H, m), 3.3 (1H, m), 2.8 (2H, t), 2.7 (1H, m), 2.6 (2H, t), 2.4 (2H, m), 2.2 (3H, s), 2.0-1.8 (2H, br, m), 0.88 (3H, t)

By using the methods described above for Examples 1-53 and by substituting the appropriate starting materials, compounds of Formula Ia, listed in Table 3 below, were similarly prepared.

TABLE 3

Preparative Examples of Compounds of Formula (Ia)

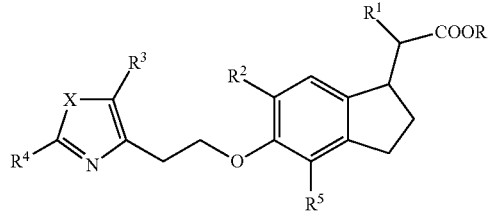

(Ia)

| Ex. No. | R | R$^1$ | R$^2$ | R$^3$ | R$^4$ | R$^5$ | X | LC-MS [M + H]$^+$ or NMR |
|---|---|---|---|---|---|---|---|---|
| 54 | H | Et | H | Me | PhOCH$_2$— | H | O | 436.2 |
| 55 | H | Et | H | Me | PhCH$_2$— | H | O | 420 |
| 56 | H | H | H | Me | Ph | H | O | 378.2 |
| 57 | Me | Ph(CH$_2$)$_3$— | H | Me | Ph | H | O | 3.45/3.52 (t, 3H), 4.10 (t, 2H), 7.3 (m, 3H), 7.83 (d, 2H) |
| 58 | Et | EtO$_2$C— | H | Me | Ph | H | O | 478.2 |
| 59 | Et | Et | H | Me | Ph | H | O | 434.3 |
| 60 | H | MeO | H | Me | Ph | H | O | 3.30 (s, 3H), 4.04 (d, 1H), 7.98 (m, 2H) |
| 61 | Et | EtO | H | Me | Ph | H | O | 450.3 |
| 62 | H | CF$_3$CH$_2$— | H | Me | Ph | H | O | 2.51 (s, 3H), 4.36 (m, 2H), 8.32 (m, 2H) |
| 63 | Et | CF$_3$CH$_2$— | H | Me | Ph | H | O | 1.18 (t, 3H), 4.21 (t, 2H), 7.98 (d, 2H) |
| 64 | Me | cyc-Pr | H | Me | Ph | H | O | 432.3 |
| 65 | H | cyc-Pr | H | Me | Ph | H | O | 0.02 (m, 1H), 0.12 (m, 1H), 4.18 (m, 2H), 7.94 (m, 2H) |
| 66 | H | benzo[d][1,3]dioxol-5-yl-C(Me)$_2$— | H | Me | Ph | H | O | 512.3 |
| 67 | H | Et | H | Me | Ph | H | S | 422.3 |
| 68 | H | benzo[d][1,3]dioxol-5-yl-C(Me)$_2$— | H | Me | Ph | H | O | 526.4 |
| 69 | H | Et | H | Me | Ph | H | S | 422.3 |
| 70 | MeNH-CH(Me)-CH(Ph)-C(Me)$_2$— | Et | H | Me | Ph | H | S | |
| 71 | Me | Et | H | Me | Ph | H | O | 0.82 (t, 3H), 3.54 (s, 3H), 4.16 (t, 2H), 7.90 (m, 2H) |
| 72 | H | Et | H | i-Pr | Ph | H | O | 434.3 |
| 73 | H | Et | H | Ph | Ph | H | O | 468.3 |
| 74 | H | Me | H | Me | Ph | H | S | 422.3 |
| 75 | Me | Me | H | Me | Ph | H | S | |
| 76 | Me | Et | MeC(O)— | Me | Ph | H | O | 462.4 |
| 77 | Me | Et | 4-MeO—Ph | Me | Ph | H | O | 526.4 |
| 78 | H | Et | 4-MeO—Ph | Me | Ph | H | O | 512.3 |
| 79 | Me | Et | 4-pyridyl | Me | Ph | H | O | 497.3 |
| 80 | H | Et | H | Me | cyc-Pentyl | H | O | 398 |

TABLE 3-continued

Preparative Examples of Compounds of Formula (Ia)

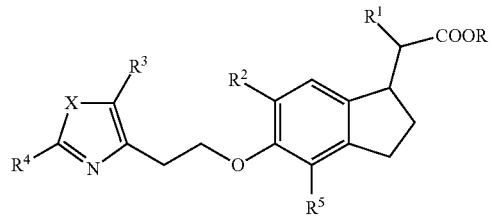

| Ex. No. | R | R¹ | R² | R³ | R⁴ | R⁵ | X | LC-MS [M + H]⁺ or NMR |
|---|---|---|---|---|---|---|---|---|
| 81 | H | Et | H | Me | cyc-Hexyl | H | O | 412 |
| 82 | H | Et | H | Me | 4-Ph—Ph— | H | O | 482 |
| 83 | Et | EtO₂C— | H | Me | 4-Me—Ph— | H | O | 492.3 |
| 84 | H | PhCH₂— | H | Me | 4-Me—Ph— | H | O | 482.4 |
| 85 | Et | n-Bu | H | Me | 4-Me—Ph— | H | O | 476.3 |
| 86 | Et | Me | H | Me | 4-Me—Ph— | H | O | 434.3 |
| 87 | Et | PhCH₂— | H | Me | 4-Me—Ph— | H | O | 510.4 |
| 88 | H | Et | H | Me | 4-MeO—Ph | H | O | 436.1 |
| 89 | H | Et | H | Me | 4-i-Pr—Ph | H | O | 448.2 |
| 90 | H | Et | H | Me | 4-F—PhCH₂— | H | O | 438.3 |
| 91 | H | Et | H | Me | 4-F—Ph | H | O | 424.3 |
| 92 | H | Et | H | Me | 4-Et—Ph | H | O | 434.3 |
| 93 | H | Et | H | Me | 4-Cl—PhOCH₂— | H | O | 470.2 |
| 94 | H | Et | H | Me | 4-Cl—Ph | H | O | 440 |
| 95 | Me | Et | H | Me | 4-Cl—Ph | H | S | 470.3 |
| 96 | Me | Et | H | Me | 4-Cl—Ph | H | S | 470.3 |
| 97 | H | Et | H | Me | 4-CF₃—Ph | H | S | 490.3 |
| 98 | Me | Et | H | Me | 4-CF₃—Ph | H | S | 504.3 |
| 99 | H | Et | H | Me | 4-CF₃—Ph | H | O | 474.3 |
| 100 | H | Et | H | Me | 4-(n-Bu)—Ph | H | O | 462.3 |
| 101 | H | Et | H | Me | 4-(t-Bu)—Ph | H | O | 462.3 |
| 102 | H | Et | H | Me | 3-Me—Ph | H | O | 420.4 |
| 103 | H | Et | H | Me | 3-MeO—Ph | H | O | 436.3 |
| 104 | H | Et | H | Me | 3-Me-5-isoxazolyl | H | O | 411.3 |
| 105 | H | Et | H | Me | 3-F—Ph | H | O | 424.2 |
| 106 | H | Et | H | Me | 3-F-4-Me—Ph | H | O | 438.2 |
| 107 | H | Et | H | Me | 4-F-3-Me—Ph | H | O | 438.3 |
| 108 | Me | Et | H | Me | 3-Cl—Ph | H | S | 470.3 |
| 109 | H | Et | H | Me | 3-Cl—Ph | H | O | 440.3 |
| 110 | H | Et | H | Me | 3-Cl—Ph | H | S | 456.3 |
| 111 | H | Et | H | Me | 3-CF₃—Ph | H | O | 474.2 |
| 112 | H | Et | H | Me | 3,5-(CF₃)₂—Ph | H | O | 542.1 |
| 113 | H | Et | H | Me | 3,4-Me₂—Ph | H | O | 434.3 |
| 114 | H | Et | H | Me | 3,4-Cl₂—Ph | H | O | 474.2 |
| 115 | H | Et | H | Me | 2,3-Cl₂—Ph | H | O | 474.1 |
| 116 | H | Et | H | Me | 3,4-(MeO)₂—Ph | H | O | 466.3 |
| 117 | H | Et | H | Me | 3,4-methylenedioxy-Ph | H | O | 466.3 |
| 118 | H | Et | H | Me | 2-thienyl | H | O | 412 |
| 119 | H | Et | H | Me | 2-naphthyl | H | O | 456.3 |
| 120 | H | Et | H | Me | 2-Me—Ph | H | O | 420.3 |
| 121 | H | Et | H | Me | 2-furyl | H | O | 396 |
| 122 | H | Et | H | Me | 2-F—Ph | H | O | 424.1 |
| 123 | H | Et | H | Me | 2-benzothienyl | H | O | 462.2 |
| 124 | H | Et | H | Me | 2,6-F₂—Ph | H | O | 442.2 |
| 125 | H | Et | H | Me | 3,4-F₂—Ph | H | O | 442.2 |
| 126 | H | Et | H | Me | 2,4-Cl₂—Ph | H | O | 473 |
| 127 | H | Et | H | Me | 1-naphthyl | H | O | 456.3 |
| 128 | Me | Et | H | Me | piperidin-1-yl | H | O | 0.90 (t, 3H), 3.45 (bs, 4H), 3.74 (s, 3H) |

Example 129

Preparation of ethyl(5-methoxy-2,3-dihydro-1H-inden-1-ylidene)ethanoate

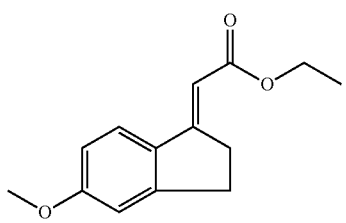

To a solution of 5-methoxyindanone (150 g, 0.91 mol) in anhydrous tetrahydrofuran (4.5 L), was added zinc (30 mesh, 103.64 g, 1.59 mol) and copper(I) chloride (4.53 g, 0.045 mol). The suspension was stirred under Ar atmosphere and refluxed for 15 minutes; approximately a 25% portion of ethyl bromoacetate (133 mL, 1.18 mol) was added to the refluxing mixture in a slow dropwise fashion. After allowing to cool and stirring overnight at rt, TLC showed the presence of desired product, indicating the formation of reactive zinc species. The remainder of ethyl bromoacetate was added dropwise; an exotherm was observed (internal temperature increased to 35° C.). After 4 hours, TLC showed complete reaction. After the solids settled to the bottom of the flask, the liquid was siphoned off leaving a small amount behind to cover the solids. The flask was re-charged with 5-methoxyindanone (157.6 g, 1.86 mol total), anhydrous tetrahydrofuran (4.5 L), and zinc (80.92 g, 2.73 mol total). Ethyl bromoacetate (140 mL, 2.36 mol total) was added dropwise. An exotherm was observed (internal temperature increased to 35° C.). When the stirred mixture cooled to rt, TLC showed the reaction to be complete. The solids were allowed to settle and the liquid was siphoned off. The combined reaction solutions were concentrated in vacuo to a volume of ~2 L. The liquid was then poured into sufficient 1N aqueous hydrochloric acid (cooled in ice water) to bring the pH to 1. The product was extracted with ethyl acetate (2×1 L, 1×500 mL). The combined extracts were washed with water, brine (1 L each), dried over sodium sulfate, filtered, and concentrated in vacuo to afford a dark red oil which solidified gradually (438.3 g; theoretical yield=432 g). $^1$H NMR (CDCl$_3$): δ 7.5 (d, 1H), 6.8 (m, 2H), 6.2 (t, 1 H), 4.2 (q, 2H), 3.8 (s, 3H), 3.3 (m, 2H), 3.0 (t, 2H), 1.3 (t, 3H). MS (CI) m/z 233 [M+H]$^+$.

Example 130

Preparation of ethyl(5-methoxy-2,3-dihydro-1H-inden-1-yl)acetate

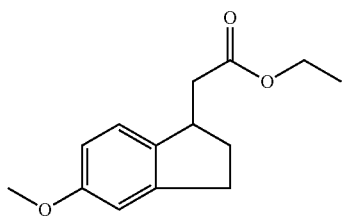

The crude product of Example 129 was dissolved in absolute ethanol (2.6 L) and hydrogenated at 40 psi of hydrogen over 10% palladium on carbon (21.6 g). Filtration through Celite and concentration of the filtrate afforded 433.3 g of brown oil (99% yield for 2 steps). $^1$H NMR (CDCl$_3$): δ 7.1 (dd, 1H), 6.8 (d, 1H), 6.7 (dd, 1H), 4.2 (q, 2H), 3.8 (s, 3H), 3.5 (m, 1H), 2.9 (m, 2H), 2.7 (dd, 1H), 2.4 (m, 2H), 1.7 (m, 1H), 1.3 (t, 3H). MS (CI) m/z 235 [M+H]$^+$.

Example 131

Preparation of (5-methoxy-2,3-dihydro-1H-inden-1-yl)acetic acid

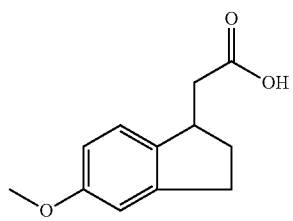

To a solution of the crude ester (416 g, 1.77 mol) prepared in Example 130 in 1 L EtOH, was added a solution of NaOH (142 g, 3.54 mol) in 1.5 L water. The cloudy reaction mixture was heated to reflux, during which time the color changed to dark red, and the reaction became homogeneous. After 1 hour, the reaction was cooled to rt, and the EtOH was removed under reduced pressure. The basic aqueous layer was washed with Et$_2$O (3×500 mL), then acidified with conc. HCl to pH ~4 upon which an oil residue formed. The mixture was extracted with Et$_2$O (4×500 mL). The combined extracts were washed with water (2×300 mL), brine, then dried over Na$_2$SO$_4$. Filtration and evaporation of solvent under reduced pressure gave the title compound (305 g, 83%) as a yellow solid after overnight drying under vacuum. $^1$H NMR (CDCl$_3$) δ 7.34(d, 1H), 6.71(s, 1H), 6.65(dd, 1H), 3.71(s, 3H), 3.47(m, 1H), 2.80(m, 3H), 2.35(m, 2H), 1.71(m, 1H). MS (CI) m/z 207 [M+H]$^+$.

Example 132

Preparation of [(1S)-5-methoxy-2,3-dihydro-1H-inden-1-yl]acetic acid

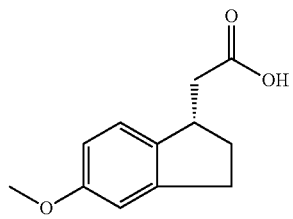

To a solution of the acid (341.0 g, 1.65 mol) prepared in Example 131 in 8.2 L reagent grade acetone, was added (S)-(−)-α-methylbenzylamine (223.8 mL, 1.74 mol) dropwise at rt with stirring. A thick white precipitate formed during the addition. An additional 500 mL acetone was added and stirring continued for 1 hour. The solids were collected by filtration, washed with 300 mL acetone, and dried under suction. The solids were then suspended in acetone (8.2 L) and warmed to reflux until all solids dissolved. The solution was cooled slowly overnight, during which time a white precipitate formed. The suspension was cooled to 0° C., then filtered, and the solids were washed with 500 mL acetone. After drying under suction, a sample analyzed by HPLC showed 95% ee. The recrystallization process was repeated as above using 6.7 L acetone. HPLC analysis showed 99% ee. After drying under suction, 192 g salt were obtained. The salt was suspended in 2 L EtOAc and 1 L of 1 N HCl solution, and shaken in a separatory funnel, whereupon the salt dissolved. The organic layer was separated, washed with 1 N HCl (500 mL), water (2×300 mL), and brine, then dried over $Na_2SO_4$. The solvent was evaporated under reduced pressure, giving an oil which soon solidified. The title product (120.5 g, 35%) was obtained as an off-white solid after vacuum drying. $^1H$ NMR ($CDCl_3$) δ 7.10(d, 1H), 6.79(d, 1H), 6.73(dd, 1H), 3.79(s, 3H), 3.55(m, 1H), 2.89(m, 2H), 2.79(dd, 1H), 2.46 (dd, 1H), 2.43(m, 1H), 1.80(m, 1H). MS (ESI) m/z 207 $[M+H]^+$.

Example 133

Preparation of [(1S)-5-methoxy-2,3-dihydro-1H-inden-1-yl]acetic acid

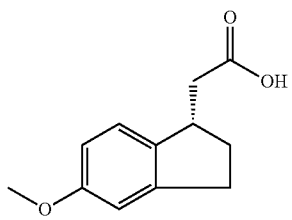

As an alternative to Example 132, the title compound may also be prepared via an enzymatic process. Thus, a cloudy mixture of the crude ester (500.0 g, 2.13 mol; 87% pure as determined by HPLC) prepared in Example 130, in 1 L reagent grade acetone, 2.5 L Phosphate Buffer (pH 7.0, 0.05 M) and 2.5 L deionized water was treated in one portion with Amano Lipase PS (150 g), and the mixture stirred efficiently at rt overnight. HPLC analysis of an aliquot (homogeneous aliquot prepared by dissolving aliquot in IPA followed by filtration) showed one peak corresponding to unreacted R-ester and another peak corresponding to desired S-acid. Trace amounts of S-ester and R-acid were noted. 2 N HCl (500 mL, ensure a pH ~2) was added in one portion to the reaction and stirred for 20 minutes. The mixture was filtered and the solids were washed with EtOAc (2×500 mL), then water (500 mL). The combined filtrates were further diluted with 1 L EtOAc, and the layers stirred together vigorously. Stirring was stopped and the layers allowed to separate. Emulsions were noted, but could be broken with the addition of solid NaCl and stirring. The aqueous layer was removed, then extracted with EtOAc (3×1 L) in the same fashion. The combined organic extractions were washed with water (4×500 mL), then with brine. The resulting organic layer was extracted with a 5% $Na_2CO_3$ solution (8×500 mL). HPLC analysis of the organic layer showed that it contained none of the 8-enantiomer acid. The combined $Na_2CO_3$ extracts were washed with EtOAc (2×1 L), then acidified to pH ~2 by the addition of 2N HCl. A white solid precipitated, accompanied by $CO_2$ evolution. The mixture was extracted with EtOAc (3×1 L). The combined extracts were washed with water (2×1 L) and brine, then dried over $Na_2SO_4$. HPLC analysis of this solution showed the material was 98% ee. The solvent was evaporated under reduced pressure, giving an oil which soon solidified. The title product (172.9 g) was obtained as an off-white solid after vacuum drying. This material was recrystallized from boiling hexanes (8.8 L). After overnight cooling, light yellow needles were collected via filtration, washed with hexanes (200 mL), and dried under suction. The title product (146.9 g, 38% from crude starting ester) was obtained as light yellow needles after vacuum drying. $^1H$ NMR results as above.

Example 134

Preparation of ethyl[(1S)-5-methoxy-2,3-dihydro-1H-inden-1-yl]acetate

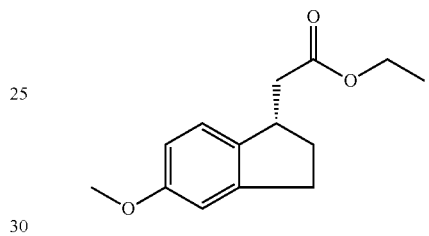

To a solution of the acid (305 g, 1.48 mol) prepared in either Example 132 or 133 in 4.8 L absolute EtOH at rt under argon, was added chlorotrimethylsilane (413 mL, 3.25 mol) dropwise. An approximate 5° C. rise in temperature was noted during the addition. The reaction was stirred overnight. EtOH was evaporated under reduced pressure, giving a bi-phasic liquid mixture. This was diluted in 500 mL ice-water, then extracted with EtOAc (2×750 mL). The combined extracts were washed with water (3×300 mL), then with saturated $NaHCO_3$ (200 mL). The organic was washed once more with water (300 mL), then brine, and dried over $Na_2SO_4$. The title compound (354 g, 102%) was obtained as a light yellow oil after solvent removal and vacuum drying. $^1H$ NMR ($CDCl_3$) δ 7.07(d, 1H), 6.78(d, 1H), 6.71(dd, 1H), 4.18(q, 2H), 3.78(s, 3H), 3.52(m, 1H), 2.89(m, 2H), 2.72(dd, 1H), 2.37(o, 2H), 1.74(m, 1H), 1.28(t, 3H). MS (CI) m/z 235 $[M+H]^+$.

Example 135

Preparation of ethyl[(1S)-5-hydroxy-2,3-dihydro-1H-inden-1-yl]acetate

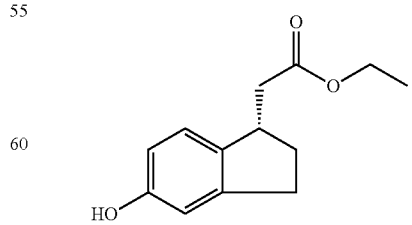

To a cold solution (ice water bath) of the compound (346 g, 1.48 mol) prepared in Example 134 in 4.2 L $CH_2Cl_2$, was added $AlCl_3$ (984.6 g, 7.38 mol) portionwise under Ar such that the reaction temperature was maintained below 10° C. The light brown suspension was stirred 10 minutes, then EtSH (546 mL, 7.38 mol) was added dropwise at such a rate that the reaction temperature was maintained below 5° C. After 2.5 hours of stirring below 10° C., the reaction mixture was slowly poured into 6 L ice water with strong agitation. The organic layer was separated, and the aqueous layer was extracted with $CH_2Cl_2$ (3×1 L). The combined $CH_2Cl_2$ layers were washed with water (2×1 L), then dried over $Na_2SO_4$. The solvent was removed under reduced pressure, giving a brown oil, which was filtered through a pad of silica gel (eluted with 0-10% EtOAc/Hexanes). Fractions were collected and the title compound (314 g, 96%) was obtained as a thick yellow oil after solvent removal and vacuum drying. $^1$H NMR (CDCl$_3$) δ 6.92(d, 1H), 6.62(d, 1H), 6.55(dd, 1H), 4.10(q, 2H), 3.43(q, 1H), 2.75(m, 2H), 2.64(dd, 1H), 2.31(dd, 1H), 2.29(m, 1H), 1.67(m, 1H), 1.20(t, 3H). MS (CI) m/z 221 [M+H]$^+$.

Example 136

Preparation of ethyl 2-((1S)-5-{2-[5-methyl-2-(4-methylphenyl)(1,3-oxazol-4-yl)]ethoxy}indanyl)acetate

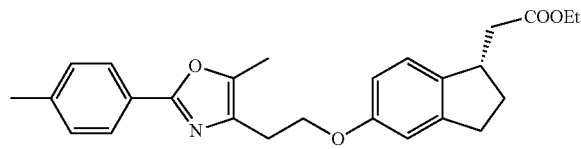 [SMILES: CCOC(=O)C[C@@H]1CCc2cc(OCCc3nc(-c4ccc(C)cc4)oc3C)ccc21]

A suspension of the ethyl[(1S)-5-hydroxy-2,3-dihydro-1H-inden-1-yl]acetate prepared in Example 135 (507.5 mg, 2.30 mmol), and 2-[5-methyl-2-(4-methylphenyl)-1,3-oxazol-4-yl]ethanol prepared in Example 10 (500 mg, 2.30 mmol), TMAD (792.6 mg, 4.60 mmol), and Ph$_3$P (1.21 g, 4.60 mmol) in 15 mL anhydrous DCM was stirred at rt under Ar for 12 hours. DCM was removed under reduced pressure. Flash chromatograph of the residue over silica gel using 1% $CH_3CN/CH_2Cl_2$ gave ethyl 2-((1S)-5-{2-[5-methyl-2-(4-methylphenyl)(1,3-oxazol-4-yl)]ethoxy}indanyl)acetate (776.3 mg, 1.85 mmol, 80.5%). HPLC/MS (M+H)$^+$ m/z 420.5.

Example 137

Preparation of 2-((1S)-5-{2-[5-methyl-2-(4-methylphenyl)(1,3-oxazol-4-yl)]ethoxy}indanyl)acetic acid

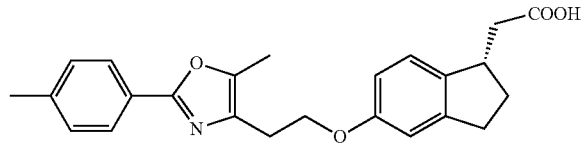 [SMILES: Cc1ccc(-c2nc(CCOc3ccc4c(c3)CC[C@H]4CC(=O)O)c(C)o2)cc1]

Ethyl 2-((1S)-5-[2-{5-methyl-2-(4-methylphenyl)(1,3-oxazol-4-yl)]ethoxy}indanyl)acetate (Example 136, 776.3 mg, 1.85 mmol) in THF (4.0 ml) was added to a mixture of aqueous LiOH (2 M, 3.7 ml, 7.4 mmol), water (2.0 ml), and EtOH (4.0 ml) at rt. The resulting mixture turned cloudy. This mixture was heated at 40° C. (oil-bath temperature). The reaction was completed after 1.5 hours. After cooling to rt, 1 N HCl solution was slowly added to the mixture until pH 4.0. The compound was extracted with EtOAc (3×20 ml). The combined EtOAc layers were dried (Na$_2$SO$_4$) and evaporated. Flash chromatography of the residue gave 2-((1S)-5-{2-[5-methyl-2-(4-methylphenyl)(1,3-oxazol-4-yl)]ethoxy}indanyl)acetic acid (616.8 mg, 1.57 mmol, 85%) as a white solid. $^1$H NMR (CDCl$_3$) δ 7.83(d, 2H), 7.21(d, 2H), 7.03(d, 1H), 6.74(d, 1H), 6.69(dd, 1H), 4.19(t, 2H), 3.45(q, 1H), 2.93(t, 2H), 2.78(m, 2H), 2.51(m, 2H), 2.30(s, 3H), 2.25(s, 3H), 1.53(m, 2H).

By using the methods described above for Examples 129-137 and by substituting the appropriate starting materials, compounds of Formula Ia, listed in Table 4 below, were similarly prepared.

TABLE 4

Preparative Examples of Compounds of Formula (Ia)

(Ia)

| Ex. No. | R$^3$ | R$^4$ | LC/MS [M + H] |
|---|---|---|---|
| 138 | Me | 4-MeO—Ph | 408.5 |
| 139 | Me | 3-MeO—Ph | 408.5 |
| 140 | Me | 4-Et—Ph | 406.5 |
| 141 | Me | 4-CF3—Ph | 446.5 |
| 142 | Me | 2-naphthyl | 428.5 |
| 143 | Me | 4-(t-Bu)—Ph | 434.6 |
| 144 | Me | 4-(n-Bu)—Ph | 434.6 |
| 145 | Me | benzodioxol | 422.5 |
| 146 | Me | 3,4-(Me)$_2$—Ph | 406.5 |
| 147 | Me | 4-Me—Ph | 392.5 |
| 148 | Me | 3-F—Ph | 396.5 |
| 149 | Me | 2-benzothienyl | 434.5 |
| 150 | Me | 4-i-Pr—Ph | 420.6 |
| 151 | Me | cyc-Pentyl | 370.5 |
| 152 | Me | cyc-hexyl | 384.5 |
| 153 | Me | PhCH$_2$ | 392.5 |
| 154 | Me | 4-F-3-Me—Ph | 410.5 |
| 155 | Me | 3-F-4-Me—Ph | 410.5 |
| 156 | Me | 4-F—Ph | 396.5 |
| 157 | Et | Ph | 392.5 |
| 158 | Me | 3,4-(Cl)$_2$—Ph | 447.4 |
| 159 | n-Pr | Ph | 406.5 |
| 160 | Me | 4-Ph—Ph | 454.5 |
| 161 | Me | 3-Cl—Ph | 412.4 |
| 162 | Me | 3-Me—Ph | 392.5 |
| 163 | Me | 4-CN—Ph | 403.4 |
| 164 | Me | 3-CN—Ph | 403.4 |
| 165 | Me | 4-Cl—Ph | 412.4 |
| 166 | Me | 3-CF3—Ph | 446.4 |
| 167 | Et | 4-Et—Ph | 420.5 |
| 168 | Et | 4-Me—Ph | 406.5 |
| 169 | Et | 4-MeO—Ph | 422.4 |

Example 170

Preparation of methyl 4-bromo-3-oxopentanoate

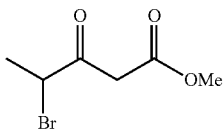

A dry three-neck flask under an Ar atmosphere was charged with a solution of methyl propionylacetate (20 g, 154 mmol) in $CHCl_3$ (100 mL). Using an addition funnel, bromine (7.9 mL, 24.6 g, 154 mmol) was added dropwise over a period of 2 hours at 0° C. The reaction was then allowed to warm slowly to rt, and the reaction mixture was stirred overnight. A saturated solution of $Na_2CO_3$ (40 mL) was slowly added, and after stirring the reaction mixture for an additional 15 minutes, the solvents layers were separated and the aqueous layer was extracted with $CH_2Cl_2$ (50 mL). The combined organic layers were dried ($Na_2SO_4$), filtered, and concentrated under reduced pressure. The residue was then purified by silica gel flash chromatography (10:1 hexanes/EtOAc) to give the desired bromide as a light yellow oil (25 g, 78%). $^1$H NMR ($CDCl_3$): δ 1.80 (d, 3H), 3.64-3.92 (m, 2H), 3.78 (s, 3H), 4.61 (q, 1H).

Example 171

Preparation of methyl(2-amino-5-methyl-1,3-thiazol-4-yl)acetate

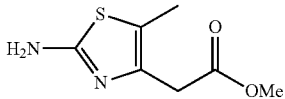

To a solution of bromide of Example 170 (18 g, 86 mmol) in toluene (100 mL) was added thiourea (10.5 g, 138 mmol). The reaction mixture was heated to 100° C. for 1 hour, cooled to rt, and the solvent removed under reduced pressure. The residue was dissolved with $CH_2Cl_2$ (100 mL), a saturated solution $NaHCO_3$ (75 mL) added, and the mixture was vigorously stirred for 10 minutes. The organic layer was separated, dried ($Na_2SO_4$), filtered, and concentrated under reduced pressure. The residue was then recrystallized from $CH_2Cl_2$/hexanes to provide the product (10 g, 63%) as a white solid. ($C_7H_{10}N_2O_2S$): LC-MS, RT 0.76 min, M+H 187.0; $^1$H NMR ($CDCl_3$): δ 2.23 (s, 3H), 3.70 (s, 2H), 3.75 (s, 3H), 4.83-4.95 (broad s, 2H).

Example 172

Preparation of methyl(2-bromo-5-methyl-1,3-thiazol-4-yl)acetate

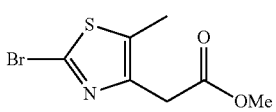

To a solution of $CuBr_2$ (4.03 g, 18.1 mmol) and t-butyl nitrite (2.82 mL, 23.8 mmol) in MeCN (210 mL) was added the compound of Example 170 (2.95 g, 15.9 mmol) at −20° C. The reaction mixture was slowly warmed to 15° C., at which point the evolution of $N_2$ was observed. After stirring for an additional 2 hours at 15° C., the reaction mixture was diluted with $Et_2O$ (400 mL) and washed with a 10% solution of HCl (200 mL). The solvent layers were separated, the aqueous re-extracted with $Et_2O$ (2×300 mL), and the combined organic layers dried ($MgSO_4$), filtered, and concentrated under reduced pressure. The residue was then purified by silica gel flash chromatography (98:2, hexanes/EtOAc) to afford bromide Example 172 (1.6 g, 40%) as a colorless oil that solidifies upon standing. ($C_7H_8BrNO_2S$): LC-MS, RT 2.56 min., M+H 250.3; $^1$H NMR ($CDCl_3$): δ 2.26 (s, 3H), 3.60 (s, 2H), 3.61 (s, 3H).

Example 173

Preparation of 2-(2-bromo-5-methyl-1,3-thiazol-4-yl)ethanol

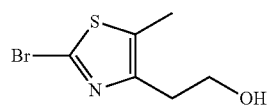

To a solution of ester prepared in Example 172 (3.80 g, 15.2 mmol) in $CH_2Cl_2$ (100 mL) was added DIBAL-H (33.4 mL, 33.4 mmol of a 1.0 M solution in toluene) at −78° C. After 15 minutes, the solution was warmed to 0° C. and stirred for an additional 90 minutes. An aqueous solution of 2 N HCl (50 mL) was then added dropwise to quench the excess DIBAL-H. The solvent layers were separated and the aqueous layer extracted with $CH_2Cl_2$ (2×200 mL). The combined organic layers were dried ($MgSO_4$), filtered, and concentrated under reduced pressure. The residue was purified by silica gel flash chromatography (5:2 hexanes/EtOAc) to yield the product (2.5 g, 74%) as a yellowish oil that solidifies upon standing. ($C_6H_8BrNOS$) LC-MS, RT 1.38 min., M+H 221.0; $^1$H NMR ($CDCl_3$): δ 2.31 (s, 3H), 2.82 (t, 2H), 2.90-3.00 (broad s, 1H), 3.89 (t, 2H).

Example 174

Preparation of ethyl{(1S)-5-[2-(2-bromo-5-methyl-1,3-thiazol-4-yl)ethoxy]-2,3-dihydro-1H-inden-1-yl}acetate

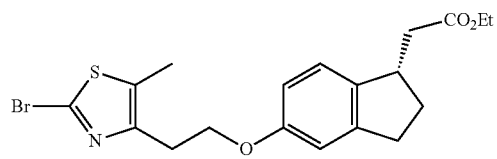 [SMILES: CCOC(=O)C[C@@H]1CCc2cc(OCCc3nc(Br)sc3C)ccc21]

Step 1. To a solution of Example 173 (975 mg, 4.39 mmol) and ethyl[(1S)-5-hydroxy-2,3-dihydro-1H-inden-1-yl]acetate (1.06 g, 4.83 mmol) in THF (20 mL) were added $Ph_3P$ (1.88 g, 7.46 mmol) and ADDP (1.96 g, 7.46 mmol). The mixture was vigorously stirred at rt for 72 hours, the solvent removed under reduced pressure, and the residue purified by silica gel flash chromatography (6:1 hexanes/EtOAc) to yield the product (1.4 g, 76%) as a colorless oil that solidifies upon standing. ($C_{19}H_{22}BrNO_3S$) LC-MS, RT 3.92 min., M+H 424.5; $^1$H NMR ($CDCl_3$): δ 1.26 (t, 3H), 1.65-1.81 (m, 1H), 2.28-2.45 (m, 2H), 2.37 (s, 3H), 2.69 (dd, 1H), 2.75-2.93 (m, 2H), 3.07 (t, 2H), 3.44-3.56 (m, 1H), 4.15 (t, 2H), 4.18 (q, 2H), 6.67 (dd, 1H), 6.73 (d, 1H), 7.03 (d, 1H).

Preparation of ethyl((1S)-5-{2-[2-(4-isopropylphenyl)-5-methyl-1,3-thiazol-4-yl]ethoxy}-2,3-dihydro-1H-inden-1-yl)acetate

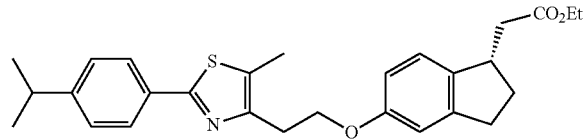 [SMILES: CCOC(=O)C[C@@H]1CCc2cc(OCCc3nc(-c4ccc(C(C)C)cc4)sc3C)ccc21]

Step 2. To a mixture of toluene (15 mL) and 1,4-dioxane (3 mL), were added the compound of step 1 (300 mg, 0.708 mmol), 4-isopropylbenzene boronic acid (464 mg, 2.83 mmol), and PdCl₂(dppf).CH₂Cl₂ (52 mg, 0.071 mmol). A flow of Ar was passed through the mixture for 30 minutes, then a 2 N solution of Na₂CO₃ (3.7 mL, 7.08 mmol) was added and the reaction was heated to 75° C. for 18 hours. The reaction mixture was then cooled to rt, diluted with EtOAc (200 mL), and washed with a saturated solution of NaHCO₃ (50 mL). The organic layer was dried (Na₂SO₄), filtered, and concentrated under reduced pressure. The residue was purified by silica gel flash chromatography (8:1 hexanes/EtOAc), to provide the product (305 mg, 93%) as a colorless oil. ($C_{28}H_{33}NO_3S$): LC-MS, RT 5.17 min., M+H 464.5; ¹H NMR (CDCl₃): δ 1.17-1.31 (m, 3H), 1.26 (s, 3H), 1.27 (s, 3H), 1.65-1.82 (m, 1H), 2.30-2.43 (m, 2H), 2.46 (s, 3H), 2.72 (dd, 1H), 2.78-3.00 (m, 3H), 3.17 (t, 2H), 3.46-3.57 (m, 1H), 4.17 (q, 2H), 4.27 (t, 2H), 6.71 (d, 1H), 6.78 (s, 1H), 7.04 (d, 1H), 7.55 (AB quartet, 4H).

Example 175

Preparation of ((1S)-5-{2-[2-(4-isopropylphenyl)-5-methyl-1,3-thiazol-4-yl]ethoxy}-2,3-dihydro-1H-inden-1-yl)acetic acid

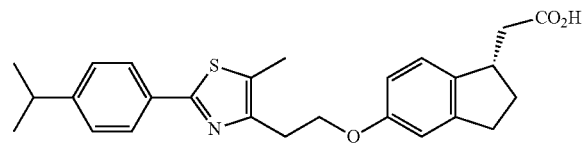 [SMILES: Cc1sc(-c2ccc(C(C)C)cc2)nc1CCOc1ccc2c(c1)CC[C@H]2CC(=O)O]

To a solution of Example 174 (305 mg, 0.657 mmol) in a mixture of THF (8 mL), water (8 mL), and EtOH (4 mL), was added LiON (63 mg, 2.63 mmol). The reaction mixture was vigorously stirred for 24 hours, diluted with water (20 mL), and washed with Et₂O (10 mL). The aqueous phase was then acidified to pH ~1 using 1 N HCl, and then extracted with CH₂Cl₂ (4×50 mL). The combined organic layers were dried (Na₂SO₄), filtered, and concentrated under reduced pressure. The residue was then purified by silica gel flash chromatography (95:5 CH₂Cl₂/MeOH) to afford product (189 mg, 66%) as a white solid. ($C_{26}H_{29}NO_3S$): LC-MS, RT 3.95 min., M+H 436.4; ¹H NMR (CDCl₃): δ 1.25 (s, 3H), 1.28 (s, 3H), 1.70-1.82 (m, 1H), 2.32-2.43 (m, 2H), 2.45 (s, 3H), 2.74-2.98 (m, 4H), 3.18 (t, 2H), 3.47-3.54 (m, 1H), 4.28 (t, 2H), 6.72 (dd, 1H), 6.78 (s, 1H), 7.08 (d, 1H), 7.51 (AB quartet, 4H).

Example 176

Preparation of methyl[5-methyl-2-(4-methylphenyl)-1,3-thiazol-4-yl]acetate

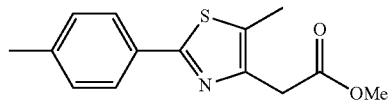 [SMILES: COC(=O)Cc1nc(-c2ccc(C)cc2)sc1C]

To a solution of bromide of Example 170 (1.15 g, 5.52 mmol) in toluene (20 mL) was added 4-methyl thiobenzamide (1.0 g, 6.6 mmol). The reaction mixture was heated to reflux for 15 hours, cooled to rt, diluted with EtOAc (150 mL), and washed with a saturated solution of NaHCO₃ (50 then with a saturated solution of NH₄Cl (50 mL). The organic layer was dried (Na₂SO₄), filtered, and concentrated under reduced pressure. The residue was then purified by silica gel flash chromatography (9:1 hexanes/EtOAc) to afford the product as a pinkish oil that solidified upon standing (1.14 g, 62%). ¹H NMR (CDCl₃): δ 2.38 (s, 3H), 3.45 (s, 3H), 3.74 (s, 3H), 3.80 (s, 2H), 7.49 (AB quartet, 4H); Rf (0.4, eluant 9:1 hexanes/EtOAc).

Example 177

Preparation of 2-[5-methyl-2-(4-methylphenyl)-1,3-thiazol-4-yl]ethanol

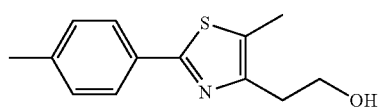 [SMILES: Cc1ccc(-c2nc(CCO)c(C)s2)cc1]

To a solution of the thiazole of Example 176 (1.14 g, 4.37 mmol) in THF (60 mL) at 0° C., was added portion-wise LiAlH₄ (663 mg, 17.5 mmol). After 30 minutes, the reaction mixture was warmed to rt and stirred for an additional 60 minutes. The reaction mixture was then cooled to 0° C., and the excess LiAlH₄ was quenched by dropwise addition of water (5 mL), 1N NaOH (10 mL), and water (5 mL) sequentially. The mixture was then diluted with a saturated solution of Rochelle salt and extracted with EtOAc (4×75 mL). The combined organic phases were dried (Na₂SO₄), filtered, and concentrated under reduced pressure. The residue was purified by silica gel flash chromatography (3:2 hexanes/EtOAc) to afford the product as a white solid (830 mg, 82%). ($C_{13}H_{15}NOS$): LC-MS, RT 2.50 min., M+H 234.2; ¹H NMR (CDCl₃): δ 2.34 (s, 3H), 2.37 (s, 3H), 2.83 (t, 2H), 3.92-4.01 (broad t, 2H), 4.04-4.15 (broad s, 1H), 7.45 (AB quartet, 4H).

The following compounds below were synthesized using one of the two procedures of Examples 170-177 described above.

Example 178

{(1S)-5-[2-(5-Methyl-2-phenyl-1,3-thiazol-4-yl)ethoxy]-2,3-dihydro-1H-inden-1-yl}acetic acid

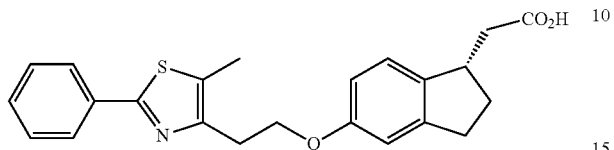

($C_{23}H_{23}NO_3S$): LC-MS RT 3.56 min., M+H 394.2; $^1$H NMR (CDCl$_3$): δ 1.61-1.78 (m, 1H), 2.19-2.50 (m, 2H), 2.30 (s, 3H), 2.62-2.91 (m, 3H), 3.12 (t, 2H), 3.17-3.26 (m, 1H), 4.12 (t, 2H), 6.70 (d, 1H), 6.79 (s, 1H), 6.98 (d, 1H), 7.21-7.40 (m, 3H), 7.74-7.83 (m, 2H).

Example 179

((1S)-5-{2-[5-Methyl-2-(4-methylphenyl)-1,3-thiazol-4-yl]ethoxy}-2,3-dihydro-1H-inden-1-yl)acetic acid

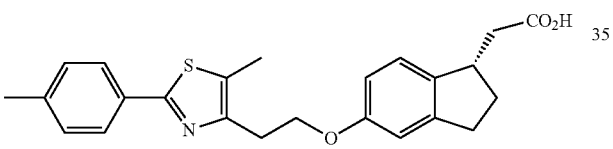

($C_{24}H_{25}NO_3S$): LC-MS, RT 3.57 min., M+H 408.5; $^1$H NMR (CDCl$_3$): δ 1.61-1.68 (m, 1H), 2.29 (s, 3H), 2.36 (s, 3H), 2.25-2.37[hidden] (m, 2H), 2.63-2.79 (m, 3H), 3.09 (t, 2H), 3.35-3.47 (m, 1H), 4.18 (t, 2H), 6.60 (dd, 1H), 6.68 (s, 1H), 6.97 (d, 1H), 7.42 (AB quartet, 4H), 7.81-8.30 (br, 1H).

Example 180

((1S)-5-{2-[2-(1,3-Benzodioxol-5-yl)-5-methyl-1,3-thiazol-4-yl]ethoxy}-2,3-dihydro-1H-inden-1-yl)acetic acid

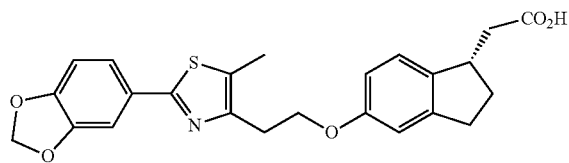 [SMILES: Cc1sc(-c2ccc3c(c2)OCO3)nc1CCOc1ccc2c(c1)CC[C@H]2CC(=O)O]

($C_{24}H_{23}NO_5S$): LC-MS, RT 4.04 min., M+H 438.5; $^1$H NMR (CDCl$_3$): δ 1.71-1.83 (m, 1H), 2.36-2.51 (m, 2H), 2.45 (s, 3H), 2.76-2.96 (m, 3H), 3.15 (t, 2H), 3.48-3.58 (m, 1H), 4.29 (t, 2H), 6.00 (s, 2H), 6.72 (dd, 1H), 6.78 (s, 1H), 6.82 (d, 1H), 7.07 (d, 1H), 7.32-7.40 (m, 2H).

Example 181

((1S)-5-{2-[2-(4-Methoxyphenyl)-5-methyl-1,3-thiazol-4-yl]ethoxy}-2,3-dihydro-1H-inden-1-yl)acetic acid

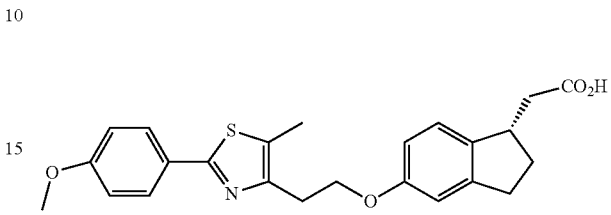

($C_{24}H_{25}NO_4S$): LC-MS, RT 4.01 min., M+H 424.5; $^1$H NMR (CDCl$_3$): δ 1.67-1.82 (m, 1H), 2.43 (s, 3H), 2.34-2.47 (m, 2H), 2.72-2.95 (m, 3H), 3.09 (t, 2H), 3.42-3.57 (m, 1H), 3.84 (s, 3H), 4.13 (t, 2H), 6.72 (d, 1H), 6.79 (s, 1H), 7.12 (d, 1H), 7.37 (AB quartet, 4H).

Example 182

[(1S)-5-(2-{5-Methyl-2-[4-(trifluoromethyl)phenyl]-1,3-thiazol-4-yl}ethoxy)-2,3-dihydro-1H-inden-1-yl]acetic acid

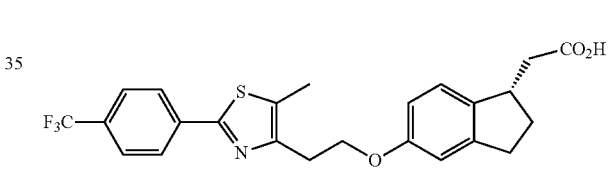

($C_{24}H_{22}F_3NO_3S$): LC-MS, RT 4.47 min., M+H 462.4; $^1$H NMR (DMSO$_{d6}$): δ 1.63-1.81 (m, 1H), 2.28-2.43 (m, 2H), 2.50 (s, 3H), 2.69 (dd, 1H), 2.74-2.95 (m, 2H), 3.19 (t, 2H), 3.31-3.36 (m, 1H), 4.31 (t, 2H), 6.71 (dd, 1H), 6.78 (s, 1H), 7.08 (d, 1H), 7.87 (AB quartet, 4H).

Example 183

((1S)-5-{2-[2-(4-Cyanophenyl)-5-methyl-1,3-thiazol-4-yl]ethoxy}-2,3-dihydro-1H-inden-1-yl)acetic acid

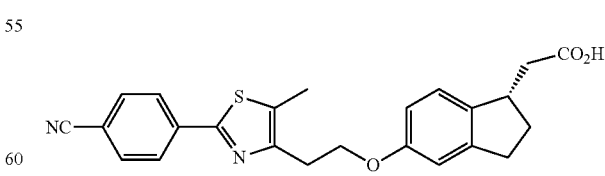

($C_{24}H_{22}N_2O_3S$): LC-MS, RT 3.43 min., M+H 419.6; $^1$H NMR (CDCl$_3$): δ 1.68-1.85 (m, 1H), 2.31-2.49 (m, 2H), 2.51 (s, 3H), 2.77 (dd, 1H), 2.83-2.94 (m, 2H), 3.18 (t, 2H), 3.43-3.56 (m, 1H), 4.31 (t, 2H), 6.71 (dd, 1H), 6.79 (s, 1H), 7.10 (d, 1H), 7.86 (AB quartet, 4H).

Example 184

((1S)-5-{2-[2-(4-Isopropylphenyl)-5-methyl-1,3-thiazol-4-yl]ethoxy}-2,3-dihydro-1H-inden-1-yl)acetic acid

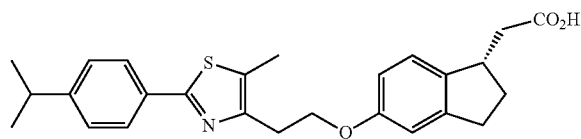 [SMILES: Cc1sc(-c2ccc(C(C)C)cc2)nc1CCOc1ccc2c(c1)CC[C@H]2CC(=O)O]

($C_{26}H_{29}NO_3S$): LC-MS, RT 3.95 min., M+H 436.4; $^1$H NMR (CDCl$_3$): δ 1.25 (s, 3H), 1.28 (s, 3H), 1.70-1.82 (m, 1H), 2.32-2.43 (m, 2H), 2.45 (s, 3H), 2.74-2.98 (m, 4H), 3.18 (t, 2H), 3.47-3.54 (m, 1H), 4.28 (t, 2H), 6.72 (dd, 1H), 6.78 (s, 1H), 7.08 (d, 1H), 7.51 (AB quartet, 4H).

Example 185

((1S)-5-{2-[2-(3-Chloro-4-fluorophenyl)-5-methyl-1,3-thiazol-4-yl]ethoxy}-2,3-dihydro-1H-inden-1-yl)acetic acid

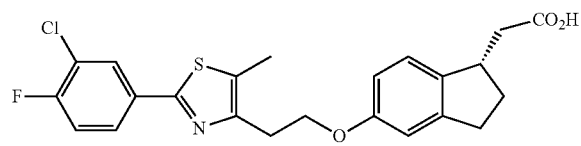 [SMILES: Cc1sc(-c2ccc(F)c(Cl)c2)nc1CCOc1ccc2c(c1)CC[C@H]2CC(=O)O]

($C_{23}H_{21}ClFNO_3S$): LC-MS, RT 3.89 min., M+H 446.4; $^1$H NMR (CDCl$_3$): δ 1.68-1.86 (m, 1H), 2.32-2.46 (m, 2H), 2.50 (s, 3H), 2.80 (dd, 1H), 2.84-2.96 (m, 2H), 3.18 (t, 2H), 3.47-3.59 (m, 1H), 4.32 (t, 2H), 6.72 (d, 1H), 6.82 (s, 1H), 7.12 (d, 1H), 7.23 (t, 1H), 7.72-7.82 (m, 1H), 7.97-8.04 (m, 1H).

Example 186

((1S)-5-{2-[2-(3,4-Dichlorophenyl)-5-methyl-1,3-thiazol-4-yl]ethoxy}-2,3-dihydro-1H-inden-1-yl)acetic acid

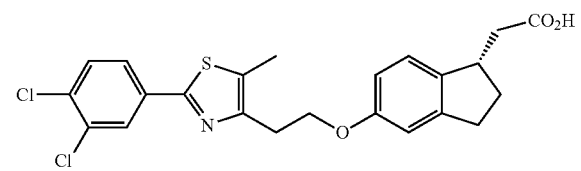 [SMILES: Cc1sc(-c2ccc(Cl)c(Cl)c2)nc1CCOc1ccc2c(c1)CC[C@H]2CC(=O)O]

(C23H$_{21}$Cl$_2$NO$_3$S): LC-MS, RT 4.12 min., M+H 462.0; $^1$H NMR (CDCl$_3$): δ 1.74-1.88 (m, 1H), 2.36-2.48 (m, 2H), 2.50 (s, 3H), 2.73-2.93 (m, 3H), 3.19 (t, 2H), 3.48-3.55 (m, 1H), 4.30 (t, 2H), 6.71 (d, 1H), 6.79 (s, 1H), 7.09 (d, 1H), 7.52 (d, 1H), 7.61 (dd, 1H), 8.02 (d, 1H).

Example 187

((1S)-5-{2-[2-(4-Fluorophenyl)-5-methyl-1,3-thiazol-4-yl]ethoxy}-2,3-dihydro-1H-inden-1-yl)acetic acid

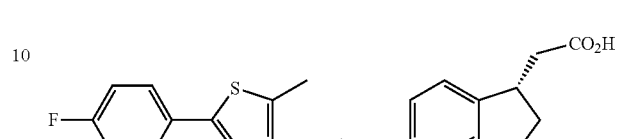

($C_{23}H_{22}FNO_3S$): LC-MS, RT 3.58 min., M+H 412.4; $^1$H NMR (CDCl$_3$): δ1.70-1.77 (m, 1H), 2.37-2.45 (m, 1H), 2.44 (s, 3H), 2.70-2.90 (m, 4H), 3.16 (t, 2H), 3.47-3.52 (m, 1H), 4.27 (t, 2H), 6.70 (d, 1H), 6.76 (s, 1H), 7.00-7.10 (m, 3H), 7.82-7.87 (m, 2H).

Example 188

((1S)-5-{2-[2-(3,4-Dimethylphenyl)-5-methyl-1,3-thiazol-4-yl]ethoxy}-2,3-dihydro-1H-inden-1-yl)acetic acid

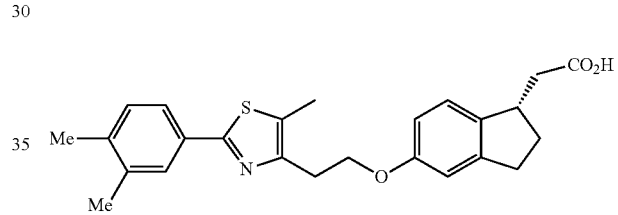

($C_{25}H_{27}NO_3S$): LC-MS, RT 4.39 min., M+H 422.3; $^1$H NMR (CDCl$_3$): δ 1.70-1.83 (m, 1H), 2.29 (s, 3H), 2.32 (s, 3H), 2.37-2.50 [hidden] (m, 2H), 2.46 (s, 3H), 2.70-2.90 (m, 3H), 3.32 (t, 2H), 3.45-3.60 (m, 1H), 4.30 (t, 2H), 6.73 (d, 1H), 6.79 (s, 1H), 7.07 (d, 1H), 7.17 (d, 1H), 7.59 (d, 1H), 7.68 (s, 1H).

Example 189

((1S)-5-{2-[2-(4-Acetylphenyl)-5-methyl-1,3-thiazol-4-yl]ethoxy}-2,3-dihydro-1H-inden-1-yl)acetic acid

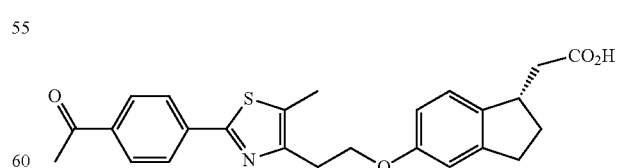

($C_{25}H_{25}NO_4S$): LC-MS, RT 4.01 min., M+H 436.3; $^1$H NMR (CDCl$_3$): δ1.70-1.82 (m, 1H), 2.37-2.49 (m, 2H), 2.50 (s, 3H), 2.63 (s, 3H), 2.70-2.90 (m, 3H), 3.20 (t, 2H), 3.45-3.60 (m, 1H), 4.30 (t, 2H), 6.72 (d, 1H), 6.78 (s, 1H), 7.08 (d, 1H), 7.95-8.03 (m, 4H).

Example 190

[(1S)-5-(2-{2-[4-(Dimethylamino)phenyl]-5-methyl-1,3-thiazol-4-yl}ethoxy)-2,3-dihydro-1H-inden-1-yl]acetic acid

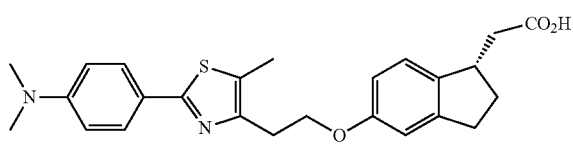

(C$_{25}$H$_{28}$N$_2$O$_3$S): LC-MS, RT 2.95 min., M+H 437.2; $^1$H NMR (DMSO$_{d6}$): δ 1.53-1.65 (m, 1H), 2.12-2.24 (m, 2H), 2.36 (s, 3H), 2.63-2.84 (m, 3H), 2.94 (s, 6H), 3.03 (t, 2H), 3.27-3.38 (m, 1H), 4.18 (t, 2H), 6.65 (d, 1H), 6.75 (s, 1H), 7.08 (d, 1H), 7.17 (AB quartet, 4H).

Example 191

((1S)-5-{2-[2-(3-Amino-4-methylphenyl)-5-methyl-1,3-thiazol-4-yl]ethoxy}-2,3-dihydro-1H-inden-1-yl)acetic acid

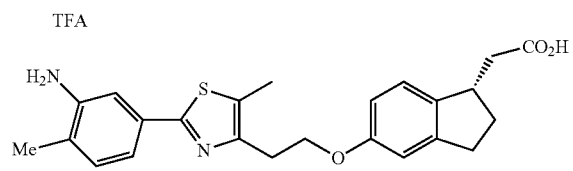 [SMILES: Cc1ccc(-c2nc(CCOc3ccc4c(c3)CC[C@H]4CC(=O)O)c(C)s2)cc1N]

C$_{24}$H$_{26}$N$_2$O$_3$S.C$_2$F$_3$O$_2$): LC-MS, RT 3.5 min., M+H 423.3; $^1$H NMR (CD$_3$OD): δ 1.67-1.82 (m, 1H), 2.25-2.37 (m, 2H), 2.38 (s, 3H), 2.50 (s, 3H), 2.67-2.90 (m, 3H), 3.20 (t, 2H), 3.41-3.56 (m, 1H), 4.32 (t, 2H), 6.71 (d, 1H), 6.79 (s, 1H), 7.09 (d, 1H), 7.42 (d, 1H), 7.69 (dd, 1H), 7.77 (d, 1H).

Example 192

((1S)-5-{2-[2-(2-Fluorophenyl)-5-methyl-1,3-thiazol-4-yl]ethoxy}-2,3-dihydro-1H-inden-1-yl)acetic acid

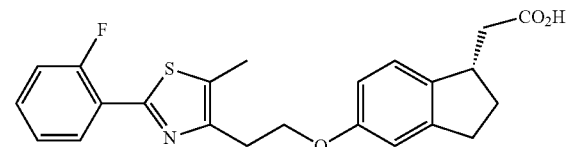

(C$_{23}$H$_{22}$FNO$_3$S): LC-MS, RT 4.25 min., M+H 412.2; $^1$H NMR (CDCl$_3$): δ 1.70-1.82 (m, 1H), 2.37-2.48 (m, 2H), 2.49 (s, 3H), 2.74-2.94 (m, 3H), 3.21 (t, 2H), 3.42-3.60 (m, 1H), 4.31 (t, 2H), 6.72 (d, 1H), 6.79 (s, 1H), 7.06-7.35 (m, 4H), 8.21 (t, 1H).

Example 193

((1S)-5-{2-[2-(4-Chlorophenyl)-5-methyl-1,3-thiazol-4-yl]ethoxy}-2,3-dihydro-1H-inden-1-yl)acetic acid

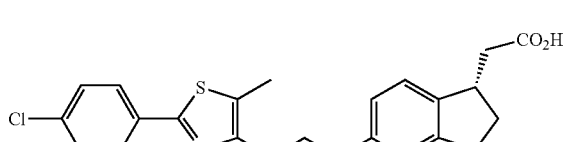

(C$_{23}$H$_{22}$ClNO$_3$S): LC-MS, RT 4.44 min., M+H 4282; $^1$H NMR (CDCl$_3$): δ 1.70-1.81 (m, 1H), 2.35-2.45 (m, 2H), 2.46 (s, 3H), 2.74-2.89 (m, 3H), 3.17 (t, 2H), 3.42-3.60 (m, 1H), 4.28 (t, 2H), 6.71 (d, 1H), 6.77 (s, 1H), 7.07 (d, 1H), 7.36 (d, 2H), 7.79 (d, 2H).

Example 194

((1S)-5-{2-[2-(4-Ethoxyphenyl)-5-methyl-1,3-thiazol-4-yl]ethoxy}-2,3-dihydro-1H-inden-1-yl)acetic acid

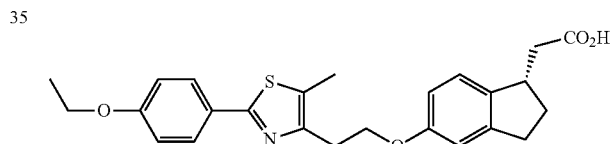

(C$_{25}$H$_{27}$NO$_4$S): LC-MS, RT 3.55 min., M+H 438.5; $^1$H NMR (CDCl$_3$): δ 1.40 (t, 3H), 1.70-1.82 (m, 1H), 2.35-2.47 (m, 2H), 2.45 (s, 3H), 2.74-2.89 (m, 3H), 3.20 (t, 2H), 3.42-3.59 (m, 1H), 4.07 (q, 2H), 4.29 (t, 2H), 6.71 (d, 1H), 6.76 (s, 1H), 6.91 (d, 1H), 7.06 (d, 2H), 7.82 (d, 2H).

Example 195

((1S)-5-{2-[2-(3,4-Dimethoxyphenyl)-5-methyl-1,3-thiazol-4-yl]ethoxy}-2,3-dihydro-1H-inden-1-yl)acetic acid

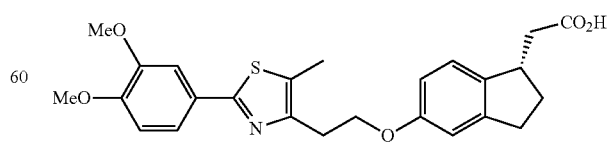

(C$_{25}$H$_{27}$NO$_3$S): LC-MS, RT 3.86 min., M+H 454.2; $^1$H NMR (CDCl$_3$): δ 1.67-1.82 (m, 1H), 2.37-2.48 (m, 2H), 2.49 (s, 3H), 2.71-2.87 (m, 3H), 3.27 (t, 2H), 3.42-3.57 (m, 1H), 3.93 (s, 3H), 3.96 (s, 3H), 4.29 (t, 2H), 6.35-6.64 (broad s, 1H), 6.67 (d, 1H), 6.75 (s, 1H), 6.89 (d, 1H), 7.05 (d, 1H), 7.39 (d, 1H), 7.56 (s, 1H).

Example 196

((1S)-5-{2-[5-Methyl-2-(3-methylphenyl)-1,3-thiazol-4-yl]ethoxy}-2,3-dihydro-1H-inden-1-yl)acetic acid

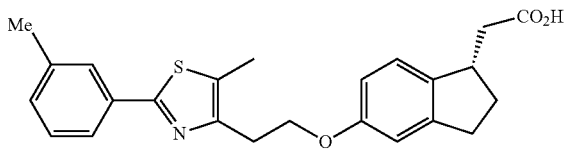

($C_{24}H_{25}NO_3S$): LC-MS, RT 3.71 min., M+H 408.2; $^1$H NMR ($CDCl_3$): δ 1.70-1.82 (m, 1H), 2.38-2.52 (m, 2H), 2.40 (s, 3H), 2.47 (s, 3H), 2.75-2.87 (m, 3H), 3.19 (t, 2H), 3.45-3.60 (m, 1H), 4.29 (t, 2H), 6.72 (d, 1H), 6.78 (s, 1H), 7.07 (d, 1H), 7.19 (d, 1H), 7.30 (t, 1H), 7.64 (d, 1H), 7.75 (s, 1H).

Example 197

[(1S)-5-(2-{5-Methyl-2-[3-(trifluoromethyl)phenyl]-1,3-thiazol-4-yl}ethoxy)-2,3-dihydro-1H-inden-1-yl]acetic acid

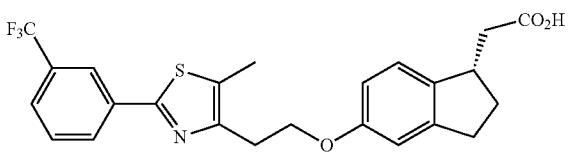 [SMILES: Cc1cccc(-c2nc(CCOc3ccc4c(c3)CC[C@H]4CC(=O)O)c(C)s2)c1]

($C_{24}H_{22}F_3NO_3S$): LC-MS, RT 3.90 min., M+H 462.1; $^1$H NMR ($CDCl_3$): δ 1.70-1.82 (m, 1H), 2.38-2.48 (m, 2H), 2.49 (s, 3H), 2.75-2.87 (m, 3H), 3.19 (t, 2H), 3.44-3.59 (m, 1H), 4.30 (t, 2H), 6.72 (d, 1H), 6.79 (s, 1H), 7.07 (d, 1H), 7.52 (t, 1H), 7.61 (d, 1H), 8.01 (d, 1H), 8.13 (s, 1H).

Example 198

((1S)-5-{2-[2-(3-Fluorophenyl)-5-methyl-1,3-thiazol-4-yl]ethoxy}-2,3-dihydro-1H-inden-1-yl)acetic acid

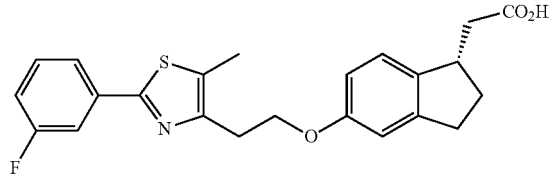 [SMILES: Cc1sc(-c2cccc(F)c2)nc1CCOc1ccc2c(c1)CC[C@H]2CC(=O)O]

($C_{23}H_{22}FNO_3S$): LC-MS, RT 3.66 min., M+H 412.1; $^1$H NMR ($CDCl_3$): δ 1.70-1.82 (m, 1H), 2.39-2.47 (m, 2H), 2.48 (s, 3H), 2.76-2.87 (m, 3H), 3.18 (t, 2H), 3.45-3.60 (m, 1H), 4.30 (t, 2H), 6.72 (d, 1H), 6.78 (s, 1H), 7.04-7.09 (m, 2H), 7.36-7.42 (m, 1H), 7.58-7.62 (m, 2H).

Example 199

((1S)-5-{2-[2-(3,5-Dimethylphenyl)-5-methyl-1,3-thiazol-4-yl]ethoxy}-2,3-dihydro-1H-inden-1-yl) acetic acid

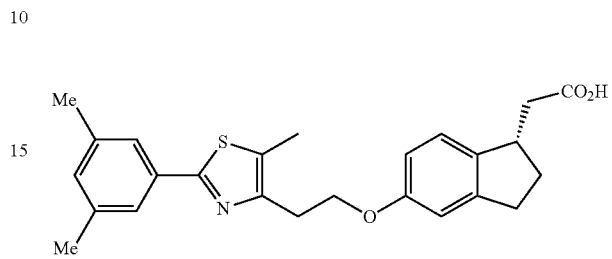

($C_{25}H_{27}NO_3S$): LC-MS, RT 3.88 min., M+H 422.2; $^1$H NMR ($CDCl_3$): δ 1.72-1.84 (m, 1H), 2.36 (s, 6H), 2.37-2.45 (m, 2H), 2.46 (s, 3H), 2.75-2.87 (m, 3H), 3.19 (t, 2H), 3.45-3.60 (m, 1H), 4.28 (t, 2H), 6.72 (d, 1H), 6.79 (s, 1H), 7.01 (s, 1H), 7.07 (d, 1H), 7.48 (s, 2H).

Example 200

[(1S)-5-(2-{5-Methyl-2-[4-(trifluoromethoxy)phenyl]-1,3-thiazol-4-yl}ethoxy)-2,3-dihydro-1H-inden-1-yl]acetic acid

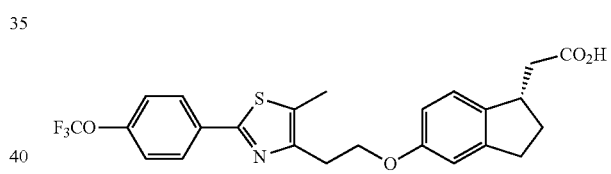

($C_{24}H_{22}F_3NO_4S$): LC-MS, RT 3.95 min., M+H 478.1; $^1$H NMR ($CDCl_3$): δ 1.72-1.84 (m, 1H), 2.38-2.46 (m, 2H), 2.47 (s, 3H), 2.75-2.87 (m, 3H), 3.18 (t, 2H), 3.45-3.60 (m, 1H), 4.29 (t, 2H), 6.72 (d, 1H), 6.77 (s, 1H), 7.07 (d, 1H), 7.24 (d, 2H), 7.88 (d, 2H).

Example 201

((1S)-5-{2-[2-(3-Methoxyphenyl)-5-methyl-1,3-thiazol-4-yl]ethoxy}-2,3-dihydro-1H-inden-1-yl) acetic acid

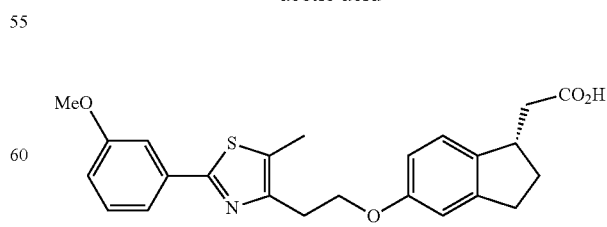

($C_{24}H_{25}NO_4S$): LC-MS, RT 3.56 min., M+H 424.2; $^1$H NMR ($CDCl_3$): δ 1.70-1.82 (m, 1H), 2.37-2.52 (m, 2H), 2.49 (s, 3H), 2.75-2.87 (m, 3H), 3.19 (t, 2H), 3.45-3.57 (m, 1H), 3.87 (s, 3H), 4.30 (t, 2H), 6.72 (d, 1H), 6.79 (s, 1H), 6.95 (d, 1H), 7.10 (d, 1H), 7.32 (t, 1H), 7.40-7.45 (m, 2H).

Example 202

((1S)-5-{2-[2-(1,1'-Biphenyl-4-yl)-5-methyl-1,3-thiazol-4-yl]ethoxy}-2,3-dihydro-1H-inden-1-yl)acetic acid

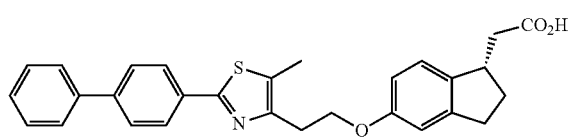 [SMILES: Cc1sc(-c2ccc(-c3ccccc3)cc2)nc1CCOc1ccc2c(c1)CC[C@H]2CC(=O)O]

($C_{29}H_{27}NO_3S$): LC-MS, RT 3.96 min., M+H 470.3; $^1$H NMR (CDCl$_3$): δ 1.70-1.81 (m, 1H), 2.38-2.48 (m, 2H), 2.49 (s, 3H), 2.75-2.87 (m, 3H), 3.20 (t, 2H), 3.43-3.59 (m, 1H), 4.31 (t, 2H), 6.72 (d, 1H), 6.79 (s, 1H), 7.08 (d, 1H), 7.36 (t, 1H), 7.45 (t, 2H), 7.61-7.65 (m, 4H), 7.93 (d, 2H).

Example 203

Preparation of ethyl{(1S)-5-[2-(4-methyl-2-phenyl-1,3-oxazol-5-yl)ethoxy]-2,3-dihydro-1H-inden-1-yl}acetate

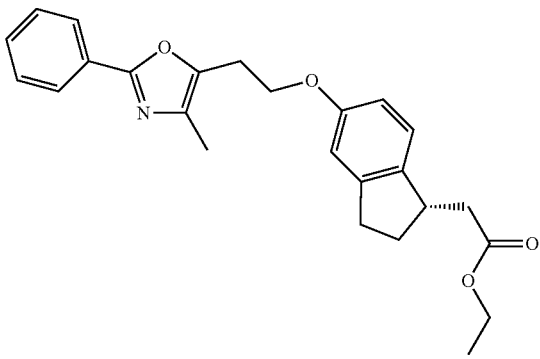 [SMILES: CCOC(=O)C[C@@H]1CCc2cc(OCCc3oc(-c4ccccc4)nc3C)ccc21]

ADDP (0.205 g, 0.81 mmol) was added to a mixture of PPh$_3$ (0.212 g, 0.81 mmol), ethyl[(1S)-5-hydroxy-2,3-dihydro-1H-inden-1-yl]acetate (0.107 g, 0.49 mmol), and 2-(4-methyl-2-phenyl-1,3-oxazol-5-yl)ethanol (step 4, Example 51, 0.110 g, 0.54 mmol) in THF (5 mL). The reaction was stirred overnight at rt, and additional ADDP (0.136 g, 0.54 mmol) and PPh$_3$ (0.141 g, 0.54 mmol) were added with CH$_2$Cl$_2$ (5 mL). The solution was stirred for 24 hours at rt and filtered. The filtrate was evaporated and the resulting mixture was purified by Biotage using a gradient 0 to 50%. EtOAc/hexane. Gave ethyl {(1S)-5-[2-(4-methyl-2-phenyl-1,3-oxazol-5-yl)ethoxy]-2,3-dihydro-1H-inden-1-yl}acetate (0.145 g, 66% yield) as yellowish oil. ES-MS m/z 406.2 ((MH)$^+$); HPLC RT (min.) 3.89; $^1$H NMR (Acetone-d$_6$) δ 7.85-7.82 (m, 2H), 7.36-7.30 (m, 3H), 6.94 (d, 1H), 6.65 (s, 1H), 6.60-6.55 (m, 1H), 4.10 (t, 2H), 3.98 (q, 2H), 3.31-3.27 (m, 1H), 3.03 (t, 2H), 3.27-2.51 (m, 3H), 2.24-2.14 (m, 2H), 2.18 (s, 3H), 1.58-1.53 (m, 1H), 1.08 (t, 3H).

Example 204

Preparation of {(1S)-5-[2-(4-methyl-2-phenyl-1,3-oxazol-5-yl)ethoxy]-2,3-dihydro-1H-inden-1-yl}acetic acid

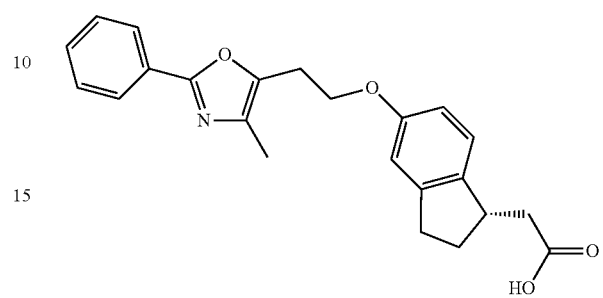

Ethyl{(1S)-5-[2-(4-methyl-2-phenyl-1,3-oxazol-5-yl)ethoxy]-2,3-dihydro-1H-inden-1-yl}acetate (0.135 g, 0.33 mmol) was dissolved in EtOH (6 mL) and LiOH (0.024 g, 1.0 mmol) was added. Water (3 mL) was added and THF was added until the cloudy solution became clear. The resulting mixture was stirred overnight at rt. HCl (2 N) was added to adjust the pH to 2, then extracted three times with ethyl acetate. The organic layers were combined, dried, and concentrated to give {(1S)-5-[2-(4-methyl-2-phenyl-1,3-oxazol-5-yl)ethoxy]-2,3-dihydro-1H-inden-1-yl}acetic acid (0.039 g, 30.6% yield) as colorless oil. ES-MS m/z 378.2 ((MH)$^+$); HPLC RT (min.) 3.22; $^1$H NMR (Acetone-d$_6$) δ 8.1 (s br 1H) 8.0-7.95 (m, 2H), 7.52-7.43 (m, 3H), 7.15 (d, 1H), 6.81 (s, 1H), 6.73 (d, 1H), 4.27 (t, 2H) 3.47-3.40 (m, 1H), 3.18 (t, 2H), 2.90-2.68 (m, 3H), 2.41-2.29 (m, 2H), 2.18 (s, 3H), 1.77-1.68 (m, 1H).

By using the procedure described above for Examples 51, 203, and 204 and substituting the appropriate starting materials, the following compounds were similarly prepared and characterized.

Example 205

Preparation of N-(4-methylbenzoyl)alanine

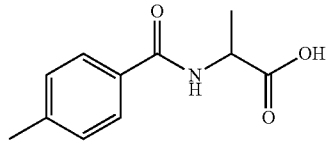

$^1$H NMR (DMSO-d$_6$) δ 12.60 (s br, 1H), 8.57 (d, 1H), 7.81 (d, 2H), 7.28 (d, 2H), 4.38 (q, 1H), 2.35 (s, 3H), 1.38 (d, 3H).

Example 206

Preparation of N-(3-fluoro-4-methylbenzoyl)alanine

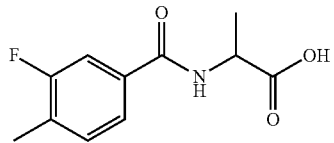 [SMILES: Cc1ccc(C(=O)NC(C)C(=O)O)cc1F]

¹H NMR (DMSO-d₆) δ 12.54 (s br, 1H), 8.67 (d, 1H), 7.65-7.62 (m, 2H), 7.39 (t, 1H), 4.38 (q, 1H), 2.27 (s, 3H), 1.38 (d, 3H).

Example 207

Preparation of N-[4-(trifluoromethyl)benzoyl]alanine

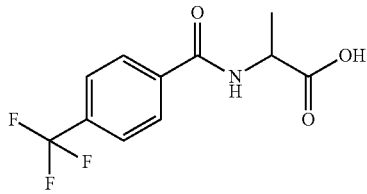 [SMILES: CC(NC(=O)c1ccc(C(F)(F)F)cc1)C(=O)O]

¹H NMR (DMSO-d₆) δ 12.64 (s br, 1H), 8.91 (d, 1H), 8.08 (d, 2H), 7.85 (d, 2H), 4.42 (q, 1H), 1.40 (d, 3H).

Example 208

Preparation of ethyl 4-[(4-methylbenzoyl)amino]-3-oxopentanoate

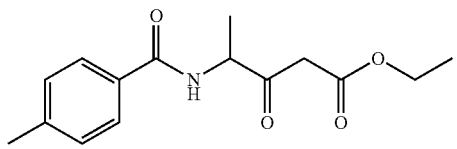 [SMILES: CCOC(=O)CC(=O)C(C)NC(=O)c1ccc(C)cc1]

ES-MS m/z 278.38 ((MH)⁺); HPLC RT (min.) 2.04. ¹H NMR (Acetone-d₆) δ 8.08 (s br, 1H), 7.90 (d, 2H), 7.28 (d, 2H), 4.72-4.67 (m, 1H), 4.13 (q, 2H), 3.66 (s, 2H), 2.40 (s, 3H), 1.41 (d, 3H), 1.12 (t, 3H).

Example 209

Preparation of ethyl 4-[(3-fluoro-4-methylbenzoyl)amino]-3-oxopentanoate

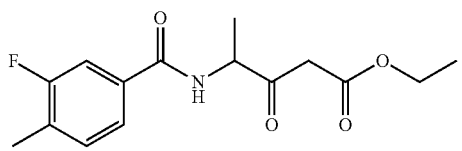 [SMILES: CCOC(=O)CC(=O)C(C)NC(=O)c1ccc(C)c(F)c1]

ES-MS m/z 296.4 ((MH)⁺); HPLC RT (min.) 2.26. ¹H NMR (Acetone-d₆) δ 7.75-7.60 (m, 2H), 7.38 (t, 1H), 4.20 (q, 2H), 3.65 (s, 2H), 2.23 (s, 3H), 1.45 (d, 3H), 1.20 (t, 3H).

Example 210

Preparation of ethyl 3-oxo-4-{[4-(trifluoromethyl)benzoyl]amino}pentanoate

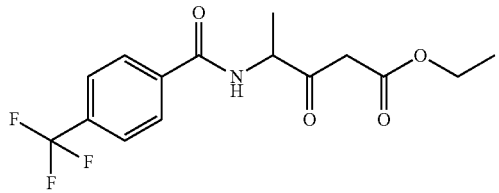 [SMILES: CCOC(=O)CC(=O)C(C)NC(=O)c1ccc(C(F)(F)F)cc1]

ES-MS m/z 332.4 ((MH)⁺); HPLC RT (min.) 2.45. ¹H NMR (Acetone-d₆) δ 8.14 (d, 2H), 7.84 (d, 2H), 4.80-4.74 (m, 2H), 4.20 (q, 2H), 3.70 (s, 2H), 1.48 (d, 3H), 1.21 (t, 3H).

Example 211

Preparation of ethyl[4-methyl-2-(4-methylphenyl)-1,3-oxazol-5-yl]acetate

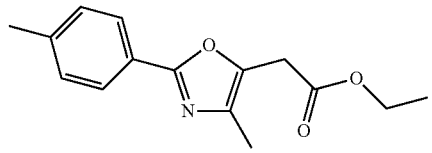 [SMILES: CCOC(=O)Cc1oc(-c2ccc(C)cc2)nc1C]

ES-MS m/z 260.2 ((MH)⁺); HPLC RT (min.) 2.96. ¹H NMR (Acetone-d₆) δ 7.86 (d, 2H), 7.30 (d, 2H), 4.15 (q, 2H), 3.81 (s, 2H), 2.37 (s, 3H), 2.14 (s, 3H), 1.24 (t, 3H).

Example 212

Preparation of ethyl[2-(3-fluoro-4-methylphenyl)-4-methyl-1,3-oxazol-5-yl]acetate

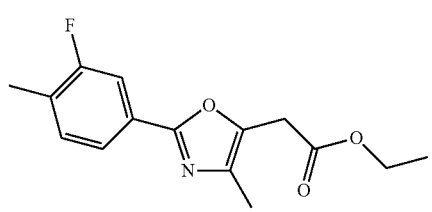 [SMILES: CCOC(=O)Cc1oc(-c2ccc(C)c(F)c2)nc1C]

ES-MS m/z 278.3 ((MH)⁺); HPLC RT (min.) 2.89. ¹H NMR (Acetone-d₆) δ 7.69 (d, 1H), 7.60 (d, 1H), 7.37 (t, 1H), 4.15 (q, 2H), 3.83 (s, 2H), 2.31 (s, 3H), 2.15 (s, 3H), 1.23 (t, 3H).

Example 213

Preparation of ethyl{4-methyl-2-[4-(trifluoromethyl)phenyl]-1,3-oxazol-5-yl}acetate

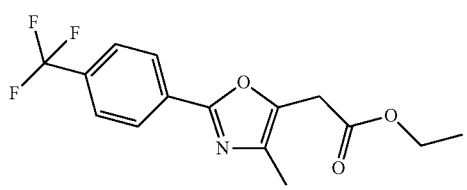 [SMILES: CCOC(=O)Cc1oc(-c2ccc(C(F)(F)F)cc2)nc1C]

ES-MS m/z 314.3 ((MH)+); HPLC RT (min.) 3.27. ¹H NMR (Acetone-d₆) δ 8.18 (d, 2H), 7.84 (d, 2H), 4.17 (q, 2H), 3.88 (s, 2H), 2.20 (s, 3H), 1.23 (t, 3H).

Example 214

Preparation of 2-[4-methyl-2-(4-methylphenyl)-1,3-oxazol-5-yl]ethanol

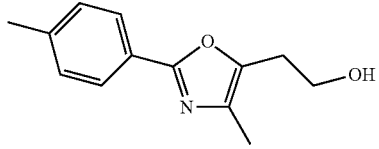 [SMILES: Cc1ccc(-c2nc(C)c(CCO)o2)cc1]

ES-MS m/z 218.2 ((MH)+); HPLC RT (min.) 2.35. ¹H NMR (Acetone d₆) δ 7.85 (d, 2H), 7.27 (d, 2H), 3.99 (s br, 1H), 3.83 (t, 2H), 2.90 (t, 2H), 2.37 (s, 3H), 2.12 (s, 3H).

Example 215

Preparation of 2-[2-(3-fluoro-4-methylphenyl)-4-methyl-1,3-oxazol-5-yl]ethanol

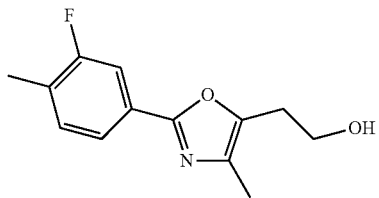 [SMILES: Cc1ccc(-c2nc(C)c(CCO)o2)cc1F]

ES-MS m/z 236.2 ((MH)+); HPLC RT (min.) 2.46. ¹H NMR (CDCl₃) δ7.54 (d, 1H), 7.43 (d, 1H), 7.17 (t, 1H), 3.91 (d, 2H), 3.09 (s br, 1H), 2.88 (t, 2H), 2.29 (s, 3H), 2.13 (s, 3H).

Example 216

Preparation of 2-{4-methyl-2-[4-(trifluoromethyl)phenyl]-1,3-oxazol-5-yl}ethanol

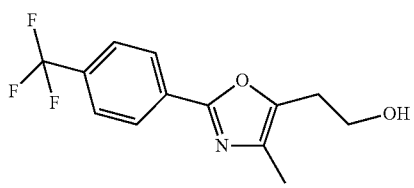 [SMILES: Cc1nc(-c2ccc(C(F)(F)F)cc2)oc1CCO]

ES-MS m/z 272.2 ((MH)+); HPLC RT (min.) 2.71. ¹H NMR (CDCl₃) δ 8.03 (2, 2H), 7.66 (d, 2H), 3.95 (t, 2H), 2.96 (t, 2H), 2.21 (s, 3H), 1.97 (s br, 1H).

Example 217

Preparation of ethyl[(1S)-5-(2-{4-methyl-2-[4-(trifluoromethyl)phenyl]-1,3-oxazol-5-yl}ethoxy)-2,3-dihydro-1H-inden-1-yl]acetate

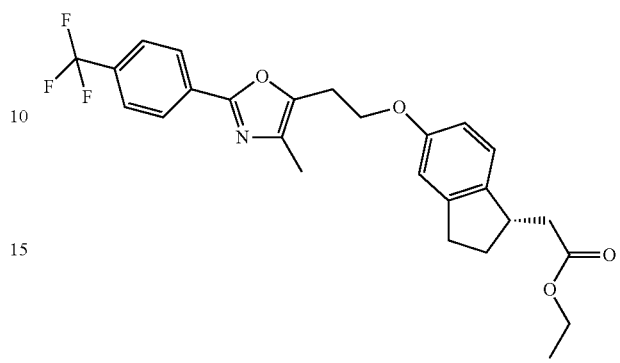

ES-MS m/z 474.5 ((MH)+); HPLC RT (min.) 4.10. ¹H NMR (Acetone-d₆) δ 8.16 (d, 2H), 7.83 (d, 2H), 7.09 (d, 1H), 6.80 (s, 1H), 6.72 (dd, 1H), 4.28 (t, 2H), 4.12 (q, 2H), 3.46-3.41 (m, 1H), 3.21 (t, 2H), 2.86-2.65 (m, 3H), 2.39-2.26 (m, 2H), 2.20 (s, 3H), 1.75-1.63 (m, 1H), 1.22 (t, 3H).

Example 218

Preparation of ethyl((1S)-5-{2-[4-methyl-2-(4-methylphenyl)-1,3-oxazol-5-yl]ethoxy}-hydro-1H-inden-1-yl)acetate

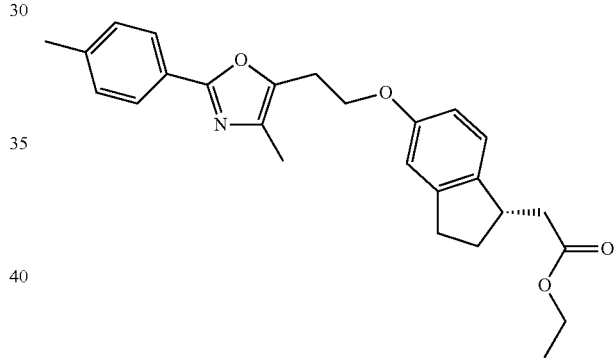

TCL Rf=0.22 Hexane/EtOAc 4:1

Example 219

Preparation of ethyl((1S)-5-{2-[4-fluoro-4-methylphenyl)-4-methyl-1,3-oxazol-5-yl]ethoxy}-2,3-dihydro-1H-inden-1-yl)acetate

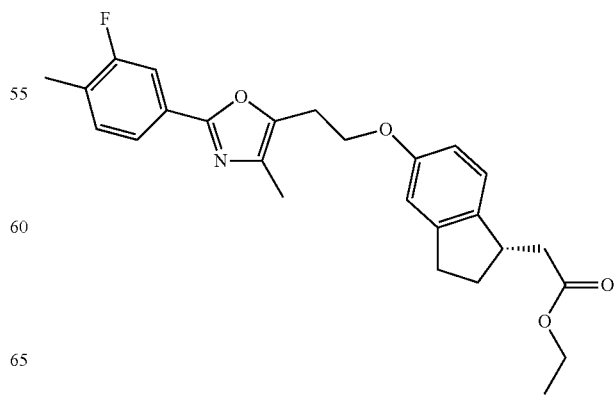

ES-MS m/z 438.2 ((MH)⁺); HPLC RT (min.) 4.18. ¹H NMR (Acetone-d₆) δ 6.67 (dd, 1H), 7.59 (dd, 1H), 7.37 (t, 1H), 7.08 (d, 1H), 6.80 (s, 1H), 6.72 (dd, 1H), 4.26 (t, 2H), 4.12 (q, 2H), 3.46-3.38 (m, 1H), 3.17 (t, 2H), 2.89-2.65 (m, 3H), 2.39-2.23 (m, 5H), 2.17 (s, 3H), 1.75-1.63 (m, 1H), 1.23 (t, 3H).

Example 220

Preparation of ((1S)-5-{2-[4-methyl-2-(4-methylphenyl)-1,3-oxazol-5-yl]ethoxy}-2,3-dihydro-1H-inden-1-yl)acetic acid

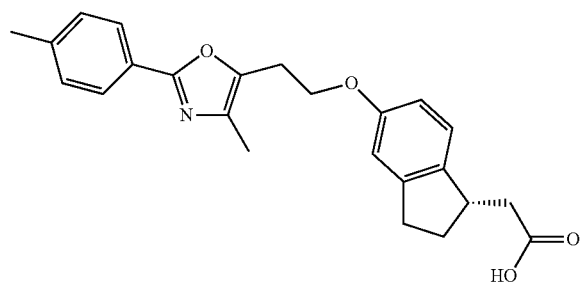 [SMILES: Cc1ccc(-c2nc(C)c(CCOc3ccc4c(c3)CC[C@H]4CC(=O)O)o2)cc1]

ES-MS m/z 392.2 ((MH)⁺); HPLC RT (min.) 3.36. ¹H NMR (Acetone-d₆) δ 7.72 (d, 2H), 7.15 (d, 2H), 6.99 (d, 1H), 6.67 (s, 1H), 6.59 (dd, 1H), 4.12 (t, 2H), 3.33-3.28 (m, 1H), 3.03 (t, 2H), 2.73-2.54 (m, 3H), 2.27-2.21 (m, 5H), 2.02 (s, 3H), 1.64-1.54 (m, 1H).

Example 221

Preparation of ((1S)-5-{2-[2-(3-fluoro-4-methylphenyl)-4-methyl-1,3-oxazol-5-yl]ethoxy}-2,3-dihydro-11-inden-1-yl)acetic acid

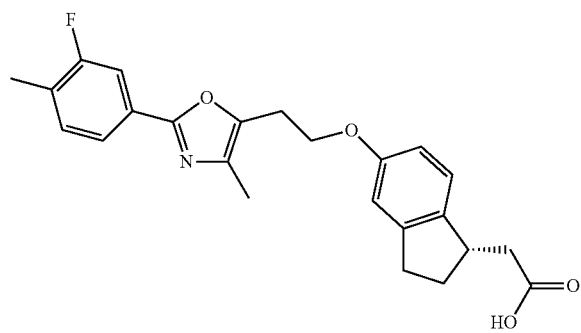 [SMILES: Cc1ccc(-c2nc(C)c(CCOc3ccc4c(c3)CC[C@H]4CC(=O)O)o2)cc1F]

ES-MS m/z 410.2 ((MH)⁺); HPLC RT (min.) 3.49. ¹H NMR (Acetone-d₆) δ 7.68 (dd, 1H), 7.59 (dd, 1H), 7.36 (t, 1H), 7.12 (d, 1H), 6.80 (s, 1H), 6.72 (dd, 1H), 4.26 (t, 2H), 3.47-3.41 (m, 1H), 3.18 (t, 2H), 2.86-2.67 (m, 3H), 2.40-2.28 (m, 5H), 2.17 (s, 3H), 1.18-1.65 (m, 1H).

Example 222

Preparation of [(1S)-5-(2-{4-methyl-2-[4-trifluoromethyl)phenyl]-1,3-oxazol-5-yl}ethoxy)-2,3-dihydro-1H-inden-1-yl]acetic acid

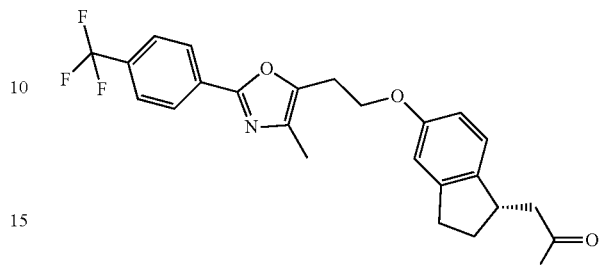

ES-MS m/z 446.5 ((MH)⁺); HPLC RT (min.) 3.47. ¹H NMR (Acetone-d₆) δ 8.17 (d, 2H), 7.84 (d, 2H), 7.13 (s, 1H), 6.80 (s, 1H), 6.72 (dd, 1H), 4.28 (t, 2H), 3.46-3.41 (m, 1H), 3.21 (t, 2H), 2.86-2.67 (m, 3H), 2.40-2.28 (m, 2H), 2.20 (s, 3H), 1.77-1.67 (m, 1H).

Example 223

Preparation of (2S)-2-{(1S)-5-[2-(5-methyl-2-phenyl-1,3-oxazol-4-yl)ethoxy]-2,3-dihydro-1H-inden-1-yl}propanoic acid and (2R)-2-{(1R)-5-[2-(5-methyl-2-phenyl-1,3-oxazol-4-yl)ethoxy]-2,3-dihydro-1H-inden-1-yl}propanoic acid

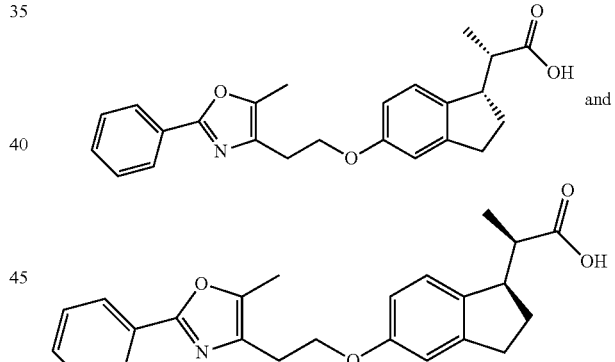

Step 1. Preparation of (2S)-2-[(1S)-5-methoxy-2,3-dihydro-1H-inden-1-yl]propanoic acid and (2R)-2-[(1R)-5-methoxy-2,3-dihydro-1H-inden-1-yl]propanoic acid

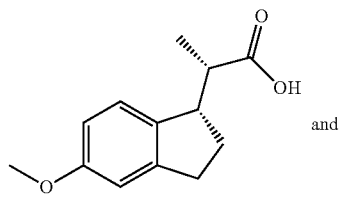

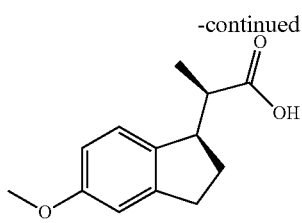

The starting acid (Example 2b) was reacted using a similar procedure as described in Example 4, under 60 psi H₂, and using 4.5 g starting material, 1.04 g catalyst, and 4.5 mL triethylamine in 45 mL ethanol and 5 mL THF. The standard extractive workup gave 3.22 g product. LC/MS retention time 2.41 min., NMR (d6-DMSO): 0.87 (d, 3H, α-methyl), 1.75 (m, 1H), 2.04 (m, 1H), 3.66 (s, 3H, methoxy), 6.65 (m, 1H, aryl), 6.76 (s, 1H, aryl), 7.04 (d, 1H, aryl,) 12.18 (bs, 1H, acid.)

Step 2: Preparation of methyl(2S)-2-[(1S)-5-methoxy-2,3-dihydro-1H-inden-1-yl]propanoate and methyl(2R)-2-[(1R))-5-methoxy-2,3-dihydro-1H-inden-1-yl]propanoate

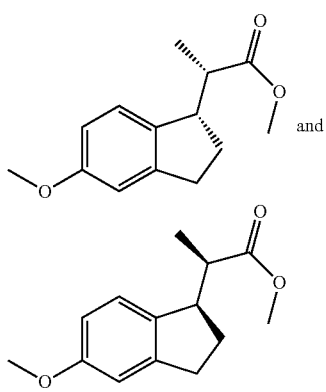

The compound was prepared by the reaction of 1.5 g starting acid, 0.93 mL iodomethane, and 1.75 g sodium bicarbonate in 10 mL methanol under standard esterification conditions as described in Example 6. Workup gave 1.53 g, 96%. (NMR (CD₂Cl₂): 1.05 (d, 3H, α-methyl), 1.88 (m, 1H), 2.19 (m, 1H), 3.44 (m, 1H), 3.68 (s, 3H, methoxy), 3.77 (s, 3H, ester).

Step 3. Preparation of: methyl(2S)-2-[(1S)-5-hydroxy-2,3-dihydro-1H-inden-1-yl]propanoate and methyl(2R)-2-[(1R)-5-hydroxy-2,3-dihydro-1H-inden-1-yl]propanoate

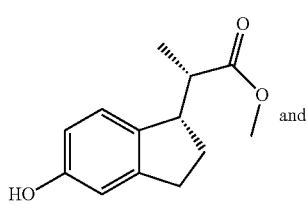

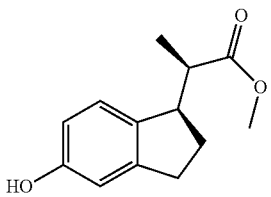

Using the demethylation conditions as described in Example 7 (1.53 g starting material, 4.35 g AlCl₃, and 2.4 mL ethanethiol in 20 mL dichloromethane), 1.21 g of product (84%) was obtained. (NMR (CD₂Cl₂): 1.05 (d, 3H, α-methyl), 1.88 (m, 1H), 2.18 (m, 1H), 3.45 (m, 1H), 3.67 (s, 3H, ester), 6.60 (m, 1H, aryl), 6.69 (s, 1H, aryl), 6.93 (d, 1H, aryl.)

Step 4: Preparation of methyl(2S)-2-{(1S)-5-[2-(5-methyl-2-phenyl-1,3-oxazol-4-yl)ethoxy]-2,3-dihydro-1H-inden-1-yl}propanoate and methyl(2R)-2-{(1R)-5-[2-(5-methyl-2-phenyl-1,3-oxazol-4-yl)ethoxy]-2,3-dihydro-1H-inden-1-yl}propanoate

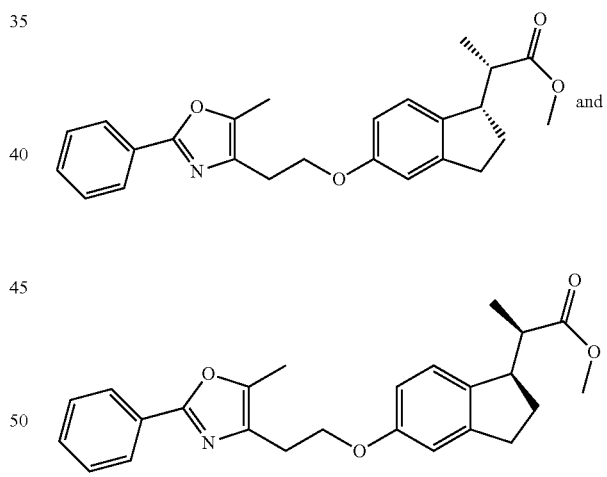

Using the standard Mitsunobu coupling procedure as described in Example 11 (0.100 g starting phenol, 0.110 g oxazolylethanol, 0.143 g triphenylphosphine, and 0.137 g ADDP in 2 mL dichloromethane), 0.107 g (58%) of product was obtained after chromatography in 15% EtOAc/hexane. NMR (CD₂Cl₂): 1.62-1.87 (m, 4H), 2.40 (s, 3H, oxazole methyl), 2.98 (t, 2H, methylene), 3.23 (m, 1H), 3.63 (s, 3H, ester), 6.60 (s, 1H, aryl), 6.64 (m, 1H, aryl), 7.42 (m, 3H, aryl), 8.00 (m, 2H, aryl).

Step 5. (2S)-2-{(1S)-5-[2-(5-methyl-2-phenyl-1,3-oxazol-4-yl)ethoxy]-2,3-dihydro-1H-inden-1-yl}propanoic acid and (2R)-2-{(1R)-5-[2-(5-methyl-2-phenyl-1,3-oxazol-4-yl)ethoxy]-2,3-dihydro-1H-inden-1-yl}propanoic acid

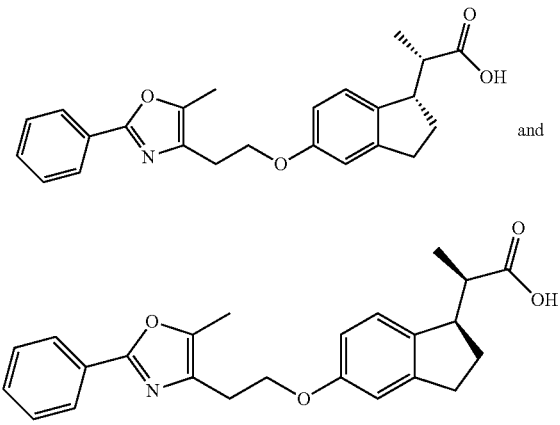
and

The LiOH hydrolysis conditions were applied to 0.090 g of starting ester, yielding 0.082 g (95%) product. NMR (CD$_3$OD): 0.4-0.75 (m, 4H), 1.18 (s, 3H), 1.75 (t, 2H, methylene), 2.00 (m, 1H), 2.99 (t, 2H, methylene), 5.39 (s, 1H, aryl), 5.48 (m, 1H, aryl), 5.83 (d, 1H, aryl), 6.27 (m, 3H, aryl), 6.76 (m, 2H, aryl).

Using the methods described above and the appropriate starting materials, additional (2S,1S) and (2R,1R) were similarly prepared, either as diastereomeric (i.e., syn, {(2S,1S)/(2R,1R)} and or anti {(2R,1S)/(2S,1R)}) mixtures, or as individual enantiomers. These compounds are summarized in Table 5.

TABLE 5

| Ex. No. | R$^3$ | R$^4$ | X | Isomer | HPLC RT (min) | LC-MS [M + H]$^+$ |
|---|---|---|---|---|---|---|
| 224 | Me | 3,4-(Cl)$_2$—Ph | O | 2S,1S | 4.10 | 460.0 |
| 225 | Me | 3,4-(Cl)$_2$—Ph | O | syn racemate | 4.10 | 460.0 |
| 226 | Me | 3,4-(Me)$_2$—Ph | O | syn racemate | 4.32 | 420.4 |
| 227 | Me | 3,4-(Me)$_2$—Ph | O | 2S,1S | 4.32 | 420.4 |
| 228 | Me | 3-Me—Ph | O | syn racemate | 4.19 | 406.3 |
| 229 | Me | 4-CF$_3$—Ph | O | syn racemate | 3.73 | 460.2 |
| 230 | Me | 4-CF$_3$—Ph | O | 2S,1S | 3.73 | 460.2 |
| 231 | Me | 4-CF$_3$—Ph | O | 2R,1R | 3.73 | 460.2 |
| 232 | Me | 4-Cl—Ph | O | syn racemate | 3.61 | 426.2 |
| 233 | Me | 4-Et—Ph | O | syn racemate | 3.70 | 420.3 |
| 234 | Me | 4-Et—Ph | O | 2S,1S | 3.70 | 420.3 |
| 235 | Me | 4-Et—Ph | O | 2R,1R | 3.70 | 420.3 |
| 236 | Me | 4-Et—Ph | O | syn/anti mixture | 3.70 | 420.3 |
| 237 | Me | 4-Et—Ph | O | 2R,1S | 3.70 | 420.3 |
| 238 | Me | 4-Et—Ph | O | 2S,1R | 3.70 | 420.3 |
| 239 | Me | 4-MeO—Ph | O | syn racemate | 3.37 | 422.3 |
| 240 | Me | 4-MeO—Ph | O | 2R,1R | 3.37 | 422.3 |
| 241 | Me | 4-MeO—Ph | O | 2S,1S | 3.37 | 422.3 |

TABLE 5-continued

| Ex. No. | R$^3$ | R$^4$ | X | Isomer | HPLC RT (min) | LC-MS [M + H]$^+$ |
|---|---|---|---|---|---|---|
| 242 | Me | 4-n-Bu—Ph | O | syn racemate | 4.08 | 448.4 |
| 243 | Me | 4-t-Bu—Ph | O | 2S,1S | 4.59 | 448.4 |
| 244 | Et | 4-t-Bu—Ph | O | syn racemate | 4.59 | 448.4 |
| 245 | Me | 4-MeO—Ph | O | 2S,1S | 3.58 | — |
| 246 | Me | 4-Cl—Ph | S | syn racemate | 3.84 | 442.2 |
| 247 | Me | 4-Me—Ph | S | syn racemate | 4.34 | 422.3 |

Example 248

Preparation of ethyl[(1S)-5-(2-{2-[4'-(5-acetyl-2-thienyl)-1,1'-biphenyl-4-yl]-5-methyl-1,3-oxazol-4-yl}ethoxy)-2,3-dihydro-1H-inden-1-yl]acetate

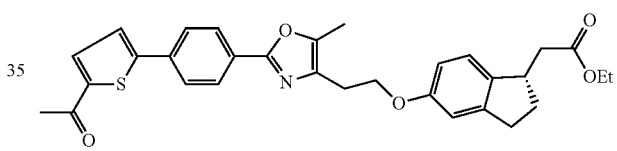

To a solution containing ethyl((1S)-5-{2-[2-(4-bromophenyl)-5-methyl-1,3-oxazol-4-yl]ethoxy}-2,3-dihydro-1H-inden-1-yl)acetate (0.100 g, 0.21 mmol) [prepared from 2-[5-methyl-2-(4-bromophenyl)-1,3-oxazol-4-yl]ethanol and ethyl [(1S)-5-hydroxy-2,3-dihydro-1H-inden-1-yl]acetate (Example 135)], 1,1'-bis(diphenylphosphino)-ferrocene] dichloro palladium(II) (16.9 mg, 0.02 mmol), and 5-acetyl-2-thienylboronic acid (0.062 g, 0.41 mmol) in degassed toluene and dioxane (4:1, 2 mL) was added aqueous 2 M sodium carbonate (0.5 mL). The mixture was heated at 85° C. for 16 hours. Solvents were evaporated under vacuum and the residue was dissolved in methanol and acetonitrile and filtered through a C8 reverse phase extraction cartridge. Solvents were evaporated and the residue was dissolved in acetonitrile and purified by HPLC to obtain ethyl[(1S)-5-(2-{2-[4'-(5-acetyl-2-thienyl)-1,1'-biphenyl-4-yl]-5-methyl-1,3-oxazol-4-yl}ethoxy)-2,3-dihydro-1H-inden-1-yl]acetate in 46% yield. (50 mg, 0.09 mmol) MS (electro spray) 530.4 (M+H)$^+$, $^1$H NMR (CDCl$_3$) δ 1.24 (t, 3H), 1.71 (m, 1H), 2.37 (m, 5H), 2.57 (s, 3H), 2.68 (m, 1H), 2.83 (m, 2H), 3.03 (m, 2H), 3.48 (m, 1H), 4.17(m, 4H), 6.67 (m, 2H), 7.02 (d, 1H), 7.39 (d, 1H), 7.67 (d, 1H), 7.73 (d, 2H), 8.01 (d, 2H).

Other compounds, prepared by using analogous starting materials and the method described in Example 248 together with the hydrolysis described in Example 11, are described below in Table 6.

TABLE 6

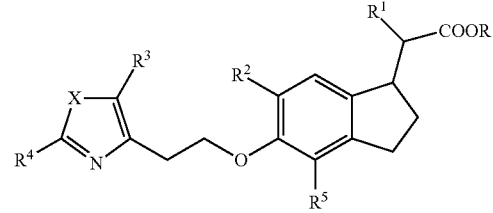

| Ex. No. | R | $R^1$ | $R^2$ | $R^3$ | $R^4$ | $R^5$ | X | LC-MS $[M + H]^+$ |
|---|---|---|---|---|---|---|---|---|
| 249 | H | H | H | Me | 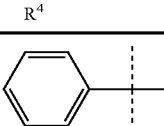 | H | O | 493.3 |
| 250 | H | H | H | Me | 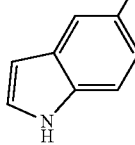 | H | O | 484.2 |
| 251 | H | H | H | Me | 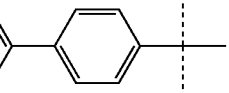 | H | O | 502.2 |

Evaluation of Compounds

Demonstration of the activity of the compounds of the present invention may be accomplished through in vitro, ex vivo, and in vivo assays that are well known in the art. For example, to demonstrate the efficacy of a pharmaceutical agent for the treatment of diabetes and related disorders such as Syndrome X, impaired glucose tolerance, impaired fasting glucose, and hyperinsulinemia or atherosclerotic disease and related disorders such as hypertriglyceridemia and hypercholesteremia, the following assays may be used.

Insulin Receptor Binding in 3T3-L1 Cells Treated with Compounds

3T3-L1 cells were seeded at 9300 cells per well in Costar flat bottom TC and incubated for 1 week until they were 2 days post-confluent (e.g., cells have reached maximum density). The cells were then treated for 2 days with differentiation media (Dulbecco's Modified Eagle Medium (DMEM), 100 μg/ml Penicillin/Streptomycin, 2 mM L-Glutamine, 10% Fetal Bovine Serum) containing 0.5 μM human Insulin-like Growth Factor (IGF-1) and test compounds. After treatment, the media was replaced with differentiation media, and the cells were incubated for 4 days. The cells were then assayed for insulin receptor activity. After washing the cells with buffer, they were incubated with 0.1 nM $^{125}$I-insulin and (+/−) 100 nM unlabeled insulin, and incubated at rt for 1 hour. The cells were then washed 3× with buffer, dissolved with 1N NaOH, and counted on a gamma counter. An EC50 value was determined if a plateau was attained and percent maximum stimulation was assessed.

In Vivo Assays

Method for Measuring Blood Glucose Levels db/db mice (obtained from Jackson Laboratories, Bar Harbor, Me.) were bled (by either eye or tail vein) and grouped according to equivalent mean blood glucose levels. They were dosed orally (by gavage in a pharmaceutically acceptable vehicle) with the test compound once daily for 14 days. At this point, the animals were bled again by eye or tail vein and blood glucose levels were determined. In each case, glucose levels were measured with a Glucometer Elite XL (Bayer Corporation, Elkhart, Ind.).

Method for Measuring Triglyceride Levels hApoA1 mice (obtained from Jackson Laboratories, Bar Harbor, Me.) were bled (by either eye or tail vein) and grouped according to equivalent mean serum triglyceride levels. They were dosed orally (by gavage in a pharmaceutically acceptable vehicle) with the test compound once daily for 8 days. The animals were then bled again by eye or tail vein, and serum triglyceride levels were determined. In each case, triglyceride levels were measured using a Technicon Axon Autoanalyzer (Bayer Corporation, Tarrytown, N.Y.).

Method for Measuring HDL-Cholesterol Levels

To determine plasma HDL-cholesterol levels, hApoA1 mice are bled and grouped with equivalent mean plasma HDL-cholesterol levels. The mice are orally dosed once daily with vehicle or test compound for 7 days, and then bled again on day 8. Plasma is analyzed for HDL-cholesterol using the Synchron Clinical System (CX4) (Beckman Coulter, Fullerton, Calif.).

Method for Measuring Total Cholesterol, HDL-Cholesterol, Triglycerides, and Glucose Levels In another in vivo assay, obese monkeys are bled, then orally dosed once daily with vehicle or test compound for 4 weeks, and then bled again. Serum is analyzed for total cholesterol, HDL-cholesterol, triglycerides, and glucose using the Synchron Clinical System (CX4) (Beckman Coulter, Fullerton, Calif.). Lipoprotein subclass analysis is performed by NMR spectroscopy as described by Oliver et al., (Proc. Natl. Acad. Sci. USA 98:5306-5311, 2001).

Method for Measuring an Effect on Cardiovascular Parameters

Cardiovascular parameters (e.g., heart rate and blood pressure) are also evaluated. SHR rats are orally dosed once daily with vehicle or test compound for 2 weeks. Blood pressure and heart rate are determined using a tail-cuff method as described by Grinsell et al., (Am. J. Hypertens. 13:370-375, 2000). In monkeys, blood pressure and heart rate are monitored as described by Shen et al, (J. Pharmacol. Exp. Therap. 278:1435-1443, 1996).

Compounds of the present invention were tested in the above assays and by the resulting activity profiles, they were found to have an effect on blood glucose levels and serum triglyceride levels, and therefore, a potential utility in the treatment of diabetes and related disorders such as Syndrome X, impaired glucose tolerance, impaired fasting glucose, and hyperinsulinemia or cardiovascular disease and related disorders such as hypertriglyceridemia and hypercholesteremia.

Pharmaceutical Compositions

Based on the above tests, or other well known assays used to determine the efficacy for treatment of conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered may generally range from about 0.001 mg/kg to about 200 mg/kg, and preferably from about 0.01 mg/kg to about 200 mg/kg body weight per day. A unit dosage may contain from about 0.05 mg to about 1500 mg of active ingredient, and may be administered one or more times per day. The daily dosage for administration by injection, including intravenous, intramuscular, subcutaneous, and parenteral injections, and use of infusion techniques may be from about 0.01 to about 200 mg/kg. The daily rectal dosage regimen may be from 0.01 to 200 mg/kg of total body weight. The transdermal concentration may be that required to maintain a daily dose of from 0.01 to 200 mg/kg.

Of course, the specific initial and continuing dosage regimen for each patient will vary according to the nature and severity of the condition as determined by the attending diagnostician, the activity of the specific compound employed, the age of the patient, the diet of the patient, time of administration, route of administration, rate of excretion of the drug, drug combinations, and the like. The desired mode of treatment and number of doses of a compound of the present invention or a pharmaceutically acceptable salt thereof may be ascertained by those skilled in the art using conventional treatment tests.

The compounds of this invention may be utilized to achieve the desired pharmacological effect by administration to a patient in need thereof in an appropriately formulated pharmaceutical composition. A patient, for the purpose of this invention, is a mammal, including a human, in need of treatment for a particular condition or disease. Therefore, the present invention includes pharmaceutical compositions which are comprised of a pharmaceutically acceptable carrier and a pharmaceutically effective amount of a compound identified by the methods described herein, or a pharmaceutically acceptable salt or ester thereof. A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient. A pharmaceutically effective amount of a compound is that amount which produces a result or exerts an influence on the particular condition being treated. The compounds identified by the methods described herein may be administered with a pharmaceutically-acceptable carrier using any effective conventional dosage unit forms, including, for example, immediate and timed release preparations, orally, parenterally, topically, or the like.

For oral administration, the compounds may be formulated into solid or liquid preparations such as, for example, capsules, pills, tablets, troches, lozenges, melts, powders, solutions, suspensions, or emulsions, and may be prepared according to methods known to the art for the manufacture of pharmaceutical compositions. The solid unit dosage forms may be a capsule which can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose, and cornstarch in combination with binders such as acacia, cornstarch, or gelatin; disintegrating agents intended to assist the break-up and dissolution of the tablet following administration such as potato starch, alginic acid, corn starch, and guar gum; lubricants intended to improve the flow of tablet granulation and to prevent the adhesion of tablet material to the surfaces of the tablet dies and punches, for example, talc, stearic acid, or magnesium, calcium or zinc stearate; dyes; coloring agents; and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and polyethylene alcohols, either with or without the addition of a pharmaceutically acceptable surfactant, suspending agent, or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent, and one or more preservatives. Suitable dispersing or wetting agents and suspending agents are exemplified by those already mentioned above. Additional excipients, for example, those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived from fatty acids and hexitol anhydrides, for example, sorbitan monooleate, and (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil, or coconut oil; or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol, or sucrose. Such formulations may also contain a demulcent, and preservative, flavoring and coloring agents.

The compounds of this invention may also be administered parenterally, that is, subcutaneously, intravenously, intramuscularly, or interperitoneally, as injectable dosages of the compound in a physiologically acceptable diluent with a pharmaceutical carrier which may be a sterile liquid or mixture of liquids such as water, saline, aqueous dextrose and related sugar solutions; an alcohol such as ethanol, isopropanol, or hexadecyl alcohol; glycols such as propylene glycol or polyethylene glycol; glycerol ketals such as 2,2-dimethyl-1,1-dioxolane-4-methanol, ethers such as poly(ethyleneglycol) 400; an oil; a fatty acid; a fatty acid ester or glyceride; or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures.

The parenteral compositions of this invention may typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters; for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadecaethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringers solution, and isotonic sodium chloride solution. In addition, sterile fixed oils are conventionally employed as solvents or suspending media. For this purpose, any bland, fixed oil may be employed including synthetic mono or diglycerides. In addition, fatty acids such as oleic acid may be used in the preparation of injectables.

A composition of the invention may also be administered in the form of suppositories for rectal administration of the drug. These compositions may be prepared by mixing the drug with a suitable non-irritation excipient which is solid at ordinary temperatures but liquid at the rectal temperature and will therefore melt in the rectum to release the drug. Such material are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, incorporated herein by reference). Such patches may be constructed for continuous, pulsatile, or on demand delivery of pharmaceutical agents.

It may be desirable or necessary to introduce the pharmaceutical composition to the patient via a mechanical delivery device. The construction and use of mechanical delivery devices for the delivery of pharmaceutical agents is well known in the art. For example, direct techniques for administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, incorporated herein by reference.

The compositions of the invention may also contain other conventional pharmaceutically acceptable compounding ingredients, generally referred to as carriers or diluents, as necessary or desired. Any of the compositions of this invention may be preserved by the addition of an antioxidant such as ascorbic acid or by other suitable preservatives. Conventional procedures for preparing such compositions in appropriate dosage forms can be utilized.

Commonly used pharmaceutical ingredients which may be used as appropriate to formulate the composition for its intended route of administration include: acidifying agents, for example, but are not limited to, acetic acid, citric acid, fumaric acid, hydrochloric acid, nitric acid; and alkalinizing agents such as, but are not limited to, ammonia solution, ammonium carbonate, diethanolamine, monoethanolamine, potassium hydroxide, sodium borate, sodium carbonate, sodium hydroxide, triethanolamine, trolamine.

Other pharmaceutical ingredients include, for example, but are not limited to, adsorbents (e.g., powdered cellulose and activated charcoal); aerosol propellants (e.g., carbon dioxide, $CCl_2F_2$, $F_2ClC$—$CClF_2$ and $CClF_3$); air displacement agents (e.g., nitrogen and argon); antifungal preservatives (e.g., benzoic acid, butylparaben, ethylparaben, methylparaben, propylparaben, sodium benzoate); antimicrobial preservatives (e.g., benzalkonium chloride, benzethonium chloride, benzyl alcohol, cetylpyridinium chloride, chlorobutanol, phenol, phenylethyl alcohol, phenylmercuric nitrate and thimerosal); antioxidants (e.g., ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite); binding materials (e.g., block polymers, natural and synthetic rubber, polyacrylates, polyurethanes, silicones and styrene-butadiene copolymers); buffering agents (e.g., potassium metaphosphate, potassium phosphate monobasic, sodium acetate, sodium citrate anhydrous and sodium citrate dihydrate); carrying agents (e.g., acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection); chelating agents (e.g., edetate disodium and edetic acid); colorants (e.g., FD&C Red No. 3, FD&C Red No. 20, FD&C Yellow No. 6, FD&C Blue No. 2, D&C Green No. 5, D&C Orange No. 5, D&C Red No. 8, caramel and ferric oxide red); clarifying agents (e.g., bentonite); emulsifying agents (but are not limited to, acacia, cetomacrogol, cetyl alcohol, glyceryl monostearate, lecithin, sorbitan monooleate, polyethylene 50 stearate); encapsulating agents (e.g., gelatin and cellulose acetate phthalate); flavorants (e.g., anise oil, cinnamon oil, cocoa, menthol, orange oil, peppermint oil and vanillin); humectants (e.g., glycerin, propylene glycol and sorbitol); levigating agents (e.g., mineral oil and glycerin); oils (e.g., arachis oil, mineral oil, olive oil, peanut oil, sesame oil and vegetable oil); ointment bases (e.g., lanolin, hydrophilic ointment, polyethylene glycol ointment, petrolatum, hydrophilic petrolatum, white ointment, yellow ointment, and rose water ointment); penetration enhancers (transdermal delivery) (e.g., monohydroxy or polyhydroxy alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas); plasticizers (e.g., diethyl phthalate and glycerin); solvents (e.g., alcohol, corn oil, cottonseed oil, glycerin, isopropyl alcohol, mineral oil, oleic acid, peanut oil, purified water, water for injection, sterile water for injection and sterile water for irrigation); stiffening agents (e.g., cetyl alcohol, cetyl esters wax, microcrystalline wax, paraffin, stearyl alcohol, white wax and yellow wax); suppository bases (e.g., cocoa butter and polyethylene glycols (mixtures)); surfactants (e.g., benzalkonium chloride, nonoxynol 10, oxtoxynol 9, polysorbate 80, sodium lauryl sulfate and sorbitan monopalmitate); suspending agents (e.g., agar, bentonite, carbomers, carboxymethylcellulose sodium, hydroxyethyl cellulose, hydroxypropyl cellulose, hydroxypropyl methylcellulose, kaolin, methylcellulose, tragacanth and veegum); sweetening e.g., aspartame, dextrose, glycerin, mannitol, propylene glycol, saccharin sodium, sorbitol and sucrose); tablet anti-adherents (e.g., magnesium stearate and talc); tablet binders (e.g., acacia, alginic acid, carboxymethylcellulose sodium, compressible sugar, ethylcellulose, gelatin, liquid glucose, methylcellulose, povidone and pregelatinized starch); tablet and capsule diluents (e.g., dibasic calcium phosphate, kaolin, lactose, mannitol, microcrystalline cellulose, powdered cellulose, precipitated calcium carbonate, sodium carbonate, sodium phosphate, sorbitol and starch); tablet coating agents (e.g., liquid glucose, hydroxyethyl cellulose, hydroxypropyl cellulose, hydroxypropyl methylcellulose, methylcellulose, ethylcellulose, cellulose acetate phthalate and shellac); tablet direct compression excipients (e.g., dibasic calcium phosphate); tablet disintegrants (e.g., alginic acid, carboxymethylcellulose calcium, microcrystalline cellulose, polacrillin potassium, sodium alginate, sodium starch glycollate and starch); tablet glidants (e.g., colloidal silica, corn starch and talc); tablet lubricants (e.g., calcium stearate, magnesium stearate, mineral oil, stearic acid and zinc stearate); tablet/capsule opaquants (e.g., titanium dioxide); tablet polishing agents (e.g., carnuba wax and white wax); Thickening agents (e.g., beeswax, cetyl alcohol and paraffin); tonicity agents (e.g., dextrose and sodium chloride); viscosity increasing agents (e.g., alginic acid, bentonite, carbomers, carboxymethylcellulose sodium, methylcellulose, povidone, sodium alginate and tragacanth); and wetting agents (e.g., heptadecaethylene oxycetanol, lecithins, polyethylene sorbitol monooleate, polyoxyethylene sorbitol monooleate, and polyoxyethylene stearate).

The compounds identified by the methods described herein may be administered as the sole pharmaceutical agent or in combination with one or more other pharmaceutical agents where the combination causes no unacceptable adverse effects. For example, the compounds of this invention can be combined with known anti-obesity, or with known antidiabetic or other indication agents, and the like, as well as with admixtures and combinations thereof.

The compounds identified by the methods described herein may also be utilized, in free base form or in compositions, in research and diagnostics, or as analytical reference standards, and the like. Therefore, the present invention includes compositions which are comprised of an inert carrier and an effective amount of a compound identified by the methods described herein, or a salt or ester thereof. An inert carrier is any material which does not interact with the compound to be carried and which lends support, means of conveyance, bulk, traceable material, and the like to the compound to be carried. An effective amount of compound is that amount which produces a result or exerts an influence on the particular procedure being performed.

Formulations suitable for subcutaneous, intravenous, intramuscular, and the like; suitable pharmaceutical carriers; and techniques for formulation and administration may be prepared by any of the methods well known in the art (see, e.g., Remington's Pharmaceutical Sciences, Mack Publishing Co., Easton, Pa., $20^{th}$ edition, 2000)

The following examples are presented to illustrate the invention described herein, but should not be construed as limiting the scope of the invention in any way.

Capsule Formulation

A capsule formula is prepared from:

| Compound of this invention | 40 mg |
|---|---|
| Starch | 109 mg |
| Magnesium stearate | 1 mg |

The components are blended, passed through an appropriate mesh sieve, and filled into hard gelatin capsules.

Tablet Formulation

A tablet is prepared from:

| Compound of this invention | 25 mg |
|---|---|
| Cellulose, microcrystaline | 200 mg |
| Colloidal silicon dioxide | 10 mg |
| Stearic acid | 5.0 mg |

The ingredients are mixed and compressed to form tablets. Appropriate aqueous and non-aqueous coatings may be applied to increase palatability, improve elegance and stability or delay absorption.

Sterile IV Solution

A 5 mg/ml solution of the desired compound of this invention is made using sterile, injectable water, and the pH is adjusted if necessary. The solution is diluted for administration to 1-2 mg/ml with sterile 5% dextrose and is administered as an IV infusion over 60 minutes.

Intramuscular Suspension

The following intramuscular suspension is prepared:

| Compound of this invention | 50 mg/ml |
|---|---|
| Sodium carboxymethylcellulose | 5 mg/ml |
| TWEEN 80 | 4 mg/ml |
| Sodium chloride | 9 mg/ml |
| Benzyl alcohol | 9 mg/ml |

The suspension is administered intramuscularly.

Hard Shell Capsules

A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Immediate Release Tablets/Capsules

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

It should be apparent to one of ordinary skill in the art that changes and modifications can be made to this invention without departing from the spirit or scope of the invention as it is set forth herein.

We claim:

1. A compound having the following structure:

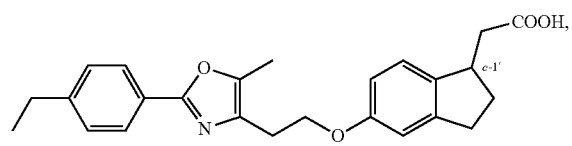 [SMILES: CCc1ccc(-c2nc(CCOc3ccc4c(c3)CCC4CC(=O)O)c(C)o2)cc1]

or a pharmaceutically acceptable salt thereof.

2. The compound according to claim 1, wherein c-1' is in the S configuration or the R configuration.

3. The compound according to claim 1, wherein the compound has the following structure:

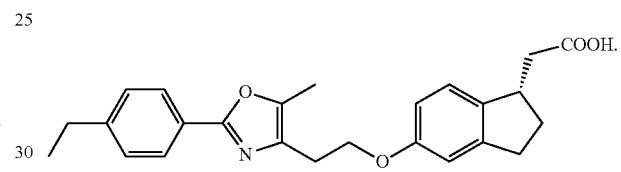

4. The compound according to claim 1, wherein the compound is a pharmaceutically acceptable salt of the following structure:

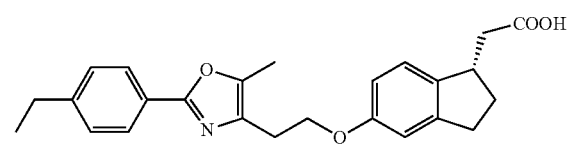

and the salt is selected from the group consisting of an alkali metal salt, an alkaline earth metal salt, a quaternized ammonium salt with an organic base, a salt of basic nitrogen containing groups in the conjugate base which is quaternized by a substituent selected from the group consisting of a lower alkyl halide, a dialkyl sulfate, a diamyl sulfate, an alkyl halide, and an aralkyl halide.

5. The compound according to claim 1, wherein the compound is a N-methyl-D-glucamine, potassium or sodium salt of the following structure:

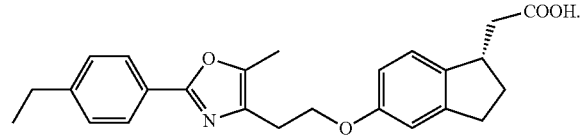

6. A pharmaceutical composition comprising an effective amount of a compound having the following structure:

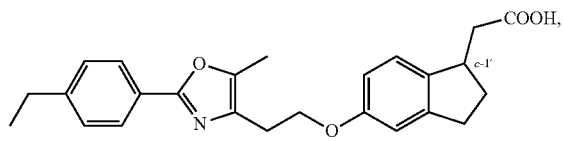

or a pharmaceutically acceptable salt thereof,
in combination with a pharmaceutically acceptable carrier.

7. The pharmaceutical composition according to claim 6, wherein the compound has the following structure:

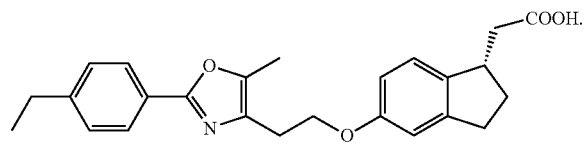

8. The pharmaceutical composition according to claim 6, wherein the compound is a N-methyl-D-glucamine, potassium or sodium salt of the following structure:

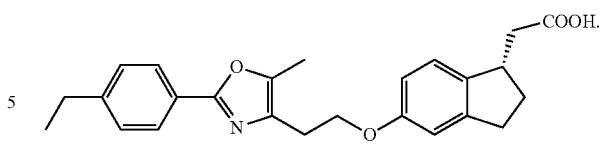

9. The pharmaceutical composition according to claim 6, further comprises at least one hypoglycemic agent.

10. The pharmaceutical composition according to claim 9, wherein said hypoglycemic agent is selected from the group consisting of insulin, biguanidines, sulfonylureas, insulin secretagogues, α-glycosidase inhibitors, and $\beta_3$-adrenoreceptor agonists.

11. The pharmaceutical composition according to claim 6 further comprising at least one agent selected from the group consisting of a HMG CoA reductase inhibitor, a bile acid binding agent, a fibric acid derivative, an agent that regulates hypertension, and an agent that regulates body weight.

* * * * *